(12) United States Patent
Prissette et al.

(10) Patent No.: US 12,209,238 B2
(45) Date of Patent: Jan. 28, 2025

(54) CRISPR/CAS SCREENING PLATFORM TO IDENTIFY GENETIC MODIFIERS OF TAU SEEDING OR AGGREGATION

(71) Applicant: Regeneron Pharmaceuticals, Inc., Tarrytown, NY (US)

(72) Inventors: Marine Prissette, Brooklyn, NY (US); Matthew Koss, Pleasantville, NY (US); Wen Fury, New York, NY (US); Brian Zambrowicz, Sleepy Hollow, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/502,499

(22) Filed: Nov. 6, 2023

(65) Prior Publication Data
US 2024/0084293 A1    Mar. 14, 2024

Related U.S. Application Data

(62) Division of application No. 16/821,453, filed on Mar. 17, 2020, now Pat. No. 11,845,931.

(60) Provisional application No. 62/820,086, filed on Mar. 18, 2019.

(51) Int. Cl.
| | |
|---|---|
| C12N 15/10 | (2006.01) |
| A61K 48/00 | (2006.01) |
| C12N 5/00 | (2006.01) |
| C12N 5/071 | (2010.01) |
| C12N 9/22 | (2006.01) |
| C12N 15/113 | (2010.01) |
| G01N 21/64 | (2006.01) |
| G01N 33/68 | (2006.01) |
| G16B 25/00 | (2019.01) |

(52) U.S. Cl.
CPC ....... *C12N 15/1082* (2013.01); *C12N 5/0018* (2013.01); *C12N 5/0686* (2013.01); *C12N 9/22* (2013.01); *C12N 15/1086* (2013.01); *C12N 15/1089* (2013.01); *C12N 15/113* (2013.01); *G01N 21/6428* (2013.01); *G01N 33/6896* (2013.01); *G16B 25/00* (2019.02); *A61K 48/00* (2013.01); *C12N 2310/20* (2017.05); *C12N 2320/12* (2013.01); *C12N 2502/99* (2013.01); *C12N 2800/80* (2013.01); *G01N 2021/6441* (2013.01); *G01N 2800/7047* (2013.01)

(58) Field of Classification Search
None
See application file for complete search history.

(56) References Cited

U.S. PATENT DOCUMENTS

| | | |
|---|---|---|
| 9,910,048 B2 | 3/2018 | Diamond et al. |
| 11,001,829 B2 | 5/2021 | Zhang et al. |
| 11,149,267 B2 | 10/2021 | Wang et al. |
| 11,781,131 B2 | 10/2023 | Prissette et al. |
| 11,845,930 B2 | 12/2023 | Fury et al. |
| 11,845,931 B2 | 12/2023 | Prissette et al. |
| 2016/0272965 A1 | 9/2016 | Zhang et al. |
| 2017/0204407 A1 | 7/2017 | Gilbert et al. |
| 2018/0291370 A1 | 10/2018 | Gersbach et al. |
| 2018/0305704 A1 | 10/2018 | Zhang |
| 2019/0032155 A1 | 1/2019 | Gong et al. |
| 2019/0284572 A1 | 9/2019 | Hunt et al. |
| 2020/0165601 A1 | 5/2020 | Zhang et al. |
| 2020/0299679 A1 | 9/2020 | Fury et al. |
| 2020/0299681 A1 | 9/2020 | Prissette et al. |
| 2020/0299682 A1 | 9/2020 | Prissette et al. |
| 2021/0009949 A1 | 1/2021 | Prissette et al. |
| 2023/0416728 A1 | 12/2023 | Prissette et al. |
| 2024/0182887 A1 | 6/2024 | Fury et al. |

FOREIGN PATENT DOCUMENTS

| | | |
|---|---|---|
| CN | 107002093 A | 8/2017 |
| CN | 108779471 A | 11/2018 |
| EP | 3011033 B1 | 2/2020 |
| WO | WO 2002/062851 A1 | 8/2002 |
| WO | WO 2014/008404 A1 | 1/2014 |
| WO | WO 2014/089104 A1 | 6/2014 |
| WO | WO 2015/122922 A1 | 8/2015 |
| WO | WO 2017/015637 A1 | 1/2017 |
| WO | WO 2017/100343 A1 | 6/2017 |
| WO | WO 2017/172764 A1 | 10/2017 |
| WO | WO 2018/127519 A1 | 7/2018 |
| WO | WO 2018/224531 A1 | 12/2018 |
| WO | WO 2019/010384 A1 | 1/2019 |
| WO | WO 2019/028032 A1 | 2/2019 |
| WO | WO 2019/183123 A1 | 9/2019 |
| WO | WO 2020/190927 A1 | 9/2020 |
| WO | WO 2020/190932 A1 | 9/2020 |
| WO | WO 2020/190944 A1 | 9/2020 |
| WO | WO 2020/252340 A1 | 12/2020 |

OTHER PUBLICATIONS

U.S. Appl. No. 62/820,086, filed Mar. 18, 2019, Expired.
U.S. Appl. No. 16/821,453, filed Mar. 17, 2020, U.S. Pat. No. 11,845,931, Issued.
PCT/US2020/023131, Mar. 17, 2020, WO 2020/190932, Expired.
EP 23215659.6 Extended European Search Report mailed Mar. 15, 2024.
"The 96th Annual Meeting of the Physiological Society of Japan," Journal of Physiological Sciences, Springer Japan KK, 69(Suppl 1), (2019).

(Continued)

*Primary Examiner* — Suzanne M Noakes
*Assistant Examiner* — Jae W Lee
(74) *Attorney, Agent, or Firm* — Yongjin Choi; Alston & Bird LLP

(57) ABSTRACT

Cas-protein-ready tau biosensor cells, CRISPR/Cas synergistic activation mediator (SAM)-ready tau biosensor cells, and methods of making and using such cells to screen for genetic modifiers of tau seeding or aggregation are provided. Reagents and methods for sensitizing such cells to tau seeding activity or tau aggregation or for causing tau aggregation are also provided.

42 Claims, 25 Drawing Sheets

Specification includes a Sequence Listing.

(56) References Cited

OTHER PUBLICATIONS

Agrotis et al., "A new age in functional genomics using CRISPR/Cas9 in arrayed library screening," Front. Genet., 6:300, (2015).
Anders et al., "Differential expression analysis for sequence count data," Genome Biol., 11:R106, pp. 1-12, (2010).
Anonymous, "Identification of genetic regulators for intracellular aggregation by genome-wide CRISPR screening," 2016 Fiscal Year Annual Research Report, The University of Tokyo, Kaken, 2 pages, (2018).
Anonymous, Abstracts: Oral Presentations, Cell Biology, ASCB Annual Meeting, 84 pages, (2016).
Bajar et al., "A Guide to Fluorescent Protein FRET Pairs," Sensors (Basel), 16:E1488, pp. 1-24, (2016).
Bennett et al., "Enhanced Tau Aggregation in the Presence of Amyloid β," Am. J. Pathol., 187(7):1601-1612, (2017).
Chakrabarti et al., "Target-Specific Precision of CRISPR-Mediated Genome Editing," Mol. Cell, 73(4):699-713, (2019).
Chen et al., "Compromised function of the ESCRT pathway promotes endolysomal escape of tau seeds and propagation of tau aggregation," J. Biol. Chem., 294(50):18952-18966, (2019).
Chen et al., "Genome-wide CRISPR Screen in a Mouse Model of Tumor Growth and Metastasis," Cell, 160(6):1246-1260 plus supplementary materials, (2015).
Chiu et al., "Identification of Calcium and Integrin-Binding Protein 1 as a Novel Regulator of Production of Amyloid β Peptide Using CRISPR/Cas9-based Screening System," FASEB J., 34(6):7661-7674 (2020).
CRISPR 101: A Desktop Resource, Addgene, 2nd ed., 195 pages, (2017).
Furman et al., "Sensitive Detection of Proteopathic Seeding Activity with FRET Flow Cytometry," J. Vis. Exp., 106:e53205, pp. 1-12, (2015).
Goedert, "Tau filaments in neurodegenerative diseases," FEBS Lett., 592(14):2383-2391, (2018).
Hart et al., "High-Resolution CRISPR Screens Reveal Fitness Genes and Genotype-Specific Cancer Liabilities," Cell, 163(6):1515-1526, (2015).
Holmes et al., "Proteopathic tau seeding predicts tauopathy in vivo," Proc. Natl. Acad. Sci. U.S.A., 111(41):E4376-E4385, (2014).
Joung et al., "Genome-scale CRISPR-Cas9 knockout and transcriptional activation screening," Nat. Protoc. 12(4):828-863, (2017).
Jjoung et al., "Genome-scale CRISPR-Cas9 knockout and transcriptional activation screening," Nat. Protoc., 12(4):828-863, (2017).
Jucker et al., "Self-propagation of pathogenic protein aggregates in neurodegenerative diseases," Nature, 501(7465):45-51, (2013).
Kampmann, "A CRISPR Approach to Neurodegenerative Diseases," Trends Mol. Med., 23(6):483-485, (2017).
Kampmann, "CRISPRi and CRISPRa Screens in Mammalian Cells for Precision Biology and Medicine," ACS Chem. Biol., 13(2):406-416, (2017).
Kaufman et al., "Tau Prion Strains Dictate Patterns of Cell Pathology, Progression Rate, and Regional Vulnerability In Vivo," Neuron, 92(4):796-812, (2016).
Kfoury et al., "Trans-cellular Propagation of Tau Aggregation by Fibrillar Species," The Journal of Biological Chemistry, 287(23):19440-19451, (2012).
Konermann et al., "Genome-scale transcriptional activation by an engineered CRISPR-Cas9 complex," Nature, 517(7536):583-588 plus supplementary materials, (2015).
Li et al., "MAGeCK enables robust identification of essential genes from genome-scale CRISPR/Cas9 knockout screens," Genome Biol., 15(12):554, 12 pages, (2014).

Miles et al., "Design, execution, and analysis of pooled in vitro CRISPR/Cas9 screens," FEBS J., 283(17):3170-3180, (2016).
Murugan et al., "The Revolution Continues: Newly Discovered Systems Expand the CRISPR-Cas Toolkit," Mol. Cell 68(1):15-25, (2017).
Nagai et al., "Astrocytes expressing ALS-linked mutated SOD1 release factors selectively toxic to motor neurons," Nat. Neurosci., 10(5):615-622, (2007).
Nakade et al., "Cas9, Cpf1 and C2c1/2/3—What's next?," Bioengineered, 8(3):265-273, (2017).
Nathaniel et al., "Elucidating Cellular Trafficking Pathways Controlling Prion-like Spread of Tau Aggregation Using CRISPR Interference Screens [abstract]," Abstracts; Poster Presentations, Cell Biology 2016, ASCB Annual Meeting, p. 887, (2016).
Nicholls et al., "Characterization of TauC3 antibody and demonstration of its potential to block tau propagation," PLOS One, 12(5):e0177914, 11 pages, (2017).
Nobuhara et al., "Tau Antibody Targeting Pathological Species Blocks Neuronal Uptake and Interneuron Propagation of Tau in Vitro," Am. J. Pathol., 187(6):1399-1412, (2017).
Jong et al., "Optimised metrics for CRISPR-KO screens with second-generation gRNA libraries," Sci. Rep., 7(1):7384, 10 pages, (2017).
Park et al., "A genome-wide CRISPR screen identifies a restricted set of HIV host dependency factors," Nat. Genet., 49(2):193-203 plus online methods, (2017).
Park et al., "Cpf1-Database: web-based genome-wide guide RNA library design for gene knockout screens using CRISPR-Cpf1," Bioinformatics, 34(6):1077-1079, (2018).
Prissette et al., "Disruption of nuclear envelope integrity as a possible initiating event in tauopathies," Cell. Rep., 40(8):111249, (Aug. 23, 2022).
Reczek et al., "A CRISPR screen identifies a pathway required for paraquat-induced cell death," Nat. Chem. Biol., 13(12):1274-1279 plus online methods, (2017).
Sanders et al., "Distinct Tau Prion Strains Propagate in Cells and Mice and Define Different Tauopathies," Neuron, 82(6):1271-1288, (2014).
Sanjana et al., "Improved vectors and genome-wide libraries for CRISPR screening," Nat. Methods, 11(8):783-784, (2014).
Shalem et al., "Genome-Scale CRISPR-Cas9 Knockout Screening in Human Cells," Science, 343:84-87 and Supplementary Material, (2014).
Tycko et al., "Pairwise library screen systematically interrogates *Staphylococcus aureus* Cas9 specificity in human cells," Nat. Commun. 9(1):2962, (2018).
Tzelepis et al., "A CRISPR Dropout Screen Identifies Genetic Vulnerabilities and Therapeutic Targets in Acute Myeloid Leukemia," Cell Reports, 17:1193-1205, (2016).
Wang et al., "Gene Essentiality Profiling Reveals Gene Networks and Synthetic Lethal Interactions with Oncogenic Ras," Cell, 168(5):890-903 plus supplemental materials, (2017).
Wang et al., "Identification and characterization of essential genes in the human genome," Science, 350(6264):1096-1101, (2015).
Wu et al., "Neuronal activity enhances tau propagation and tau pathology in vivo," Nat. Neurosci., 19(8):1085-1092, (2016).
U.S. Appl. No. 16/821,453, Non-Final Office Action mailed Feb. 14, 2023.
U.S. Appl. No. 16/821,453, Notice of Allowance and Interview Summary mailed Aug. 9, 2010.
U.S. Appl. No. 16/821,453, Requirement for Restriction/Election mailed Sep. 30, 2022.
WIPO Application No. PCT/US2020/023131, PCT International Search Report and Written Opinion of the International Searching Authority mailed Jul. 21, 2020.
WIPO Application No. PCT/US2020/023131, PCT Invitation to Pay Additional Fees mailed May 27, 2020.

CRISPR/CAS SCREENING PLATFORM TO IDENTIFY GENETIC MODIFIERS OF TAU SEEDING OR AGGREGATION

CROSS-REFERENCE TO RELATED APPLICATIONS

This application is a divisional of U.S. application Ser. No. 16/821,453, filed Mar. 17, 2020, which claims the benefit of U.S. Application No. 62/820,086, filed Mar. 18, 2019, each of which is herein incorporated by reference in its entirety for all purposes.

REFERENCE TO A SEQUENCE LISTING SUBMITTED AS AN XML FILE

The Sequence Listing written in file 602866SEQLIST.txt is 87,439 bytes, was created on Nov. 6, 2023, and is hereby incorporated by reference.

BACKGROUND

Abnormal aggregation or fibrillization of proteins is a defining feature of many diseases, notably including a number of neurodegenerative diseases such as Alzheimer's disease (AD), Parkinson's disease (PD), frontotemporal dementia (FTD), amyotrophic lateral sclerosis (ALS), chronic traumatic encephalopathy (CTE), Creutzfeldt-Jakob disease (CJD), and others. In many of these diseases, the fibrillization of certain proteins into insoluble aggregates is not only a hallmark of disease, but has also been implicated as a causative factor of neurotoxicity. Furthermore, these diseases are characterized by propagation of aggregate pathology through the central nervous system following stereotypical patterns, a process which correlates with disease progression. The identification of genes and genetic pathways that modify the processes of abnormal protein aggregation, or cell-to-cell propagation of aggregates, are therefore of great value in better understanding neurodegenerative disease etiology as well as in devising strategies for therapeutic intervention.

SUMMARY

Provided herein are methods of screening for genetic modifiers of tau aggregation, methods of producing a conditioned medium for inducing or sensitizing to tau aggregation, and methods of generating a population of tau-aggregation-positive cells. Also provided herein are Cas-tau biosensor cells or populations of such cells and in vitro cultures of Cas-tau biosensor cells and conditioned medium. Also provided herein are CRISPR/Cas synergistic activation mediator (SAM)-tau biosensor cells or populations of such cells and in vitro cultures of SAM-tau biosensor cells and conditioned medium.

In one aspect, provided are methods of screening for genetic modifiers of tau aggregation. Some such methods (CRISPRn) can comprise: (a) providing a population of cells comprising a Cas protein, a first tau repeat domain linked to a first reporter, and a second tau repeat domain linked to a second reporter; (b) introducing into the population of cells a library comprising a plurality of unique guide RNAs that target a plurality of genes; (c) culturing the population of cells to allow genome editing and expansion, wherein the plurality of unique guide RNAs form complexes with the Cas protein, and the Cas protein cleaves the plurality of genes resulting in knockout of gene function to produce a genetically modified population of cells; (d) contacting the genetically modified population of cells with a tau seeding agent to produce a seeded population of cells; (e) culturing the seeded population of cells to allow tau aggregates to form, wherein aggregates of the first tau repeat domain and the second tau repeat domain form in a subset of the seeded population of cells to produce an aggregation-positive population of cells; and (f) determining abundance of each of the plurality of unique guide RNAs in the aggregation-positive population of cells identified in step (e) relative to the genetically modified population of cells in step (c), wherein enrichment of a guide RNA in the aggregation-positive population of cells identified in step (e) relative to the cultured population of cells in step (c) indicates that the gene targeted by the guide RNA is a genetic modifier of tau aggregation, wherein disruption of the gene targeted by the guide RNA enhances tau aggregation, or is a candidate genetic modifier of tau aggregation (e.g., for further testing via secondary screens), wherein disruption of the gene targeted by the guide RNA is expected to enhance tau aggregation.

In some such methods, the first tau repeat domain and/or the second tau repeat domain is a human tau repeat domain. In some such methods, the first tau repeat domain and/or the second tau repeat domain comprises a pro-aggregation mutation. Optionally, the first tau repeat domain and/or the second tau repeat domain comprises a tau P301S mutation.

In some such methods, the first tau repeat domain and/or the second tau repeat domain comprises a tau four-repeat domain. In some such methods, the first tau repeat domain and/or the second tau repeat domain comprises SEQ ID NO: 11. In some such methods, the first tau repeat domain and the second tau repeat domain are the same. In some such methods, the first tau repeat domain and the second tau repeat domain are the same and each comprises tau four-repeat domain comprising a tau P301S mutation.

In some such methods, first reporter and the second reporter are fluorescent proteins. Optionally, the first reporter and the second reporter are a fluorescence resonance energy transfer (FRET) pair. Optionally, the first reporter is cyan fluorescent protein (CFP) and the second reporter is yellow fluorescent protein (YFP).

In some such methods, the Cas protein is a Cas9 protein. Optionally, the Cas protein is *Streptococcus pyogenes* Cas9. Optionally, the Cas protein comprises SEQ ID NO: 21. Optionally, the Cas protein is encoded by a coding sequence comprising the sequence set forth in SEQ ID NO: 22.

In some such methods, the Cas protein, the first tau repeat domain linked to the first reporter, and the second tau repeat domain linked to the second reporter are stably expressed in the population of cells. In some such methods, nucleic acids encoding the Cas protein, the first tau repeat domain linked to the first reporter, and the second tau repeat domain linked to the second reporter are genomically integrated in the population of cells.

In some such methods, the cells are eukaryotic cells. Optionally, the cells are mammalian cells. Optionally, the cells are human cells. Optionally, the cells are HEK293T cells.

In some such methods, the plurality of unique guide RNAs are introduced at a concentration selected such that a majority of the cells receive only one of the unique guide RNAs. In some such methods, the plurality of unique guide RNAs target 100 or more genes, 1000 or more genes, or 10000 or more genes. In some such methods, the library is a genome-wide library.

In some such methods, a plurality of target sequences are targeted on average in each of the targeted plurality of genes. Optionally, at least three target sequences are targeted on average in each of the targeted plurality of genes. Optionally, about three to about six target sequences (e.g., about three, about four, or about six) are targeted on average in each of the targeted plurality of genes.

In some such methods, each guide RNA targets a constitutive exon. Optionally, each guide RNA targets a 5' constitutive exon. In some such methods, each guide RNA targets a first exon, a second exon, or a third exon.

In some such methods, the plurality of unique guide RNAs are introduced into the population of cells by viral transduction. Optionally, each of the plurality of unique guide RNAs is in a separate viral vector. Optionally, the plurality of unique guide RNAs are introduced into the population of cells by lentiviral transduction. In some such methods, the population of cells is infected at a multiplicity of infection of less than about 0.3.

In some such methods, the plurality of unique guide RNAs are introduced into the population of cells together with a selection marker, and step (b) further comprises selecting cells that comprise the selection marker. Optionally, the selection marker imparts resistance to a drug. Optionally, the selection marker imparts resistance to puromycin or zeocin. Optionally, the selection marker is selected from neomycin phosphotransferase, hygromycin B phosphotransferase, puromycin-N-acetyltransferase, and blasticidin S deaminase. Optionally, the selection marker is selected from neomycin phosphotransferase, hygromycin B phosphotransferase, puromycin-N-acetyltransferase, blasticidin S deaminase, and bleomycin resistance protein.

In some such methods, the population of cells into which the plurality of unique guide RNAs are introduced in step (b) comprises greater than about 300 cells per unique guide RNA.

In some such methods, step (c) is about 3 days to about 9 days. Optionally, step (c) is about 6 days.

In some such methods, step (d) comprises culturing the genetically modified population of cells in the presence of conditioned medium harvested from cultured tau-aggregation-positive cells in which a tau repeat domain stably presents in an aggregated state. Optionally, the conditioned medium was harvested after being on confluent tau-aggregation-positive cells for about 1 to about 7 days. Optionally, the conditioned medium was harvested after being on confluent tau-aggregation-positive cells for about 4 days. Optionally, step (d) comprises culturing the genetically modified population of cells in about 75% conditioned medium and about 25% fresh medium. In some such methods, the genetically modified population of cells is not co-cultured with the tau-aggregation-positive cells in which a tau repeat domain stably presents in an aggregated state.

In some such methods, step (e) is about 2 days to about 6 days. Optionally, step (e) is about 4 days. In some such methods, the first reporter and the second reporter are a fluorescence resonance energy transfer (FRET) pair, and the aggregation-positive population of cells in step (e) is identified by flow cytometry.

In some such methods, abundance is determined by next-generation sequencing. In some such methods, a guide RNA is considered enriched if the abundance of the guide RNA relative to the total population of the plurality of unique guide RNAs is at least 1.5-fold higher in the aggregation-positive population of cells in step (e) relative to the cultured population of cells in step (c).

In some such methods, step (f) comprises determining abundance of each of the plurality of unique guide RNAs in the aggregation-positive population of cells in step (e) relative to the cultured population of cells in step (c) at a first time point in step (c) and/or a second time point in step (c). Optionally, the first time point in step (c) is at a first passage of culturing the population of cells, and the second time point is in the middle of culturing the population of cells to allow genome editing and expansion. Optionally, the first time point in step (c) is after about three days of culturing, and the second time point in step (c) is after about six days of culturing.

In some such methods, a gene is considered a genetic modifier of tau aggregation, wherein disruption of the gene enhances tau aggregation (or a candidate genetic modifier of tau aggregation, wherein disruption of the gene is expected to enhance tau aggregation), if: (1) the abundance of a guide RNA targeting the gene relative to the total population of the plurality of unique guide RNAs is at least 1.5-fold higher in the aggregation-positive population of cells in step (e) relative to the cultured population of cells in step (c) at both the first time point in step (c) and the second time point in step (c); and/or (2) the abundance of at least two unique guide RNAs targeting the gene relative to the total population of the plurality of unique guide RNAs is at least 1.5-fold higher in the aggregation-positive population of cells in step (e) relative to the cultured population of cells in step (c) at either the first time point in step (c) or the second time point in step (c).

In some such methods, the following steps are taken in step (f) to identify a gene as a genetic modifier of tau aggregation, wherein disruption of the gene enhances tau aggregation (or a candidate genetic modifier of tau aggregation, wherein disruption of the gene is expected to enhance tau aggregation): (1) identifying which of the plurality of unique guide RNAs are present in the aggregation-positive population of cells produced in step (e); (2) calculating the random chance of the guide RNAs identified in step (f)(1) being present using the formula $nCn'* (x-n') C(m-n)/xCm$, wherein x is the variety of unique guide RNAs introduced into the population of cells in step (b), wherein m is the variety of unique guide RNAs identified in step (f)(1), wherein n is the variety of unique guide RNAs introduced into the population of cells in step (b) that target the gene, and wherein n' is the variety of unique guide RNAs identified in step (f)(1) that target the gene; (3) calculating average enrichment scores for the guide RNAs identified in step (f)(1), wherein the enrichment score for a guide RNA is the relative abundance of the guide RNA in the aggregation-positive population of cells produced in step (e) divided by the relative abundance of the guide RNA in the cultured population of cells in step (c), and wherein relative abundance is the read count of the guide RNA divided by the read count of the total population of the plurality of unique guide RNAs; and (4) selecting the gene if a guide RNA targeting the gene is significantly below the random chance of being present and above a threshold enrichment score.

Some such methods (CRISPRa) can comprise: (a) providing a population of cells comprising a chimeric Cas protein comprising a nuclease-inactive Cas protein fused to one or more transcriptional activation domains, a chimeric adaptor protein comprising an adaptor protein fused to one or more transcriptional activation domains, a first tau repeat domain linked to a first reporter, and a second tau repeat domain linked to a second reporter; (b) introducing into the population of cells a library comprising a plurality of unique guide RNAs that target a plurality of genes; (c) culturing the population of cells to allow transcriptional activation and expansion, wherein the plurality of unique guide RNAs form complexes with the chimeric Cas protein and the chimeric adaptor protein, and the complexes activate transcription of the plurality of genes resulting in increased gene expression to produce a genetically modified population of cells; (d) contacting the genetically modified population of cells with a tau seeding agent to produce a seeded population of cells; (e) culturing the seeded population of cells to allow tau aggregates to form, wherein aggregates of the first tau repeat domain and the second tau repeat domain form in a subset of the seeded population of cells to produce an aggregation-positive population of cells; and (f) determining abundance of each of the plurality of unique guide RNAs in the aggregation-positive population of cells identified in step (e) relative to the genetically modified population of cells in step (c), wherein enrichment of a guide RNA in the aggregation-positive population of cells identified in step (e) relative to the cultured population of cells in step (c) indicates that the gene targeted by the guide RNA is a genetic modifier of tau aggregation, wherein transcriptional activation of the gene targeted by the guide RNA enhances tau aggregation, or is a candidate genetic modifier of tau aggregation (e.g., for further testing via secondary screens), wherein transcriptional activation of the gene targeted by the guide RNA is expected to enhance tau aggregation.

In some such methods, the first tau repeat domain and/or the second tau repeat domain is a human tau repeat domain. In some such methods, the first tau repeat domain and/or the second tau repeat domain comprises a pro-aggregation mutation. Optionally, the first tau repeat domain and/or the second tau repeat domain comprises a tau P301S mutation.

In some such methods, the first tau repeat domain and/or the second tau repeat domain comprises a tau four-repeat domain. In some such methods, the first tau repeat domain and/or the second tau repeat domain comprises SEQ ID NO: 11. In some such methods, the first tau repeat domain and the second tau repeat domain are the same. In some such methods, the first tau repeat domain and the second tau repeat domain are the same and each comprises tau four-repeat domain comprising a tau P301S mutation.

In some such methods, first reporter and the second reporter are fluorescent proteins. Optionally, the first reporter and the second reporter are a fluorescence resonance energy transfer (FRET) pair. Optionally, the first reporter is cyan fluorescent protein (CFP) and the second reporter is yellow fluorescent protein (YFP).

In some such methods, the Cas protein is a Cas9 protein. Optionally, the Cas protein is *Streptococcus pyogenes* Cas9. In some such methods, the chimeric Cas protein comprises the nuclease-inactive Cas protein fused to a VP64 transcriptional activation domain, optionally wherein the chimeric Cas protein comprises from N-terminus to C-terminus: the nuclease-inactive Cas protein; a nuclear localization signal; and the VP64 transcriptional activator domain. In some such methods, the adaptor protein is an MS2 coat protein, and wherein the one or more transcriptional activation domains in the chimeric adaptor protein comprise a p65 transcriptional activation domain and an HSF1 transcriptional activation domain, optionally wherein the chimeric adaptor protein comprises from N-terminus to C-terminus: the MS2 coat protein; a nuclear localization signal; the p65 transcriptional activation domain; and the HSF1 transcriptional activation domain. In some such methods, the chimeric Cas protein comprises SEQ ID NO: 36, optionally wherein the chimeric Cas protein is encoded by a coding sequence comprising the sequence set forth in SEQ ID NO: 38. In some such methods, the chimeric adaptor protein comprises SEQ ID NO: 37, optionally wherein the chimeric adaptor protein is encoded by a coding sequence comprising the sequence set forth in SEQ ID NO: 39.

In some such methods, the chimeric Cas protein, the chimeric adaptor protein, the first tau repeat domain linked to the first reporter, and the second tau repeat domain linked to the second reporter are stably expressed in the population of cells. In some such methods, nucleic acids encoding the chimeric Cas protein, the chimeric adaptor protein, the first tau repeat domain linked to the first reporter, and the second tau repeat domain linked to the second reporter are genomically integrated in the population of cells.

In some such methods, the cells are eukaryotic cells. Optionally, the cells are mammalian cells. Optionally, the cells are human cells. Optionally, the cells are HEK293T cells.

In some such methods, the plurality of unique guide RNAs are introduced at a concentration selected such that a majority of the cells receive only one of the unique guide RNAs. In some such methods, the plurality of unique guide RNAs target 100 or more genes, 1000 or more genes, or 10000 or more genes. In some such methods, the library is a genome-wide library.

In some such methods, a plurality of target sequences are targeted on average in each of the targeted plurality of genes. Optionally, at least three target sequences are targeted on average in each of the targeted plurality of genes. Optionally, about three to about six target sequences (e.g., about three, about four, or about six) are targeted on average in each of the targeted plurality of genes. Optionally, about three target sequences are targeted on average in each of the targeted plurality of genes.

In some such methods, each guide RNA targets a guide RNA target sequence within 200 bp upstream of a transcription start site. In some such methods, each guide RNA comprises one or more adaptor-binding elements to which the chimeric adaptor protein can specifically bind. Optionally, each guide RNA comprises two adaptor-binding elements to which the chimeric adaptor protein can specifically bind. Optionally, a first adaptor-binding element is within a first loop of each of the one or more guide RNAs, and a second adaptor-binding element is within a second loop of each of the one or more guide RNAs. Optionally, the adaptor-binding element comprises the sequence set forth in SEQ ID NO: 33. In some such methods, wherein each of one or more guide RNAs is a single guide RNA comprising a CRISPR RNA (crRNA) portion fused to a transactivating CRISPR RNA (tracrRNA) portion, and the first loop is the tetraloop corresponding to residues 13-16 of SEQ ID NO: 17, and the second loop is the stem loop 2 corresponding to residues 53-56 of SEQ ID NO: 17.

In some such methods, the plurality of unique guide RNAs are introduced into the population of cells by viral transduction. Optionally, each of the plurality of unique guide RNAs is in a separate viral vector. Optionally, the plurality of unique guide RNAs are introduced into the population of cells by lentiviral transduction. In some such methods, the population of cells is infected at a multiplicity of infection of less than about 0.3.

In some such methods, the plurality of unique guide RNAs are introduced into the population of cells together with a selection marker, and step (b) further comprises selecting cells that comprise the selection marker. Optionally, the selection marker imparts resistance to a drug. Optionally, the selection marker imparts resistance to puromycin or zeocin. Optionally, the selection marker is selected from neomycin phosphotransferase, hygromycin B phosphotransferase, puromycin-N-acetyltransferase, and blasticidin S deaminase. Optionally, the selection marker is selected from neomycin phosphotransferase, hygromycin B phosphotransferase, puromycin-N-acetyltransferase, blasticidin S deaminase, and bleomycin resistance protein.

In some such methods, the population of cells into which the plurality of unique guide RNAs are introduced in step (b) comprises greater than about 300 cells per unique guide RNA.

In some such methods, step (c) is about 3 days to about 9 days. Optionally, step (c) is about 6 days.

In some such methods, step (d) comprises culturing the genetically modified population of cells in the presence of conditioned medium harvested from cultured tau-aggregation-positive cells in which a tau repeat domain stably presents in an aggregated state. Optionally, the conditioned medium was harvested after being on confluent tau-aggregation-positive cells for about 1 to about 7 days. Optionally, the conditioned medium was harvested after being on confluent tau-aggregation-positive cells for about 4 days. Optionally, step (d) comprises culturing the genetically modified population of cells in about 75% conditioned medium and about 25% fresh medium. In some such methods, the genetically modified population of cells is not co-cultured with the tau-aggregation-positive cells in which a tau repeat domain stably presents in an aggregated state.

In some such methods, step (e) is about 2 days to about 6 days. Optionally, step (e) is about 4 days. In some such methods, the first reporter and the second reporter are a fluorescence resonance energy transfer (FRET) pair, and the aggregation-positive population of cells in step (e) is identified by flow cytometry.

In some such methods, abundance is determined by next-generation sequencing. In some such methods, a guide RNA is considered enriched if the abundance of the guide RNA relative to the total population of the plurality of unique guide RNAs is at least 1.5-fold higher in the aggregation-positive population of cells in step (e) relative to the cultured population of cells in step (c).

In some such methods, step (f) comprises determining abundance of each of the plurality of unique guide RNAs in the aggregation-positive population of cells in step (e) relative to the cultured population of cells in step (c) at a first time point in step (c) and/or a second time point in step (c). Optionally, the first time point in step (c) is at a first passage of culturing the population of cells, and the second time point is in the middle of culturing the population of cells to allow genome editing and expansion. Optionally, the first time point in step (c) is after about three days of culturing, and the second time point in step (c) is after about six days of culturing.

In some such methods, a gene is considered a genetic modifier of tau aggregation, wherein transcriptional activation of the gene enhances tau aggregation (or a candidate genetic modifier of tau aggregation, wherein transcriptional activation of the gene is expected to enhance tau aggregation), if: (1) the abundance of a guide RNA targeting the gene relative to the total population of the plurality of unique guide RNAs is at least 1.5-fold higher in the aggregation-positive population of cells in step (e) relative to the cultured population of cells in step (c) at both the first time point in step (c) and the second time point in step (c); and/or (2) the abundance of at least two unique guide RNAs targeting the gene relative to the total population of the plurality of unique guide RNAs is at least 1.5-fold higher in the aggregation-positive population of cells in step (e) relative to the cultured population of cells in step (c) at either the first time point in step (c) or the second time point in step (c).

In some such methods, the following steps are taken in step (f) to identify a gene as a genetic modifier of tau aggregation, wherein transcriptional activation of the gene enhances tau aggregation (or a candidate genetic modifier of tau aggregation, wherein transcriptional activation of the gene is expected to enhance tau aggregation): (1) identifying which of the plurality of unique guide RNAs are present in the aggregation-positive population of cells produced in step (e); (2) calculating the random chance of the guide RNAs identified in step (f)(1) being present using the formula $nCn'*(x-n')C(m-n)/xCm$, wherein x is the variety of unique guide RNAs introduced into the population of cells in step (b), wherein m is the variety of unique guide RNAs identified in step (f)(1), wherein n is the variety of unique guide RNAs introduced into the population of cells in step (b) that target the gene, and wherein n' is the variety of unique guide RNAs identified in step (f)(1) that target the gene; (3) calculating average enrichment scores for the guide RNAs identified in step (f)(1), wherein the enrichment score for a guide RNA is the relative abundance of the guide RNA in the aggregation-positive population of cells produced in step (e) divided by the relative abundance of the guide RNA in the cultured population of cells in step (c), and wherein relative abundance is the read count of the guide RNA divided by the read count of the total population of the plurality of unique guide RNAs; and (4) selecting the gene if a guide RNA targeting the gene is significantly below the random chance of being present and above a threshold enrichment score.

In another aspect, provided are additional methods of screening for genetic modifiers of tau aggregation. Some such methods (CRISPRn) can comprise: (a) providing a population of cells comprising a Cas protein, a first tau repeat domain linked to a first reporter, and a second tau repeat domain linked to a second reporter; (b) introducing into the population of cells a library comprising a plurality of unique guide RNAs that target a plurality of genes; (c) culturing the population of cells to allow genome editing and expansion, wherein the plurality of unique guide RNAs form complexes with the Cas protein, and the Cas protein cleaves the plurality of genes resulting in knockout of gene function to produce a genetically modified population of cells; (d) contacting the genetically modified population of cells with a tau seeding agent to produce a seeded population of cells; (e) culturing the seeded population of cells to allow tau aggregates to form, wherein aggregates of the first tau repeat domain and the second tau repeat domain form in a first subset of the seeded population of cells to produce an aggregation-positive population of cells and do not form in a second subset of the seeded population of cells to produce an aggregation-negative population of cells; and (f) determining abundance of each of the plurality of unique guide RNAs in the aggregation-positive population of cells identified in step (e) relative to the aggregation-negative population of cells identified in step (e) and/or the seeded population of cells in step (d), and/or determining abundance of each of the plurality of unique guide RNAs in the aggregation-negative population of cells identified in step (e) relative to the aggregation-positive population of cells identified in step (e) and/or the seeded population of cells in step (d), wherein enrichment of a guide RNA in the aggregation-negative population of cells identified in step (e) relative to the aggregation-positive population of cells identified in step (e) and/or the seeded population of cells in step (d) or wherein depletion of a guide RNA in the aggregation-positive population of cells identified in step (e) relative to the aggregation-negative population of cells identified in step (e) and/or the seeded population of cells in step (d) indicates that the gene targeted by the guide RNA is a genetic modifier of tau aggregation, wherein disruption of the gene targeted by the guide RNA prevents tau aggregation, or is a candidate genetic modifier of tau aggregation (e.g., for further testing via secondary screens), wherein disruption of the gene targeted by the guide RNA is expected to prevent tau aggregation, and/or wherein enrichment of a guide RNA in the aggregation-positive population of cells identified in step (e) relative to the aggregation-negative population of cells identified in step (e) and/or the seeded population of cells in step (d) or wherein depletion of a guide RNA in the aggregation-negative population of cells identified in step (e) relative to the aggregation-positive population of cells identified in step (e) and/or the seeded population of cells in step (d) indicates that the gene targeted by the guide RNA is a genetic modifier of tau aggregation, wherein disruption of the gene targeted by the guide RNA promotes or enhances tau aggregation, or is a candidate genetic modifier of tau aggregation (e.g., for further testing via secondary screens), wherein disruption of the gene targeted by the guide RNA is expected to promote or enhance tau aggregation.

In some such methods, the Cas protein is a Cas9 protein. Optionally, Cas protein is *Streptococcus pyogenes* Cas9. In some such methods, the Cas protein comprises SEQ ID NO: 21, optionally wherein the Cas protein is encoded by a coding sequence comprising the sequence set forth in SEQ ID NO: 22.

In some such methods, the Cas protein, the first tau repeat domain linked to the first reporter, and the second tau repeat domain linked to the second reporter are stably expressed in the population of cells. In some such methods, nucleic acids encoding the Cas protein, the first tau repeat domain linked to the first reporter, and the second tau repeat domain linked to the second reporter are genomically integrated in the population of cells.

In some such methods, each guide RNA targets a constitutive exon. Optionally, each guide RNA targets a 5' constitutive exon. In some such methods, each guide RNA targets a first exon, a second exon, or a third exon.

Some such methods (CRISPRa) comprise: (a) providing a population of cells comprising a chimeric Cas protein comprising a nuclease-inactive Cas protein fused to one or more transcriptional activation domains, a chimeric adaptor protein comprising an adaptor protein fused to one or more transcriptional activation domains, a first tau repeat domain linked to a first reporter, and a second tau repeat domain linked to a second reporter; (b) introducing into the population of cells a library comprising a plurality of unique guide RNAs that target a plurality of genes; (c) culturing the population of cells to allow transcriptional activation and expansion, wherein the plurality of unique guide RNAs form complexes with the chimeric Cas protein and the chimeric adaptor protein, and the complexes activate transcription of the plurality of genes resulting in increased gene expression to produce a genetically modified population of cells; (d) contacting the genetically modified population of cells with a tau seeding agent to produce a seeded population of cells; (e) culturing the seeded population of cells to allow tau aggregates to form, wherein aggregates of the first tau repeat domain and the second tau repeat domain form in a first subset of the seeded population of cells to produce an aggregation-positive population of cells and do not form in a second subset of the seeded population of cells to produce an aggregation-negative population of cells; and (f) determining abundance of each of the plurality of unique guide RNAs in the aggregation-positive population of cells identified in step (e) relative to the aggregation-negative population of cells identified in step (e) and/or the seeded population of cells in step (d), and/or determining abundance of each of the plurality of unique guide RNAs in the aggregation-negative population of cells identified in step (e) relative to the aggregation-positive population of cells identified in step (e) and/or the seeded population of cells in step (d), wherein enrichment of a guide RNA in the aggregation-negative population of cells identified in step (e) relative to the aggregation-positive population of cells identified in step (e) and/or the seeded population of cells in step (d) or wherein depletion of a guide RNA in the aggregation-positive population of cells identified in step (e) relative to the aggregation-negative population of cells identified in step (e) and/or the seeded population of cells in step (d) indicates that the gene targeted by the guide RNA is a genetic modifier of tau aggregation, wherein transcriptional activation of the gene targeted by the guide RNA prevents tau aggregation, or is a candidate genetic modifier of tau aggregation (e.g., for further testing via secondary screens), wherein transcriptional activation of the gene targeted by the guide RNA is expected to prevent tau aggregation, and/or wherein enrichment of a guide RNA in the aggregation-positive population of cells identified in step (e) relative to the aggregation-negative population of cells identified in step (e) and/or the seeded population of cells in step (d) or wherein depletion of a guide RNA in the aggregation-negative population of cells identified in step (e) relative to the aggregation-positive population of cells identified in step (e) and/or the seeded population of cells in step (d) indicates that the gene targeted by the guide RNA is a genetic modifier of tau aggregation, wherein transcriptional activation of the gene targeted by the guide RNA promotes or enhances tau aggregation, or is a candidate genetic modifier of tau aggregation (e.g., for further testing via secondary screens), wherein transcriptional activation of the gene targeted by the guide RNA is expected to promote or enhance tau aggregation.

In some such methods, the Cas protein is a Cas9 protein. Optionally, the Cas protein is *Streptococcus pyogenes* Cas9. In some such methods, the chimeric Cas protein comprises the nuclease-inactive Cas protein fused to a VP64 transcriptional activation domain, optionally wherein the chimeric Cas protein comprises from N-terminus to C-terminus: the nuclease-inactive Cas protein; a nuclear localization signal; and the VP64 transcriptional activator domain. In some such methods, the adaptor protein is an MS2 coat protein, and wherein the one or more transcriptional activation domains in the chimeric adaptor protein comprise a p65 transcriptional activation domain and an HSF1 transcriptional activation domain, optionally wherein the chimeric adaptor protein comprises from N-terminus to C-terminus: the MS2 coat protein; a nuclear localization signal; the p65 transcriptional activation domain; and the HSF1 transcriptional activation domain. In some such methods, the chimeric Cas protein comprises SEQ ID NO: 36, optionally wherein the chimeric Cas protein is encoded by a coding sequence comprising the sequence set forth in SEQ ID NO: 38. In some such methods, the chimeric adaptor protein comprises SEQ ID NO: 37, optionally wherein the chimeric adaptor protein is encoded by a coding sequence comprising the sequence set forth in SEQ ID NO: 39.

In some such methods, the chimeric Cas protein, the chimeric adaptor protein, the first tau repeat domain linked to the first reporter, and the second tau repeat domain linked to the second reporter are stably expressed in the population of cells. In some such methods, nucleic acids encoding the chimeric Cas protein, the chimeric adaptor protein, the first tau repeat domain linked to the first reporter, and the second tau repeat domain linked to the second reporter are genomically integrated in the population of cells.

In some such methods, each guide RNA targets a guide RNA target sequence within 200 bp upstream of a transcription start site. In some such methods, each guide RNA comprises one or more adaptor-binding elements to which the chimeric adaptor protein can specifically bind. Optionally, each guide RNA comprises two adaptor-binding elements to which the chimeric adaptor protein can specifically bind. Optionally, a first adaptor-binding element is within a first loop of each of the one or more guide RNAs, and a second adaptor-binding element is within a second loop of each of the one or more guide RNAs. Optionally, the adaptor-binding element comprises the sequence set forth in SEQ ID NO: 33. Optionally, each of one or more guide RNAs is a single guide RNA comprising a CRISPR RNA (crRNA) portion fused to a transactivating CRISPR RNA (tracrRNA) portion, and the first loop is the tetraloop corresponding to residues 13-16 of SEQ ID NO: 17, and the second loop is the stem loop 2 corresponding to residues 53-56 of SEQ ID NO: 17.

In some such methods, step (c) is about 3 days to about 13 days. In some such methods, step (c) is about 7 days to about 10 days, is about 7 days, or is about 10 days.

In some such methods, step (d) comprises culturing the genetically modified population of cells in the presence of a medium comprising a cell lysate from cultured tau-aggregation-positive cells in which a tau repeat domain stably presents in an aggregated state. Optionally, the cell lysate in the medium is at a concentration of about 1 to about 5 µg/mL. In some such methods, the medium comprising the cell lysate further comprises lipofectamine or another transfection reagent. Optionally, the medium comprising the cell lysate comprises lipofectamine at a concentration of about 1.5 to about 4 µL/mL. In some such methods, the genetically modified population of cells is not co-cultured with the tau-aggregation-positive cells in which a tau repeat domain stably presents in an aggregated state.

In some such methods, step (e) is about 1 day to about 3 days. Optionally, step (e) is about 2 days. In some such methods, the first reporter and the second reporter are a fluorescence resonance energy transfer (FRET) pair, and the aggregation-positive population of cells and the aggregation-negative population of cells in step (e) is identified by flow cytometry. In some such methods, abundance is determined by next-generation sequencing.

In some such methods, a guide RNA is considered enriched in the aggregation-negative population of cells in step (e) if the abundance of the guide RNA relative to the total population of the plurality of unique guide RNAs is at least 1.5-fold higher in the aggregation-negative population of cells in step (e) relative to the aggregation-positive population of cells in step (e) and/or the seeded population of cells in step (d), and wherein a guide RNA is considered depleted in the aggregation-positive population of cells in step (e) if the abundance of the guide RNA relative to the total population of the plurality of unique guide RNAs is at least 1.5-fold lower in the aggregation-positive population of cells in step (e) relative to the aggregation-negative population of cells in step (e) and/or the seeded population of cells in step (d), or wherein a guide RNA is considered enriched in the aggregation-positive population of cells in step (e) if the abundance of the guide RNA relative to the total population of the plurality of unique guide RNAs is at least 1.5-fold higher in the aggregation-positive population of cells in step (e) relative to the aggregation-negative population of cells in step (e) and/or the seeded population of cells in step (d), and wherein a guide RNA is considered depleted in the aggregation-negative population of cells in step (e) if the abundance of the guide RNA relative to the total population of the plurality of unique guide RNAs is at least 1.5-fold lower in the aggregation-negative population of cells in step (e) relative to the aggregation-positive population of cells in step (e) and/or the seeded population of cells in step (d).

In some such methods, step (f) comprises determining abundance of each of the plurality of unique guide RNAs in the aggregation-negative population of cells in step (e) relative to the aggregation-positive population of cells in step (e), the cultured population of cells in step (c) at a first time point, and the seeded population of cells in step (d) at a second time point, and/or wherein step (f) comprises determining abundance of each of the plurality of unique guide RNAs in the aggregation-positive population of cells in step (e) relative to the aggregation-negative population of cells in step (e), the cultured population of cells in step (c) at a first time point, and the seeded population of cells in step (d) at a second time point. Optionally, the first time point in step (c) is at a first passage of culturing the population of cells. Optionally, the first time point in step (c) is after about 3 days of culturing, and the second time point in step (c) is after about 7 days of culturing or about 10 days of culturing.

In some such methods, a gene is considered a genetic modifier of tau aggregation, wherein disruption (CRISPRn) or transcriptional activation (CRISPRa) of the gene prevents tau aggregation (or a candidate genetic modifier of tau aggregation, wherein disruption or transcriptional activation of the gene is expected to prevent tau aggregation), if. (1) the abundance of a guide RNA targeting the gene relative to the total population of the plurality of unique guide RNAs is at least 1.5-fold higher in the aggregation-negative population of cells in step (e) relative to the aggregation-positive population of cells in step (e), the cultured population of cells in step (c) at the first time point, and the seeded population of cells in step (d) at the second time point; and/or (2) the abundance of a guide RNA targeting the gene relative to the total population of the plurality of unique guide RNAs is at least 1.5-fold higher in the aggregation-negative population of cells in step (e) relative to the aggregation-positive population of cells in step (e) and the seeded population of cells in step (d) at the second time point; and/or (3) the abundance of a guide RNA targeting the gene relative to the total population of the plurality of unique guide RNAs is at least 1.5-fold lower in the aggregation-positive population of cells in step (e) relative to the aggregation-negative population of cells in step (e), the cultured population of cells in step (c) at the first time point, and the seeded population of cells in step (d) at the second time point; and/or (4) the abundance of a guide RNA targeting the gene relative to the total population of the plurality of unique guide RNAs is at least 1.5-fold lower in the aggregation-positive population of cells in step (e) relative to the aggregation-negative population of cells in step (e) and the seeded population of cells in step (d) at the second time point. In some such methods, a gene is considered a genetic modifier of tau aggregation, wherein disruption (CRISPRn) or transcriptional activation (CRISPRa) of the gene promotes or enhances tau aggregation (or a candidate genetic modifier of tau aggregation, wherein disruption or transcriptional activation of the gene is expected to promote or enhance tau aggregation), if: (1) the abundance of a guide RNA targeting the gene relative to the total population of the plurality of unique guide RNAs is at least 1.5-fold higher in the aggregation-positive population of cells in step (e) relative to the aggregation-negative population of cells in step (e), the cultured population of cells in step (c) at the first time point, and the seeded population of cells in step (d) at the second time point; and/or (2) the abundance of a guide RNA targeting the gene relative to the total population of the plurality of unique guide RNAs is at least 1.5-fold higher in the aggregation-positive population of cells in step (e) relative to the aggregation-negative population of cells in step (e) and the seeded population of cells in step (d) at the second time point; and/or (3) the abundance of a guide RNA targeting the gene relative to the total population of the plurality of unique guide RNAs is at least 1.5-fold lower in the aggregation-negative population of cells in step (e) relative to the aggregation-positive population of cells in step (e), the cultured population of cells in step (c) at the first time point, and the seeded population of cells in step (d) at the second time point; and/or (4) the abundance of a guide RNA targeting the gene relative to the total population of the plurality of unique guide RNAs is at least 1.5-fold lower in the aggregation-negative population of cells in step (e) relative to the aggregation-positive population of cells in step (e) and the seeded population of cells in step (d) at the second time point.

In some such methods, the following steps are taken in step (f) to identify a gene as a genetic modifier of tau aggregation, wherein disruption (CRISPRn) or transcriptional activation (CRISPRa) of the gene prevents tau aggregation (or as a candidate genetic modifier of tau aggregation, wherein disruption (CRISPRn) or transcriptional activation (CRISPRa) of the gene is expected to prevent tau aggregation): (1) identifying which of the plurality of unique guide RNAs are present in the aggregation-negative population of cells produced in step (e); (2) calculating the random chance of the guide RNAs identified in step (f)(1) being present using the formula $nC_{n'}*(x-n')C(m-n)/xC_m$, wherein x is the variety of unique guide RNAs introduced into the population of cells in step (b), wherein m is the variety of unique guide RNAs identified in step (f)(1), wherein n is the variety of unique guide RNAs introduced into the population of cells in step (b) that target the gene, and wherein n' is the variety of unique guide RNAs identified in step (f)(1) that target the gene; (3) calculating average enrichment scores for the guide RNAs identified in step (f)(1), wherein the enrichment score for a guide RNA is the relative abundance of the guide RNA in the aggregation-negative population of cells produced in step (e) divided by the relative abundance of the guide RNA in the aggregation-positive population of cells produced in step (e) or the seeded population of cells in step (d), and wherein relative abundance is the read count of the guide RNA divided by the read count of the total population of the plurality of unique guide RNAs; and (4) selecting the gene if a guide RNA targeting the gene is significantly below the random chance of being present and above a threshold enrichment score. In some such methods, the following steps are taken in step (f) to identify a gene as a genetic modifier of tau aggregation, wherein disruption (CRISPRn) or transcriptional activation (CRISPRa) of the gene promotes or enhances tau aggregation (or as a candidate genetic modifier of tau aggregation, wherein disruption or transcriptional activation of the gene is expected to promote or enhance tau aggregation): (1) identifying which of the plurality of unique guide RNAs are present in the aggregation-positive population of cells produced in step (e); (2) calculating the random chance of the guide RNAs identified in step (f)(1) being present using the formula $nC_{n'}*(x-n')C(m-n)/xC_m$, wherein x is the variety of unique guide RNAs introduced into the population of cells in step (b), wherein m is the variety of unique guide RNAs identified in step (f)(1), wherein n is the variety of unique guide RNAs introduced into the population of cells in step (b) that target the gene, and wherein n' is the variety of unique guide RNAs identified in step (f)(1) that target the gene; (3) calculating average enrichment scores for the guide RNAs identified in step (f)(1), wherein the enrichment score for a guide RNA is the relative abundance of the guide RNA in the aggregation-positive population of cells produced in step (e) divided by the relative abundance of the guide RNA in the aggregation-negative population of cells produced in step (e) or the seeded population of cells in step (d), and wherein relative abundance is the read count of the guide RNA divided by the read count of the total population of the plurality of unique guide RNAs; and (4) selecting the gene if a guide RNA targeting the gene is significantly below the random chance of being present and above a threshold enrichment score.

In some such methods, the first tau repeat domain and/or the second tau repeat domain is a human tau repeat domain. In some such methods, the first tau repeat domain and/or the second tau repeat domain comprises a pro-aggregation mutation. Optionally, the first tau repeat domain and/or the second tau repeat domain comprises a tau P301S mutation.

In some such methods, the first tau repeat domain and/or the second tau repeat domain comprises a tau four-repeat domain. In some such methods, the first tau repeat domain and/or the second tau repeat domain comprises SEQ ID NO: 11. In some such methods, the first tau repeat domain and the second tau repeat domain are the same. In some such methods, the first tau repeat domain and the second tau repeat domain are the same and each comprises tau four-repeat domain comprising a tau P301S mutation.

In some such methods, first reporter and the second reporter are fluorescent proteins. Optionally, the first reporter and the second reporter are a fluorescence resonance energy transfer (FRET) pair. Optionally, the first reporter is cyan fluorescent protein (CFP) and the second reporter is yellow fluorescent protein (YFP).

In some such methods, the cells are eukaryotic cells. Optionally, the cells are mammalian cells. Optionally, the cells are human cells. Optionally, the cells are HEK293T cells.

In some such methods, the plurality of unique guide RNAs are introduced at a concentration selected such that a majority of the cells receive only one of the unique guide RNAs. In some such methods, the plurality of unique guide RNAs target 100 or more genes, 1000 or more genes, or 10000 or more genes. In some such methods, the library is a genome-wide library.

In some such methods, a plurality of target sequences are targeted on average in each of the targeted plurality of genes. Optionally, at least three target sequences are targeted on average in each of the targeted plurality of genes. Optionally, about three to about six target sequences (e.g., about three, about four, or about six) are targeted on average in each of the targeted plurality of genes. Optionally, about three target sequences are targeted on average in each of the targeted plurality of genes.

In some such methods, the plurality of unique guide RNAs are introduced into the population of cells by viral transduction. Optionally, each of the plurality of unique guide RNAs is in a separate viral vector. Optionally, the plurality of unique guide RNAs are introduced into the population of cells by lentiviral transduction. In some such methods, the population of cells is infected at a multiplicity of infection of less than about 0.3.

In some such methods, the plurality of unique guide RNAs are introduced into the population of cells together with a selection marker, and step (b) further comprises selecting cells that comprise the selection marker. Optionally, the selection marker imparts resistance to a drug. Optionally, the selection marker imparts resistance to puromycin or zeocin. Optionally, the selection marker is selected from neomycin phosphotransferase, hygromycin B phosphotransferase, puromycin-N-acetyltransferase, and blasticidin S deaminase. Optionally, the selection marker is selected from neomycin phosphotransferase, hygromycin B phosphotransferase, puromycin-N-acetyltransferase, blasticidin S deaminase, and bleomycin resistance protein.

In some such methods, the population of cells into which the plurality of unique guide RNAs are introduced in step (b) comprises greater than about 300 cells per unique guide RNA.

In another aspect, provided are methods of screening for genetic modifiers of tau aggregation and/or disaggregation. Some such methods (CRISPRn) comprise: (a) providing a population of cells comprising a Cas protein, a first tau repeat domain linked to a first reporter, and a second tau repeat domain linked to a second reporter, wherein the cells are tau-aggregation-positive cells in which a tau repeat domain stably presents in an aggregated state; (b) introducing into the population of cells a library comprising a plurality of unique guide RNAs that target a plurality of genes; (c) culturing the population of cells to allow genome editing and expansion, wherein the plurality of unique guide RNAs form complexes with the Cas protein, and the Cas protein cleaves the plurality of genes resulting in knockout of gene function to produce a genetically modified population of cells, and wherein the culturing results in an aggregation-positive population of cells and an aggregation-negative population of cells; (d) identifying the aggregation-positive population of cells and the aggregation-negative population of cells; and (e) determining abundance of each of the plurality of unique guide RNAs in the aggregation-positive population of cells identified in step (d) relative to the aggregation-negative population of cells identified in step (d) and/or the cultured population of cells at one or more time points in step (c), and/or determining abundance of each of the plurality of unique guide RNAs in the aggregation-negative population of cells identified in step (d) relative to the aggregation-positive population of cells identified in step (d) and/or the cultured population of cells at one or more time points in step (c), wherein enrichment of a guide RNA in the aggregation-negative population of cells identified in step (d) relative to the aggregation-positive population of cells identified in step (d) and/or the cultured population of cells at one or more time points in step (c) or wherein depletion of a guide RNA in the aggregation-positive population of cells identified in step (d) relative to the aggregation-negative population of cells identified in step (d) and/or cultured population of cells at one or more time points in step (c) indicates that the gene targeted by the guide RNA is a genetic modifier of tau disaggregation, wherein disruption of the gene targeted by the guide RNA promotes tau disaggregation, or is a candidate genetic modifier of tau disaggregation (e.g., for further testing via secondary screens), wherein disruption of the gene targeted by the guide RNA is expected to promote tau disaggregation, and/or wherein enrichment of a guide RNA in the aggregation-positive population of cells identified in step (d) relative to the aggregation-negative population of cells identified in step (d) and/or the cultured population of cells at one or more time points in step (c) or wherein depletion of a guide RNA in the aggregation-negative population of cells identified in step (d) relative to the aggregation-positive population of cells identified in step (d) and/or cultured population of cells at one or more time points in step (c) indicates that the gene targeted by the guide RNA is a genetic modifier of tau aggregation, wherein disruption of the gene targeted by the guide RNA promotes or enhances tau aggregation, or is a candidate genetic modifier of tau aggregation (e.g., for further testing via secondary screens), wherein disruption of the gene targeted by the guide RNA is expected to promote or enhance tau aggregation.

In some such methods, the Cas protein is a Cas9 protein. Optionally, Cas protein is *Streptococcus pyogenes* Cas9. In some such methods, the Cas protein comprises SEQ ID NO: 21, optionally wherein the Cas protein is encoded by a coding sequence comprising the sequence set forth in SEQ ID NO: 22.

In some such methods, the Cas protein, the first tau repeat domain linked to the first reporter, and the second tau repeat domain linked to the second reporter are stably expressed in the population of cells. In some such methods, nucleic acids encoding the Cas protein, the first tau repeat domain linked to the first reporter, and the second tau repeat domain linked to the second reporter are genomically integrated in the population of cells.

In some such methods, each guide RNA targets a constitutive exon. Optionally, each guide RNA targets a 5' constitutive exon. In some such methods, each guide RNA targets a first exon, a second exon, or a third exon.

Some such methods (CRISPRa) comprise: (a) providing a population of cells comprising a chimeric Cas protein comprising a nuclease-inactive Cas protein fused to one or more transcriptional activation domains, a chimeric adaptor protein comprising an adaptor protein fused to one or more transcriptional activation domains, a first tau repeat domain linked to a first reporter, and a second tau repeat domain linked to a second reporter, wherein the cells are tau-aggregation-positive cells in which a tau repeat domain stably presents in an aggregated state; (b) introducing into the population of cells a library comprising a plurality of unique guide RNAs that target a plurality of genes; (c) culturing the population of cells to allow transcriptional activation and expansion, wherein the plurality of unique guide RNAs form complexes with the chimeric Cas protein and the chimeric adaptor protein, and the complexes activate transcription of the plurality of genes resulting in increased gene expression to produce a genetically modified population of cells, and wherein the culturing results in an aggregation-positive population of cells and an aggregation-negative population of cells; (d) identifying the aggregation-positive population of cells and the aggregation-negative population of cells; and (e) determining abundance of each of the plurality of unique guide RNAs in the aggregation-positive population of cells identified in step (d) relative to the aggregation-negative population of cells identified in step (d) and/or the cultured population of cells at one or more time points in step (c), and/or determining abundance of each of the plurality of unique guide RNAs in the aggregation-negative population of cells identified in step (d) relative to the aggregation-positive population of cells identified in step (d) and/or the cultured population of cells at one or more time points in step (c), wherein enrichment of a guide RNA in the aggregation-negative population of cells identified in step (d) relative to the aggregation-positive population of cells identified in step (d) and/or the cultured population of cells at one or more time points in step (c) or wherein depletion of a guide RNA in the aggregation-positive population of cells identified in step (d) relative to the aggregation-negative population of cells identified in step (d) and/or cultured population of cells at one or more time points in step (c) indicates that the gene targeted by the guide RNA is a genetic modifier of tau disaggregation, wherein transcriptional activation of the gene targeted by the guide RNA promotes tau disaggregation, or is a candidate genetic modifier of tau disaggregation (e.g., for further testing via secondary screens), wherein transcriptional activation of the gene targeted by the guide RNA is expected to promote tau disaggregation, and/or wherein enrichment of a guide RNA in the aggregation-positive population of cells identified in step (d) relative to the aggregation-negative population of cells identified in step (d) and/or the cultured population of cells at one or more time points in step (c) or wherein depletion of a guide RNA in the aggregation-negative population of cells identified in step (d) relative to the aggregation-positive population of cells identified in step (d) and/or cultured population of cells at one or more time points in step (c) indicates that the gene targeted by the guide RNA is a genetic modifier of tau aggregation, wherein transcriptional activation of the gene targeted by the guide RNA promotes or enhances tau aggregation, or is a candidate genetic modifier of tau aggregation (e.g., for further testing via secondary screens), wherein transcriptional activation of the gene targeted by the guide RNA is expected to promote or enhance tau aggregation.

In some such methods, the Cas protein is a Cas9 protein. Optionally, the Cas protein is *Streptococcus pyogenes* Cas9. In some such methods, the chimeric Cas protein comprises the nuclease-inactive Cas protein fused to a VP64 transcriptional activation domain, optionally wherein the chimeric Cas protein comprises from N-terminus to C-terminus: the nuclease-inactive Cas protein; a nuclear localization signal; and the VP64 transcriptional activator domain. In some such methods, the adaptor protein is an MS2 coat protein, and wherein the one or more transcriptional activation domains in the chimeric adaptor protein comprise a p65 transcriptional activation domain and an HSF1 transcriptional activation domain, optionally wherein the chimeric adaptor protein comprises from N-terminus to C-terminus: the MS2 coat protein; a nuclear localization signal; the p65 transcriptional activation domain; and the HSF1 transcriptional activation domain. In some such methods, the chimeric Cas protein comprises SEQ ID NO: 36, optionally wherein the chimeric Cas protein is encoded by a coding sequence comprising the sequence set forth in SEQ ID NO: 38. In some such methods, the chimeric adaptor protein comprises SEQ ID NO: 37, optionally wherein the chimeric adaptor protein is encoded by a coding sequence comprising the sequence set forth in SEQ ID NO: 39.

In some such methods, the chimeric Cas protein, the chimeric adaptor protein, the first tau repeat domain linked to the first reporter, and the second tau repeat domain linked to the second reporter are stably expressed in the population of cells. In some such methods, nucleic acids encoding the chimeric Cas protein, the chimeric adaptor protein, the first tau repeat domain linked to the first reporter, and the second tau repeat domain linked to the second reporter are genomically integrated in the population of cells.

In some such methods, each guide RNA targets a guide RNA target sequence within 200 bp upstream of a transcription start site. In some such methods, each guide RNA comprises one or more adaptor-binding elements to which the chimeric adaptor protein can specifically bind. Optionally, each guide RNA comprises two adaptor-binding elements to which the chimeric adaptor protein can specifically bind. Optionally, a first adaptor-binding element is within a first loop of each of the one or more guide RNAs, and a second adaptor-binding element is within a second loop of each of the one or more guide RNAs. Optionally, the adaptor-binding element comprises the sequence set forth in SEQ ID NO: 33. Optionally, each of one or more guide RNAs is a single guide RNA comprising a CRISPR RNA (crRNA) portion fused to a transactivating CRISPR RNA (tracrRNA) portion, and the first loop is the tetraloop corresponding to residues 13-16 of SEQ ID NO: 17, and the second loop is the stem loop 2 corresponding to residues 53-56 of SEQ ID NO: 17.

In some such methods, step (c) is about 3 days to about 14 days. Optionally, step (c) is about 10 days to about 14 days or about 12 days to about 14 days.

In some such methods, step (d) comprises synchronizing cell cycle progression to obtain a cell population predominantly enriched in S phase. Optionally, the synchronization is achieved by double thymidine block.

In some such methods, the first reporter and the second reporter are a fluorescence resonance energy transfer (FRET) pair, and the aggregation-positive population of cells and the aggregation-negative population of cells in step (d) is identified by flow cytometry. In some such methods, abundance is determined by next-generation sequencing.

In some such methods, a guide RNA is considered enriched in the aggregation-negative population of cells in step (d) if the abundance of the guide RNA relative to the total population of the plurality of unique guide RNAs is at least 1.5-fold higher in the aggregation-negative population of cells in step (d) relative to the aggregation-positive population of cells in step (d) and/or the cultured population of cells at one or more time points in step (c), and wherein a guide RNA is considered depleted in the aggregation-positive population of cells in step (d) if the abundance of the guide RNA relative to the total population of the plurality of unique guide RNAs is at least 1.5-fold lower in the aggregation-positive population of cells in step (d) relative to the aggregation-negative population of cells in step (d) and/or the cultured population of cells at one or more time points in step (c), or wherein a guide RNA is considered enriched in the aggregation-positive population of cells in step (d) if the abundance of the guide RNA relative to the total population of the plurality of unique guide RNAs is at least 1.5-fold higher in the aggregation-positive population of cells in step (d) relative to the aggregation-negative population of cells in step (d) and/or the cultured population of cells at one or more time points in step (c), and wherein a guide RNA is considered depleted in the aggregation-negative population of cells in step (d) if the abundance of the guide RNA relative to the total population of the plurality of unique guide RNAs is at least 1.5-fold lower in the aggregation-negative population of cells in step (d) relative to the aggregation-positive population of cells in step (d) and/or the cultured population of cells at one or more time points in step (c).

In some such methods, step (e) comprises determining abundance of each of the plurality of unique guide RNAs in the aggregation-negative population of cells in step (d) relative to the aggregation-positive population of cells in step (d), the cultured population of cells in step (c) at a first time point, and the cultured population of cells in step (c) at a second time point, and/or wherein step (e) comprises determining abundance of each of the plurality of unique guide RNAs in the aggregation-positive population of cells in step (d) relative to the aggregation-negative population of cells in step (e), the cultured population of cells in step (c) at a first time point, and the cultured population of cells in step (c) at a second time point. Optionally, the first time point in step (c) is at a first passage of culturing the population of cells, and the second time point is in the middle of culturing the population of cells to allow genome editing and expansion or transcriptional activation and expansion. Optionally, the first time point in step (c) is after about 7 days of culturing, and the second time point in step (c) is after about 10 days of culturing.

In some such methods, a gene is considered a genetic modifier of tau disaggregation, wherein disruption (CRISPRn) or transcriptional activation (CRISPRa) of the gene promotes tau disaggregation (or a candidate genetic modifier of tau disaggregation, wherein disruption or transcriptional activation of the gene is expected to promote tau disaggregation), if: (1) the abundance of a guide RNA targeting the gene relative to the total population of the plurality of unique guide RNAs is at least 1.5-fold higher in the aggregation-negative population of cells in step (d) relative to the aggregation-positive population of cells in step (d), the cultured population of cells in step (c) at the first time point, and the cultured population of cells in step (c) at the second time point; and/or (2) the abundance of a guide RNA targeting the gene relative to the total population of the plurality of unique guide RNAs is at least 1.5-fold higher in the aggregation-negative population of cells in step (d) relative to the aggregation-positive population of cells in step (d) and the cultured population of cells in step (c) at the second time point; and/or (3) the abundance of a guide RNA targeting the gene relative to the total population of the plurality of unique guide RNAs is at least 1.5-fold lower in the aggregation-positive population of cells in step (d) relative to the aggregation-negative population of cells in step (d), the cultured population of cells in step (c) at the first time point, and the cultured population of cells in step (c) at the second time point; and/or (4) the abundance of a guide RNA targeting the gene relative to the total population of the plurality of unique guide RNAs is at least 1.5-fold lower in the aggregation-positive population of cells in step (d) relative to the aggregation-negative population of cells in step (d) and the cultured population of cells in step (c) at the second time point. In some such methods, a gene is considered a genetic modifier of tau aggregation, wherein disruption (CRISPRn) or transcriptional activation (CRISPRa) of the gene promotes or enhances tau aggregation (or a candidate genetic modifier of tau aggregation, wherein disruption or transcriptional activation of the gene is expected to promote or enhance tau aggregation), if: (1) the abundance of a guide RNA targeting the gene relative to the total population of the plurality of unique guide RNAs is at least 1.5-fold higher in the aggregation-positive population of cells in step (d) relative to the aggregation-negative population of cells in step (d), the cultured population of cells in step (c) at the first time point, and the cultured population of cells in step (c) at the second time point; and/or (2) the abundance of a guide RNA targeting the gene relative to the total population of the plurality of unique guide RNAs is at least 1.5-fold higher in the aggregation-positive population of cells in step (d) relative to the aggregation-negative population of cells in step (d) and the cultured population of cells in step (c) at the second time point; and/or (3) the abundance of a guide RNA targeting the gene relative to the total population of the plurality of unique guide RNAs is at least 1.5-fold lower in the aggregation-negative population of cells in step (d) relative to the aggregation-positive population of cells in step (d), the cultured population of cells in step (c) at the first time point, and the cultured population of cells in step (c) at the second time point; and/or (4) the abundance of a guide RNA targeting the gene relative to the total population of the plurality of unique guide RNAs is at least 1.5-fold lower in the aggregation-negative population of cells in step (d) relative to the aggregation-positive population of cells in step (d) and the cultured population of cells in step (c) at the second time point.

In some such methods, the following steps are taken in step (e) to identify a gene as a genetic modifier of tau disaggregation, wherein disruption (CRISPRn) or transcriptional activation (CRISPRa) of the gene promotes tau disaggregation (or a candidate genetic modifier of tau disaggregation, wherein disruption or transcriptional activation of the gene is expected to promote tau disaggregation): (1) identifying which of the plurality of unique guide RNAs are present in the aggregation-negative population of cells identified in step (d); (2) calculating the random chance of the guide RNAs identified in step (e)(1) being present using the formula $nC_{n'}*(x-n')C(m-n)/xC_m$, wherein x is the variety of unique guide RNAs introduced into the population of cells in step (b), wherein m is the variety of unique guide RNAs identified in step (e)(1), wherein n is the variety of unique guide RNAs introduced into the population of cells in step (b) that target the gene, and wherein n' is the variety of unique guide RNAs identified in step (e)(1) that target the gene; (3) calculating average enrichment scores for the guide RNAs identified in step (e)(1), wherein the enrichment score for a guide RNA is the relative abundance of the guide RNA in the aggregation-negative population of cells identified in step (d) divided by the relative abundance of the guide RNA in the aggregation-positive population of cells identified in step (d) or the cultured population of cells in step (c) at the first time point or the second time point, and wherein relative abundance is the read count of the guide RNA divided by the read count of the total population of the plurality of unique guide RNAs; and (4) selecting the gene if a guide RNA targeting the gene is significantly below the random chance of being present and above a threshold enrichment score. In some such methods, the following steps are taken in step (e) to identify a gene as a genetic modifier of tau aggregation, wherein disruption (CRISPRn) or transcriptional activation (CRISPRa) of the gene promotes or enhances tau aggregation (or a candidate genetic modifier of tau aggregation, wherein disruption or transcriptional activation of the gene is expected to promote or enhance tau aggregation): (1) identifying which of the plurality of unique guide RNAs are present in the aggregation-positive population of cells identified in step (d); (2) calculating the random chance of the guide RNAs identified in step (e)(1) being present using the formula $nC_{n'}*(x-n')C(m-n)/xC_m$, wherein x is the variety of unique guide RNAs introduced into the population of cells in step (b), wherein m is the variety of unique guide RNAs identified in step (e)(1), wherein n is the variety of unique guide RNAs introduced into the population of cells in step (b) that target the gene, and wherein n' is the variety of unique guide RNAs identified in step (e)(1) that target the gene; (3) calculating average enrichment scores for the guide RNAs identified in step (e)(1), wherein the enrichment score for a guide RNA is the relative abundance of the guide RNA in the aggregation-positive population of cells identified in step (d) divided by the relative abundance of the guide RNA in the aggregation-negative population of cells identified in step (d) or the cultured population of cells in step (c) at the first time point or the second time point, and wherein relative abundance is the read count of the guide RNA divided by the read count of the total population of the plurality of unique guide RNAs; and (4) selecting the gene if a guide RNA targeting the gene is significantly below the random chance of being present and above a threshold enrichment score.

In some such methods, the first tau repeat domain and/or the second tau repeat domain is a human tau repeat domain. In some such methods, the first tau repeat domain and/or the second tau repeat domain comprises a pro-aggregation mutation. Optionally, the first tau repeat domain and/or the second tau repeat domain comprises a tau P301S mutation.

In some such methods, the first tau repeat domain and/or the second tau repeat domain comprises a tau four-repeat domain. In some such methods, the first tau repeat domain and/or the second tau repeat domain comprises SEQ ID NO: 11. In some such methods, the first tau repeat domain and the second tau repeat domain are the same. In some such methods, the first tau repeat domain and the second tau repeat domain are the same and each comprises tau four-repeat domain comprising a tau P301S mutation.

In some such methods, first reporter and the second reporter are fluorescent proteins. Optionally, the first reporter and the second reporter are a fluorescence resonance energy transfer (FRET) pair. Optionally, the first reporter is cyan fluorescent protein (CFP) and the second reporter is yellow fluorescent protein (YFP).

In some such methods, the cells are eukaryotic cells. Optionally, the cells are mammalian cells. Optionally, the cells are human cells. Optionally, the cells are HEK293T cells.

In some such methods, the plurality of unique guide RNAs are introduced at a concentration selected such that a majority of the cells receive only one of the unique guide RNAs. In some such methods, the plurality of unique guide RNAs target 100 or more genes, 1000 or more genes, or 10000 or more genes. In some such methods, the library is a genome-wide library.

In some such methods, a plurality of target sequences are targeted on average in each of the targeted plurality of genes. Optionally, at least three target sequences are targeted on average in each of the targeted plurality of genes. Optionally, about three to about six target sequences (e.g., about three, about four, or about six) are targeted on average in each of the targeted plurality of genes. Optionally, about three target sequences are targeted on average in each of the targeted plurality of genes.

In some such methods, the plurality of unique guide RNAs are introduced into the population of cells by viral transduction. Optionally, each of the plurality of unique guide RNAs is in a separate viral vector. Optionally, the plurality of unique guide RNAs are introduced into the population of cells by lentiviral transduction. In some such methods, the population of cells is infected at a multiplicity of infection of less than about 0.3.

In some such methods, the plurality of unique guide RNAs are introduced into the population of cells together with a selection marker, and step (b) further comprises selecting cells that comprise the selection marker. Optionally, the selection marker imparts resistance to a drug. Optionally, the selection marker imparts resistance to puromycin or zeocin. Optionally, the selection marker is selected from neomycin phosphotransferase, hygromycin B phosphotransferase, puromycin-N-acetyltransferase, and blasticidin S deaminase. Optionally, the selection marker is selected from neomycin phosphotransferase, hygromycin B phosphotransferase, puromycin-N-acetyltransferase, blasticidin S deaminase, and bleomycin resistance protein.

In some such methods, the population of cells into which the plurality of unique guide RNAs are introduced in step (b) comprises greater than about 300 cells per unique guide RNA.

In another aspect, provided are Cas-tau biosensor cells or populations of such cells. Some such cells comprise a population of one or more cells comprising a Cas protein, a first tau repeat domain linked to a first reporter, and a second tau repeat domain linked to a second reporter.

In some such cells, the first tau repeat domain and/or the second tau repeat domain is a human tau repeat domain. In some such cells, the first tau repeat domain and/or the second tau repeat domain comprises a pro-aggregation mutation. Optionally, the first tau repeat domain and/or the second tau repeat domain comprises a tau P301S mutation.

In some such cells, the first tau repeat domain and/or the second tau repeat domain comprises a tau four-repeat domain. In some such cells, the first tau repeat domain and/or the second tau repeat domain comprises SEQ ID NO: 11. In some such cells, the first tau repeat domain and the second tau repeat domain are the same. In some such cells, the first tau repeat domain and the second tau repeat domain are the same and each comprises tau four-repeat domain comprising a tau P301S mutation.

In some such cells, the first reporter and the second reporter are fluorescent proteins. Optionally, the first reporter and the second reporter are a fluorescence resonance energy transfer (FRET) pair. Optionally, the first reporter is cyan fluorescent protein (CFP) and the second reporter is yellow fluorescent protein (YFP).

In some such cells, the Cas protein is a Cas9 protein. Optionally, the Cas protein is *Streptococcus pyogenes* Cas9. Optionally, the Cas protein comprises SEQ ID NO: 21. Optionally, the Cas protein is encoded by a coding sequence comprising the sequence set forth in SEQ ID NO: 22.

In some such cells, the Cas protein, the first tau repeat domain linked to the first reporter, and the second tau repeat domain linked to the second reporter are stably expressed in the cell. In some such cells, nucleic acids encoding the Cas protein, the first tau repeat domain linked to the first reporter, and the second tau repeat domain linked to the second reporter are genomically integrated in the cell.

In some such cells, the cells are eukaryotic cells. Optionally, the cells are mammalian cells. Optionally, the cells are human cells. Optionally, the cells are HEK293T cells. Some such cells are in vitro.

In some such cells, wherein the first tau repeat domain linked to the first reporter and the second tau repeat domain linked to the second reporter are not stably present in an aggregated state. In some such cells, the first tau repeat domain linked to the first reporter and the second tau repeat domain linked to the second reporter stably present in an aggregated state.

In another aspect, provided are in vitro cultures of Cas-tau biosensor cells and conditioned medium. Some such in vitro cultures comprise any of the populations of cells described above or elsewhere herein and a culture medium comprising a conditioned medium harvested from cultured tau-aggregation-positive cells in which a tau repeat domain stably presents in an aggregated state.

In some such in vitro cultures, the conditioned medium was harvested after being on confluent tau-aggregation-positive cells for about 1 to about 7 days. Optionally, the conditioned medium was harvested after being on confluent tau-aggregation-positive cells for about 4 days.

In some such in vitro cultures, the culture medium comprises about 75% conditioned medium and about 25% fresh medium. In some such in vitro cultures, the population of cells is not co-cultured with the cultured tau-aggregation-positive cells in which a tau repeat domain stably presents in an aggregated state.

In another aspect, provided are SAM-tau biosensor cells or populations of such cells. Some such cells comprise a population of one or more cells comprising a chimeric Cas protein comprising a nuclease-inactive Cas protein fused to one or more transcriptional activation domains, a chimeric adaptor protein comprising an adaptor protein fused to one or more transcriptional activation domains, a first tau repeat domain linked to a first reporter, and a second tau repeat domain linked to a second reporter.

In some such cells, the first tau repeat domain and/or the second tau repeat domain is a human tau repeat domain. In some such cells, the first tau repeat domain and/or the second tau repeat domain comprises a pro-aggregation mutation. Optionally, the first tau repeat domain and/or the second tau repeat domain comprises a tau P301S mutation.

In some such cells, the first tau repeat domain and/or the second tau repeat domain comprises a tau four-repeat domain. In some such cells, the first tau repeat domain and/or the second tau repeat domain comprises SEQ ID NO: 11. In some such cells, the first tau repeat domain and the second tau repeat domain are the same. In some such cells, the first tau repeat domain and the second tau repeat domain are the same and each comprises tau four-repeat domain comprising a tau P301S mutation.

In some such cells, the first reporter and the second reporter are fluorescent proteins. Optionally, the first reporter and the second reporter are a fluorescence resonance energy transfer (FRET) pair. Optionally, the first reporter is cyan fluorescent protein (CFP) and the second reporter is yellow fluorescent protein (YFP).

In some such cells, the Cas protein is a Cas9 protein. Optionally, the Cas protein is *Streptococcus pyogenes* Cas9. In some such cells, the chimeric Cas protein comprises the nuclease-inactive Cas protein fused to a VP64 transcriptional activation domain, optionally wherein the chimeric Cas protein comprises from N-terminus to C-terminus: the nuclease-inactive Cas protein; a nuclear localization signal; and the VP64 transcriptional activator domain. In some such cells, the adaptor protein is an MS2 coat protein, and wherein the one or more transcriptional activation domains in the chimeric adaptor protein comprise a p65 transcriptional activation domain and an HSF1 transcriptional activation domain, optionally wherein the chimeric adaptor protein comprises from N-terminus to C-terminus: the MS2 coat protein; a nuclear localization signal; the p65 transcriptional activation domain; and the HSF1 transcriptional activation domain. In some such cells, the chimeric Cas protein comprises SEQ ID NO: 36, optionally wherein the chimeric Cas protein is encoded by a coding sequence comprising the sequence set forth in SEQ ID NO: 38. In some such cells, the chimeric adaptor protein comprises SEQ ID NO: 37, optionally wherein the chimeric adaptor protein is encoded by a coding sequence comprising the sequence set forth in SEQ ID NO: 39.

In some such cells, the chimeric Cas protein, the chimeric adaptor protein, the first tau repeat domain linked to the first reporter, and the second tau repeat domain linked to the second reporter are stably expressed in the cell. In some such cells, nucleic acids encoding the chimeric Cas protein, the chimeric adaptor protein, the first tau repeat domain linked to the first reporter, and the second tau repeat domain linked to the second reporter are genomically integrated in the cell.

In some such cells, the cells are eukaryotic cells. Optionally, the cells are mammalian cells. Optionally, the cells are human cells. Optionally, the cells are HEK293T cells. Some such cells are in vitro.

In some such cells, wherein the first tau repeat domain linked to the first reporter and the second tau repeat domain linked to the second reporter are not stably present in an aggregated state. In some such cells, the first tau repeat domain linked to the first reporter and the second tau repeat domain linked to the second reporter stably present in an aggregated state.

In another aspect, provided are in vitro cultures of SAM-tau biosensor cells and conditioned medium. Some such in vitro cultures comprise any of the populations of cells described above or elsewhere herein and a culture medium comprising a conditioned medium harvested from cultured tau-aggregation-positive cells in which a tau repeat domain stably presents in an aggregated state.

In some such in vitro cultures, the conditioned medium was harvested after being on confluent tau-aggregation-positive cells for about 1 to about 7 days. Optionally, the conditioned medium was harvested after being on confluent tau-aggregation-positive cells for about 4 days.

In some such in vitro cultures, the culture medium comprises about 75% conditioned medium and about 25% fresh medium. In some such in vitro cultures, the population of cells is not co-cultured with the cultured tau-aggregation-positive cells in which a tau repeat domain stably presents in an aggregated state.

In another aspect, provided are in vitro cultures of Cas-tau biosensor cells or SAM-tau biosensor cells and a culture medium comprising a cell lysate from cultured tau-aggregation-positive cells in which a tau repeat domain stably presents in an aggregated state. Some such in vitro cultures comprise any of the populations of cells described above or elsewhere herein.

In some such in vitro cultures, the cell lysate in the medium is at a concentration of about 1 to about 5 µg/mL. In some such in vitro cultures, the medium comprising the cell lysate further comprises lipofectamine or another transfection reagent. Optionally, the medium comprising the cell lysate comprises lipofectamine at a concentration of about 1.5 to about 4 L/mL. In some such in vitro cultures, the cell lysate was produced by sonication of the tau-aggregation-positive cells for about 2 minutes to about 4 minutes after collecting the cells in a buffer comprising protease inhibitors.

In another aspect, provided are methods of producing conditioned medium for inducing or sensitizing to tau aggregation. Some such methods comprise: (a) providing a population of tau-aggregation-positive cells in which a tau repeat domain stably presents in an aggregated state; (b) culturing the population of tau-aggregation-positive cells in a medium to produce a conditioned medium; and (c) harvesting the conditioned medium.

In some such methods, the tau-aggregation-positive cells are cultured in step (b) to confluence. Optionally, the conditioned medium is harvested after being on the confluent tau-aggregation-positive cells in step (c) for about 1 to about 7 days. Optionally, the conditioned medium is harvested after being on the confluent tau-aggregation-positive cells in step (c) for about 4 days.

In another aspect, provided are methods of generating a population of tau-aggregation-positive cells. Some such methods comprise: (a) producing a conditioned medium for inducing tau aggregation according to any of the methods described above or elsewhere herein; and (b) culturing a population of cells comprising a protein comprising a tau repeat domain in a culture medium comprising the conditioned medium to produce the population of tau-aggregation-positive cells.

In some such methods, the culture medium comprises about 75% conditioned medium and about 25% fresh medium. In some such methods, the population of cells is not co-cultured with the tau-aggregation-positive cells used in the method to produce the conditioned medium.

In some such methods, the tau repeat domain comprises a pro-aggregation mutation. In some such methods, the tau repeat domain comprises a tau P301S mutation. In some such methods, the tau repeat domain comprises a tau four-repeat domain. In some such methods, the tau repeat domain comprises SEQ ID NO: 11.

In another aspect, provided are methods of producing a medium comprising a cell lysate from cultured tau-aggregation-positive cells for inducing tau aggregation. Some such methods comprise: (a) providing a population of tau-aggregation-positive cells in which a tau repeat domain stably presents in an aggregated state; (b) collecting the tau-aggregation-positive cells in a buffer comprising protease inhibitors; (c) sonicating the tau-aggregation-positive cells for about 2 minutes to about 4 minutes to produce the cell lysate; and (d) adding the cell lysate to a growth medium.

In some such methods, the cell lysate in the growth medium is at a concentration of about 1 to about 5 µg/mL. Some such methods further comprise adding lipofectamine or another transfection reagent to the growth medium in step (d). Optionally, step (d) comprising adding lipofectamine at a concentration of about 1.5 to about 4 µL/mL.

In another aspect, provided are methods of generating a population of tau-aggregation-positive cells. Some such methods comprise: (a) producing a medium comprising a cell lysate from cultured tau-aggregation-positive cells according to the any of the above methods; and (b) culturing a population of cells comprising a protein comprising a tau repeat domain in the medium comprising a cell lysate from cultured tau-aggregation-positive cells.

In some such methods, the population of cells is not co-cultured with the tau-aggregation-positive cells used in the method to produce the conditioned medium.

In some such methods, the tau repeat domain comprises a pro-aggregation mutation. In some such methods, the tau repeat domain comprises a tau P301S mutation. In some such methods, the tau repeat domain comprises a tau four-repeat domain. In some such methods, the tau repeat domain comprises SEQ ID NO: 11.

TCY biosensor cells as assessed by western blot at Day 13 following transduction with the lentiviral sgRNA expression constructs.

Figure 15:
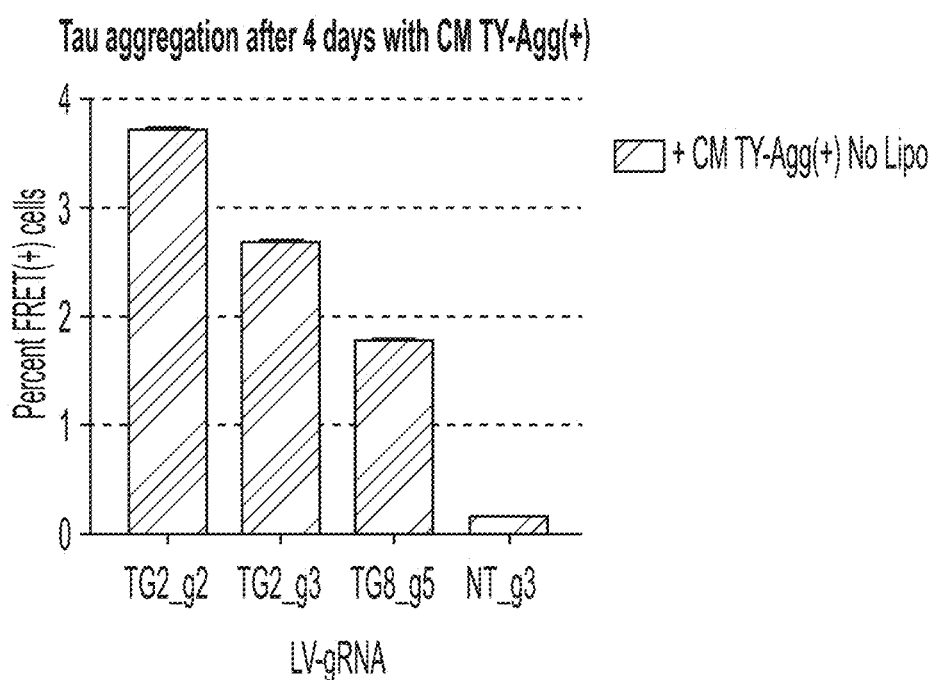

FIG. 15 shows tau aggregation as measured by percent FRET[+] cells in Cas9 TCY biosensor cells at Day 10 following transduction with the lentiviral sgRNA expression constructs. No lipofectamine was used.

Figure 16:
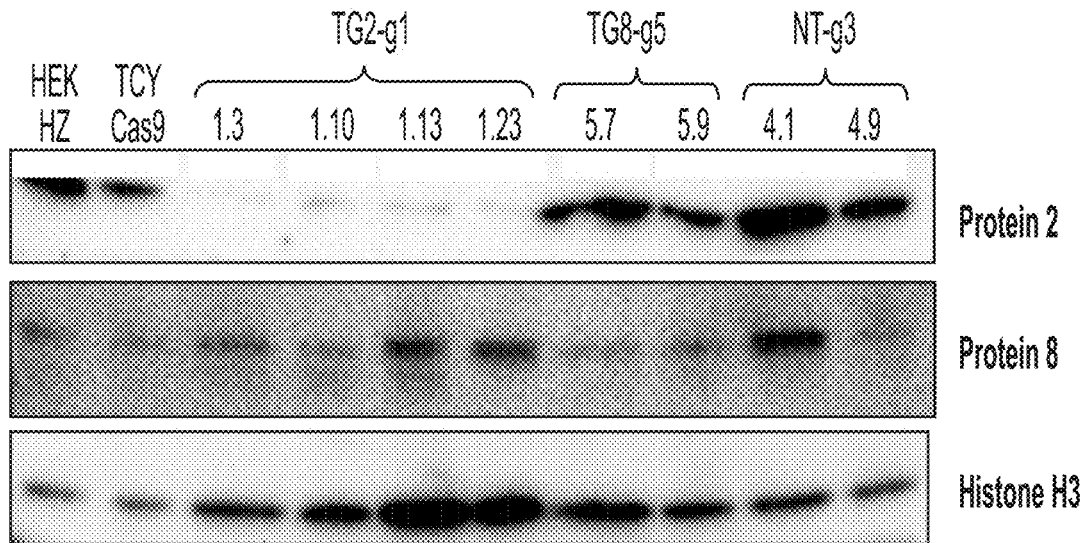

FIG. 16 shows expression of Target Gene 2 and Target Gene 8 in the knockdown Cas9 TCY cell clones as assessed by western blot.

Figure 17:
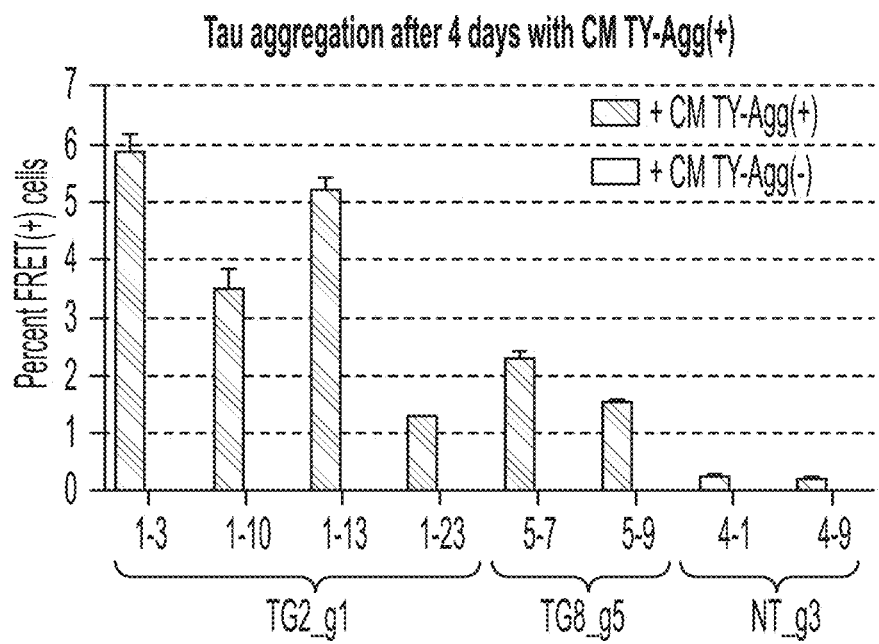

FIG. 17 shows expression of tau aggregation in the Target Gene 2 and Target Gene 8 knockdown Cas9 TCY cell clones as assessed by FRET.

Figure 18:
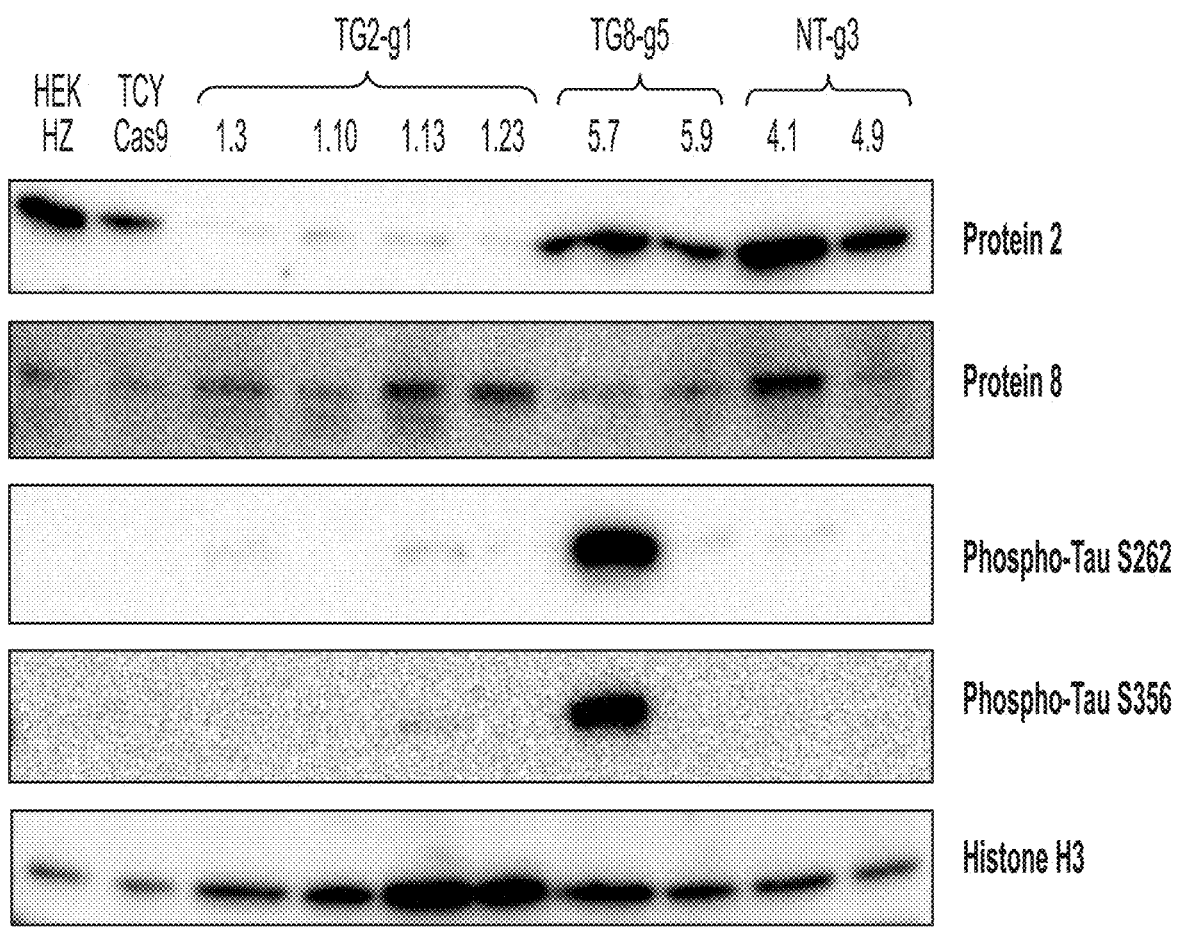

FIG. 18 shows expression of Target Gene 2 and Target Gene 8 in the knockdown Cas9 TCY cell clones as assessed by western blot and phosphorylation of tau at positions S262 and S356 in those clones as assessed by western blot.

Figure 19:
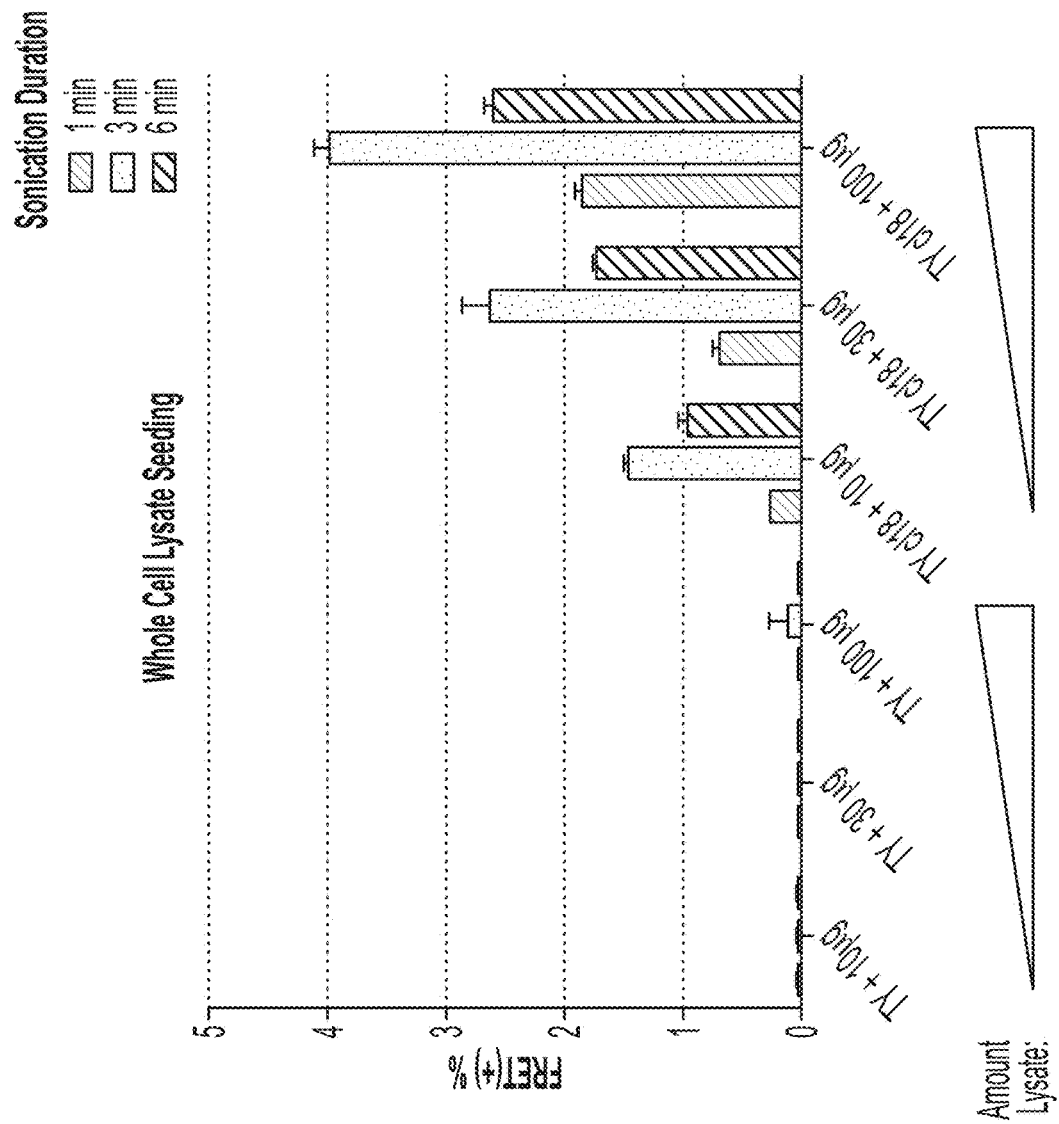

FIG. 19 shows whole cell lysate from tau-YFP Agg[+] clone18 can induce tau aggregation and FRET signal in tau biosensor cells. Different amounts of whole cell lysate were tested, and different sonication conditions for producing the lysate were tested.

Figure 20:
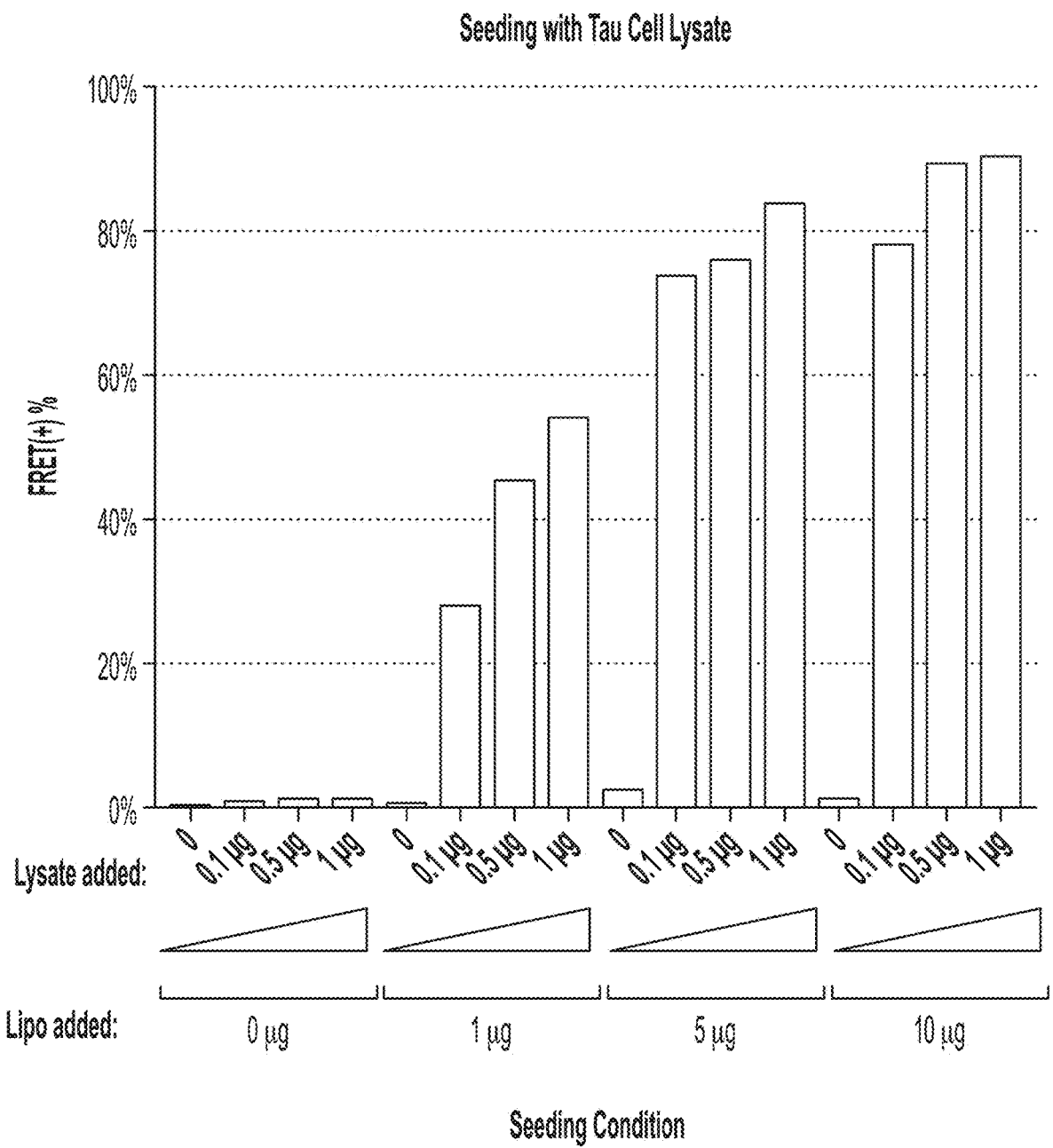

FIG. 20 shows whole cell lysate from tau-YFP Agg[+] clone18 can induce tau aggregation and FRET signal in tau biosensor cells. Different amounts of whole cell lysate were tested, and different amounts of lipofectamine were tested.

Figure 21:
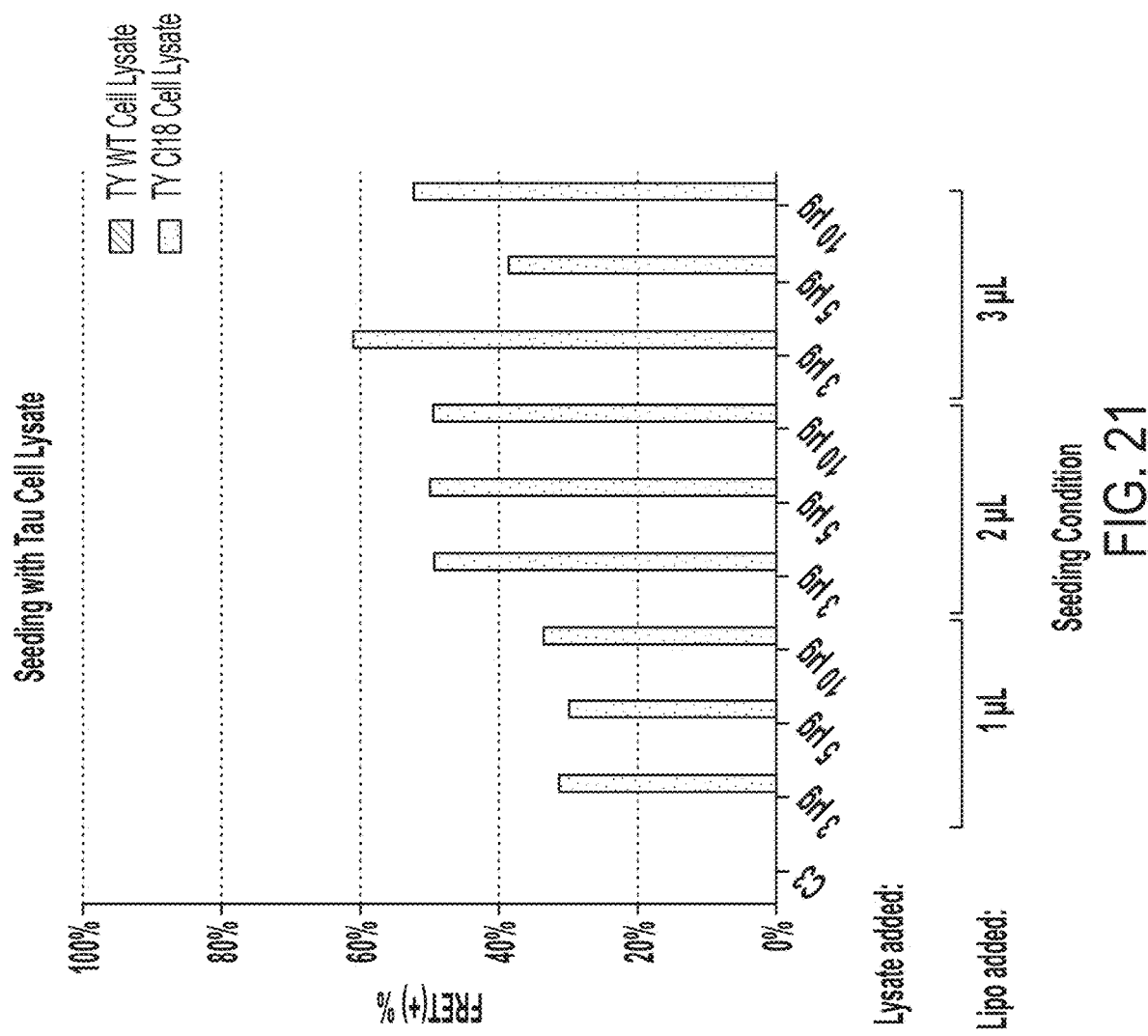

FIG. 21 shows whole cell lysate from tau-YFP Agg[+] clone18 can induce tau aggregation and FRET signal in tau biosensor cells but whole cell lysate from Agg[−] clones cannot. Different amounts of whole cell lysate were tested, and different amounts of lipofectamine were tested.

Figure 22:
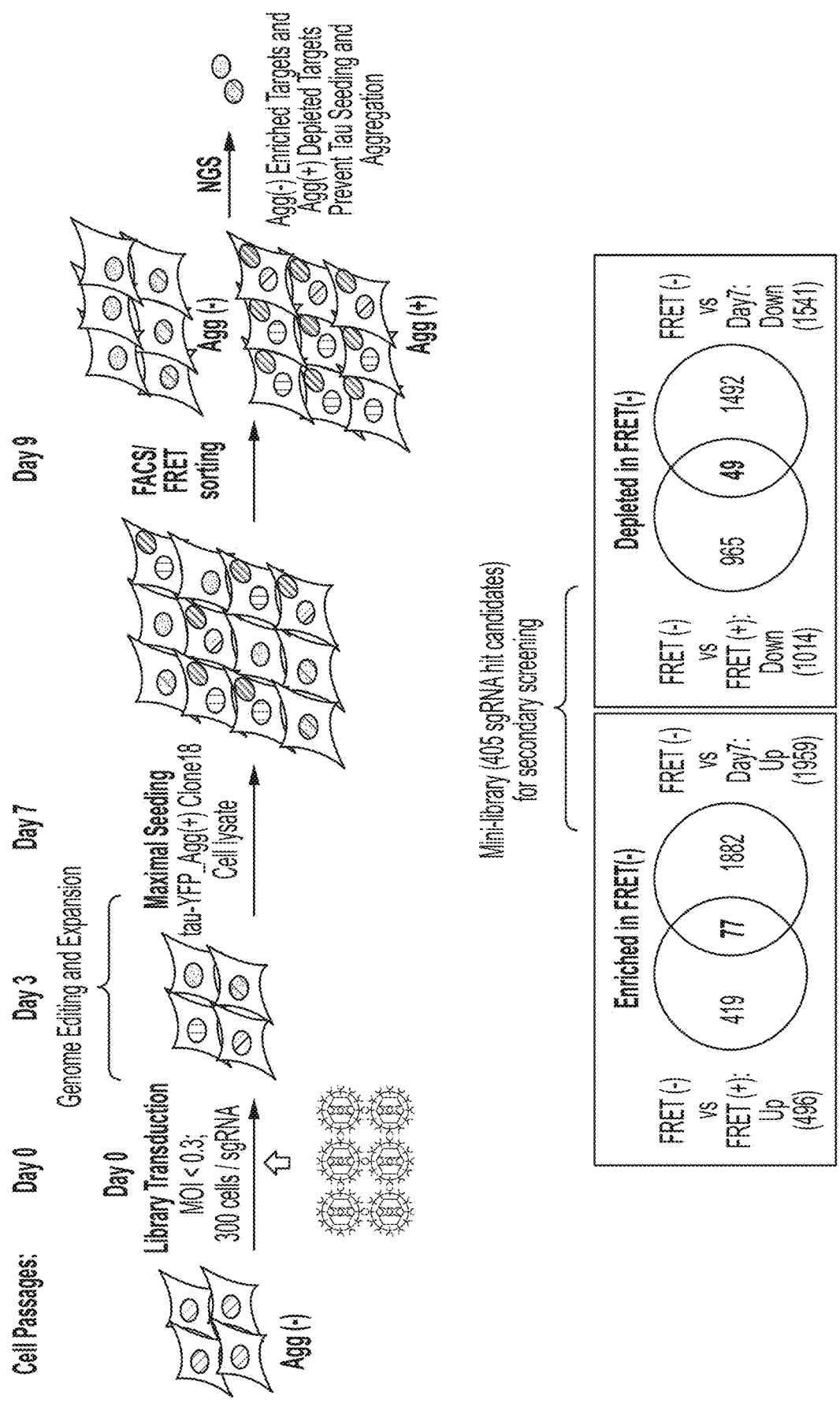

FIG. 22 shows a schematic showing the strategy for a genome-wide CRISPR nuclease (CRISPRn) screen to identify modifier genes that prevent tau aggregation.

Figure 23:
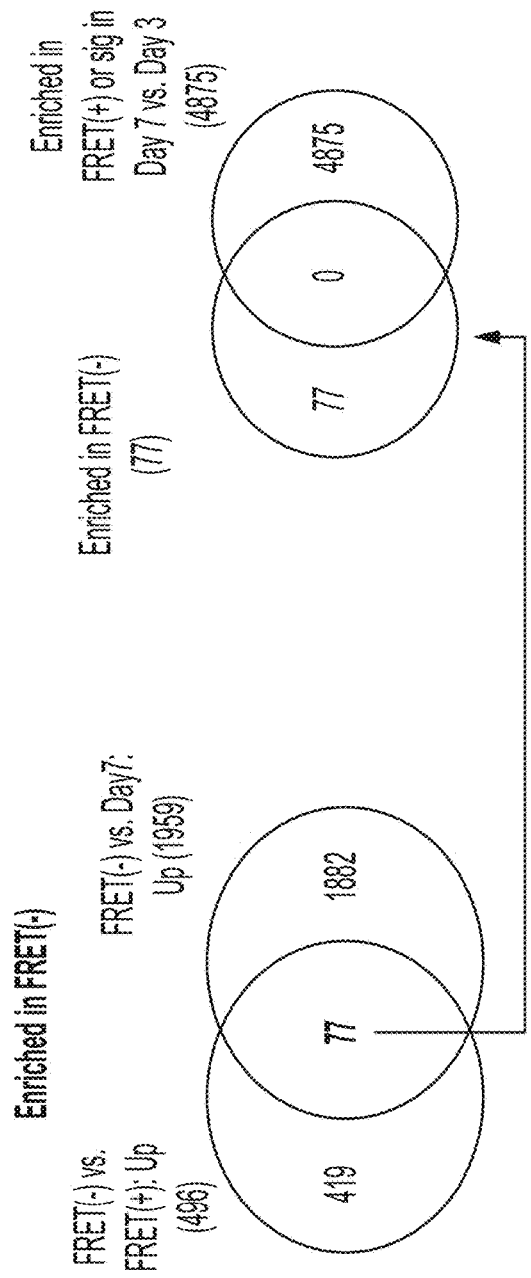

FIG. 23 is a graph showing the identification of genes with uniquely enriched sgRNAs in FRET[−] samples.

Figure 24:
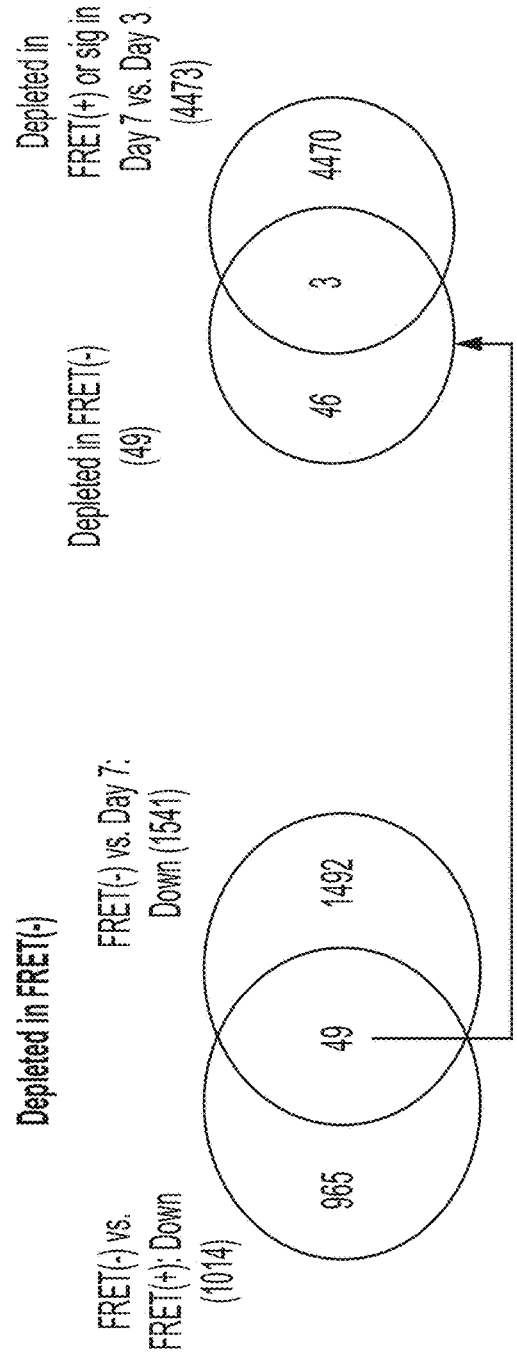

FIG. 24 is a graph showing the identification of genes with uniquely depleted sgRNAs in FRET[−] samples.

Figure 25:
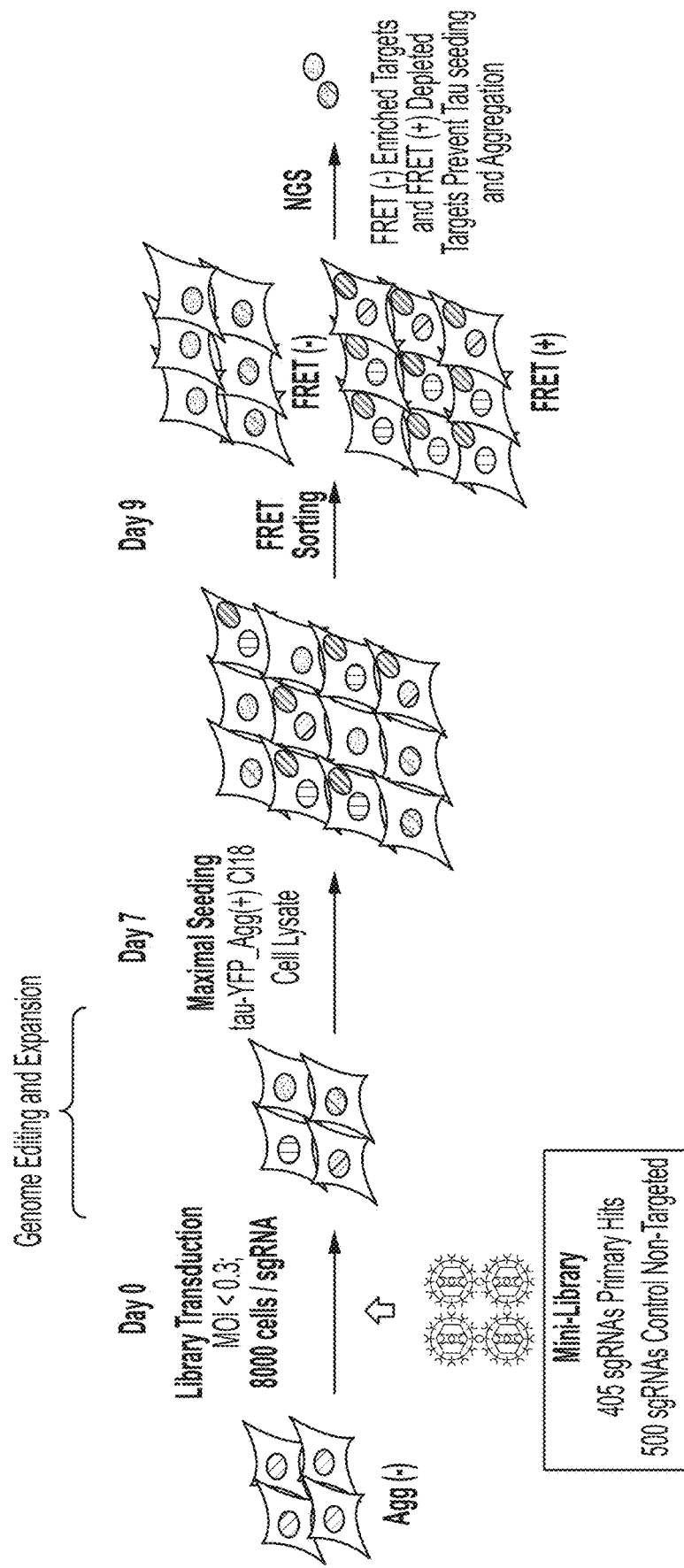

FIG. 25 shows a schematic showing the strategy for secondary screening to confirm identified modifier genes that prevent tau aggregation.

Figure 26:
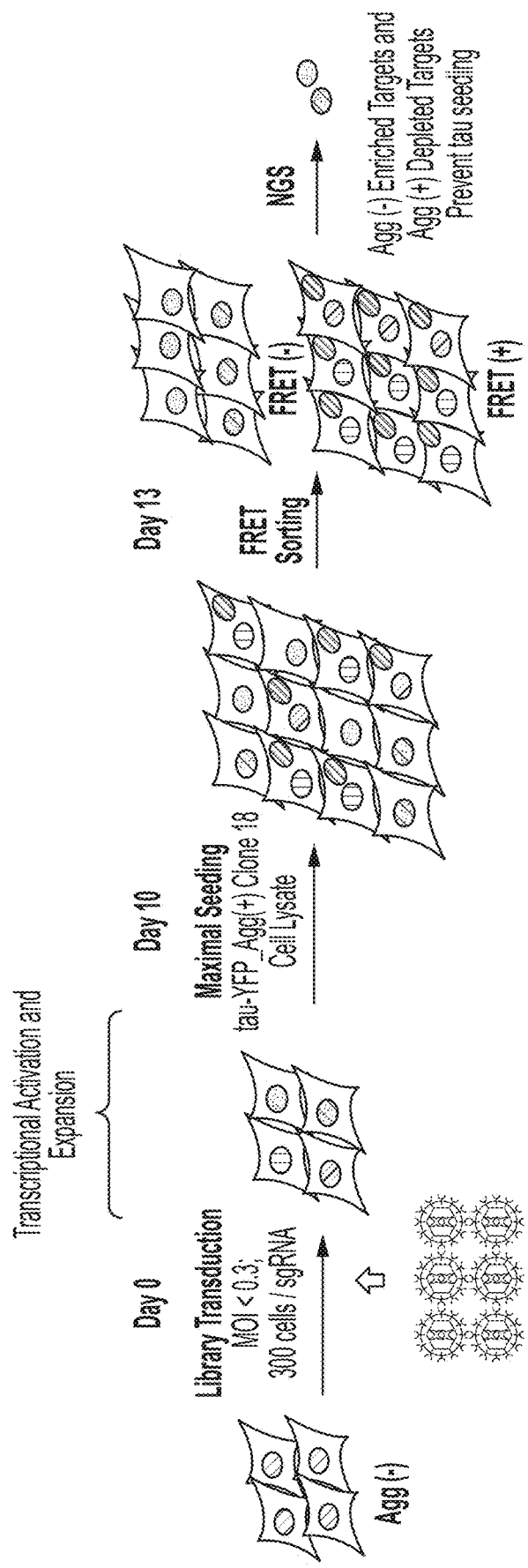

FIG. 26 shows a schematic showing the strategy for a genome-wide CRISPR activation (CRISPRa) screen to identify modifier genes that prevent tau aggregation.

Figure 27:
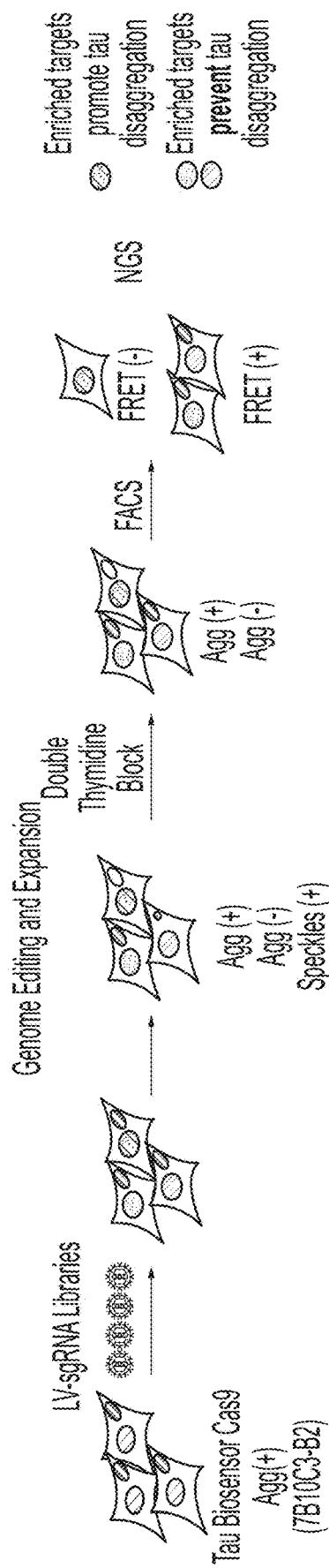

FIG. 27 shows a schematic showing the strategy for a genome-wide CRISPR nuclease (CRISPRn) screen to identify modifier genes that promote tau disaggregation.

Figure 28:
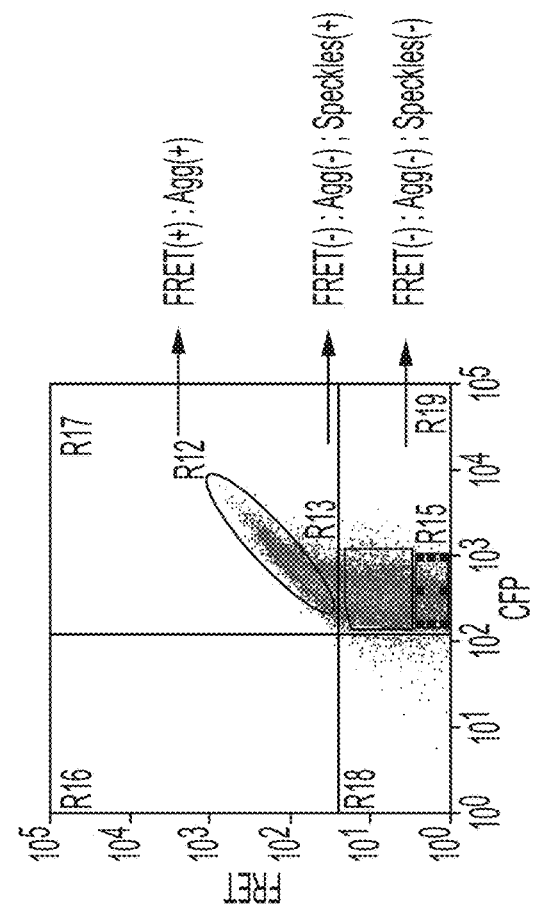

FIG. 28 shows gating used for sorting Agg[+], speckles [+], and Agg[−] cell populations.

Figure 29:
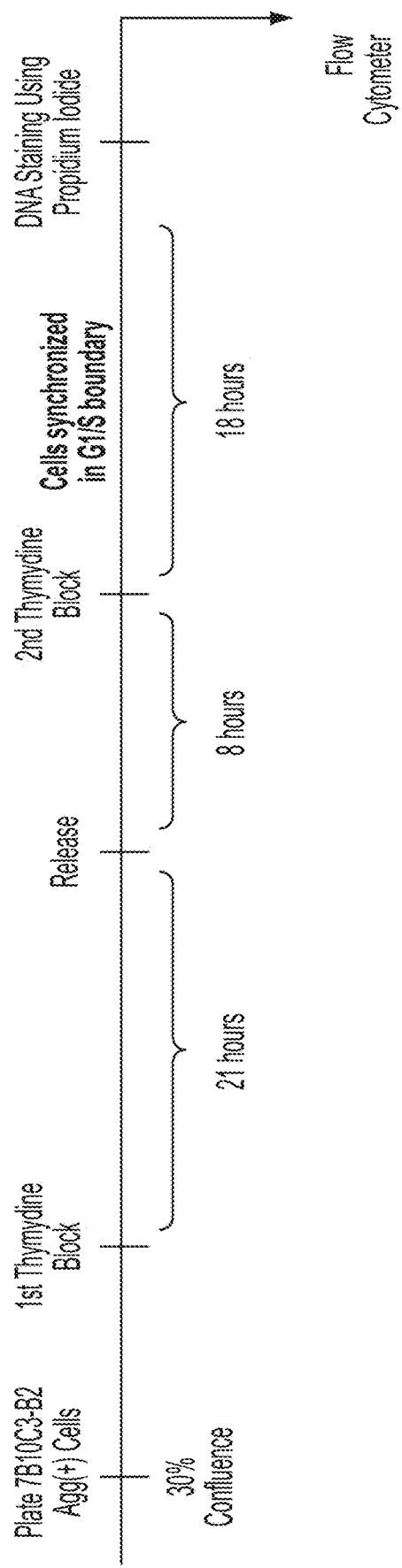

FIG. 29 shows a schematic for a thymidine block strategy used in the genome-wide CRISPR nuclease (CRISPRn) screen to identify modifier genes that promote tau disaggregation.

DEFINITIONS

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "genomically integrated" refers to a nucleic acid that has been introduced into a cell such that the nucleotide sequence integrates into the genome of the cell. Any protocol may be used for the stable incorporation of a nucleic acid into the genome of a cell.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells either ex vivo or in vivo. Numerous forms of viral vectors are known.

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a cell or organism. For example, an endogenous MAPT sequence of a cell or organism refers to a native MAPT sequence that naturally occurs at the MAPT locus in the cell or organism.

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

The term "locus" refers to a specific location of a gene (or significant sequence), DNA sequence, polypeptide-encoding sequence, or position on a chromosome of the genome of an organism. For example, a "MAPT locus" may refer to the specific location of a MAPT gene, MAPTDNA sequence, microtubule-associated-protein-tau-encoding sequence, or MAPT position on a chromosome of the genome of an organism that has been identified as to where such a sequence resides. A "MAPT locus" may comprise a regulatory element of a MAPT gene, including, for example, an enhancer, a promoter, 5' and/or 3' untranslated region (UTR), or a combination thereof.

The term "gene" refers to a DNA sequence in a chromosome that codes for a product (e.g., an RNA product and/or a polypeptide product) and includes the coding region interrupted with non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a human cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

The term "variant" refers to a nucleotide sequence differing from the sequence most prevalent in a population (e.g., by one nucleotide) or a protein sequence different from the sequence most prevalent in a population (e.g., by one amino acid).

The term "fragment" when referring to a protein means a protein that is shorter or has fewer amino acids than the full-length protein. The term "fragment" when referring to a nucleic acid means a nucleic acid that is shorter or has fewer nucleotides than the full-length nucleic acid. A fragment can be, for example, an N-terminal fragment (i.e., removal of a portion of the C-terminal end of the protein), a C-terminal fragment (i.e., removal of a portion of the N-terminal end of the protein), or an internal fragment.

"Sequence identity" or "identity" in the context of two polynucleotides or polypeptide sequences refers to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

TABLE 1

Amino Acid Categorizations.

| Alanine | Ala | A | Nonpolar | Neutral | 1.8 |
| --- | --- | --- | --- | --- | --- |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |

TABLE 1-continued

Amino Acid Categorizations.

| Tryptophan | Trp | W | Nonpolar | Neutral | −0.9 |
| --- | --- | --- | --- | --- | --- |
| Tyrosine | Tyr | Y | Polar | Neutral | −1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube or an isolated cell or cell line). The term "in vivo" includes natural environments (e.g., a cell or organism or body) and to processes or reactions that occur within a natural environment. The term "ex vivo" includes cells that have been removed from the body of an individual and to processes or reactions that occur within such cells.

The term "reporter gene" refers to a nucleic acid having a sequence encoding a gene product (typically an enzyme) that is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include, but are not limited, to genes encoding beta-galactosidase (lacZ), the bacterial chloramphenicol acetyl-transferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreenl), yellow fluorescent proteins (e.g., YFP, eYFP, Citrine, Venus, YPet, PhiYFP, and ZsYellowl), blue fluorescent proteins (e.g., BFP, eBFP, eBFP2, Azurite, mKalamal, GFPuv, Sapphire, and T-sapphire), cyan fluorescent proteins (e.g., CFP, eCFP, Cerulean, CyPet, AmCyanl, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, and Jred), orange fluorescent proteins (e.g., mOrange, mKO, Kusabira- Orange, Monomeric Kusabira-Orange, mTangerine, and tdTomato), and any other suitable fluorescent protein whose presence in cells can be detected by flow cytometry methods.

Repair in response to double-strand breaks (DSBs) occurs principally through two conserved DNA repair pathways: homologous recombination (HR) and non-homologous end joining (NHEJ). See Kasparek & Humphrey (2011) *Seminars in Cell & Dev. Biol.* 22:886-897, herein incorporated by reference in its entirety for all purposes. Likewise, repair of a target nucleic acid mediated by an exogenous donor nucleic acid can include any process of exchange of genetic information between the two polynucleotides.

The term "recombination" includes any process of exchange of genetic information between two polynucleotides and can occur by any mechanism. Recombination can occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLOS ONE* 7: e45768:1-9; and Wang et al. (2013) *Nat Biotechnol.* 31:530-532, each of which is herein incorporated by reference in its entirety for all purposes.

NHEJ includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by a nuclease agent in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which it does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means $p<0.05$.

DETAILED DESCRIPTION

I. Overview

Cas-protein-ready tau biosensor cells and methods of making and using such cells to screen for genetic modifiers of tau seeding or aggregation are provided. CRISPR/Cas synergistic activation mediator (SAM)-ready tau biosensor cells and methods of making and using such cells to screen for genetic modifiers of tau seeding or aggregation are provided. Cas-protein-ready tau biosensor cells and methods of making and using such cells to screen for genetic modifiers of tau disaggregation are provided. CRISPR/Cas synergistic activation mediator (SAM)-ready tau biosensor cells and methods of making and using such cells to screen for genetic modifiers of tau disaggregation are provided. Reagents and methods for sensitizing such cells to tau seeding activity or tau aggregation are also provided. Reagents and methods for inducing tau aggregation are also provided.

To identify genes and pathways that modify the processes of abnormal tau protein aggregation, a platform was developed for performing screens with CRISPR (e.g., CRISPR/Cas9) nuclease (CRISPRn) sgRNA libraries to identify genes that regulate the potential of cells to be "seeded" by tau disease-associated protein aggregates (e.g., genes which, when disrupted, cause cells to be more susceptible to tau aggregate formation when exposed to a source of tau fibrilized protein). To further identify genes and pathways that modify the processes of abnormal tau protein aggregation, a platform was developed for performing screens with CRISPR activation (CRISPRa) sgRNA libraries to identify genes that regulate the potential of cells to be "seeded" by tau disease-associated protein aggregates (e.g., genes which, when transcriptionally activated, cause cells to be more susceptible to tau aggregate formation when exposed to a source of tau fibrillized protein). Likewise, a platform was developed for performing screens with CRISPR (e.g., CRISPR/Cas9) nuclease (CRISPRn) sgRNA libraries to identify genes that, when disrupted, prevent tau aggregation or promote tau disaggregation. Likewise, a platform was developed for performing screens with CRISPR activation (CRISPRa) sgRNA libraries to identify genes that, when transcriptionally activated, prevent tau aggregation or promote tau disaggregation. A "seed" refers to one or more proteins that nucleate aggregation of other proteins with a similar aggregation domain. The seeding activity of a sample refers to the ability of a sample to nucleate (i.e. induce) aggregation of a protein with a similar aggregation domain. The identification of such genes may elucidate the mechanisms of tau cell-to-cell aggregate propagation and genetic pathways that govern the susceptibility of neurons to form tau aggregates in the context of neurodegenerative diseases.

The screens employ a tau biosensor cell line (e.g., human cell line, or HEK293T) consisting of cells stably expressing tau repeat domain (e.g., tau four-repeat domain, tau_4RD) with a pathogenic mutation (e.g., the P301S pathogenic mutation), linked to unique reporters that can act together as an intracellular biosensor that produces a detectable signal when aggregated. In one non-limiting example, the cell lines contain two transgenes stably expressing disease-associated protein variants fused to the fluorescent protein CFP (e.g., eCFP) or the fluorescent protein YFP (e.g., eYFP): $tau^{4RD}$-CFP/$tau^{4RD}$-YFP (TCY), wherein the tau repeat domain (4RD) comprises the P301S pathogenic mutation. In these biosensor lines, tau-CFP/tau-YFP protein aggregation produces a fluorescence resonance energy transfer (FRET) signal, the result of a transfer of fluorescent energy from donor CFP to acceptor YFP. The term CFP (cyan fluorescent protein) when used herein includes eCFP (enhanced cyan fluorescent protein), and the term YFP (yellow fluorescent protein) when used herein includes eYFP (enhanced yellow fluorescent protein). FRET-positive cells, which contain tau aggregates, can be sorted and isolated by flow cytometry. At baseline, unstimulated cells express the reporters in a stable, soluble state with minimal FRET signal. Upon stimulation (e.g., liposome transfection of seed particles), the reporter proteins form aggregates, producing a FRET signal. Aggregate-containing cells can be isolated by FACS. Stably propagating aggregate-containing cell lines, Agg[+], can be isolated by clonal serial dilution of Agg[−] cell lines.

Several modifications were made to this tau biosensor cell line to make it useful for genetic screening using CRISPRn libraries. First, these tau biosensor cells were modified by introducing a Cas-expressing transgene (e.g., Cas9 or SpCas9) for use in the CRISPRn screens. Second, reagents and a method were developed for sensitizing cells to tau seeding activity and tau aggregation. A cell line was developed in which tau aggregates stably persist in all cells with growth and multiple passages over time. These cells were used to produce conditioned medium by collecting medium that has been on confluent cells for a period of time. This conditioned medium can then be applied onto naïve tau biosensor tau cells at a ratio of so that tau aggregation could be induced in a small percentage of these recipient cells, thereby sensitizing them to tau seeding activity and tau aggregation. Conditioned medium without co-culturing has not been used in this context as a seeding agent before. However, the conditioned medium is particularly useful for large-scale genome-wide screens because tau fibrils produced in vitro are a limited resource. In addition, conditioned medium is more physiologically relevant because it is produced and secreted by cells rather than in vitro.

These cell lines were used to develop a method of screening in which Cas-expressing tau biosensor cells without aggregates (Agg[−]) were transduced with a CRISPR guide RNA library to introduce knock-out mutations at each target gene. After culturing the cells to allow genome editing and expansion, the cells were grown in conditioned medium to sensitize them to the seeding activity, and cells were identified in which tau aggregation occurred. Guide RNAs were identified that were enriched in the aggregation-positive sub-population relative to earlier time points during genome editing and expansion to identify genes that can regulate the susceptibility of cells to tau seeding when exposed to an external source of tau seeding activity.

Likewise, several modifications were made to this tau biosensor cell line to make it useful for genetic screening using CRISPRa libraries (e.g., for use with a CRISPR/Cas synergistic activation mediator (SAM) system). In an exemplary SAM system, several activation domains interact to cause a greater transcriptional activation than could be induced by any one factor alone. For example, an exemplary SAM system comprises a chimeric Cas protein comprising a nuclease-inactive Cas protein fused to one or more transcriptional activation domains (e.g., VP64) and a chimeric adaptor protein comprising an adaptor protein (e.g., MS2 coat protein (MCP)) fused to one or more transcriptional activation domains (e.g., fused to p65 and HSF1). The MCP naturally binds to MS2 stem loops. In an exemplary SAM system, MCP interacts MS2 stem loops engineered into the CRISPR-associated sgRNA and thereby shuttles the bound transcription factors to the appropriate genomic location.

First, these tau biosensor cells were modified by introducing one or more transgenes expressing the chimeric Cas protein comprising the nuclease-inactive Cas protein fused to one or more transcriptional activation domains (e.g., VP64) and the chimeric adaptor protein comprising the adaptor protein (e.g., MS2 coat protein (MCP)) fused to one or more transcriptional activation domains (e.g., fused to p65 and HSF1). Although SAM systems are described herein, other CRISPRa systems such as a nuclease-inactive Cas protein fused to one or more transcriptional activation domains, wherein such systems do not also include a chimeric adaptor protein, can also be used. In such cases, the tau biosensor cells would be modified by introducing a transgene expressing the chimeric Cas protein.

Second, reagents and a method were developed for sensitizing cells to tau seeding activity and tau aggregation. A cell line was developed in which tau aggregates stably persist in all cells with growth and multiple passages over time. These cells were used to produce conditioned medium by collecting medium that has been on confluent cells for a period of time. This conditioned medium can then be applied onto naïve tau biosensor tau cells at a ratio of so that tau aggregation could be induced in a small percentage of these recipient cells, thereby sensitizing them to tau seeding activity and tau aggregation. Conditioned medium without co-culturing has not been used in this context as a seeding agent before. However, the conditioned medium is particularly useful for large-scale genome-wide screens because tau fibrils produced in vitro are a limited resource. In addition, conditioned medium is more physiologically relevant because it is produced and secreted by cells rather than in vitro.

These cell lines were used to develop a method of screening in which SAM-expressing tau biosensor cells without aggregates (Agg[−]) were transduced with a CRISPRa guide RNA library to transcriptionally activate each target gene. After culturing the cells to allow genome editing and expansion, the cells were grown in conditioned medium to sensitize them to the seeding activity, and cells were identified in which tau aggregation occurred. Guide RNAs were identified that were enriched in the aggregation-positive sub-population relative to earlier time points during genome editing and expansion to identify genes that can regulate the susceptibility of cells to tau seeding when exposed to an external source of tau seeding activity.

II. Cas/Tau Biosensor and SAM/Tau Biosensor Cell Lines and Methods of Generating A. Cas/Tau Biosensor Cells and SAM/Tau Biosensor Cells Disclosed herein are cells not only expressing a first tau repeat domain (e.g., comprising the tau microtubule binding domain (MBD)) linked to a first reporter and a second tau repeat domain linked to a second reporter, but also expressing a Cas protein, such as Cas9. Also disclosed herein are cells not only expressing a first tau repeat domain (e.g., comprising the tau microtubule binding domain (MBD)) linked to a first reporter and a second tau repeat domain linked to a second reporter, but also expressing a chimeric Cas protein comprising a nuclease-inactive Cas protein fused to one or more transcriptional activation domains and a chimeric adaptor protein comprising an adaptor protein fused to one or more transcriptional activation domains. The first tau repeat domain linked to the first reporter can be stably expressed, and the second tau repeat domain linked to the second reporter can be stably expressed. For example, DNA encoding the first tau repeat domain linked to the first reporter can be genomically integrated, and DNA encoding the second tau repeat domain linked to the second reporter can be genomically integrated. Similarly, the Cas protein can be stably expressed in the Cas/tau biosensor cells. For example, DNA encoding the Cas protein can be genomically integrated. Likewise, the chimeric Cas protein and/or the chimeric adaptor protein can be stably expressed in the SAM/tau biosensor cells. For example, DNA encoding the chimeric Cas protein can be genomically integrated and/or DNA encoding the chimeric adaptor protein can be genomically integrated. The cells can be tau-aggregation-negative or can be tau-aggregation-positive.

1. Tau and Tau Repeat Domains Linked to Reporters

Microtubule-associated protein tau is a protein that promotes microtubule assembly and stability and is predominantly expressed in neurons. Tau has a role in stabilizing neuronal microtubules and thus in promoting axonal outgrowth. In Alzheimer's disease (AD) and a family of related neurodegenerative diseases called tauopathies, tau protein is abnormally hyperphosphorylated and aggregated into bundles of filaments (paired helical filaments), which manifest as neurofibrillary tangles. Tauopathies are a group of heterogeneous neurodegenerative conditions characterized by deposition of abnormal tau in the brain.

The tau repeat domain can be from a tau protein from any animal or mammal, such as human, mouse, or rat. In one specific example, the tau repeat domain is from a human tau protein. An exemplary human tau protein is assigned UniProt accession number P10636. The tau proteins are the products of alternate splicing from a single gene that in humans is designated MAPT (microtubule-associated protein tau). The tau repeat domain carries the sequence motifs responsible for aggregation (i.e., it is the aggregation-prone domain from tau). Depending on splicing, the repeat domain of the tau protein has either three or four repeat regions that constitute the aggregation-prone core of the protein, which is often termed the repeat domain (RD). Specifically, the repeat domain of tau represents the core of the microtubule binding region and harbors the hexapeptide motifs in R2 and R3 that are responsible for Tau aggregation. In the human brain, there are six tau isoforms ranging from 352 to 441 amino acids in length. These isoforms vary at the carboxyl terminal according to the presence of either three repeat or four repeat domains (R1-R4), in addition to the presence or absence of one or two insert domains at the amino-terminus. The repeat domains, located at the carboxyl-terminal half of tau, are believed to be important for microtubule binding as well as for the pathological aggregation of tau into paired helical filaments (PHFs), which are the core constituents of the neurofibrillary tangles found in tauopathies. Exemplary sequences for the four repeat domains (R1-R4) are provided in SEQ ID NOS: 1-4, respectively. Exemplary coding sequences for the four repeat domains (R1-R4) are provided in SEQ ID NOS: 5-8. An exemplary sequence for the Tau four-repeat domain is provided in SEQ ID NO: 9. An exemplary coding sequence for the Tau four-repeat domain is provided in SEQ ID NO: 10. An exemplary sequence for the Tau four-repeat domain with the P301S mutation is provided in SEQ ID NO: 11. An exemplary coding sequence for the Tau four-repeat domain with the P301S mutation is provided in SEQ ID NO: 12.

The tau repeat domain used in the Cas/tau biosensor cells or the SAM/tau biosensor cells can comprise the tau microtubule binding domain (MBD). The tau repeat domain used in the Cas/tau biosensor cells or the SAM/tau biosensor cells can comprise one or more or all of the four repeat domains (R1-R4). For example, the tau repeat domain can comprise, consist essentially of, or consist of one or more or all of SEQ ID NOS: 1, 2, 3, and 4, or sequences at least about 90%, 91%, 92%, 93%, 94%, 95%, 96%, 97%, 98%, or 99% identical to SEQ ID NOS: 1, 2, 3, and 4. In one specific example, the tau repeat domain is the tau four-repeat domain (R1-R4) found in several tau isoforms. The tau four-repeat domain can be used instead of full-length tau because it reliably forms fibrils in cultured cells. For example, the tau repeat domain can comprise, consist essentially of, or consist of SEQ ID NO: 9 or SEQ ID NO: 11 or a sequence at least about 90%, 91%, 92%, 93%, 94%, 95%, 96%, 97%, 98%, or 99% identical to SEQ ID NO: 9 or SEQ ID NO: 11. In one specific example, the nucleic acid encoding the tau repeat domain can comprise, consist essentially of, or consist of SEQ ID NO: 12 or a sequence at least about 90%, 91%, 92%, 93%, 94%, 95%, 96%, 97%, 98%, or 99% identical to SEQ ID NO: 12, optionally wherein the nucleic acid encodes a protein comprising, consisting essentially of, or consisting of SEQ ID NO: 11. In another specific example, the nucleic acid encoding the second tau repeat domain linked to the second reporter can comprise, consist essentially of, or consist of SEQ ID NO: 10 or a sequence at least about 90%, 91%, 92%, 93%, 94%, 95%, 96%, 97%, 98%, or 99% identical to SEQ ID NO: 10, optionally wherein the nucleic acid encodes a protein comprising, consisting essentially of, or consisting of SEQ ID NO: 9. The first and second tau repeat domains in the cells disclosed herein can be the same, similar, or different.

One or both of the first tau repeat domain linked to the first reporter and the second tau repeat domain linked to the second reporter can be stably expressed in the cells. For example, nucleic acids encoding one or both of the first tau repeat domain linked to the first reporter and the second tau repeat domain linked to the second reporter can be genomically integrated in the population of cells and operably linked to promoters active in the cell.

The tau repeat domains used in the cells disclosed herein can also comprise a tau pathogenic mutation, such as a pro-aggregation mutation. Such a mutation can be, for example, a mutation that is associated with (e.g., segregates with) or causes a tauopathy. As one example, the mutation can be an aggregation-sensitizing mutation that sensitizes tau to seeding but does not result in tau readily aggregating on its own. For example, the mutation can be the disease-associated P301S mutation. By P301S mutation is meant the human tau P301S mutation or a corresponding mutation in another tau protein when optimally aligned with the human tau protein. The P301S mutation in tau exhibits high sensitivity to seeding, but it does not readily aggregate on its own. Thus, although at baseline tau reporter proteins comprising the P301S mutation exist in a stable, soluble form within the cell, exposure to exogenous tau seeds leads to tau reporter protein aggregation. Other tau mutations include, for example, K280del, P301L, V337M, P301L/V337M, and K280del/I227P/I308P.

The first tau repeat domain can be linked to the first reporter and the second tau repeat domain can be linked to the second reporter by any means. For example, the reporter can be fused to the tau repeat domain (e.g., as part of a fusion protein).

The first reporter and second reporter can be and pair of unique reporters that can act together as an intracellular biosensor that produces a detectable signal when the first and second proteins are aggregated. As one example, the reporters can be fluorescent proteins, and fluorescence resonance energy transfer (FRET) can be used to measure protein aggregation. Specifically, the first and second reporters can be a FRET pair. Examples of FRET pairs (donor and acceptor fluorophores) are well known. See, e.g., Bajar et al. (2016) *Sensors (Basel)* 16(9):1488, herein incorporated by reference in its entirety for all purposes. Typical fluorescence microscopy techniques rely upon the absorption by a fluorophore of light at one wavelength (excitation), followed by the subsequent emission of secondary fluorescence at a longer wavelength. The mechanism of fluorescence resonance energy transfer involves a donor fluorophore in an excited electronic state, which may transfer its excitation energy to a nearby acceptor chromophore in a non-radiative fashion through long-range dipole-dipole interactions. For example, the FRET energy donor may be the first reporter, and the FRET energy acceptor may be the second reporter. Alternatively, the FRET energy donor may be the second reporter, and the FRET energy acceptor may be the first reporter. In a specific example, the first and second reporters are CFP and YFP. Exemplary protein and coding sequences for CFP are provided, e.g., in SEQ ID NOS: 13 and 14, respectively. Exemplary protein and coding sequences for YFP are provided, e.g., in SEQ ID NOS: 15 and 16, respectively. As a specific example, the CFP can comprise, consist essentially of, or consist of SEQ ID NO: 13 or a sequence at least about 90%, 91%, 92%, 93%, 94%, 95%, 96%, 97%, 98%, or 99% identical to SEQ ID NO: 13. As another specific example, the YFP can comprise, consist essentially of, or consist of SEQ ID NO: 15 or a sequence at least about 90%, 91%, 92%, 93%, 94%, 95%, 96%, 97%, 98%, or 99% identical to SEQ ID NO: 15.

As another example, a protein fragment complementation strategy can be used to detect aggregation. For example, a split-luciferase can be used to produce bioluminescence from a substrate, and the first and second reporters can be amino-(NLuc) and carboxy-(CLuc) terminal fragments of the luciferase. Examples of luciferase include *Renilla*, firefly, click beetle, and *Metridia* luciferase.

In one non-limiting example, the biosensor cells disclosed herein contain two transgenes stably expressing disease-associated tau protein variants fused to the fluorescent protein CFP or the fluorescent protein YFP, respectively ($tau^{4RD}$-CFP/$tau^{4RD}$-YFP (TCY)), wherein the tau four repeat domain (4RD) comprises the P301S pathogenic mutation. In these biosensor lines, tau-CFP/tau-YFP protein aggregation produces a FRET signal, the result of a transfer of fluorescent energy from donor CFP to acceptor YFP. FRET-positive cells, which contain tau aggregates, can be sorted and isolated by flow cytometry. At baseline, unstimulated cells express the reporters in a stable, soluble state with minimal FRET signal. Upon stimulation (e.g., liposome transfection of seed particles), the reporter proteins form aggregates, producing a FRET signal.

The Cas/tau biosensor cells disclosed herein can be aggregation-positive (Agg[+]) cells in which the tau repeat domain stably presents in an aggregated state, meaning that the tau repeat domain aggregates stably persist in all cells with growth and multiple passages over time. Alternatively, the Cas/tau biosensor cells disclosed herein can be aggregation-negative (Agg[−]).

2. Cas Proteins and Chimeric Cas Proteins

The Cas/tau biosensor cells disclosed herein also comprise nucleic acids (DNA or RNA) encoding Cas proteins. Optionally, the Cas protein is stably expressed. Optionally, the cells comprise a genomically integrated Cas coding sequence. Likewise, the SAM/tau biosensor cells disclosed herein also comprise nucleic acids (DNA or RNA) encoding chimeric Cas proteins comprising a nuclease-inactive Cas protein fused to one or more transcriptional activation domains (e.g., VP64). Optionally, the chimeric Cas protein is stably expressed. Optionally, the cells comprise a genomically integrated chimeric Cas coding sequence.

Cas proteins are part of Clustered Regularly Interspersed Short Palindromic Repeats (CRISPR)/CRISPR-associated (Cas) systems. CRISPR/Cas systems include transcripts and other elements involved in the expression of, or directing the activity of, Cas genes. A CRISPR/Cas system can be, for example, a type I, a type II, a type III system, or a type V system (e.g., subtype V-A or subtype V-B). The methods and compositions disclosed herein can employ CRISPR/Cas systems by utilizing CRISPR complexes (comprising a guide RNA (gRNA) complexed with a Cas protein) for site-directed binding or cleavage of nucleic acids.

CRISPR/Cas systems used in the compositions and methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together, employ a Cas protein that does not occur naturally, or employ a gRNA that does not occur naturally.

Cas proteins generally comprise at least one RNA recognition or binding domain that can interact with guide RNAs. Cas proteins can also comprise nuclease domains (e.g., DNase domains or RNase domains), DNA-binding domains, helicase domains, protein-protein interaction domains, dimerization domains, and other domains. Some such domains (e.g., DNase domains) can be from a native Cas protein. Other such domains can be added to make a modified Cas protein. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break at a target genomic locus (e.g., a double-strand break with blunt ends), or it can be a nickase that creates a single-strand break at a target genomic locus.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

An exemplary Cas protein is a Cas9 protein or a protein derived from a Cas9 protein. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes*, *Streptococcus thermophilus*, *Streptococcus* sp., *Staphylococcus aureus*, *Nocardiopsis dassonvillei*, *Streptomyces pristinaespiralis*, *Streptomyces viridochromogenes*, *Streptomyces viridochromogenes*, *Streptosporangium roseum*, *Streptosporangium roseum*, *Alicyclobacillus acidocaldarius*, *Bacillus pseudomycoides*, *Bacillus selenitireducens*, *Exiguobacterium sibiricum*, *Lactobacillus delbrueckii*, *Lactobacillus salivarius*, *Microscilla marina*, Burkholderiales *bacterium*, *Polaromonas naphthalenivorans*, *Polaromonas* sp., *Crocosphaera watsonii*, *Cyanothece* sp., *Microcystis aeruginosa*, *Synechococcus sp.*, *Acetohalobium arabaticum*, *Ammonfex degensii*, *Caldicelulosiruptor becscii*, *Candidatus Desulforudis*, *Clostridium botulinum*, *Clostridium difficile*, *Finegoldia magna*, *Natranaerobius thermophilus*, *Pelotomaculum thermopropionicum*, *Acidithiobacillus caldus*, *Acidithiobacillus ferrooxidans*, *Allochromatium vinosum*, *Marinobacter* sp., *Nitrosococcus halophilus*, *Nitrosococcus watsoni*, *Pseudoalteromonas haloplanktis*, *Ktedonobacter racemifer*, *Methanohalobium evestigatum*, *Anabaena variabilis*, *Nodularia spumigena*, *Nostoc* sp., *Arthrospira maxima*, *Arthrospira platensis*, *Arthrospira* sp., *Lyngbya* sp., *Microcoleus chthonoplastes*, *Oscillatoria* sp., *Petrotoga mobilis*, *Thermosipho africanus*, *Acaryochloris marina*, *Neisseria meningitidis*, or *Campylobacter jejuni*. Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Exemplary SpCas9 protein and coding sequence are set forth in SEQ ID NOS: 21 and 22, respectively. Cas9 from *S. aureus* (SaCas9) (assigned UniProt accession number J7RUA5) is another exemplary Cas9 protein. Cas9 from *Campylobacter jejuni* (CjCas9) (assigned UniProt accession number Q0P897) is another exemplary Cas9 protein. See, e.g., Kim et al. (2017) *Nat. Comm.* 8: 14500, herein incorporated by reference in its entirety for all purposes. SaCas9 is smaller than SpCas9, and CjCas9 is smaller than both SaCas9 and SpCas9. Cas9 from *Neisseria meningitidis* (Nme2Cas9) is another exemplary Cas9 protein. See, e.g., Edraki et al. (2019) *Mol. Cell* 73(4):714-726, herein incorporated by reference in its entirety for all purposes. Cas9 proteins from *Streptococcus thermophilus* (e.g., *Streptococcus thermophilus* LMD-9 Cas9 encoded by the CRISPR1 locus (St1Cas9) or *Streptococcus thermophilus* Cas9 from the CRISPR3 locus (St3Cas9)) are other exemplary Cas9 proteins. Cas9 from *Francisella novicida* (FnCas9) or the RHA *Francisella novicida* Cas9 variant that recognizes an alternative PAM (E1369R/E1449H/R1556A substitutions) are other exemplary Cas9 proteins. These and other exemplary Cas9 proteins are reviewed, e.g., in Cebrian-Serrano and Davies (2017) *Mamm. Genome* 28(7):247-261, herein incorporated by reference in its entirety for all purposes.

As one example, the Cas protein can be a Cas9 protein. For example, the Cas9 protein can be a *Streptococcus pyogenes* Cas9 protein. As one specific example, the Cas protein can comprise, consist essentially of, or consist of SEQ ID NO: 21 or a sequence at least about 90%, 91%, 92%, 93%, 94%, 95%, 96%, 97%, 98%, or 99% identical to SEQ ID NO: 21. As another specific example, a chimeric Cas protein comprising a nuclease-inactive Cas protein and one or more transcriptional activation domains can comprise, consist essentially of, or consist of SEQ ID NO: 36 or a sequence at least about 90%, 91%, 92%, 93%, 94%, 95%, 96%, 97%, 98%, or 99% identical to SEQ ID NO: 36.

Another example of a Cas protein is a Cpf1 (CRISPR from Prevotella and Francisella 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) Cell 163(3): 759-771, herein incorporated by reference in its entirety for all purposes. Exemplary Cpf1 proteins are from *Francisella tularensis* 1, *Francisella tularensis* subsp. *novicida*, *Prevotella albensis*, Lachnospiraceae *bacterium* MC20171, *Butyrivibrio proteoclasticus*, Peregrinibacteria *bacterium* GW2011_GWA2_33_10, Parcubacteria *bacterium* GW2011_GWC2_44_17, Smithella sp. SCADC, *Acidaminococcus sp.* BV3L6, Lachnospiraceae *bacterium* MA2020, Candidatus Methanoplasma *termitum*, *Eubacterium eligens*, *Moraxella bovoculi* 237, *Leptospira inadai*, Lachnospiraceae *bacterium* ND2006, *Porphyromonas crevioricanis* 3, *Prevotella disiens*, and *Porphyromonas macacae*. Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain double-strand-break-inducing activity. Assays for double-strand-break-inducing activity are known and generally measure the overall activity and specificity of the Cas protein on DNA substrates containing the cleavage site.

One example of a modified Cas protein is the modified SpCas9-HF1 protein, which is a high-fidelity variant of Streptococcus pyogenes Cas9 harboring alterations (N497A/R661A/Q695A/Q926A) designed to reduce non-specific DNA contacts. See, e.g., Kleinstiver et al. (2016) Nature 529(7587):490-495, herein incorporated by reference in its entirety for all purposes. Another example of a modified Cas protein is the modified eSpCas9 variant (K848A/K1003A/R1060A) designed to reduce off-target effects. See, e.g., Slaymaker et al. (2016) Science 351(6268):84-88, herein incorporated by reference in its entirety for all purposes. Other SpCas9 variants include K855A and K810A/K1003A/R1060A. These and other modified Cas proteins are reviewed, e.g., in Cebrian-Serrano and Davies (2017) Mamm. Genome 28(7):247-261, herein incorporated by reference in its entirety for all purposes. Another example of a modified Cas9 protein is xCas9, which is a SpCas9 variant that can recognize an expanded range of PAM sequences. See, e.g., Hu et al. (2018) Nature 556:57-63, herein incorporated by reference in its entirety for all purposes.

Cas proteins can be modified to increase or decrease one or more of nucleic acid binding affinity, nucleic acid binding specificity, and enzymatic activity. Cas proteins can also be modified to change any other activity or property of the protein, such as stability. For example, a Cas protein can be truncated to remove domains that are not essential for the function of the protein or to optimize (e.g., enhance or reduce) the activity of or a property of the Cas protein. As another example, one or more nuclease domains of the Cas protein can be modified, deleted, or inactivated (e.g., for use in the SAM/tau biosensor cells comprising a nuclease-inactive Cas protein).

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) Science 337:816-821, herein incorporated by reference in its entirety for all purposes.

One or more or all of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break within a double-stranded target DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null or nuclease-inactive Cas protein, or a catalytically dead Cas protein (dCas)). An example of a mutation that converts Cas9 into a nickase is a D10A (aspartate to alanine at position 10 of Cas9) mutation in the RuvC domain of Cas9 from S. pyogenes. Likewise, H939A (histidine to alanine at amino acid position 839), H840A (histidine to alanine at amino acid position 840), or N863A (asparagine to alanine at amino acid position N863) in the HNH domain of Cas9 from S. pyogenes can convert the Cas9 into a nickase. Other examples of mutations that convert Cas9 into a nickase include the corresponding mutations to Cas9 from S. thermophilus. See, e.g., Sapranauskas et al. (2011) Nucleic Acids Res. 39(21):9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes. If all of the nuclease domains are deleted or mutated in a Cas protein (e.g., both of the nuclease domains are deleted or mutated in a Cas9 protein), the resulting Cas protein (e.g., Cas9) will have a reduced ability to cleave both strands of a double-stranded DNA (e.g., a nuclease-null or nuclease-inactive Cas protein). One specific example is a D10A/H840A S. pyogenes Cas9 double mutant or a corresponding double mutant in a Cas9 from another species when optimally aligned with S. pyogenes Cas9. Another specific example is a D10A/N863A S. pyogenes Cas9 double mutant or a corresponding double mutant in a Cas9 from another species when optimally aligned with S. pyogenes Cas9.

Examples of inactivating mutations in the catalytic domains of xCas9 are the same as those described above for SpCas9. Examples of inactivating mutations in the catalytic domains of Staphylococcus aureus Cas9 proteins are also known. For example, the Staphylococcus aureus Cas9 enzyme (SaCas9) may comprise a substitution at position N580 (e.g., N580A substitution) and a substitution at position D10 (e.g., D10A substitution) to generate a nuclease-inactive Cas protein. See, e.g., WO 2016/106236, herein incorporated by reference in its entirety for all purposes. Examples of inactivating mutations in the catalytic domains of Nme2Cas9 are also known (e.g., combination of D16A and H588A). Examples of inactivating mutations in the catalytic domains of St1Cas9 are also known (e.g., combination of D9A, D598A, H599A, and N622A). Examples of inactivating mutations in the catalytic domains of St3Cas9 are also known (e.g., combination of D10A and N870A). Examples of inactivating mutations in the catalytic domains of CjCas9 are also known (e.g., combination of D8A and H559A). Examples of inactivating mutations in the catalytic domains of FnCas9 and RHA FnCas9 are also known (e.g., N995A).

Examples of inactivating mutations in the catalytic domains of Cpf1 proteins are also known. With reference to Cpf1 proteins from Francisella novicida U112 (FnCpf1), Acidaminococcus sp. BV3L6 (AsCpf1), Lachnospiraceae bacterium ND2006 (LbCpf1), and Moraxella bovoculi 237 (MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas proteins can also be operably linked to heterologous polypeptides as fusion proteins. For example, a Cas protein can be fused to a cleavage domain, an epigenetic modification domain, a transcriptional activation domain, or a transcriptional repressor domain. See WO 2014/089290, herein incorporated by reference in its entirety for all purposes. For example, Cas proteins can be operably linked or fused to a transcriptional activation domain for use in the SAM/tau biosensor cells. Examples of transcriptional activation domains include a herpes simplex virus VP16 activation domain, VP64 (which is a tetrameric derivative of VP16), a NFκB p65 activation domain, p53 activation domains 1 and 2, a CREB (cAMP response element binding protein) activation domain, an E2A activation domain, and an NFAT (nuclear factor of activated T-cells) activation domain. Other examples include activation domains from Oct1, Oct-2A, SP1, AP-2, CTF1, P300, CBP, PCAF, SRC1, PvALF, ERF-2, OsGAI, HALF-1, C1, AP1, ARF-5, ARF-6, ARF-7, ARF-8, CPRF1, CPRF4, MYC-RP/GP, TRAB1PC4, and HSF1. See, e.g., US 2016/0237456, EP3045537, and WO 2011/146121, each of which is incorporated by reference in its entirety for all purposes. In some cases, a transcriptional activation system can be used comprising a dCas9-VP64 fusion protein paired with MS2-p65-HSF1. Guide RNAs in such systems can be designed with aptamer sequences appended to sgRNA tetraloop and stem-loop 2 designed to bind dimerized MS2 bacteriophage coat proteins. See, e.g., Konermann et al. (2015) *Nature* 517(7536):583-588, herein incorporated by reference in its entirety for all purposes. Examples of transcriptional repressor domains include inducible cAMP early repressor (ICER) domains, Kruppel-associated box A (KRAB-A) repressor domains, YY1 glycine rich repressor domains, Sp1-like repressors, E(spl) repressors, IκB repressor, and MeCP2. Other examples include transcriptional repressor domains from A/B, KOX, TGF-beta-inducible early gene (TIEG), v-erbA, SID, SID4X, MBD2, MBD3, DNMT1, DNMG3A, DNMT3B, Rb, ROM2, See, e.g., EP3045537 and WO 2011/146121, each of which is incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

Cas proteins can also be operably linked to heterologous polypeptides as fusion proteins. As one example, a Cas protein can be fused to one or more heterologous polypeptides that provide for subcellular localization. Such heterologous polypeptides can include, for example, one or more nuclear localization signals (NLS) such as the monopartite SV40 NLS and/or a bipartite alpha-importin NLS for targeting to the nucleus, a mitochondrial localization signal for targeting to the mitochondria, an ER retention signal, and the like. See, e.g., Lange et al. (2007) *J. Biol. Chem.* 282:5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence. Optionally, a Cas protein can comprise two or more NLSs, including an NLS (e.g., an alpha-importin NLS or a monopartite NLS) at the N-terminus and an NLS (e.g., an SV40 NLS or a bipartite NLS) at the C-terminus. A Cas protein can also comprise two or more NLSs at the N-terminus and/or two or more NLSs at the C-terminus.

Cas proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290 and WO 2013/176772, each of which is herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreenl), yellow fluorescent proteins (e.g., YFP, eYFP, Citrine, Venus, YPet, PhiYFP, ZsYellowl), blue fluorescent proteins (e.g., eBFP, eBFP2, Azurite, mKalamal, GFPuv, Sapphire, T-sapphire), cyan fluorescent proteins (e.g., eCFP, Cerulean, CyPet, AmCyanl, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas proteins can be provided in any form. For example, a Cas protein can be provided in the form of a protein. For example, a Cas protein can be provided as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. For example, the nucleic acid encoding the Cas protein can be codon optimized for expression in a human cell. When a nucleic acid encoding the Cas protein is introduced into the cell, the Cas protein can be transiently, conditionally, or constitutively expressed in the cell.

Cas proteins provided as mRNAs can be modified for improved stability and/or immunogenicity properties. The modifications may be made to one or more nucleosides within the mRNA. Examples of chemical modifications to mRNA nucleobases include pseudouridine, 1-methyl-pseudouridine, and 5-methyl-cytidine. For example, capped and polyadenylated Cas mRNA containing N1-methyl pseudouridine can be used. Likewise, Cas mRNAs can be modified by depletion of uridine using synonymous codons.

Nucleic acids encoding Cas proteins can be stably integrated in the genome of a cell and operably linked to a promoter active in the cell. In one specific example, the nucleic acid encoding the Cas protein can comprise, consist essentially of, or consist of SEQ ID NO: 22 or a sequence at least about 90%, 91%, 92%, 93%, 94%, 95%, 96%, 97%, 98%, or 99% identical to SEQ ID NO: 22, optionally wherein the nucleic acid encodes a protein comprising, consisting essentially of, or consisting of SEQ ID NO: 21. In another specific example, the nucleic acid encoding a chimeric Cas protein comprising a nuclease-inactive Cas protein and one or more transcriptional activation domains can comprise, consist essentially of, or consist of SEQ ID NO: 38 or a sequence at least about 90%, 91%, 92%, 93%, 94%, 95%, 96%, 97%, 98%, or 99% identical to SEQ ID NO: 38, optionally wherein the nucleic acid encodes a protein comprising, consisting essentially of, or consisting of SEQ ID NO: 36. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters.

3. Chimeric Adaptor Proteins

The SAM/tau biosensor cells disclosed herein can comprise not only nucleic acids (DNA or RNA) encoding a chimeric Cas protein comprising a nuclease-inactive Cas protein fused to one or more transcriptional activation domains (e.g., VP64) but optionally also nucleic acids (DNA or RNA) encoding a chimeric adaptor protein comprising an adaptor protein (e.g., MS2 coat protein (MCP)) fused to one or more transcriptional activation domains (e.g., fused to p65 and HSF1). Optionally, the chimeric Cas protein and/or the chimeric adaptor protein is stably expressed. Optionally, the cells comprise a genomically integrated chimeric Cas protein coding sequence and/or a genomically integrated chimeric adaptor protein coding sequence.

Such chimeric adaptor proteins comprise: (a) an adaptor (i.e., adaptor domain or adaptor protein) that specifically binds to an adaptor-binding element within a guide RNA; and (b) one or more heterologous transcriptional activation domains. For example, such fusion proteins can comprise 1, 2, 3, 4, 5, or more transcriptional activation domains (e.g., two or more heterologous transcriptional activation domains or three or more heterologous transcriptional activation domains). In one example, such chimeric adaptor proteins can comprise: (a) an adaptor (i.e., an adaptor domain or adaptor protein) that specifically binds to an adaptor-binding element in a guide RNA; and (b) two or more transcriptional activation domains. For example, the chimeric adaptor protein can comprise: (a) an MS2 coat protein adaptor that specifically binds to one or more MS2 aptamers in a guide RNA (e.g., two MS2 aptamers in separate locations in a guide RNA); and (b) one or more (e.g., two or more transcriptional activation domains). For example, the two transcriptional activation domains can be p65 and HSF1 transcriptional activation domains or functional fragments or variants thereof. However, chimeric adaptor proteins in which the transcriptional activation domains comprise other transcriptional activation domains or functional fragments or variants thereof are also provided.

The one or more transcriptional activation domains can be fused directly to the adaptor. Alternatively, the one or more transcriptional activation domains can be linked to the adaptor via a linker or a combination of linkers or via one or more additional domains. Likewise, if two or more transcriptional activation domains are present, they can be fused directly to each other or can be linked to each other via a linker or a combination of linkers or via one or more additional domains. Linkers that can be used in these fusion proteins can include any sequence that does not interfere with the function of the fusion proteins. Exemplary linkers are short (e.g., 2-20 amino acids) and are typically flexible (e.g., comprising amino acids with a high degree of freedom such as glycine, alanine, and serine).

The one or more transcriptional activation domains and the adaptor can be in any order within the chimeric adaptor protein. As one option, the one or more transcriptional activation domains can be C-terminal to the adaptor and the adaptor can be N-terminal to the one or more transcriptional activation domains. For example, the one or more transcriptional activation domains can be at the C-terminus of the chimeric adaptor protein, and the adaptor can be at the N-terminus of the chimeric adaptor protein. However, the one or more transcriptional activation domains can be C-terminal to the adaptor without being at the C-terminus of the chimeric adaptor protein (e.g., if a nuclear localization signal is at the C-terminus of the chimeric adaptor protein). Likewise, the adaptor can be N-terminal to the one or more transcriptional activation domains without being at the N-terminus of the chimeric adaptor protein (e.g., if a nuclear localization signal is at the N-terminus of the chimeric adaptor protein). As another option, the one or more transcriptional activation domains can be N-terminal to the adaptor and the adaptor can be C-terminal to the one or more transcriptional activation domains. For example, the one or more transcriptional activation domains can be at the N-terminus of the chimeric adaptor protein, and the adaptor can be at the C-terminus of the chimeric adaptor protein. As yet another option, if the chimeric adaptor protein comprises two or more transcriptional activation domains, the two or more transcriptional activation domains can flank the adaptor.

Chimeric adaptor proteins can also be operably linked or fused to additional heterologous polypeptides. The fused or linked heterologous polypeptide can be located at the N-terminus, the C-terminus, or anywhere internally within the chimeric adaptor protein. For example, a chimeric adaptor protein can further comprise a nuclear localization signal. A specific example of such a protein comprises an MS2 coat protein (adaptor) linked (either directly or via an NLS) to a p65 transcriptional activation domain C-terminal to the MS2 coat protein (MCP), and HSF1 transcriptional activation domain C-terminal to the p65 transcriptional activation domain. Such a protein can comprise from N-terminus to C-terminus: an MCP; a nuclear localization signal; a p65 transcriptional activation domain; and an HSF1 transcriptional activation domain. For example, a chimeric adaptor protein can comprise, consist essentially of, or consist of an amino acid sequence at least 85%, 90%, 91%, 92%, 93%, 94%, 95%, 96%, 97%, 98%, 99%, or 100% identical to the MCP-p65-HSF1 chimeric adaptor protein sequence set forth in SEQ ID NO: 37. Likewise, a nucleic acid encoding a chimeric adaptor protein can comprise, consist essentially of, or consist of a sequence at least 85%, 90%, 91%, 92%, 93%, 94%, 95%, 96%, 97%, 98%, 99%, or 100% identical to the MCP-p65-HSF1 chimeric adaptor protein coding sequence set forth in SEQ ID NO: 39

Adaptors (i.e., adaptor domains or adaptor proteins) are nucleic-acid-binding domains (e.g., DNA-binding domains and/or RNA-binding domains) that specifically recognize and bind to distinct sequences (e.g., bind to distinct DNA and/or RNA sequences such as aptamers in a sequence-specific manner). Aptamers include nucleic acids that, through their ability to adopt a specific three-dimensional conformation, can bind to a target molecule with high affinity and specificity. Such adaptors can bind, for example, to a specific RNA sequence and secondary structure. These sequences (i.e., adaptor-binding elements) can be engineered into a guide RNA. For example, an MS2 aptamer can be engineered into a guide RNA to specifically bind an MS2 coat protein (MCP). For example, the adaptor can comprise, consist essentially of, or consist of an amino acid sequence at least 85%, 90%, 91%, 92%, 93%, 94%, 95%, 96%, 97%, 98%, 99%, or 100% identical to the MCP sequence set forth in SEQ ID NO: 40. Likewise, a nucleic acid encoding the adaptor can comprise, consist essentially of, or consist of an amino acid sequence at least 85%, 90%, 91%, 92%, 93%, 94%, 95%, 96%, 97%, 98%, 99%, or 100% identical to the MCP coding sequence set forth in SEQ ID NO: 41. Specific examples of adaptors and targets include, for example, RNA-binding protein/aptamer combinations that exist within the diversity of bacteriophage coat proteins. See, e.g., US 2019-0284572 and WO 2019/183123, each of which is herein incorporated by reference in its entirety for all purposes.

The chimeric adaptor proteins disclosed herein comprise one or more transcriptional activation domains. Such transcriptional activation domains can be naturally occurring transcriptional activation domains, can be functional fragments or functional variants of naturally occurring transcriptional activation domains, or can be engineered or synthetic transcriptional activation domains. Transcriptional activation domains that can be used include those described, for example, in US 2019-0284572 and WO 2019/183123, each of which is herein incorporated by reference in its entirety for all purposes.

4. Cell Types

The Cas/tau biosensor cells disclosed herein can be any type of cell and can be in vitro, ex vivo, or in vivo. A Cas/tau biosensor cell line or population of cells can be a monoclonal cell line or population of cells. Likewise, the SAM/tau biosensor cells disclosed herein can be any type of cell and can be in vitro, ex vivo, or in vivo. A SAM/tau biosensor cell line or population of cells can be a monoclonal cell line or population of cells. The cell can be from any source. For example, the cell can be a eukaryotic cell, an animal cell, a plant cell, or a fungal (e.g., yeast) cell. Such cells can be fish cells or bird cells, or such cells can be mammalian cells, such as human cells, non-human mammalian cells, rodent cells, mouse cells, or rat cells. Mammals include, for example, humans, non-human primates, monkeys, apes, cats dogs, horses, bulls, deer, bison, sheep, rodents (e.g., mice, rats, hamsters, guinea pigs), livestock (e.g., bovine species such as cows and steer; ovine species such as sheep and goats; and porcine species such as pigs and boars). Birds include, for example, chickens, turkeys, ostrich, geese, and ducks. Domesticated animals and agricultural animals are also included. The term "non-human animal" excludes humans. In a specific example, the Cas/tau biosensor cells are human cells (e.g., HEK293T cells). Likewise, in a specific example, the SAM/tau biosensor cells are human cells (e.g., HEK293T cells).

The cell can be, for example, a totipotent cell or a pluripotent cell (e.g., an embryonic stem (ES) cell such as a rodent ES cell, a mouse ES cell, or a rat ES cell). Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The cell can also be a primary somatic cell, or a cell that is not a primary somatic cell. Somatic cells can include any cell that is not a gamete, germ cell, gametocyte, or undifferentiated stem cell. The cell can also be a primary cell. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, somatic cells, hematopoietic cells, endothelial cells, epithelial cells, fibroblasts, mesenchymal cells, keratinocytes, melanocytes, monocytes, mononuclear cells, adipocytes, preadipocytes, neurons, glial cells, hepatocytes, skeletal myoblasts, and smooth muscle cells. For example, primary cells can be derived from connective tissues, muscle tissues, nervous system tissues, or epithelial tissues.

Such cells also include would normally not proliferate indefinitely but, due to mutation or alteration, have evaded normal cellular senescence and instead can keep undergoing division. Such mutations or alterations can occur naturally or be intentionally induced. Examples of immortalized cells include Chinese hamster ovary (CHO) cells, human embryonic kidney cells (e.g., HEK293T cells), and mouse embryonic fibroblast cells (e.g., 3T3 cells). Numerous types of immortalized cells are well known. Immortalized or primary cells include cells that are typically used for culturing or for expressing recombinant genes or proteins.

The cell can also be a differentiated cell, such as a neuronal cell (e.g., a human neuronal cell).

B. Methods of Generating Cas/Tau Biosensor Cells and SAM/Tau Biosensor Cells

The Cas/tau biosensor cells disclosed herein can be generated by any known means. The first tau repeat domain linked to the first reporter, the second tau repeat domain linked to the second reporter, and the Cas protein can be introduced into the cell in any form (e.g., DNA, RNA, or protein) by any known means. Likewise, the SAM/tau biosensor cells disclosed herein can be generated by any known means. The first tau repeat domain linked to the first reporter, the second tau repeat domain linked to the second reporter, the chimeric Cas protein, and the chimeric adaptor protein can be introduced into the cell in any form (e.g., DNA, RNA, or protein) by any known means. "Introducing" includes presenting to the cell the nucleic acid or protein in such a manner that the sequence gains access to the interior of the cell. The methods provided herein do not depend on a particular method for introducing a nucleic acid or protein into the cell, only that the nucleic acid or protein gains access to the interior of a least one cell. Methods for introducing nucleic acids and proteins into various cell types are known and include, for example, stable transfection methods, transient transfection methods, and virus-mediated methods. Optionally, targeting vectors can be used.

Transfection protocols as well as protocols for introducing nucleic acids or proteins into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of nucleic acids or proteins into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of nucleic acids or proteins into a cell can also be accomplished by microinjection. Microinjection of an mRNA is preferably into the cytoplasm (e.g., to deliver mRNA directly to the translation machinery), while microinjection of a protein or a DNA encoding a protein is preferably into the nucleus. Alternatively, microinjection can be carried out by injection into both the nucleus and the cytoplasm: a needle can first be introduced into the nucleus and a first amount can be injected, and while removing the needle from the cell a second amount can be injected into the cytoplasm. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York: Cold Spring Harbor Laboratory Press); Meyer et al. (2010) *Proc. Natl. Acad. Sci. USA* 107:15022-15026 and Meyer et al. (2012) *Proc. Natl. Acad. Sci. USA* 109:9354-9359.

Other methods for introducing nucleic acid or proteins into a cell can include, for example, vector delivery, particle-mediated delivery, exosome-mediated delivery, lipid-nanoparticle-mediated delivery, cell-penetrating-peptide-mediated delivery, or implantable-device-mediated delivery. Methods of administering nucleic acids or proteins to a subject to modify cells in vivo are disclosed elsewhere herein.

In one example, the first tau repeat domain linked to the first reporter, the second tau repeat domain linked to the second reporter, and the Cas protein can be introduced via viral transduction such as lentiviral transduction.

Screening for cells comprising the first tau repeat domain linked to the first reporter, the second tau repeat domain linked to the second reporter, and the Cas protein can be performed by any known means.

As one example, reporter genes can be used to screen for cells that have the Cas protein, the first tau repeat domain linked to the first reporter, or the second tau repeat domain linked to the second reporter. Exemplary reporter genes include those encoding luciferase, β-galactosidase, green fluorescent protein (GFP), enhanced green fluorescent protein (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, ZsGreen, MmGFP, mPlum, mCherry, tdTomato, mStrawberry, J-Red, mOrange, mKO, mCitrine, Venus, YPet, Emerald, CyPet, Cerulean, T-Sapphire, and alkaline phosphatase. For example, if the first reporter and the second reporter are fluorescent proteins (e.g., CFP and YFP), cells comprising these reporters can be selected by flow cytometry to select for dual-positive cells. The dual-positive cells can then be combined to generate a polyclonal line, or monoclonal lines can be generated from single dual-positive cells.

As another example, selection markers can be used to screen for cells that have the Cas protein, the first tau repeat domain linked to the first reporter, or the second tau repeat domain linked to the second reporter. Exemplary selection markers include neomycin phosphotransferase (neo), hygromycin B phosphotransferase ($hyg^r$), puromycin-N-acetyl-transferase ($puro^r$), blasticidin S deaminase ($bsr^r$), xanthine/guanine phosphoribosyl transferase (gpt), or herpes simplex virus thymidine kinase (HSV-k). Another exemplary selection marker is bleomycin resistance protein, encoded by the Sh ble gene (*Streptoalloteichus hindustanus* bleomycin gene), which confers zeocin (phleomycin D1) resistance.

Aggregation-positive (Agg[+]) cells in which the tau repeat domain stably presents in an aggregated state, meaning that the tau repeat domain aggregates stably persist in all cells with growth and multiple passages over time, can be generated, for example, by seeding with tau aggregates. For example, naïve aggregation-negative (Agg[−]) Cas/tau biosensor cells disclosed herein can be treated with recombinant fibrillized tau (e.g., recombinant fibrillized tau repeat domain) to seed the aggregation of the tau repeat domain protein stably expressed by these cells. Likewise, naïve aggregation-negative (Agg[−]) SAM/tau biosensor cells disclosed herein can be treated with recombinant fibrillized tau (e.g., recombinant fibrillized tau repeat domain) to seed the aggregation of the tau repeat domain protein stably expressed by these cells. The fibrillized tau repeat domain can be the same as, similar to, or different from the tau repeat domain stably expressed by the cells. Optionally, the recombinant fibrillized tau can be mixed with lipofectamine reagent. The seeded cells can then be serially diluted to obtain single-cell-derived clones and to identify clonal cell lines in which tau repeat domain aggregates stably persist in all cells with growth and multiple passages over time.

As another example, aggregation-positive (Agg[+]) cells in which the tau repeat domain stably presents in an aggregated state, meaning that the tau repeat domain aggregates stably persist in all cells with growth and multiple passages over time, can be generated, for example, by seeding cells (e.g., tau aggregation-negative cells) with cell lysate from tau aggregation-positive cells. This is the "maximal seeding" described in the examples herein. For example, the cells can be seeded using a medium comprising the cell lysate (e.g., fresh medium comprising the cell lysate). "Maximal seeding" can refer to seeding that, by itself, induces tau aggregation in a majority of aggregation-negative tau biosensor cells. "Minimal seeding" can refer to seeding that, by itself, is insufficient to induce tau aggregation in aggregation-negative tau biosensor cells (or only minimally induces tau aggregation) but sensitizes such cells to induction of aggregation.

The amount or concentration of the cell lysate in the medium can be any suitable amount or concentration. For example, the concentration of cell lysate in the medium can be between about 0.1 µg/mL and about 50 µg/mL, between about 0.1 µg/mL and about 25 µg/mL, between about 0.1 µg/mL and about 10 µg/mL, between about 0.1 µg/mL and about 5 µg/mL, between about 0.1 µg/mL and about 4.5 µg/mL, between about 0.1 µg/mL and about 4 µg/mL, between about 0.1 µg/mL and about 3.5 µg/mL, between about 0.1 µg/mL and about 3 µg/mL, between about 0.1 µg/mL and about 2.5 µg/mL, between about 0.1 µg/mL and about 2 µg/mL, between about 0.1 µg/mL and about 1.5 µg/mL, between about 0.1 µg/mL and about 1 µg/mL, between about 0.5 µg/mL and about 50 µg/mL, between about 0.5 µg/mL and about 25 µg/mL, between about 0.5 µg/mL and about 10 µg/mL, between about 0.5 µg/mL and about 5 µg/mL, between about 0.5 µg/mL and about 4.5 µg/mL, between about 0.5 µg/mL and about 4 µg/mL, between about 0.5 µg/mL and about 3.5 µg/mL, between about 0.5 µg/mL and about 3 µg/mL, between about 0.5 µg/mL and about 2.5 µg/mL, between about 0.5 µg/mL and about 2 µg/mL, between about 0.5 µg/mL and about 1.5 µg/mL, between about 0.5 µg/mL and about 1 µg/mL, between about 1 µg/mL and about 50 µg/mL, between about 1 µg/mL and about 25 µg/mL, between about 1 µg/mL and about 10 µg/mL, between about 1 µg/mL and about 5 µg/mL, between about 1 µg/mL and about 4.5 µg/mL, between about 1 µg/mL and about 4 µg/mL, between about 1 µg/mL and about 3.5 µg/mL, between about 1 µg/mL and about 3 µg/mL, between about 1 µg/mL and about 2.5 µg/mL, between about 1 µg/mL and about 2 µg/mL, between about 1 µg/mL and about 1.5 µg/mL, between about 1.5 µg/mL and about 50 µg/mL, between about 1.5 µg/mL and about 25 µg/mL, between about 1.5 µg/mL and about 10 µg/mL, between about 1.5 µg/mL and about 5 µg/mL, between about 1.5 µg/mL and about 4.5 µg/mL, between about 1.5 µg/mL and about 4 µg/mL, between about 1.5 µg/mL and about 3.5 µg/mL, between about 1.5 µg/mL and about 3 µg/mL, between about 1.5 µg/mL and about 2.5 µg/mL, between about 1.5 µg/mL and about 2 µg/mL, between about 2 µg/mL and about 50 µg/mL, between about 2 µg/mL and about 25 µg/mL, between about 2 µg/mL and about 10 µg/mL, between about 2 µg/mL and about 5 µg/mL, between about 2 µg/mL and about 4.5 µg/mL, between about 2 µg/mL and about 4 µg/mL, between about 2 µg/mL and about 3.5 µg/mL, between about 2 µg/mL and about 3 µg/mL, between about 2 µg/mL and about 2.5 µg/mL, between about 2.5 µg/mL and about 50 µg/mL, between about 2.5 µg/mL and about 25 µg/mL, between about 2.5 µg/mL and about 10 µg/mL, between about 2.5 µg/mL and about 5 µg/mL, between about 2.5 µg/mL and about 4.5 µg/mL, between about 2.5 µg/mL and about 4 µg/mL, between about 2.5 µg/mL and about 3.5 µg/mL, or between about 2.5 µg/mL and about 3 µg/mL of medium (e.g., fresh culture medium). For example, the cell lysate in the culture medium can be at a concentration of between about 1 µg/mL and about 5 µg/mL or can be at a concentration of about 1.5 µg/mL, about 2 µg/mL, about 2.5 µg/mL, about 3 µg/mL, about 3.5 µg/mL, about 4 µg/mL, about 4.5 µg/mL, or about 5 µg/mL. Optionally, the cell lysate can be in a buffer, such as phosphate-buffered saline. Optionally, the buffer can comprise protease inhibitors. Examples of protease inhibitors include, but are not limited to, AEBSF, aprotinin, bestatin, E-64, leupeptin, pepstatin A, and ethylenediaminetetracetic acid (EDTA). The buffer can comprise any of these inhibitors or any combination thereof (e.g., the buffer can comprise all of these protease inhibitors).

The cells for producing the lysate can be collected in a buffer, such as phosphate-buffered saline. Optionally, the buffer can comprise protease inhibitors. Examples of protease inhibitors include, but are not limited to, AEBSF, aprotinin, bestatin, E-64, leupeptin, pepstatin A, and ethylenediaminetetracetic acid (EDTA). The buffer can comprise any of these inhibitors or any combination thereof (e.g., the buffer can comprise all of these protease inhibitors).

The cell lysate can, for example, be collected by sonicating the tau-aggregation-positive cells (e.g., cells collected in a buffer and protease inhibitors as described above) for any suitable amount of time. For example, the cells can be sonicated for between about 1 minute and about 6 minutes, between about 1 minute and about 5 minutes, between about 1 minute and about 4 minutes, between about 1 minute and about 3 minutes, between about 2 minutes and about 6 minutes, between about 2 minutes and about 5 minutes, between about 2 minutes and about 4 minutes, between about 2 minutes and about 3 minutes, between about 2 minutes and about 6 minutes, between about 3 minutes and about 5 minutes, or between about 3 minutes and about 4 minutes. For example, the cells can be sonicated for between about 2 minutes and about 4 minutes or for about 3 minutes.

Optionally, the medium comprises lipofectamine or liposomes (e.g., cationic liposomes) or phospholipids or another transfection agent. Optionally, the medium comprises lipofectamine. Optionally, the medium does not comprise lipofectamine or liposomes (e.g., cationic liposomes) or phospholipids or another transfection agent. Optionally, the medium does not comprise lipofectamine. The amount or concentration of the lipofectamine or liposomes (e.g., cationic liposomes) or phospholipids or other transfection agent in the medium can be any suitable amount or concentration. For example, the concentration of lipofectamine or liposomes (e.g., cationic liposomes) or phospholipids or other transfection agent in the medium can be between about 0.5 µL/mL to about 10 µL/mL, between about 0.5 µL/mL to about 5 µL/mL, between about 0.5 µL/mL to about 4.5 µL/mL, between about 0.5 µL/mL to about 4 µL/mL, between about 0.5 µL/mL to about 3.5 µL/mL, between about 0.5 µL/mL to about 3 µL/mL, between about 0.5 µL/mL to about 2.5 µL/mL, between about 0.5 µL/mL to about 2 µL/mL, between about 0.5 µL/mL to about 1.5 µL/mL, between about 0.5 µL/mL to about 1 µL/mL, between about 1 µL/mL to about 10 µL/mL, between about 1 µL/mL to about 5 µL/mL, between about 1 µL/mL to about 4.5 µL/mL, between about 1 µL/mL to about 4 µL/mL, between about 1 L/mL to about 3.5 µL/mL, between about 1 µL/mL to about 3 µL/mL, between about 1 µL/mL to about 2.5 µL/mL, between about 1 µL/mL to about 2 µL/mL, between about 1 µL/mL to about 1.5 µL/mL, between about 1.5 µL/mL to about 10 µL/mL, between about 1.5 µL/mL to about 5 L/mL, between about 1.5 µL/mL to about 4.5 µL/mL, between about 1.5 µL/mL to about 4 L/mL, between about 1.5 µL/mL to about 3.5 µL/mL, between about 1.5 µL/mL to about 3 L/mL, between about 1.5 µL/mL to about 2.5 µL/mL, between about 1.5 µL/mL to about 2 L/mL, between about 2 µL/mL to about 10 µL/mL, between about 2 µL/mL to about 5 µL/mL, between about 2 µL/mL to about 4.5 µL/mL, between about 2 µL/mL to about 4 µL/mL, between about 2 µL/mL to about 3.5 µL/mL, between about 2 µL/mL to about 3 µL/mL, or between about 2 µL/mL to about 2.5 µL/mL of medium (e.g., fresh medium). For example, the concentration of lipofectamine or liposomes (e.g., cationic liposomes) or phospholipids or other transfection agent in the medium can be between about 1.5 µL/mL and about 4 µL/mL or it can be about 1.5 L/mL, about 2 µL/mL, about 2.5 µL/mL, about 3 µL/mL, about 3.5 µL/mL, or about 4 µL/mL.

Tau cell-to-cell propagation may also result from tau aggregation activity secreted by aggregate-containing cells. For example, Agg[+] cells, or cells sensitized to becoming Agg[+] cells (e.g., sensitized to tau seeding or tau aggregation activity), can be generated by co-culturing Agg[−] Cas/tau biosensor cells with Agg[+] cells. Likewise, Agg[+] cells, or cells sensitized to becoming Agg[+] cells (e.g., sensitized to tau seeding or tau aggregation activity), can be generated by co-culturing Agg[−] SAM/tau biosensor cells with Agg[+] cells.

Agg[+] cells, or cells sensitized to becoming Agg[+] cells (e.g., sensitized to tau seeding or tau aggregation activity), can also be generated using conditioned medium harvested from cultured tau-aggregation-positive cells in which a tau repeat domain stably presents in an aggregated state as described herein. This is the "minimal seeding" disclosed in the examples herein. Conditioned medium refers to spent medium harvested from cultured cells. It contains metabolites, growth factors, and extracellular matrix proteins secreted into the medium by the cultured cells. Use of conditioned medium does not involve co-culturing with Agg[+] cells (i.e., the naïve Agg[−] cells are not co-cultured with Agg[+] cells). As one example, conditioned medium can be generated by collecting medium that has been on confluent Agg[+] cells. The medium can have been on the confluent Agg[+] cells for about 12 hours, about 24 hours, about 2 days, about 3 days, about 4 days, about 5 days, about 6 days, about 7 days, about 8 days, about 9 days, or about 10 days. For example, the medium can have been on the confluent Agg[+] cells for about 1 to about 7, about 2 to about 6, about 3 to about 5, or about 4 days. Conditioned medium can then be applied to naïve (Agg[−]) Cas/tau biosensor cells in combination with fresh medium. Likewise, conditioned medium can then be applied to naïve (Agg[−]) SAM/tau biosensor cells in combination with fresh medium. The ratio of conditioned medium to fresh medium can be, for example, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10. For example, the ratio of conditioned medium of fresh medium can be from about 5:1 to about 1:1, about 4:1 to about 2:1, or about 3:1. For example, it can comprise culturing the genetically modified population of cells in about 90% conditioned medium and about 10% fresh medium, about 85% conditioned medium and about 15% fresh medium, about 80% conditioned medium and about 20% fresh medium, about 75% conditioned medium and about 25% fresh medium, about 70% conditioned medium and about 30% fresh medium, about 65% conditioned medium and about 35% fresh medium, about 60% conditioned medium and about 40% fresh medium, about 55% conditioned medium and about 45% fresh medium, about 50% conditioned medium and about 50% fresh medium, about 45% conditioned medium and about 55% fresh medium, about 40% conditioned medium and about 60% fresh medium, about 35% conditioned medium and about 65% fresh medium, about 30% conditioned medium and about 70% fresh medium, about 25% conditioned medium and about 75% fresh medium, about 20% conditioned medium and about 80% fresh medium, about 15% conditioned medium and about 85% fresh medium, or about 10% conditioned medium and about 90% fresh medium. In one example, it can comprise culturing the genetically modified population of cells in a medium that comprises at least about 50% conditioned medium and no more than about 50% fresh medium. In a specific example, it can comprise culturing the genetically modified population of cells in about 75% conditioned medium and about 25% fresh medium. Optionally, the conditioned medium is applied to the naïve Agg[−] cells without lipofectamine or without liposomes (e.g., cationic liposomes) or without phospholipids. Optionally, the genetically modified population of cells is not co-cultured with the tau-aggregation-positive cells in which a tau repeat domain stably presents in an aggregated state.

Conditioned medium without co-culturing has not been used in this context as a seeding agent before. However, conditioned medium is particularly useful for large-scale genome-wide screens because tau fibrils produced in vitro are a limited resource. In addition, conditioned medium is more physiologically relevant because it is produced and secreted by cells rather than in vitro. Use of conditioned medium as described herein provides a boost of tau seeding activity (e.g., ~0.1% as measured by FRET induction as disclosed elsewhere herein) to sensitize cells to tau aggregation.

C. In Vitro Cultures and Conditioned Medium

Also disclosed herein are in vitro cultures or compositions comprising the Cas/tau biosensor cells disclosed herein and medium for culturing those cells. Also disclosed herein are in vitro cultures or compositions comprising the SAM/tau biosensor cells disclosed herein and medium for culturing those cells. The cells can be Agg[−] cells or Agg[+] cells. For example, the culture or composition can comprise Agg[−] cells. In one example, the medium comprises conditioned medium from Agg[+] cells as disclosed elsewhere herein. Optionally, the cells in the culture or composition are Agg[−] cells and are not being co-cultured with Agg[+] cells. The medium can comprise a mixture of conditioned medium and fresh medium. As one example, the ratio of conditioned medium to fresh medium can be, for example, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10. For example, the ratio of conditioned medium of fresh medium can be from about 5:1 to about 1:1, about 4:1 to about 2:1, or about 3:1. For example, it can comprise culturing the genetically modified population of cells in about 90% conditioned medium and about 10% fresh medium, about 85% conditioned medium and about 15% fresh medium, about 80% conditioned medium and about 20% fresh medium, about 75% conditioned medium and about 25% fresh medium, about 70% conditioned medium and about 30% fresh medium, about 65% conditioned medium and about 35% fresh medium, about 60% conditioned medium and about 40% fresh medium, about 55% conditioned medium and about 45% fresh medium, about 50% conditioned medium and about 50% fresh medium, about 45% conditioned medium and about 55% fresh medium, about 40% conditioned medium and about 60% fresh medium, about 35% conditioned medium and about 65% fresh medium, about 30% conditioned medium and about 70% fresh medium, about 25% conditioned medium and about 75% fresh medium, about 20% conditioned medium and about 80% fresh medium, about 15% conditioned medium and about 85% fresh medium, or about 10% conditioned medium and about 90% fresh medium. In one example, it can comprise culturing the genetically modified population of cells in a medium that comprises at least about 50% conditioned medium and no more than about 50% fresh medium. In a specific example, it can comprise culturing the genetically modified population of cells in about 75% conditioned medium and about 25% fresh medium. Optionally, the medium comprises lipofectamine or liposomes (e.g., cationic liposomes) or phospholipids. Optionally, the medium does not comprise lipofectamine or liposomes (e.g., cationic liposomes) or phospholipids. Optionally, the medium does not comprise lipofectamine.

D. In Vitro Cultures and Medium Comprising Lysate from Tau-Aggregation-Positive Cells Also disclosed herein are in vitro cultures or compositions comprising the Cas/tau biosensor cells disclosed herein and medium for culturing those cells. Also disclosed herein are in vitro cultures or compositions comprising the SAM/tau biosensor cells disclosed herein and medium for culturing those cells. In one example, the medium comprises a cell lysate from cultured tau-aggregation-positive cells in which a tau repeat domain stably presents in an aggregated state. The cells can be Agg[−] cells or Agg[+] cells. For example, the culture or composition can comprise Agg[−] cells. Optionally, the cells in the culture or composition are Agg[−] cells and are not being co-cultured with Agg[+] cells. The medium can comprise a mixture of fresh medium and the cell lysate.

The amount or concentration of the cell lysate in the medium can be any suitable amount or concentration. For example, the concentration of cell lysate in the medium can be between about 0.1 µg/mL and about 50 µg/mL, between about 0.1 µg/mL and about 25 µg/mL, between about 0.1 µg/mL and about 10 µg/mL, between about 0.1 µg/mL and about 5 µg/mL, between about 0.1 µg/mL and about 4.5 µg/mL, between about 0.1 µg/mL and about 4 µg/mL, between about 0.1 µg/mL and about 3.5 µg/mL, between about 0.1 µg/mL and about 3 µg/mL, between about 0.1 µg/mL and about 2.5 µg/mL, between about 0.1 µg/mL and about 2 µg/mL, between about 0.1 µg/mL and about 1.5 µg/mL, between about 0.1 µg/mL and about 1 µg/mL, between about 0.5 µg/mL and about 50 µg/mL, between about 0.5 µg/mL and about 25 µg/mL, between about 0.5 µg/mL and about 10 µg/mL, between about 0.5 µg/mL and about 5 µg/mL, between about 0.5 µg/mL and about 4.5 µg/mL, between about 0.5 µg/mL and about 4 µg/mL, between about 0.5 µg/mL and about 3.5 µg/mL, between about 0.5 µg/mL and about 3 µg/mL, between about 0.5 µg/mL and about 2.5 µg/mL, between about 0.5 µg/mL and about 2 µg/mL, between about 0.5 µg/mL and about 1.5 µg/mL, between about 0.5 µg/mL and about 1 µg/mL, between about 1 µg/mL and about 50 µg/mL, between about 1 µg/mL and about 25 µg/mL, between about 1 µg/mL and about 10 µg/mL, between about 1 µg/mL and about 5 µg/mL, between about 1 µg/mL and about 4.5 µg/mL, between about 1 µg/mL and about 4 µg/mL, between about 1 µg/mL and about 3.5 µg/mL, between about 1 µg/mL and about 3 µg/mL, between about 1 µg/mL and about 2.5 µg/mL, between about 1 µg/mL and about 2 µg/mL, between about 1 µg/mL and about 1.5 µg/mL, between about 1.5 µg/mL and about 50 µg/mL, between about 1.5 µg/mL and about 25 µg/mL, between about 1.5 µg/mL and about 10 µg/mL, between about 1.5 µg/mL and about 5 µg/mL, between about 1.5 µg/mL and about 4.5 µg/mL, between about 1.5 µg/mL and about 4 µg/mL, between about 1.5 µg/mL and about 3.5 µg/mL, between about 1.5 µg/mL and about 3 µg/mL, between about 1.5 µg/mL and about 2.5 µg/mL, between about 1.5 µg/mL and about 2 µg/mL, between about 2 µg/mL and about 50 µg/mL, between about 2 µg/mL and about 25 µg/mL, between about 2 µg/mL and about 10 µg/mL, between about 2 µg/mL and about 5 µg/mL, between about 2 µg/mL and about 4.5 µg/mL, between about 2 µg/mL and about 4 µg/mL, between about 2 µg/mL and about 3.5 µg/mL, between about 2 µg/mL and about 3 µg/mL, between about 2 µg/mL and about 2.5 µg/mL, between about 2.5 µg/mL and about 50 µg/mL, between about 2.5 µg/mL and about 25 µg/mL, between about 2.5 µg/mL and about 10 µg/mL, between about 2.5 µg/mL and about 5 µg/mL, between about 2.5 µg/mL and about 4.5 µg/mL, between about 2.5 µg/mL and about 4 µg/mL, between about 2.5 µg/mL and about 3.5 µg/mL, or between about 2.5 µg/mL and about 3 µg/mL of medium (e.g., fresh culture medium). For example, the cell lysate in the culture medium can be at a concentration of between about 1 µg/mL and about 5 µg/mL or can be at a concentration of about 1.5 µg/mL, about 2 µg/mL, about 2.5 µg/mL, about 3 µg/mL, about 3.5 µg/mL, about 4 µg/mL, about 4.5 µg/mL, or about 5 µg/mL. Optionally, the cell lysate can be in a buffer, such as phosphate-buffered saline. Optionally, the buffer can comprise protease inhibitors. Examples of protease inhibitors include, but are not limited to, AEBSF, aprotinin, bestatin, E-64, leupeptin, pepstatin A, and ethylenediaminetetracetic acid (EDTA). The buffer can comprise any of these inhibitors or any combination thereof (e.g., the buffer can comprise all of these protease inhibitors).

The cells for producing the lysate can be collected in a buffer, such as phosphate-buffered saline. Optionally, the buffer can comprise protease inhibitors. Examples of protease inhibitors include, but are not limited to, AEBSF, aprotinin, bestatin, E-64, leupeptin, pepstatin A, and ethylenediaminetetracetic acid (EDTA). The buffer can comprise any of these inhibitors or any combination thereof (e.g., the buffer can comprise all of these protease inhibitors).

The cell lysate can, for example, be collected by sonicating the tau-aggregation-positive cells (e.g., cells collected in a buffer and protease inhibitors as described above) for any suitable amount of time. For example, the cells can be sonicated for between about 1 minute and about 6 minutes, between about 1 minute and about 5 minutes, between about 1 minute and about 4 minutes, between about 1 minute and about 3 minutes, between about 2 minutes and about 6 minutes, between about 2 minutes and about 5 minutes, between about 2 minutes and about 4 minutes, between about 2 minutes and about 3 minutes, between about 2 minutes and about 6 minutes, between about 3 minutes and about 5 minutes, or between about 3 minutes and about 4 minutes. For example, the cells can be sonicated for between about 2 minutes and about 4 minutes or for about 3 minutes.

Optionally, the medium comprises lipofectamine or liposomes (e.g., cationic liposomes) or phospholipids or another transfection agent. Optionally, the medium comprises lipofectamine. Optionally, the medium does not comprise lipofectamine or liposomes (e.g., cationic liposomes) or phospholipids or another transfection agent. Optionally, the medium does not comprise lipofectamine. The amount or concentration of the lipofectamine or liposomes (e.g., cationic liposomes) or phospholipids or other transfection agent in the medium can be any suitable amount or concentration. For example, the concentration of lipofectamine or liposomes (e.g., cationic liposomes) or phospholipids or other transfection agent in the medium can be between about 0.5 µL/mL to about 10 µL/mL, between about 0.5 µL/mL to about 5 µL/mL, between about 0.5 µL/mL to about 4.5 µL/mL, between about 0.5 µL/mL to about 4 µL/mL, between about 0.5 µL/mL to about 3.5 µL/mL, between about 0.5 µL/mL to about 3 µL/mL, between about 0.5 µL/mL to about 2.5 µL/mL, between about 0.5 µL/mL to about 2 µL/mL, between about 0.5 µL/mL to about 1.5 µL/mL, between about 0.5 µL/mL to about 1 µL/mL, between about 1 µL/mL to about 10 µL/mL, between about 1 µL/mL to about 5 µL/mL, between about 1 µL/mL to about 4.5 µL/mL, between about 1 µL/mL to about 4 µL/mL, between about 1 L/mL to about 3.5 µL/mL, between about 1 µL/mL to about 3 µL/mL, between about 1 µL/mL to about 2.5 µL/mL, between about 1 µL/mL to about 2 µL/mL, between about 1 µL/mL to about 1.5 µL/mL, between about 1.5 µL/mL to about 10 µL/mL, between about 1.5 µL/mL to about 5 µL/mL, between about 1.5 µL/mL to about 4.5 µL/mL, between about 1.5 µL/mL to about 4 µL/mL, between about 1.5 µL/mL to about 3.5 µL/mL, between about 1.5 µL/mL to about 3 µL/mL, between about 1.5 µL/mL to about 2.5 µL/mL, between about 1.5 µL/mL to about 2 µL/mL, between about 2 µL/mL to about 10 L/mL, between about 2 µL/mL to about 5 µL/mL, between about 2 µL/mL to about 4.5 µL/mL, between about 2 µL/mL to about 4 µL/mL, between about 2 µL/mL to about 3.5 µL/mL, between about 2 µL/mL to about 3 µL/mL, or between about 2 µL/mL to about 2.5 µL/mL of medium (e.g., fresh medium). For example, the concentration of lipofectamine or liposomes (e.g., cationic liposomes) or phospholipids or other transfection agent in the medium can be between about 1.5 µL/mL and about 4 µL/mL or it can be about 1.5 µL/mL, about 2 µL/mL, about 2.5 µL/mL, about 3 µL/mL, about 3.5 µL/mL, or about 4 µL/mL.

III. Guide RNA Knockout Libraries

The CRISPRn screening methods disclosed herein make use of CRISPR guide RNA (gRNA) knockout libraries such as genome-wide gRNA knockout libraries. Cas nucleases such as Cas9 can be programmed to induce double-strand breaks at specific genomic loci through gRNAs designed to target specific target sequences. Because the targeting specificity of Cas proteins is conferred by short gRNAs, pooled genome-scale functional screening is possible. Such libraries have several advantages over libraries such as shRNA libraries, which reduce protein expression by targeting mRNA. In contrast, gRNA libraries achieve knockout via frameshift mutations introduced in genomic coding regions of genes.

The CRISPRa screening methods disclosed herein make use of CRISPR guide RNA (gRNA) transcriptional activation libraries such as genome-wide gRNA transcriptional activation libraries. SAM systems can be programmed to activate transcription of genes at specific genomic loci through gRNAs designed to target specific target sequences. Because the targeting specificity of Cas proteins is conferred by short gRNAs, pooled genome-scale functional screening is possible.

The gRNAs in a library can target any number of genes. For example, the gRNAs can target about 50 or more genes, about 100 or more genes, about 200 or more genes, about 300 or more genes, about 400 or more genes, about 500 or more genes, about 1000 or more genes, about 2000 or more genes, about 3000 or more genes, about 4000 or more genes, about 5000 or more genes, about 10000 or more genes, or about 20000 or more genes. In some libraries, the gRNAs can be selected to target genes in a particular signaling pathway. Some libraries are genome-wide libraries.

The genome-wide libraries include one or more gRNAs (e.g., sgRNAs) targeting each gene in the genome. The genome being targeted can any type of genome. For example, the genome can be a eukaryotic genome, a mammalian genome, a non-human mammalian genome, a rodent genome, a mouse genome, a rat genome, or a human genome. In one example, the targeted genome is a human genome.

The gRNAs can target any number of sequences within each individual targeted gene. In some libraries, a plurality of target sequences are targeted on average in each of the targeted plurality of genes. For example, about 2 to about 10, about 2 to about 9, about 2 to about 8, about 2 to about 7, about 2 to about 6, about 2 to about 5, about 2 to about 4, or about 2 to about 3 unique target sequences can be targeted on average in each of the targeted plurality of genes. For example, at least about 2, at least about 3, at least about 4, at least about 5, or at least about 6 unique target sequences can be targeted on average in each of the targeted plurality of genes. As a specific example, about 6 target sequences can be targeted on average in each of the targeted plurality of genes. As another specific example, about 3 to about 6 or about 4 to about 6 target sequences are targeted on average in each of the targeted plurality of genes.

For example, the libraries can target genes with an average coverage of about 1, about 2, about 3, about 4, about 5, about 6, about 7, about 8, about 9, or about 10 gRNAs per gene. In a specific example a library can target genes with an average coverage of about 3-4 gRNAs per gene or about 6 gRNAs per gene.

The gRNAs can target any desired location in the target genes. The CRISPRn gRNAs can be designed to target coding regions of genes so that cleavage by the corresponding Cas protein will result in frameshift insertion/deletion (indel) mutations that result in a loss-of-function allele. More specifically, frameshift mutations can be achieved through targeted DNA double strand breaks and subsequent mutagenic repair via the non-homologous end joining (NHEJ) pathway, which produces indels at the site of break. The indel being introduced into the DSB is random, with some indels leading to frameshift mutations that cause premature termination of the gene.

In some CRISPRn libraries, each gRNA targets a constitutive exon if possible. In some CRISPRn libraries, each gRNA targets a 5' constitutive exon if possible. In some methods, each gRNA targets a first exon, a second exon, or a third exon (from the 5' end of the gene) if possible.

As one example, the gRNAs in the CRISPRn library can target constitutive exons. Constitutive exons are exons that are consistently conserved after splicing. Exons expressed across all tissues can be considered constitutive exons for gRNA targeting. The gRNAs in the library can target constitutive exons near the 5' end of each gene. Optionally, the first and last exons of each gene can be excluded as potential targets. Optionally, any exon containing an alternative splicing site can be excluded as potential targets. Optionally, the two earliest exons meeting the above criteria are selected as potential targets. Optionally, exons 2 and 3 are selected as potential targets (e.g., if no constitutive exons are identified). In addition, the gRNAs in the library can be selected and designed to minimize off-target effects.

In a specific example, the genome-wide CRISPRn gRNA library or libraries comprise sgRNAs targeting 5' constitutive exons of >18,000 genes in the human genome with an average coverage of ~6 sgRNAs per gene, with each target site was selected to minimize off-target modification.

The CRISPRa gRNAs can be designed to target sequences adjacent to the transcription start site of a gene. For example, the target sequence can be within 1000, 900, 800, 700, 600, 500, 400, 300, 200, 190, 180, 170, 160, 150, 140, 130, 120, 110, 100, 90, 80, 70, 60, 50, 40, 30, 20, 10, 5, or 1 base pair of the transcription start site. For example, each gRNA in the CRISPRa library can target a sequence within 200 bp upstream of a transcription start site. Optionally, the target sequence is within the region 200 base pairs upstream of the transcription start site and 1 base pair downstream of the transcription start site (−200 to +1).

The gRNAs in the genome-wide library can be in any form. For example, the gRNA library can be packaged in a viral vector, such as retroviral vectors, lentiviral vectors, or adenoviral vectors. In a specific example, the gRNA library is packaged in lentiviral vectors. The vectors can further comprise reporter genes or selection markers to facilitate selection of cells that receive the vectors. Examples of such reporter genes and selection markers are disclosed elsewhere herein. As one example, the selection marker can be one that imparts resistance to a drug, such as neomycin phosphotransferase, hygromycin B phosphotransferase, puromycin-N-acetyltransferase, and blasticidin S deaminase. Another exemplary selection marker is bleomycin resistance protein, encoded by the Sh ble gene (*Streptoalloteichus hindustanus* bleomycin gene), which confers zeocin (phleomycin D1) resistance. For example, cells can be selected with a drug (e.g., puromycin) so that only cells transduced with a guide RNA construct are preserved for being used to carry out screening.

A. Guide RNAs

A "guide RNA" or "gRNA" is an RNA molecule that binds to a Cas protein (e.g., Cas9 protein) and targets the Cas protein to a specific location within a target DNA. Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to a target sequence. The terms "guide RNA" and "gRNA" include both double-molecule (i.e., modular) gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides that forms one half of the dsRNA duplex of the protein-binding segment of the gRNA. An example of a crRNA tail, located downstream (3') of the DNA-targeting segment, comprises, consists essentially of, or consists of GUUUUAGAGCUAUGCU (SEQ ID NO: 23). Any of the DNA-targeting segments disclosed herein can be joined to the 5' end of SEQ ID NO: 23 to form a crRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. An example of a tracrRNA sequence comprises, consists essentially of, or consists of AGCAUAGCAAGUUAAAAUAAGGCUAGUCCGUUAUCAACUUGAAAAAGUGGCACCGAGUCGGUGCUUU (SEQ ID NO: 24). Other examples of tracrRNA sequences comprise, consist essentially of, or consist of any one of AAACAGCAUAGCAAGUUAAAAUAAGGCUAGUCCGUUAUCAACUUGAAAAAGUGGCACCGAGUCGGUGCUUUU (SEQ ID NO: 28), or GUUGGAACCAUUCAAAACAGCAUAGCAAGUUAAAAUAAGGCUAGUCCGUUAUCAACUUGAAAAAGUGGCACCGAGUCGGUGC (SEQ ID NO: 29).

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that hybridizes to the complementary strand of a target DNA. If used for modification within a cell, the exact sequence of a given crRNA or tracrRNA molecule can be designed to be specific to the species in which the RNA molecules will be used. See, e.g., Mali et al. (2013) *Science* 339:823-826; Jinek et al. (2012) *Science* 337:816-821; Hwang et al. (2013) *Nat. Biotechnol.* 31:227-229; Jiang et al. (2013) *Nat. Biotechnol.* 31:233-239; and Cong et al. (2013) *Science* 339:819-823, each of which is herein incorporated by reference in its entirety for all purposes.

The DNA-targeting segment (crRNA) of a given gRNA comprises a nucleotide sequence that is complementary to a sequence on the complementary strand of the target DNA, as described in more detail below. The DNA-targeting segment of a gRNA interacts with the target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of *S. pyogenes*, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have, for example, a length of at least about 12, 15, 17, 18, 19, 20, 25, 30, 35, or 40 nucleotides. Such DNA-targeting segments can have, for example, a length from about 12 to about 100, from about 12 to about 80, from about 12 to about 50, from about 12 to about 40, from about 12 to about 30, from about 12 to about 25, or from about 12 to about 20 nucleotides. For example, the DNA targeting segment can be from about 15 to about 25 nucleotides (e.g., from about 17 to about 20 nucleotides, or about 17, 18, 19, or 20 nucleotides). See, e.g., US 2016/0024523, herein incorporated by reference in its entirety for all purposes. For Cas9 from *S. pyogenes*, a typical DNA-targeting segment is between 16 and 20 nucleotides in length or between 17 and 20 nucleotides in length. For Cas9 from *S. aureus*, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise, consist essentially of, or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from *S. pyogenes* include 171-nucleotide, 89-nucleotide, 75-nucleotide, and 65-nucleotide versions. See, e.g., Deltcheva et al. (2011) *Nature* 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting segment of the guide RNA and the complementary strand of the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting segment and the complementary strand of the target DNA can be at least 60% over about 20 contiguous nucleotides. As an example, the percent complementarity between the DNA-targeting segment and the complementary strand of the target DNA can be 100% over the 14 contiguous nucleotides at the 5' end of the complementary strand of the target DNA and as low as 0% over the remainder. In such a case, the DNA-targeting segment can be considered to be 14 nucleotides in length. As another example, the percent complementarity between the DNA-targeting segment and the complementary strand of the target DNA can be 100% over the seven contiguous nucleotides at the 5' end of the complementary strand of the target DNA and as low as 0% over the remainder. In such a case, the DNA-targeting segment can be considered to be 7 nucleotides in length. In some guide RNAs, at least 17 nucleotides within the DNA-targeting segment are complementary to the complementary strand of the target DNA. For example, the DNA-targeting segment can be 20 nucleotides in length and can comprise 1, 2, or 3 mismatches with the complementary strand of the target DNA. In one example, the mismatches are not adjacent to the region of the complementary strand corresponding to the protospacer adjacent motif (PAM) sequence (i.e., the reverse complement of the PAM sequence) (e.g., the mismatches are in the 5' end of the DNA-targeting segment of the guide RNA, or the mismatches are at least 2, 3, 4, 5, 6, 7, 8, 9, 10, 11, 12, 13, 14, 15, 16, 17, 18, or 19 base pairs away from the region of the complementary strand corresponding to the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs can comprise a DNA-targeting segment and a scaffold sequence (i.e., the protein-binding or Cas-binding sequence of the guide RNA). For example, such guide RNAs can have a 5' DNA-targeting segment joined to a 3' scaffold sequence. Exemplary scaffold sequences comprise, consist essentially of, or consist of:

```
                                  (version 1; SEQ ID NO: 17)
GUUUUAGAGCUAGAAAUAGCAAGUUAAAAUAAGGCUAGUCCGUUAUCAAC

UUGAAAAAGUGGCACCGAGUCGGUGCU;

(version 2; SEQ ID NO: 18)
GUUGGAACCAUUCAAAACAGCAUAGCAAGUUAAAAUAAGGCUAGUCCGUU

AUCAACUUGAAAAAGUGGCACCGAGUCGGUGC;

(version 3; SEQ ID NO: 19)
GUUUUAGAGCUAGAAAUAGCAAGUUAAAAUAAGGCUAGUCCGUUAUCAAC

UUGAAAAAGUGGCACCGAGUCGGUGC;
and (version 4; SEQ ID NO: 20)
GUUUAAGAGCUAUGCUGGAAACAGCAUAGCAAGUUUAAAUAAGGCUAGUC

CGUUAUCAACUUGAAAAAGUGGCACCGAGUCGGUGC.

Other exemplary scaffold sequences comprise,
consist essentially of, or consist of:
                                  (version 5; SEQ ID NO: 30)
GUUUUAGAGCUAGAAAUAGCAAGUUAAAAUAAGGCUAGUCCGUUAUCAAC

UUGAAAAAGUGGCACCGAGUCGGUGCUUUUUUU;

(version 6; SEQ ID NO: 31)
GUUUUAGAGCUAGAAAUAGCAAGUUAAAAUAAGGCUAGUCCGUUAUCAAC

UUGAAAAAGUGGCACCGAGUCGGUGCUUUU;
or (version 7; SEQ ID NO: 32)
GUUUAAGAGCUAUGCUGGAAACAGCAUAGCAAGUUUAAAUAAGGCUAGUC

CGUUAUCAACUUGAAAAAGUGGCACCGAGUCGGUGCUUUUUU.
```

Guide RNAs targeting any of the guide RNA target sequences disclosed herein can include, for example, a DNA-targeting segment on the 5' end of the guide RNA fused to any of the exemplary guide RNA scaffold sequences on the 3' end of the guide RNA. That is, any of the DNA-targeting segments disclosed herein can be joined to the 5' end of any one of the above scaffold sequences to form a single guide RNA (chimeric guide RNA).

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

In some cases, a transcriptional activation system can be used comprising a dCas9-VP64 fusion protein paired with MS2-p65-HSF1. Guide RNAs in such systems can be designed with aptamer sequences appended to sgRNA tetraloop and stem-loop 2 designed to bind dimerized MS2 bacteriophage coat proteins. See, e.g., Konermann et al. (2015) Nature 517(7536):583-588, herein incorporated by reference in its entirety for all purposes.

Unmodified nucleic acids can be prone to degradation. Exogenous nucleic acids can also induce an innate immune response. Modifications can help introduce stability and reduce immunogenicity. Guide RNAs can comprise modified nucleosides and modified nucleotides including, for example, one or more of the following: (1) alteration or replacement of one or both of the non-linking phosphate oxygens and/or of one or more of the linking phosphate oxygens in the phosphodiester backbone linkage; (2) alteration or replacement of a constituent of the ribose sugar such as alteration or replacement of the 2' hydroxyl on the ribose sugar; (3) replacement of the phosphate moiety with dephospho linkers; (4) modification or replacement of a naturally occurring nucleobase; (5) replacement or modification of the ribose-phosphate backbone; (6) modification of the 3' end or 5' end of the oligonucleotide (e.g., removal, modification or replacement of a terminal phosphate group or conjugation of a moiety); and (7) modification of the sugar. Other possible guide RNA modifications include modifications of or replacement of uracils or poly-uracil tracts. See, e.g., WO 2015/048577 and US 2016/0237455, each of which is herein incorporated by reference in its entirety for all purposes. Similar modifications can be made to Cas-encoding nucleic acids, such as Cas mRNAs. For example, Cas mRNAs can be modified by depletion of uridine using synonymous codons.

As one example, nucleotides at the 5' or 3' end of a guide RNA can include phosphorothioate linkages (e.g., the bases can have a modified phosphate group that is a phosphorothioate group). For example, a guide RNA can include phosphorothioate linkages between the 2, 3, or 4 terminal nucleotides at the 5' or 3' end of the guide RNA. As another example, nucleotides at the 5' and/or 3' end of a guide RNA can have 2'-O-methyl modifications. For example, a guide RNA can include 2'-O-methyl modifications at the 2, 3, or 4 terminal nucleotides at the 5' and/or 3' end of the guide RNA (e.g., the 5' end). See, e.g., WO 2017/173054 A1 and Finn et al. (2018) Cell Reports 22:1-9, each of which is herein incorporated by reference in its entirety for all purposes. Other possible modifications are described in more detail elsewhere herein. In a specific example, a guide RNA includes 2'-O-methyl analogs and 3' phosphorothioate internucleotide linkages at the first three 5' and 3' terminal RNA residues. Such chemical modifications can, for example, provide greater stability and protection from exonucleases to guide RNAs, allowing them to persist within cells for longer than unmodified guide RNAs. Such chemical modifications can also, for example, protect against innate intracellular immune responses that can actively degrade RNA or trigger immune cascades that lead to cell death.

In some guide RNAs (e.g., single guide RNAs), at least one loop (e.g., two loops) of the guide RNA is modified by insertion of a distinct RNA sequence that binds to one or more adaptors (i.e., adaptor proteins or domains). Such adaptor proteins can be used to further recruit one or more heterologous functional domains, such as transcriptional activation domains (e.g., for use in CRISPRa screening in the SAM/tau biosensor cells). Examples of fusion proteins comprising such adaptor proteins (i.e., chimeric adaptor proteins) are disclosed elsewhere herein. For example, an MS2-binding loop ggccAACAUGAGGAUCACCCAUGU-CUGCAGggcc (SEQ ID NO: 33) may replace nucleotides +13 to +16 and nucleotides +53 to +56 of the sgRNA scaffold (backbone) set forth in SEQ ID NO: 17 or SEQ ID NO: 19 (or SEQ ID NO: 30 or 31) or the sgRNA backbone for the S. pyogenes CRISPR/Cas9 system described in WO 2016/049258 and Konermann et al. (2015) Nature 517 (7536):583-588, each of which is herein incorporated by reference in its entirety for all purposes. See also US 2019-0284572 and WO 2019/183123, each of which is herein incorporated by reference in its entirety for all purposes. The guide RNA numbering used herein refers to the nucleotide numbering in the guide RNA scaffold sequence (i.e., the sequence downstream of the DNA-targeting segment of the guide RNA). For example, the first nucleotide of the guide RNA scaffold is +1, the second nucleotide of the scaffold is +2, and so forth. Residues corresponding with nucleotides +13 to +16 in SEQ ID NO: 17 or SEQ ID NO: 19 (or SEQ ID NO: 30 or 31) are the loop sequence in the region spanning nucleotides +9 to +21 in SEQ ID NO: 17 or SEQ ID NO: 19 (or SEQ ID NO: 30 or 31), a region referred to herein as the tetraloop. Residues corresponding with nucleotides +53 to +56 in SEQ ID NO: 17 or SEQ ID NO: 19 (or SEQ ID NO: 30 or 31) are the loop sequence in the region spanning nucleotides +48 to +61 in SEQ ID NO: 17 or SEQ ID NO: 19 (or SEQ ID NO: 30 or 31), a region referred to herein as the stem loop 2. Other stem loop sequences in in SEQ ID NO: 17 or SEQ ID NO: 19 (or SEQ ID NO: 30 or 31) comprise stem loop 1 (nucleotides +33 to +41) and stem loop 3 (nucleotides +63 to +75). The resulting structure is an sgRNA scaffold in which each of the tetraloop and stem loop 2 sequences have been replaced by an MS2 binding loop. The tetraloop and stem loop 2 protrude from the Cas9 protein in such a way that adding an MS2-binding loop should not interfere with any Cas9 residues. Additionally, the proximity of the tetraloop and stem loop 2 sites to the DNA indicates that localization to these locations could result in a high degree of interaction between the DNA and any recruited protein, such as a transcriptional activator. Thus, in some sgRNAs, nucleotides corresponding to +13 to +16 and/or nucleotides corresponding to +53 to +56 of the guide RNA scaffold set forth in SEQ ID NO: 17 or SEQ ID NO: 19 (or SEQ ID NO: 30 or 31) or corresponding residues when optimally aligned with any of these scaffold/backbones are replaced by the distinct RNA sequences capable of binding to one or more adaptor proteins or domains. Alternatively or additionally, adaptor-binding sequences can be added to the 5' end or the 3' end of a guide RNA. An exemplary guide RNA scaffold comprising MS2-binding loops in the tetraloop and stem loop 2 regions can comprise, consist essentially of, or consist of the sequence set forth in SEQ ID NO: 34. An exemplary generic single guide RNA comprising MS2-binding loops in the tetraloop and stem loop 2 regions can comprise, consist essentially of, or consist of the sequence set forth in SEQ ID NO: 35.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising a heterologous nucleic acid, such as a nucleic acid encoding a Cas protein. Alternatively, it can be in a vector or a plasmid that is separate from the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

Alternatively, gRNAs can be prepared by various other methods. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be a synthetically produced molecule prepared by chemical synthesis. For example, a guide RNA can be chemically synthesized to include 2'-O-methyl analogs and 3' phosphorothioate internucleotide linkages at the first three 5' and 3' terminal RNA residues.

Guide RNAs (or nucleic acids encoding guide RNAs) can be in compositions comprising one or more guide RNAs (e.g., 1, 2, 3, 4, or more guide RNAs) and a carrier increasing the stability of the guide RNA (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly (lactic acid) (PLA) microspheres, poly(D,L-lactic-coglycolic-acid) (PLGA) microspheres, liposomes, micelles, inverse micelles, lipid cochleates, and lipid microtubules. Such compositions can further comprise a Cas protein, such as a Cas9 protein, or a nucleic acid encoding a Cas protein.

B. Guide RNA Target Sequences

Target DNAs for guide RNAs include nucleic acid sequences present in a DNA to which a DNA-targeting segment of a gRNA will bind, provided sufficient conditions for binding exist. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the gRNA can be called the "complementary strand," and the strand of the target DNA that is complementary to the "complementary strand" (and is therefore not complementary to the Cas protein or gRNA) can be called "noncomplementary strand" or "template strand."

The target DNA includes both the sequence on the complementary strand to which the guide RNA hybridizes and the corresponding sequence on the non-complementary strand (e.g., adjacent to the protospacer adjacent motif (PAM)). The term "guide RNA target sequence" as used herein refers specifically to the sequence on the non-complementary strand corresponding to (i.e., the reverse complement of) the sequence to which the guide RNA hybridizes on the complementary strand. That is, the guide RNA target sequence refers to the sequence on the non-complementary strand adjacent to the PAM (e.g., upstream or 5' of the PAM in the case of Cas9). A guide RNA target sequence is equivalent to the DNA-targeting segment of a guide RNA, but with thymines instead of uracils. As one example, a guide RNA target sequence for an SpCas9 enzyme can refer to the sequence upstream of the 5'-NGG-3' PAM on the non-complementary strand. A guide RNA is designed to have complementarity to the complementary strand of a target DNA, where hybridization between the DNA-targeting segment of the guide RNA and the complementary strand of the target DNA promotes the formation of a CRISPR complex. Full complementarity is not necessarily required, provided that there is sufficient complementarity to cause hybridization and promote formation of a CRISPR complex. If a guide RNA is referred to herein as targeting a guide RNA target sequence, what is meant is that the guide RNA hybridizes to the complementary strand sequence of the target DNA that is the reverse complement of the guide RNA target sequence on the non-complementary strand.

A target DNA or guide RNA target sequence can comprise any polynucleotide, and can be located, for example, in the nucleus or cytoplasm of a cell or within an organelle of a cell, such as a mitochondrion or chloroplast. A target DNA or guide RNA target sequence can be any nucleic acid sequence endogenous or exogenous to a cell. The guide RNA target sequence can be a sequence coding a gene product (e.g., a protein) or a non-coding sequence (e.g., a regulatory sequence) or can include both.

For CRISPRa and SAM systems, it can be preferable for the target sequence to be adjacent to the transcription start site of a gene. For example, the target sequence can be within 1000, 900, 800, 700, 600, 500, 400, 300, 200, 190, 180, 170, 160, 150, 140, 130, 120, 110, 100, 90, 80, 70, 60, 50, 40, 30, 20, 10, 5, or 1 base pair of the transcription start site. Optionally, the target sequence is within the region 200 base pairs upstream of the transcription start site and 1 base pair downstream of the transcription start site (−200 to +1).

Site-specific binding and cleavage of a target DNA by a Cas protein can occur at locations determined by both (i) base-pairing complementarity between the guide RNA and the complementary strand of the target DNA and (ii) a short motif, called the protospacer adjacent motif (PAM), in the non-complementary strand of the target DNA. The PAM can flank the guide RNA target sequence. Optionally, the guide RNA target sequence can be flanked on the 3' end by the PAM (e.g., for Cas9). Alternatively, the guide RNA target sequence can be flanked on the 5' end by the PAM (e.g., for Cpf1). For example, the cleavage site of Cas proteins can be about 1 to about 10 or about 2 to about 5 base pairs (e.g., 3 base pairs) upstream or downstream of the PAM sequence (e.g., within the guide RNA target sequence). In the case of SpCas9, the PAM sequence (i.e., on the non-complementary strand) can be 5'-$N_1$GG-3', where $N_1$ is any DNA nucleotide, and where the PAM is immediately 3' of the guide RNA target sequence on the non-complementary strand of the target DNA. As such, the sequence corresponding to the PAM on the complementary strand (i.e., the reverse complement) would be 5'-$CCN_2$-3', where N2 is any DNA nucleotide and is immediately 5' of the sequence to which the DNA-targeting segment of the guide RNA hybridizes on the complementary strand of the target DNA. In some such cases, $N_1$ and N2 can be complementary and the $N_1$-N2 base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from *S. aureus*, the PAM can be NNGRRT or NNGRR, where N can A, G, C, or T, and R can be G or A. In the case of Cas9 from *C. jejuni*, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

An example of a guide RNA target sequence is a 20-nucleotide DNA sequence immediately preceding an NGG motif recognized by an SpCas9 protein. For example, two examples of guide RNA target sequences plus PAMs are $GN_{19}$NGG (SEQ ID NO: 25) or $N_{20}$NGG (SEQ ID NO: 26). See, e.g., WO 2014/165825, herein incorporated by reference in its entirety for all purposes. The guanine at the 5' end can facilitate transcription by RNA polymerase in cells. Other examples of guide RNA target sequences plus PAMs can include two guanine nucleotides at the 5' end (e.g., $GGN_{20}$NGG; SEQ ID NO: 27) to facilitate efficient transcription by T7 polymerase in vitro. See, e.g., WO 2014/065596, herein incorporated by reference in its entirety for all purposes. Other guide RNA target sequences plus PAMs can have between 4-22 nucleotides in length of SEQ ID NOS: 25-27, including the 5' G or GG and the 3' GG or NGG. Yet other guide RNA target sequences plus PAMs can have between 14 and 20 nucleotides in length of SEQ ID NOS: 25-27.

Formation of a CRISPR complex hybridized to a target DNA can result in cleavage of one or both strands of the target DNA within or near the region corresponding to the guide RNA target sequence (i.e., the guide RNA target sequence on the non-complementary strand of the target DNA and the reverse complement on the complementary strand to which the guide RNA hybridizes). For example, the cleavage site can be within the guide RNA target sequence (e.g., at a defined location relative to the PAM sequence). The "cleavage site" includes the position of a target DNA at which a Cas protein produces a single-strand break or a double-strand break. The cleavage site can be on only one strand (e.g., when a nickase is used) or on both strands of a double-stranded DNA. Cleavage sites can be at the same position on both strands (producing blunt ends; e.g. Cas9)) or can be at different sites on each strand (producing staggered ends (i.e., overhangs); e.g., Cpf1). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA target sequence or cleavage site of the nickase on the first strand is separated from the guide RNA target sequence or cleavage site of the nickase on the second strand by at least 2, 3, 4, 5, 6, 7, 8, 9, 10, 15, 20, 25, 30, 40, 50, 75, 100, 250, 500, or 1,000 base pairs.

IV. Methods of Screening for Genetic Modifiers of Tau Seeding or Aggregation

The Cas/tau biosensor cell lines disclosed herein can be used in methods of screening for genetic modifiers of tau seeding or aggregation. Such methods can comprise providing a population of Cas/tau biosensor cells as disclosed elsewhere herein, introducing a library comprising a plurality of unique guide RNAs, and assessing tau seeding or aggregation in the targeted cells.

As one example, a method can comprise providing a population of Cas/tau biosensor cells (e.g., a population of cells comprising a Cas protein, a first tau repeat domain linked to a first reporter, and a second tau repeat domain linked to a second reporter), introducing into the population of cells a library comprising a plurality of unique guide RNAs that target a plurality of genes, and culturing the population of cells to allow genome editing and expansion. The plurality of unique guide RNAs form complexes with the Cas protein, and the Cas protein cleaves the plurality of genes resulting in knockout of gene function to produce a genetically modified population of cells. The genetically modified population of cells can then be contacted with a tau seeding agent to produce a seeded population of cells. The seeded population of cells can be cultured to allow tau aggregates to form, wherein aggregates of the first tau repeat domain and the second tau repeat domain form in a subset of the seeded population of cells to produce an aggregation-positive population of cells. Finally, abundance of each of the plurality of unique guide RNAs can be determined in the aggregation-positive population of cells relative to the population of cells being cultured after introduction of the guide RNA library. Enrichment of a guide RNA in the aggregation-positive population of cells relative to the population of cells being cultured after introduction of the guide RNA library indicates that the gene targeted by the guide RNA is a genetic modifier of tau aggregation, wherein disruption of the gene targeted by the guide RNA enhances tau aggregation, or is a candidate genetic modifier of tau aggregation (e.g., for further testing via secondary screens), wherein disruption of the gene targeted by the guide RNA is expected to enhance tau aggregation.

Similarly, the SAM/tau biosensor cell lines disclosed herein can be used in methods of screening for genetic modifiers of tau seeding or aggregation. Such methods can comprise providing a population of SAM/tau biosensor cells as disclosed elsewhere herein, introducing a library comprising a plurality of unique guide RNAs, and assessing tau seeding or aggregation in the targeted cells.

As one example, a method can comprise providing a population of SAM/tau biosensor cells (e.g., a population of cells comprising a chimeric Cas protein comprising a nuclease-inactive Cas protein fused to one or more transcriptional activation domains, a chimeric adaptor protein comprising an adaptor protein fused to one or more transcriptional activation domains, a first tau repeat domain linked to a first reporter, and a second tau repeat domain linked to a second reporter), introducing into the population of cells a library comprising a plurality of unique guide RNAs that target a plurality of genes, and culturing the population of cells to allow transcriptional activation and expansion. The plurality of unique guide RNAs form complexes with the chimeric Cas protein and the chimeric adaptor protein, and the complexes activate transcription of the plurality of genes resulting in increased gene expression and a modified population of cells. The modified population of cells can then be contacted with a tau seeding agent to produce a seeded population of cells. The seeded population of cells can be cultured to allow tau aggregates to form, wherein aggregates of the first tau repeat domain and the second tau repeat domain form in a subset of the seeded population of cells to produce an aggregation-positive population of cells. Finally, abundance of each of the plurality of unique guide RNAs can be determined in the aggregation-positive population of cells relative to the population of cells being cultured after introduction of the guide RNA library. Enrichment of a guide RNA in the aggregation-positive population of cells relative to the population of cells being cultured after introduction of the guide RNA library indicates that the gene targeted by the guide RNA is a genetic modifier of tau aggregation, wherein transcriptional activation of the gene targeted by the guide RNA enhances tau aggregation, or is a candidate genetic modifier of tau aggregation (e.g., for further testing via secondary screens), wherein transcriptional activation of the gene targeted by the guide RNA is expected to enhance tau aggregation.

The Cas/tau biosensor cells used in the method can be any of the Cas/tau biosensor cells disclosed elsewhere herein. Likewise, the SAM/tau biosensor cells used in the method can be any of the SAM/tau biosensor cells disclosed elsewhere herein. The first tau repeat domain and the second tau repeat domain can be different or can be similar or the same. The tau repeat domain can be any of the tau repeat domains disclosed elsewhere herein. For example, the first tau repeat domain and/or the second tau repeat domain can be a wild type tau repeat domain or can comprise a pro-aggregation mutation (e.g., a pathogenic, pro-aggregation mutation), such as a tau P301S mutation. The first tau repeat domain and/or the second tau repeat domain can comprise a tau four-repeat domain. As one specific example, the first tau repeat domain and/or the second tau repeat domain can comprise, consist essentially of, or consist of SEQ ID NO: 11 or a sequence at least about 90%, 91%, 92%, 93%, 94%, 95%, 96%, 97%, 98%, or 99% identical to SEQ ID NO: 11. In one specific example, the nucleic acid encoding the tau repeat domain can comprise, consist essentially of, or consist of SEQ ID NO: 12 or a sequence at least about 90%, 91%, 92%, 93%, 94%, 95%, 96%, 97%, 98%, or 99% identical to SEQ ID NO: 12, optionally wherein the nucleic acid encodes a protein comprising, consisting essentially of, or consisting of SEQ ID NO: 11.

The first tau repeat domain can be linked to the first reporter and the second tau repeat domain can be linked to the second reporter by any means. For example, the reporter can be fused to the tau repeat domain (e.g., as part of a fusion protein). The reporter proteins can be any pair of reporter proteins that produce a detectable signal when the first tau repeat domain linked to the first reporter is aggregated with the second tau repeat domain linked to the second reporter. As one example, the first and second reporters can be a split luciferase protein. As another example, the first and second reporter proteins can be a fluorescence resonance energy transfer (FRET) pair. FRET is a physical phenomenon in which a donor fluorophore in its excited state non-radiatively transfers its excitation energy to a neighboring acceptor fluorophore, thereby causing the acceptor to emit its characteristic fluorescence. Examples of FRET pairs (donor and acceptor fluorophores) are well known. See, e.g., Bajar et al. (2016) *Sensors (Basel)* 16(9):1488, herein incorporated by reference in its entirety for all purposes. As one specific example of a FRET pair, the first reporter can be cyan fluorescent protein (CFP) and the second reporter can be yellow fluorescent protein (YFP). As a specific example, the CFP can comprise, consist essentially of, or consist of SEQ ID NO: 13 or a sequence at least about 90%, 91%, 92%, 93%, 94%, 95%, 96%, 97%, 98%, or 99% identical to SEQ ID NO: 13. As another specific example, the YFP can comprise, consist essentially of, or consist of SEQ ID NO: 15 or a sequence at least about 90%, 91%, 92%, 93%, 94%, 95%, 96%, 97%, 98%, or 99% identical to SEQ ID NO: 15.

For the Cas/tau biosensor cells, the Cas protein can be any Cas protein disclosed elsewhere herein. As one example, the Cas protein can be a Cas9 protein. For example, the Cas9 protein can be a *Streptococcus pyogenes* Cas9 protein. As one specific example, the Cas protein can comprise, consist essentially of, or consist of SEQ ID NO: 21 or a sequence at least about 90%, 91%, 92%, 93%, 94%, 95%, 96%, 97%, 98%, or 99% identical to SEQ ID NO: 21.

One or more or all of the Cas protein, the first tau repeat domain linked to the first reporter, and the second tau repeat domain linked to the second reporter can be stably expressed in the population of cells. For example, nucleic acids encoding one or more or all of the Cas protein, the first tau repeat domain linked to the first reporter, and the second tau repeat domain linked to the second reporter can be genomically integrated in the population of cells. In one specific example, the nucleic acid encoding the Cas protein can comprise, consist essentially of, or consist of SEQ ID NO: 22 or a sequence at least about 90%, 91%, 92%, 93%, 94%, 95%, 96%, 97%, 98%, or 99% identical to SEQ ID NO: 22, optionally wherein the nucleic acid encodes a protein comprising, consisting essentially of, or consisting of SEQ ID NO: 21.

For the SAM/tau biosensor cells, the Cas protein can be any Cas protein disclosed elsewhere herein. As one example, the Cas protein can be a Cas9 protein. For example, the Cas9 protein can be a *Streptococcus pyogenes* Cas9 protein. As one specific example, the chimeric Cas protein can comprise the nuclease-inactive Cas protein fused to a VP64 transcriptional activation domain. For example, the chimeric Cas protein can comprise from N-terminus to C-terminus: the nuclease-inactive Cas protein; a nuclear localization signal; and the VP64 transcriptional activator domain. As one specific example, the adaptor protein can be an MS2 coat protein, and the one or more transcriptional activation domains in the chimeric adaptor protein can comprise a p65 transcriptional activation domain and an HSF1 transcriptional activation domain. For example, the chimeric adaptor protein can comprise from N-terminus to C-terminus: the MS2 coat protein; a nuclear localization signal; the p65 transcriptional activation domain; and the HSF1 transcriptional activation domain. In one specific example, the nucleic acid encoding the chimeric Cas protein can comprise, consist essentially of, or consist of SEQ ID NO: 38 or a sequence at least about 90%, 91%, 92%, 93%, 94%, 95%, 96%, 97%, 98%, or 99% identical to SEQ ID NO: 38, optionally wherein the nucleic acid encodes a protein comprising, consisting essentially of, or consisting of SEQ ID NO: 36. In one specific example, the nucleic acid encoding the chimeric adaptor protein can comprise, consist essentially of, or consist of SEQ ID NO: 39 or a sequence at least about 90%, 91%, 92%, 93%, 94%, 95%, 96%, 97%, 98%, or 99% identical to SEQ ID NO: 39, optionally wherein the nucleic acid encodes a protein comprising, consisting essentially of, or consisting of SEQ ID NO: 37.

One or more or all of the chimeric Cas protein, the chimeric adaptor protein, the first tau repeat domain linked to the first reporter, and the second tau repeat domain linked to the second reporter can be stably expressed in the population of cells. For example, nucleic acids encoding one or more or all of the chimeric Cas protein, the chimeric adaptor protein, the first tau repeat domain linked to the first reporter, and the second tau repeat domain linked to the second reporter can be genomically integrated in the population of cells.

As disclosed elsewhere herein, the cells can be any type of cells. For example, the cells can be eukaryotic cells, mammalian cells, or human cells (e.g., HEK293T cells or neuronal cells).

The plurality of unique guide RNAs can be introduced into the population of cells by any known means. In some methods, the guide RNAs are introduced into the population of cells by viral transduction, such as retroviral, adenoviral, or lentiviral transduction. In a specific example, the guide RNAs can be introduced by lentiviral transduction. Each of the plurality of unique guide RNAs can be in a separate viral vector. The population of cells can be infected at any multiplicity of infection. For example, the multiplicity of infection can be between about 0.1 and about 1.0, between about 0.1 and about 0.9, between about 0.1 and about 0.8, between about 0.1 and about 0.7, between about 0.1 and about 0.6, between about 0.1 and about 0.5, between about 0.1 and about 0.4, or between about 0.1 and about 0.3. Alternatively, the multiplicity of infection can be less than about 1.0, less than about 0.9, less than about 0.8, less than about 0.7, less than about 0.6, less than about 0.5, less than about 0.4, less than about 0.3, or less than about 0.2. In a specific example, the multiplicity of infection can be less than about 0.3.

The guide RNAs can be introduced into the population of cells together with a selection marker or reporter gene to select for cells that have the guide RNAs, and the method can further comprise selecting cells that comprise the selection marker or reporter gene. Examples of selection markers and reporter genes are provided elsewhere herein. As one example, the selection marker can be one that imparts resistance to a drug, such as neomycin phosphotransferase, hygromycin B phosphotransferase, puromycin-N-acetyl-transferase, and blasticidin S deaminase. Another exemplary selection marker is bleomycin resistance protein, encoded by the Sh ble gene (*Streptoalloteichus hindustanus* bleomycin gene), which confers zeocin (phleomycin D1) resistance. For example, cells can be selected with a drug (e.g., puromycin) so that only cells transduced with a guide RNA construct are preserved for being used to carry out screening. For example, the drug can be puromycin or zeocin (phleomycin D1).

In some methods, the plurality of unique guide RNAs are introduced at a concentration selected such that a majority of the cells receive only one of the unique guide RNAs. For example, if the guide RNAs are being introduced by viral transduction, the cells can be infected at a low multiplicity of infection to ensure that most cells receive only one viral construct with high probability. As one specific example, the multiplicity of infection can be less than about 0.3.

The population of cells into which the plurality of unique guide RNAs is introduced can be any suitable number of cells. For example, the population of cells can comprise greater than about 50, greater than about 100, greater than about 200, greater than about 300, greater than about 400, greater than about 500, greater than about 600, greater than about 700, greater than about 800, greater than about 900, or greater than about 1000 cells per unique guide RNA. In a specific example, the population of cells comprises greater than about 300 cells or greater than about 500 cells per unique guide RNA.

The plurality of unique guide RNAs can target any number of genes. For example, the plurality of unique guide RNAs can target about 50 or more genes, about 100 or more genes, about 200 or more genes, about 300 or more genes, about 400 or more genes, about 500 or more genes, about 1000 or more genes, about 2000 or more genes, about 3000 or more genes, about 4000 or more genes, about 5000 or more genes, about 10000 or more genes, or about 20000 or more genes. In some methods, the guide RNAs can be selected to target genes in a particular signaling pathway. In some methods, the library of unique guide RNAs is a genome-wide library.

The plurality of unique guide RNAs can target any number of sequences within each individual targeted gene. In some methods, a plurality of target sequences are targeted on average in each of the targeted plurality of genes. For example, about 2 to about 10, about 2 to about 9, about 2 to about 8, about 2 to about 7, about 2 to about 6, about 2 to about 5, about 2 to about 4, or about 2 to about 3 unique target sequences can be targeted on average in each of the targeted plurality of genes. For example, at least about 2, at least about 3, at least about 4, at least about 5, or at least about 6 unique target sequences can be targeted on average in each of the targeted plurality of genes. As a specific example, about 6 target sequences can be targeted on average in each of the targeted plurality of genes. As another specific example, about 3 to about 6 or about 4 to about 6 target sequences are targeted on average in each of the targeted plurality of genes.

The guide RNAs can target any desired location in the target genes. In some CRISPRn methods using the Cas/tau biosensor cells, each guide RNA targets a constitutive exon if possible. In some methods, each guide RNA targets a 5' constitutive exon if possible. In some methods, each guide RNA targets a first exon, a second exon, or a third exon (from the 5' end of the gene) if possible. In some CRISPRa methods using the SAM/tau biosensor cells, each guide RNA can target a guide RNA target sequence within 200 bp upstream of a transcription start site, if possible. In some CRISPRa methods using the SAM/tau biosensor cells, wherein each guide RNA can comprise one or more adaptor-binding elements to which the chimeric adaptor protein can specifically bind. In one example, each guide RNA comprises two adaptor-binding elements to which the chimeric adaptor protein can specifically bind, optionally wherein a first adaptor-binding element is within a first loop of each of the one or more guide RNAs, and a second adaptor-binding element is within a second loop of each of the one or more guide RNAs. For example, the adaptor-binding element can comprise the sequence set forth in SEQ ID NO: 33. In a specific example, each of one or more guide RNAs is a single guide RNA comprising a CRISPR RNA (crRNA) portion fused to a transactivating CRISPR RNA (tracrRNA) portion, and the first loop is the tetraloop corresponding to residues 13-16 of SEQ ID NO: 17, 19, 30, or 31, and the second loop is the stem loop 2 corresponding to residues 53-56 of SEQ ID NO: 17, 19, 30, or 31.

The step of culturing the population of cells to allow genome editing and expansion can be any suitable period of time. For example, the culturing can be for between about 2 days and about 10 days, between about 3 days and about 9 days, between about 4 days and about 8 days, between about 5 days and about 7 days, or about 6 days. Likewise, the step of culturing the population of cells to allow transcriptional activation and expansion can be any suitable period of time. For example, the culturing can be for between about 2 days and about 10 days, between about 3 days and about 9 days, between about 4 days and about 8 days, between about 5 days and about 7 days, or about 6 days.

Any suitable tau seeding agent can be used to produce a seeded population of cells. Suitable tau seeding agents are disclosed elsewhere herein. Some suitable seeding agents comprise a tau repeat domain that can be, for example, different from or similar to or the same as the first tau repeat domain and/or the second tau repeat domain. In one example, the seeding step comprises culturing the genetically modified population of cells in the presence of conditioned medium harvested from cultured tau-aggregation-positive cells in which a tau repeat domain stably presents in an aggregated state. For example, the conditioned medium can have been harvested from confluent tau-aggregation-positive cells after being on the confluent cells for about 1 to about 7 days, about 2 to about 6 days, about 3 to about 5 days, or about 4 days. The seeding step can comprise culturing the genetically modified population of cells in any suitable ratio of conditioned medium to fresh medium. For example, it can comprise culturing the genetically modified population of cells in about 90% conditioned medium and about 10% fresh medium, about 85% conditioned medium and about 15% fresh medium, about 80% conditioned medium and about 20% fresh medium, about 75% conditioned medium and about 25% fresh medium, about 70% conditioned medium and about 30% fresh medium, about 65% conditioned medium and about 35% fresh medium, about 60% conditioned medium and about 40% fresh medium, about 55% conditioned medium and about 45% fresh medium, about 50% conditioned medium and about 50% fresh medium, about 45% conditioned medium and about 55% fresh medium, about 40% conditioned medium and about 60% fresh medium, about 35% conditioned medium and about 65% fresh medium, about 30% conditioned medium and about 70% fresh medium, about 25% conditioned medium and about 75% fresh medium, about 20% conditioned medium and about 80% fresh medium, about 15% conditioned medium and about 85% fresh medium, or about 10% conditioned medium and about 90% fresh medium. In one example, it can comprise culturing the genetically modified population of cells in a medium that comprises at least about 50% conditioned medium and no more than about 50% fresh medium. In a specific example, it can comprise culturing the genetically modified population of cells in about 75% conditioned medium and about 25% fresh medium. Optionally, the genetically modified population of cells is not co-cultured with the tau-aggregation-positive cells in which a tau repeat domain stably presents in an aggregated state.

The step of culturing the seeded population of cells to allow tau aggregates to form, wherein aggregates of the first tau repeat domain and the second tau repeat domain form in a subset of the seeded population of cells to produce an aggregation-positive population of cells, can be any suitable length of time. For example, the culturing can be for between about 1 day and about 7 days, between about 2 days and about 6 days, between about 3 days and about 5 days, or about 4 days. Aggregation can be determined by any suitable means, depending on the reporters used. For example, in methods in which the first reporter and the second reporter are a fluorescence resonance energy transfer (FRET) pair, the aggregation-positive population of cells can be identified by flow cytometry.

Abundance of guide RNAs can be determined by any suitable means. In a specific example, abundance is determined by next-generation sequencing. Next-generation sequencing refers to non-Sanger-based high-throughput DNA sequencing technologies. For example, determining abundance of a guide RNA can comprise measuring read counts of the guide RNA.

In some methods, a guide RNA is considered enriched if the abundance of the guide RNA relative to the total population of the plurality of unique guide RNAs is at least about 1.5-fold higher in the aggregation-positive population of cells relative to the population of cells being cultured after introduction of the guide RNA library. Different enrichment thresholds can also be used. For example, an enrichment threshold can be set higher to be more stringent (e.g., at least about 1.6-fold, at least about 1.7-fold, at least about 1.8-fold, at least about 1.9-fold, at least about 2-fold, at least about 2.5-fold, or at least about 2.5-fold). Alternatively, an enrichment threshold can be set lower to be less stringent (e.g., at least about 1.4-fold, at least about 1.3-fold, or at least about 1.2-fold).

In one example, the step of determining abundance can comprise determining abundance of the plurality of unique guide RNAs in the aggregation-positive population relative to the population of cells cultured after introduction of the guide RNA library at a first time point during the culturing and/or a second time point during the culturing. For example, the first time point can be at a first passage of culturing the population of cells, and the second time point can be in the middle of culturing the population of cells to allow genome editing and expansion. For example, the first time point can be after a sufficient amount of time for the guide RNAs to form complexes with the Cas protein, and for the Cas protein to cleave the plurality of genes resulting in knockout of gene function (CRISPRn) or to transcriptionally activate the plurality of genes (CRISPRa). However, the first time point should ideally be at the first cell passage to determine the gRNA library representation soon after infection (i.e., before further expansion and genome editing) and to determine if each gRNA representation evolves from the first time point to the second time points and to any additional time points to a final time point. This allows ruling out enriched gRNAs/targets due to cell growth advantages during the course of the screen by verifying gRNA abundance is unchanged between the first and second time points. As a specific example, the first time point can be after about 1 day, about 2 days, about 3 days, or about 4 days of culturing and expansion, and the second time point can be after about 3 days, about 4 days, about 5 days, or about 6 days of culturing and expansion. For example, the first time point can be after about 3 days of culturing and expansion, and the second time point can be after about 6 days of culturing and expansion. In some methods, a gene can then be considered a genetic modifier of tau aggregation, wherein disruption (CRISPRn) or transcriptional activation (CRISPRa) of the gene enhances (or is expected to enhance) tau aggregation, if the abundance of a guide RNA targeting the gene relative to the total population of the plurality of unique guide RNAs is at least 1.5-fold higher (or higher than a different selected enrichment threshold) in the aggregation-positive population of cells relative to the population of cells cultured after introduction of the guide RNA library at both the first time point and the second time point. Alternatively or additionally, a gene can be considered a genetic modifier of tau aggregation, wherein disruption (CRISPRn) or transcriptional activation (CRISPRa) of the gene enhances (or is expected to enhance) tau aggregation, if the abundance of at least two unique guide RNAs targeting the gene relative to the total population of the plurality of unique guide RNAs is at least 1.5-fold higher (or higher than a different selected enrichment threshold) in the aggregation-positive population of cells relative to the population of cells cultured after introduction of the guide RNA library at either the first time point or the second time point.

In some CRISPRn methods, the following steps are taken to identify a gene as a genetic modifier of tau aggregation, wherein disruption (CRISPRn) or transcriptional activation (CRISPRa) of the gene enhances (or is expected to enhance) tau aggregation. Likewise, in some CRISPRa methods, the following steps are taken to identify a gene as a genetic modifier of tau aggregation, wherein transcriptional activation of the gene enhances tau aggregation. The first step comprises identifying which of the plurality of unique guide RNAs are present in the aggregation-positive population of cells. The second step comprises calculating the random chance of the guide RNAs identified being present using the formula $nC_{n'}*(x-n')C(m-n)/xC_m$, where x is the variety of unique guide RNAs introduced into the population of cells, m is the variety of unique guide RNAs identified in step (1), n is the variety of unique guide RNAs introduced into the population of cells that target the gene, and n' is the variety of unique guide RNAs identified in step (1) that target the gene. The third step comprises calculating average enrichment scores for the guide RNAs identified in step (1). The enrichment score for a guide RNA is the relative abundance of the guide RNA in the aggregation-positive population of cells divided by the relative abundance of the guide RNA in the population of cells cultured after introduction of the guide RNA library. The relative abundance is the read count of the guide RNA divided by the read count of the total population of the plurality of unique guide RNAs. The fourth step comprises selecting the gene if a guide RNA targeting the gene is significantly below the random chance of being present and above a threshold enrichment score. Possible threshold enrichment scores are discussed above. As a specific example, the threshold enrichment score can be set at about 1.5-fold.

Variety when used in the phrase variety of unique guide RNAs means the number of unique guide RNA sequences. It is not the abundance, but rather the qualitative "present" or "not present." Variety of unique guide RNAs means the number of unique guide RNA sequence. The variety of unique guide RNA is determined by next generation sequencing (NGS) to identify all the unique guide RNAs present in a cell population. It is done by using two primers that recognize the constant regions of the viral vector to amplify the gRNA that is between the constant regions and a primer that recognizes one constant region for sequencing. Each unique guide RNA present in the sample will generate read counts using the sequencing primer. The NGS results will include the sequence and also the number of reads corresponding to the sequence. The number of reads will be used for the enrichment score calculation for each guide RNA, and the presence of each unique sequence will tell us which guide RNAs are present. For instance, if there are three unique guide RNAs for a gene before selection, and all three are retained post-selection, then both n and n' are 3. These numbers are used for calculating the statistics but not the actual read counts. However, the read counts for each guide RNA (in one example, 100, 200, 50, which correspond to each of the 3 unique guide RNAs) will be used for the calculation of enrichment score.

V. Methods of Screening for Genetic Modifiers of Tau Aggregation that Prevent Tau Aggregation The Cas/tau biosensor cell lines disclosed herein can be used in methods of screening for genetic modifiers of tau aggregation (e.g., that prevent tau aggregation or are expected to prevent tau aggregation). Such methods can comprise providing a population of Cas/tau biosensor cells as disclosed elsewhere herein, introducing a library comprising a plurality of unique guide RNAs, and assessing tau aggregation in the targeted cells.

As one example, a method can comprise providing a population of Cas/tau biosensor cells (e.g., a population of cells comprising a Cas protein, a first tau repeat domain linked to a first reporter, and a second tau repeat domain linked to a second reporter), introducing into the population of cells a library comprising a plurality of unique guide RNAs that target a plurality of genes, and culturing the population of cells to allow genome editing and expansion. The plurality of unique guide RNAs form complexes with the Cas protein, and the Cas protein cleaves the plurality of genes resulting in knockout of gene function to produce a genetically modified population of cells. The genetically modified population of cells can then be contacted with a tau seeding agent to produce a seeded population of cells. For example, the tau seeding agent can be a "maximum seeding" agent as described elsewhere herein, such as cell lysates from tau-aggregation-positive cells. The seeded population of cells can be cultured to allow tau aggregates to form, wherein aggregates of the first tau repeat domain and the second tau repeat domain form in a subset of the seeded population of cells to produce an aggregation-positive population of cells and wherein aggregates do not form in a second subset of the seeded population of cells to produce an aggregation-negative population of cells. Finally, abundance of each of the plurality of unique guide RNAs can be determined in the aggregation-positive population of cells relative to the aggregation-negative population of cells and/or relative to the population of cells after being seeded and/or relative to the population of cells being cultured after introduction of the guide RNA library. Enrichment of a guide RNA in the aggregation-negative population of cells relative to the aggregation-positive population of cells and/or relative to the population of cells after being seeded and/or relative to the population of cells being cultured after introduction of the guide RNA library indicates that the gene targeted by the guide RNA is a genetic modifier of tau aggregation, wherein disruption of the gene targeted by the guide RNA prevents tau aggregation, or is a candidate genetic modifier of tau aggregation (e.g., for further testing via secondary screens), wherein disruption of the gene targeted by the guide RNA is expected to prevent tau aggregation. Likewise, depletion of a guide RNA in the aggregation-positive population of cells relative to the aggregation-negative population of cells and/or relative to the population of cells after being seeded and/or relative to the population of cells being cultured after introduction of the guide RNA library indicates that the gene targeted by the guide RNA is a genetic modifier of tau aggregation, wherein disruption of the gene targeted by the guide RNA prevents tau aggregation, or is a candidate genetic modifier of tau aggregation (e.g., for further testing via secondary screens), wherein disruption of the gene targeted by the guide RNA is expected to prevent tau aggregation. Enrichment of a guide RNA in the aggregation-positive population of cells relative to the aggregation-negative population of cells and/or relative to the population of cells after being seeded and/or relative to the population of cells being cultured after introduction of the guide RNA library indicates that the gene targeted by the guide RNA is a genetic modifier of tau aggregation, wherein disruption of the gene targeted by the guide RNA promotes or enhances tau aggregation, or is a candidate genetic modifier of tau aggregation (e.g., for further testing via secondary screens), wherein disruption of the gene targeted by the guide RNA is expected to promote or enhance tau aggregation. Likewise, depletion of a guide RNA in the aggregation-negative population of cells relative to the aggregation-positive population of cells and/or relative to the population of cells after being seeded and/or relative to the population of cells being cultured after introduction of the guide RNA library indicates that the gene targeted by the guide RNA is a genetic modifier of tau aggregation, wherein disruption of the gene targeted by the guide RNA promotes or enhances tau aggregation, or is a candidate genetic modifier of tau aggregation (e.g., for further testing via secondary screens), wherein disruption of the gene targeted by the guide RNA is expected to promote or enhance tau aggregation.

Similarly, the SAM/tau biosensor cell lines disclosed herein can be used in methods of screening for genetic modifiers of tau aggregation (e.g., that prevent tau aggregation or are expected to prevent tau aggregation). Such methods can comprise providing a population of SAM/tau biosensor cells as disclosed elsewhere herein, introducing a library comprising a plurality of unique guide RNAs, and assessing tau aggregation in the targeted cells.

As one example, a method can comprise providing a population of SAM/tau biosensor cells (e.g., a population of cells comprising a chimeric Cas protein comprising a nuclease-inactive Cas protein fused to one or more transcriptional activation domains, a chimeric adaptor protein comprising an adaptor protein fused to one or more transcriptional activation domains, a first tau repeat domain linked to a first reporter, and a second tau repeat domain linked to a second reporter), introducing into the population of cells a library comprising a plurality of unique guide RNAs that target a plurality of genes, and culturing the population of cells to allow transcriptional activation and expansion. The plurality of unique guide RNAs form complexes with the chimeric Cas protein and the chimeric adaptor protein, and the complexes activate transcription of the plurality of genes resulting in increased gene expression and a modified population of cells. The modified population of cells can then be contacted with a tau seeding agent to produce a seeded population of cells. For example, the tau seeding agent can be a "maximum seeding" agent as described elsewhere herein, such as cell lysates from tau-aggregation-positive cells. The seeded population of cells can be cultured to allow tau aggregates to form, wherein aggregates of the first tau repeat domain and the second tau repeat domain form in a subset of the seeded population of cells to produce an aggregation-positive population of cells and wherein aggregates do not form in a second subset of the seeded population of cells to produce an aggregation-negative population of cells. Finally, abundance of each of the plurality of unique guide RNAs can be determined in the aggregation-positive population of cells relative to the aggregation-negative population of cells and/or relative to the population of cells after being seeded and/or relative to the population of cells being cultured after introduction of the guide RNA library. Enrichment of a guide RNA in the aggregation-negative population of cells relative to the aggregation-positive population of cells and/or relative to the population of cells after being seeded and/or relative to the population of cells being cultured after introduction of the guide RNA library indicates that the gene targeted by the guide RNA is a genetic modifier of tau aggregation, wherein transcriptional activation of the gene targeted by the guide RNA prevents tau aggregation, or is a candidate genetic modifier of tau aggregation (e.g., for further testing via secondary screens), wherein transcriptional activation of the gene targeted by the guide RNA is expected to prevent tau aggregation. Likewise, depletion of a guide RNA in the aggregation-positive population of cells relative to the aggregation-negative population of cells and/or relative to the population of cells after being seeded and/or relative to the population of cells being cultured after introduction of the guide RNA library indicates that the gene targeted by the guide RNA is a genetic modifier of tau aggregation, wherein transcriptional activation of the gene targeted by the guide RNA prevents tau aggregation, or is a candidate genetic modifier of tau aggregation (e.g., for further testing via secondary screens), wherein transcriptional activation of the gene targeted by the guide RNA is expected to prevent tau aggregation. Enrichment of a guide RNA in the aggregation-positive population of cells relative to the aggregation-negative population of cells and/or relative to the population of cells after being seeded and/or relative to the population of cells being cultured after introduction of the guide RNA library indicates that the gene targeted by the guide RNA is a genetic modifier of tau aggregation, wherein transcriptional activation of the gene targeted by the guide RNA promotes or enhances tau aggregation, or is a candidate genetic modifier of tau aggregation (e.g., for further testing via secondary screens), wherein transcriptional activation of the gene targeted by the guide RNA is expected to promote or enhance tau aggregation. Likewise, depletion of a guide RNA in the aggregation-negative population of cells relative to the aggregation-positive population of cells and/or relative to the population of cells after being seeded and/or relative to the population of cells being cultured after introduction of the guide RNA library indicates that the gene targeted by the guide RNA is a genetic modifier of tau aggregation, wherein transcriptional activation of the gene targeted by the guide RNA promotes or enhances tau aggregation, or is a candidate genetic modifier of tau aggregation (e.g., for further testing via secondary screens), wherein transcriptional activation of the gene targeted by the guide RNA is expected to promote or enhance tau aggregation.

The Cas/tau biosensor cells used in the method can be any of the Cas/tau biosensor cells disclosed elsewhere herein. Likewise, the SAM/tau biosensor cells used in the method can be any of the SAM/tau biosensor cells disclosed elsewhere herein. The first tau repeat domain and the second tau repeat domain can be different or can be similar or the same. The tau repeat domain can be any of the tau repeat domains disclosed elsewhere herein. For example, the first tau repeat domain and/or the second tau repeat domain can be a wild type tau repeat domain or can comprise a pro-aggregation mutation (e.g., a pathogenic, pro-aggregation mutation), such as a tau P301S mutation. The first tau repeat domain and/or the second tau repeat domain can comprise a tau four-repeat domain. As one specific example, the first tau repeat domain and/or the second tau repeat domain can comprise, consist essentially of, or consist of SEQ ID NO: 11 or a sequence at least about 90%, 91%, 92%, 93%, 94%, 95%, 96%, 97%, 98%, or 99% identical to SEQ ID NO: 11. In one specific example, the nucleic acid encoding the tau repeat domain can comprise, consist essentially of, or consist of SEQ ID NO: 12 or a sequence at least about 90%, 91%, 92%, 93%, 94%, 95%, 96%, 97%, 98%, or 99% identical to SEQ ID NO: 12, optionally wherein the nucleic acid encodes a protein comprising, consisting essentially of, or consisting of SEQ ID NO: 11.

The first tau repeat domain can be linked to the first reporter and the second tau repeat domain can be linked to the second reporter by any means. For example, the reporter can be fused to the tau repeat domain (e.g., as part of a fusion protein). The reporter proteins can be any pair of reporter proteins that produce a detectable signal when the first tau repeat domain linked to the first reporter is aggregated with the second tau repeat domain linked to the second reporter. As one example, the first and second reporters can be a split luciferase protein. As another example, the first and second reporter proteins can be a fluorescence resonance energy transfer (FRET) pair. FRET is a physical phenomenon in which a donor fluorophore in its excited state non-radiatively transfers its excitation energy to a neighboring acceptor fluorophore, thereby causing the acceptor to emit its characteristic fluorescence. Examples of FRET pairs (donor and acceptor fluorophores) are well known. See, e.g., Bajar et al. (2016) Sensors (Basel) 16(9):1488, herein incorporated by reference in its entirety for all purposes. As one specific example of a FRET pair, the first reporter can be cyan fluorescent protein (CFP) and the second reporter can be yellow fluorescent protein (YFP). As a specific example, the CFP can comprise, consist essentially of, or consist of SEQ ID NO: 13 or a sequence at least about 90%, 91%, 92%, 93%, 94%, 95%, 96%, 97%, 98%, or 99% identical to SEQ ID NO: 13. As another specific example, the YFP can comprise, consist essentially of, or consist of SEQ ID NO: 15 or a sequence at least about 90%, 91%, 92%, 93%, 94%, 95%, 96%, 97%, 98%, or 99% identical to SEQ ID NO: 15.

For the Cas/tau biosensor cells, the Cas protein can be any Cas protein disclosed elsewhere herein. As one example, the Cas protein can be a Cas9 protein. For example, the Cas9 protein can be a *Streptococcus pyogenes* Cas9 protein. As one specific example, the Cas protein can comprise, consist essentially of, or consist of SEQ ID NO: 21 or a sequence at least about 90%, 91%, 92%, 93%, 94%, 95%, 96%, 97%, 98%, or 99% identical to SEQ ID NO: 21.

One or more or all of the Cas protein, the first tau repeat domain linked to the first reporter, and the second tau repeat domain linked to the second reporter can be stably expressed in the population of cells. For example, nucleic acids encoding one or more or all of the Cas protein, the first tau repeat domain linked to the first reporter, and the second tau repeat domain linked to the second reporter can be genomically integrated in the population of cells. In one specific example, the nucleic acid encoding the Cas protein can comprise, consist essentially of, or consist of SEQ ID NO: 22 or a sequence at least about 90%, 91%, 92%, 93%, 94%, 95%, 96%, 97%, 98%, or 99% identical to SEQ ID NO: 22, optionally wherein the nucleic acid encodes a protein comprising, consisting essentially of, or consisting of SEQ ID NO: 21.

For the SAM/tau biosensor cells, the Cas protein can be any Cas protein disclosed elsewhere herein. As one example, the Cas protein can be a Cas9 protein. For example, the Cas9 protein can be a *Streptococcus pyogenes* Cas9 protein. As one specific example, the chimeric Cas protein can comprise the nuclease-inactive Cas protein fused to a VP64 transcriptional activation domain. For example, the chimeric Cas protein can comprise from N-terminus to C-terminus: the nuclease-inactive Cas protein; a nuclear localization signal; and the VP64 transcriptional activator domain. As one specific example, the adaptor protein can be an MS2 coat protein, and the one or more transcriptional activation domains in the chimeric adaptor protein can comprise a p65 transcriptional activation domain and an HSF1 transcriptional activation domain. For example, the chimeric adaptor protein can comprise from N-terminus to C-terminus: the MS2 coat protein; a nuclear localization signal; the p65 transcriptional activation domain; and the HSF1 transcriptional activation domain. In one specific example, the nucleic acid encoding the chimeric Cas protein can comprise, consist essentially of, or consist of SEQ ID NO: 38 or a sequence at least about 90%, 91%, 92%, 93%, 94%, 95%, 96%, 97%, 98%, or 99% identical to SEQ ID NO: 38, optionally wherein the nucleic acid encodes a protein comprising, consisting essentially of, or consisting of SEQ ID NO: 36. In one specific example, the nucleic acid encoding the chimeric adaptor protein can comprise, consist essentially of, or consist of SEQ ID NO: 39 or a sequence at least about 90%, 91%, 92%, 93%, 94%, 95%, 96%, 97%, 98%, or 99% identical to SEQ ID NO: 39, optionally wherein the nucleic acid encodes a protein comprising, consisting essentially of, or consisting of SEQ ID NO: 37.

One or more or all of the chimeric Cas protein, the chimeric adaptor protein, the first tau repeat domain linked to the first reporter, and the second tau repeat domain linked to the second reporter can be stably expressed in the population of cells. For example, nucleic acids encoding one or more or all of the chimeric Cas protein, the chimeric adaptor protein, the first tau repeat domain linked to the first reporter, and the second tau repeat domain linked to the second reporter can be genomically integrated in the population of cells.

As disclosed elsewhere herein, the cells can be any type of cells. For example, the cells can be eukaryotic cells, mammalian cells, or human cells (e.g., HEK293T cells or neuronal cells).

The plurality of unique guide RNAs can be introduced into the population of cells by any known means. In some methods, the guide RNAs are introduced into the population of cells by viral transduction, such as retroviral, adenoviral, or lentiviral transduction. In a specific example, the guide RNAs can be introduced by lentiviral transduction. Each of the plurality of unique guide RNAs can be in a separate viral vector. The population of cells can be infected at any multiplicity of infection. For example, the multiplicity of infection can be between about 0.1 and about 1.0, between about 0.1 and about 0.9, between about 0.1 and about 0.8, between about 0.1 and about 0.7, between about 0.1 and about 0.6, between about 0.1 and about 0.5, between about 0.1 and about 0.4, or between about 0.1 and about 0.3. Alternatively, the multiplicity of infection can be less than about 1.0, less than about 0.9, less than about 0.8, less than about 0.7, less than about 0.6, less than about 0.5, less than about 0.4, less than about 0.3, or less than about 0.2. In a specific example, the multiplicity of infection can be less than about 0.3.

The guide RNAs can be introduced into the population of cells together with a selection marker or reporter gene to select for cells that have the guide RNAs, and the method can further comprise selecting cells that comprise the selection marker or reporter gene. Examples of selection markers and reporter genes are provided elsewhere herein. As one example, the selection marker can be one that imparts resistance to a drug, such as neomycin phosphotransferase, hygromycin B phosphotransferase, puromycin-N-acetyl-transferase, and blasticidin S deaminase. Another exemplary selection marker is bleomycin resistance protein, encoded by the Sh ble gene (*Streptoalloteichus hindustanus* bleomycin gene), which confers zeocin (phleomycin D1) resistance. For example, cells can be selected with a drug (e.g., puromycin) so that only cells transduced with a guide RNA construct are preserved for being used to carry out screening. For example, the drug can be puromycin or zeocin (phleomycin D1).

In some methods, the plurality of unique guide RNAs are introduced at a concentration selected such that a majority of the cells receive only one of the unique guide RNAs. For example, if the guide RNAs are being introduced by viral transduction, the cells can be infected at a low multiplicity of infection to ensure that most cells receive only one viral construct with high probability. As one specific example, the multiplicity of infection can be less than about 0.3.

The population of cells into which the plurality of unique guide RNAs is introduced can be any suitable number of cells. For example, the population of cells can comprise greater than about 50, greater than about 100, greater than about 200, greater than about 300, greater than about 400, greater than about 500, greater than about 600, greater than about 700, greater than about 800, greater than about 900, or greater than about 1000 cells per unique guide RNA. In a specific example, the population of cells comprises greater than about 300 cells or greater than about 500 cells per unique guide RNA.

The plurality of unique guide RNAs can target any number of genes. For example, the plurality of unique guide RNAs can target about 50 or more genes, about 100 or more genes, about 200 or more genes, about 300 or more genes, about 400 or more genes, about 500 or more genes, about 1000 or more genes, about 2000 or more genes, about 3000 or more genes, about 4000 or more genes, about 5000 or more genes, about 10000 or more genes, or about 20000 or more genes. In some methods, the guide RNAs can be selected to target genes in a particular signaling pathway. In some methods, the library of unique guide RNAs is a genome-wide library.

The plurality of unique guide RNAs can target any number of sequences within each individual targeted gene. In some methods, a plurality of target sequences are targeted on average in each of the targeted plurality of genes. For example, about 2 to about 10, about 2 to about 9, about 2 to about 8, about 2 to about 7, about 2 to about 6, about 2 to about 5, about 2 to about 4, or about 2 to about 3 unique target sequences can be targeted on average in each of the targeted plurality of genes. For example, at least about 2, at least about 3, at least about 4, at least about 5, or at least about 6 unique target sequences can be targeted on average in each of the targeted plurality of genes. As a specific example, about 6 target sequences can be targeted on average in each of the targeted plurality of genes. As another specific example, about 3 to about 6 or about 4 to about 6 target sequences are targeted on average in each of the targeted plurality of genes.

The guide RNAs can target any desired location in the target genes. In some CRISPRn methods using the Cas/tau biosensor cells, each guide RNA targets a constitutive exon if possible. In some methods, each guide RNA targets a 5' constitutive exon if possible. In some methods, each guide RNA targets a first exon, a second exon, or a third exon (from the 5' end of the gene) if possible. In some CRISPRa methods using the SAM/tau biosensor cells, each guide RNA can target a guide RNA target sequence within 200 bp upstream of a transcription start site, if possible. In some CRISPRa methods using the SAM/tau biosensor cells, wherein each guide RNA can comprise one or more adaptor-binding elements to which the chimeric adaptor protein can specifically bind. In one example, each guide RNA comprises two adaptor-binding elements to which the chimeric adaptor protein can specifically bind, optionally wherein a first adaptor-binding element is within a first loop of each of the one or more guide RNAs, and a second adaptor-binding element is within a second loop of each of the one or more guide RNAs. For example, the adaptor-binding element can comprise the sequence set forth in SEQ ID NO: 33. In a specific example, each of one or more guide RNAs is a single guide RNA comprising a CRISPR RNA (crRNA) portion fused to a transactivating CRISPR RNA (tracrRNA) portion, and the first loop is the tetraloop corresponding to residues 13-16 of SEQ ID NO: 17, 19, 30, or 31, and the second loop is the stem loop 2 corresponding to residues 53-56 of SEQ ID NO: 17, 19, 30, or 31.

The step of culturing the population of cells to allow genome editing and expansion can be any suitable period of time. For example, the culturing can be for between about 2 days and about 15 days, between about 3 days and about 13 days, between about 5 days and about 12 days, between about 7 days and about 11 days, or about 7 days or about 11 days. As another example, the culturing can be for between about 2 days and about 14 days, between about 3 days and about 12 days, between about 5 days and about 11 days, between about 7 days and about 10 days, or about 7 days or about 10 days. Likewise, the step of culturing the population of cells to allow transcriptional activation and expansion can be any suitable period of time. For example, the culturing can be for between about 2 days and about 15 days, between about 3 days and about 13 days, between about 5 days and about 12 days, between about 7 days and about 11 days, or about 7 days or about 11 days. Likewise, the step of culturing the population of cells to allow transcriptional activation and expansion can be any suitable period of time. For example, the culturing can be for between about 2 days and about 14 days, between about 3 days and about 12 days, between about 5 days and about 11 days, between about 7 days and about 10 days, or about 7 days or about 10 days.

Any suitable tau seeding agent can be used to produce a seeded population of cells. Suitable tau seeding agents are disclosed elsewhere herein. Some suitable seeding agents comprise a tau repeat domain that can be, for example, different from or similar to or the same as the first tau repeat domain and/or the second tau repeat domain. In one example, the seeding step comprises culturing the genetically modified population of cells in the presence of comprising a cell lysate from cultured tau-aggregation-positive cells in which a tau repeat domain stably presents in an aggregated state. Optionally, the genetically modified population of cells is not co-cultured with the tau-aggregation-positive cells in which a tau repeat domain stably presents in an aggregated state.

The amount or concentration of the cell lysate in the medium can be any suitable amount or concentration. For example, the concentration of cell lysate in the medium can be between about 0.1 µg/mL and about 50 µg/mL, between about 0.1 µg/mL and about 25 µg/mL, between about 0.1 µg/mL and about 10 µg/mL, between about 0.1 µg/mL and about 5 µg/mL, between about 0.1 µg/mL and about 4.5 µg/mL, between about 0.1 µg/mL and about 4 µg/mL, between about 0.1 µg/mL and about 3.5 µg/mL, between about 0.1 µg/mL and about 3 µg/mL, between about 0.1 µg/mL and about 2.5 µg/mL, between about 0.1 µg/mL and about 2 µg/mL, between about 0.1 µg/mL and about 1.5 µg/mL, between about 0.1 µg/mL and about 1 µg/mL, between about 0.5 µg/mL and about 50 µg/mL, between about 0.5 µg/mL and about 25 µg/mL, between about 0.5 µg/mL and about 10 µg/mL, between about 0.5 µg/mL and about 5 µg/mL, between about 0.5 µg/mL and about 4.5

μg/mL, between about 0.5 μg/mL and about 4 μg/mL, between about 0.5 μg/mL and about 3.5 μg/mL, between about 0.5 μg/mL and about 3 μg/mL, between about 0.5 μg/mL and about 2.5 μg/mL, between about 0.5 μg/mL and about 2 μg/mL, between about 0.5 μg/mL and about 1.5 μg/mL, between about 0.5 μg/mL and about 1 μg/mL, between about 1 μg/mL and about 50 μg/mL, between about 1 μg/mL and about 25 μg/mL, between about 1 μg/mL and about 10 μg/mL, between about 1 μg/mL and about 5 μg/mL, between about 1 μg/mL and about 4.5 μg/mL, between about 1 μg/mL and about 4 μg/mL, between about 1 μg/mL and about 3.5 μg/mL, between about 1 μg/mL and about 3 μg/mL, between about 1 μg/mL and about 2.5 μg/mL, between about 1 μg/mL and about 2 μg/mL, between about 1 μg/mL and about 1.5 μg/mL, between about 1.5 μg/mL and about 50 μg/mL, between about 1.5 μg/mL and about 25 μg/mL, between about 1.5 μg/mL and about 10 μg/mL, between about 1.5 μg/mL and about 5 μg/mL, between about 1.5 μg/mL and about 4.5 μg/mL, between about 1.5 μg/mL and about 4 μg/mL, between about 1.5 μg/mL and about 3.5 μg/mL, between about 1.5 μg/mL and about 3 μg/mL, between about 1.5 μg/mL and about 2.5 μg/mL, between about 1.5 μg/mL and about 2 μg/mL, between about 2 μg/mL and about 50 μg/mL, between about 2 μg/mL and about 25 μg/mL, between about 2 μg/mL and about 10 μg/mL, between about 2 μg/mL and about 5 μg/mL, between about 2 μg/mL and about 4.5 μg/mL, between about 2 μg/mL and about 4 μg/mL, between about 2 μg/mL and about 3.5 μg/mL, between about 2 μg/mL and about 3 μg/mL, between about 2 μg/mL and about 2.5 μg/mL, between about 2.5 μg/mL and about 50 μg/mL, between about 2.5 μg/mL and about 25 μg/mL, between about 2.5 μg/mL and about 10 μg/mL, between about 2.5 μg/mL and about 5 μg/mL, between about 2.5 μg/mL and about 4.5 μg/mL, between about 2.5 μg/mL and about 4 μg/mL, between about 2.5 μg/mL and about 3.5 μg/mL, or between about 2.5 μg/mL and about 3 μg/mL of medium (e.g., fresh culture medium). For example, the cell lysate in the culture medium can be at a concentration of between about 1 μg/mL and about 5 μg/mL or can be at a concentration of about 1.5 μg/mL, about 2 μg/mL, about 2.5 μg/mL, about 3 μg/mL, about 3.5 μg/mL, about 4 μg/mL, about 4.5 μg/mL, or about 5 μg/mL. Optionally, the cell lysate can be in a buffer, such as phosphate-buffered saline. Optionally, the buffer can comprise protease inhibitors. Examples of protease inhibitors include, but are not limited to, AEBSF, aprotinin, bestatin, E-64, leupeptin, pepstatin A, and ethylenediaminetetracetic acid (EDTA). The buffer can comprise any of these inhibitors or any combination thereof (e.g., the buffer can comprise all of these protease inhibitors).

The cells for producing the lysate can be collected in a buffer, such as phosphate-buffered saline. Optionally, the buffer can comprise protease inhibitors. Examples of protease inhibitors include, but are not limited to, AEBSF, aprotinin, bestatin, E-64, leupeptin, pepstatin A, and ethylenediaminetetracetic acid (EDTA). The buffer can comprise any of these inhibitors or any combination thereof (e.g., the buffer can comprise all of these protease inhibitors).

The cell lysate can, for example, be collected by sonicating the tau-aggregation-positive cells (e.g., cells collected in a buffer and protease inhibitors as described above) for any suitable amount of time. For example, the cells can be sonicated for between about 1 minute and about 6 minutes, between about 1 minute and about 5 minutes, between about 1 minute and about 4 minutes, between about 1 minute and about 3 minutes, between about 2 minutes and about 6 minutes, between about 2 minutes and about 5 minutes, between about 2 minutes and about 4 minutes, between about 2 minutes and about 3 minutes, between about 2 minutes and about 6 minutes, between about 3 minutes and about 5 minutes, or between about 3 minutes and about 4 minutes. For example, the cells can be sonicated for between about 2 minutes and about 4 minutes or for about 3 minutes.

Optionally, the medium comprises lipofectamine or liposomes (e.g., cationic liposomes) or phospholipids or another transfection agent. Optionally, the medium comprises lipofectamine. Optionally, the medium does not comprise lipofectamine or liposomes (e.g., cationic liposomes) or phospholipids or another transfection agent. Optionally, the medium does not comprise lipofectamine. The amount or concentration of the lipofectamine or liposomes (e.g., cationic liposomes) or phospholipids or other transfection agent in the medium can be any suitable amount or concentration. For example, the concentration of lipofectamine or liposomes (e.g., cationic liposomes) or phospholipids or other transfection agent in the medium can be between about 0.5 μL/mL to about 10 μL/mL, between about 0.5 μL/mL to about 5 μL/mL, between about 0.5 μL/mL to about 4.5 μL/mL, between about 0.5 μL/mL to about 4 μL/mL, between about 0.5 μL/mL to about 3.5 μL/mL, between about 0.5 μL/mL to about 3 μL/mL, between about 0.5 μL/mL to about 2.5 μL/mL, between about 0.5 μL/mL to about 2 μL/mL, between about 0.5 μL/mL to about 1.5 μL/mL, between about 0.5 μL/mL to about 1 μL/mL, between about 1 μL/mL to about 10 μL/mL, between about 1 μL/mL to about 5 μL/mL, between about 1 μL/mL to about 4.5 μL/mL, between about 1 μL/mL to about 4 μL/mL, between about 1 L/mL to about 3.5 μL/mL, between about 1 μL/mL to about 3 μL/mL, between about 1 μL/mL to about 2.5 μL/mL, between about 1 μL/mL to about 2 μL/mL, between about 1 μL/mL to about 1.5 μL/mL, between about 1.5 μL/mL to about 10 μL/mL, between about 1.5 μL/mL to about 5 L/mL, between about 1.5 μL/mL to about 4.5 μL/mL, between about 1.5 μL/mL to about 4 L/mL, between about 1.5 μL/mL to about 3.5 μL/mL, between about 1.5 μL/mL to about 3 L/mL, between about 1.5 μL/mL to about 2.5 μL/mL, between about 1.5 μL/mL to about 2 L/mL, between about 2 μL/mL to about 10 μL/mL, between about 2 μL/mL to about 5 μL/mL, between about 2 μL/mL to about 4.5 μL/mL, between about 2 μL/mL to about 4 μL/mL, between about 2 μL/mL to about 3.5 μL/mL, between about 2 μL/mL to about 3 μL/mL, or between about 2 μL/mL to about 2.5 μL/mL of medium (e.g., fresh medium). For example, the concentration of lipofectamine or liposomes (e.g., cationic liposomes) or phospholipids or other transfection agent in the medium can be between about 1.5 μL/mL and about 4 μL/mL or it can be about 1.5 L/mL, about 2 L/mL, about 2.5 L/mL, about 3 L/mL, about 3.5 L/mL, or about 4 L/mL.

The step of culturing the seeded population of cells to allow tau aggregates to form, wherein aggregates of the first tau repeat domain and the second tau repeat domain form in a subset of the seeded population of cells to produce an aggregation-positive population of cells, can be any suitable length of time. For example, the culturing can be for between about 1 day and about 7 days, between about 2 days and about 6 days, between about 3 days and about 5 days, between about 1 day and about 3 days, or about 2 days. Aggregation can be determined by any suitable means, depending on the reporters used. For example, in methods in which the first reporter and the second reporter are a fluorescence resonance energy transfer (FRET) pair, the aggregation-positive population of cells can be identified by flow cytometry.

Abundance of guide RNAs can be determined by any suitable means. In a specific example, abundance is determined by next-generation sequencing. Next-generation sequencing refers to non-Sanger-based high-throughput DNA sequencing technologies. For example, determining abundance of a guide RNA can comprise measuring read counts of the guide RNA.

In some methods, a guide RNA is considered enriched in aggregation-negative cells if the abundance of the guide RNA relative to the total population of the plurality of unique guide RNAs is at least 1.5-fold higher in the aggregation-negative population of cells relative to the aggregation-positive population of cells and/or the seeded population of cells. In some methods, a guide RNA is considered depleted in aggregation-positive cells if the abundance of the guide RNA relative to the total population of the plurality of unique guide RNAs is at least 1.5-fold lower in the aggregation-positive population of cells relative to the aggregation-negative population of cells and/or the seeded population of cells. Different enrichment/depletion thresholds can also be used. For example, an enrichment/depletion threshold can be set higher to be more stringent (e.g., at least about 1.6-fold, at least about 1.7-fold, at least about 1.8-fold, at least about 1.9-fold, at least about 2-fold, at least about 2.5-fold, or at least about 2.5-fold). Alternatively, an enrichment/depletion threshold can be set lower to be less stringent (e.g., at least about 1.4-fold, at least about 1.3-fold, or at least about 1.2-fold).

Alternatively, in some methods, a guide RNA is considered enriched in aggregation-positive cells if the abundance of the guide RNA relative to the total population of the plurality of unique guide RNAs is at least 1.5-fold higher in the aggregation-positive population of cells relative to the aggregation-negative population of cells and/or the seeded population of cells. In some methods, a guide RNA is considered depleted in aggregation-negative cells if the abundance of the guide RNA relative to the total population of the plurality of unique guide RNAs is at least 1.5-fold lower in the aggregation-negative population of cells relative to the aggregation-positive population of cells and/or the seeded population of cells. Different enrichment/depletion thresholds can also be used. For example, an enrichment/depletion threshold can be set higher to be more stringent (e.g., at least about 1.6-fold, at least about 1.7-fold, at least about 1.8-fold, at least about 1.9-fold, at least about 2-fold, at least about 2.5-fold, or at least about 2.5-fold). Alternatively, an enrichment/depletion threshold can be set lower to be less stringent (e.g., at least about 1.4-fold, at least about 1.3-fold, or at least about 1.2-fold).

In one example, the step of determining abundance can comprise determining abundance of the plurality of unique guide RNAs in the aggregation-positive population relative to the aggregation-negative population and/or relative to the population of cells cultured after introduction of the guide RNA library at a first time point and/or relative to the seeded population of cells at a second time point. Likewise, the step of determining abundance can comprise determining abundance of the plurality of unique guide RNAs in the aggregation-negative population relative to the aggregation-positive population and/or relative to the population of cells cultured after introduction of the guide RNA library at a first time point and/or relative to the seeded population of cells at a second time point. For example, the first time point can be at a first passage of culturing the population of cells or in the middle of culturing the population of cells to allow genome editing and expansion. For example, the first time point can be after a sufficient amount of time for the guide RNAs to form complexes with the Cas protein, and for the Cas protein to cleave the plurality of genes resulting in knockout of gene function (CRISPRn) or to transcriptionally activate the plurality of genes (CRISPRa). However, in some cases, the first time point should ideally be at the first cell passage to determine the gRNA library representation soon after infection (i.e., before further expansion and genome editing) and to determine if each gRNA representation evolves from the first time point to the second time points and to any additional time points to a final time point. This allows ruling out enriched gRNAs/targets due to cell growth advantages during the course of the screen by verifying gRNA abundance is unchanged between the first and second time points. As a specific example, the first time point can be after about 1 day, about 2 days, about 3 days, or about 4 days of culturing and expansion (e.g., at about 3 days of culture and expansion), and the second time point can be after about 5 days, about 6 days, about 7 days, about 8 days, about 9 days, about 10 days, or about 11 days of culturing and expansion. For example, the first time point can be after about 3 days of culturing and expansion, and the second time point can be after about 7 days or about 10 days of culturing and expansion.

In some methods, a gene can then be considered a genetic modifier of tau aggregation, wherein disruption (CRISPRn) or transcriptional activation (CRISPRa) of the gene prevents (or is expected to prevent) tau aggregation, if the abundance of a guide RNA targeting the gene relative to the total population of the plurality of unique guide RNAs is at least 1.5-fold higher in the aggregation-negative population of cells relative to the aggregation-positive population of cells, the cultured population of cells at the first time point, and the seeded population of cells at the second time point. Alternatively or additionally, a gene can then be considered a genetic modifier of tau aggregation, wherein disruption (CRISPRn) or transcriptional activation (CRISPRa) of the gene prevents (or is expected to prevent) tau aggregation, if the abundance of a guide RNA targeting the gene relative to the total population of the plurality of unique guide RNAs is at least 1.5-fold higher in the aggregation-negative population of cells relative to the aggregation-positive population of cells and the seeded population of cells at the second time point. Alternatively or additionally, a gene can then be considered a genetic modifier of tau aggregation, wherein disruption (CRISPRn) or transcriptional activation (CRISPRa) of the gene prevents (or is expected to prevent) tau aggregation, if the abundance of a guide RNA targeting the gene relative to the total population of the plurality of unique guide RNAs is at least 1.5-fold lower in the aggregation-positive population of cells relative to the aggregation-negative population of cells, the cultured population of cells at the first time point, and the seeded population of cells at the second time point. Alternatively or additionally, a gene can then be considered a genetic modifier of tau aggregation, wherein disruption (CRISPRn) or transcriptional activation (CRISPRa) of the gene prevents (or is expected to prevent) tau aggregation, if the abundance of a guide RNA targeting the gene relative to the total population of the plurality of unique guide RNAs is at least 1.5-fold lower in the aggregation-positive population of cells relative to the aggregation-negative population of cells and the seeded population of cells at the second time point.

Alternatively, in one example, the step of determining abundance can comprise determining abundance of the plurality of unique guide RNAs in the aggregation-negative population relative to the aggregation-positive population and/or relative to the population of cells cultured after introduction of the guide RNA library at a first time point and/or relative to the seeded population of cells at a second time point. Likewise, the step of determining abundance can comprise determining abundance of the plurality of unique guide RNAs in the aggregation-positive population relative to the aggregation-negative population and/or relative to the population of cells cultured after introduction of the guide RNA library at a first time point and/or relative to the seeded population of cells at a second time point. For example, the first time point can be at a first passage of culturing the population of cells or in the middle of culturing the population of cells to allow genome editing and expansion. For example, the first time point can be after a sufficient amount of time for the guide RNAs to form complexes with the Cas protein, and for the Cas protein to cleave the plurality of genes resulting in knockout of gene function (CRISPRn) or to transcriptionally activate the plurality of genes (CRISPRa). However, in some cases, the first time point should ideally be at the first cell passage to determine the gRNA library representation soon after infection (i.e., before further expansion and genome editing) and to determine if each gRNA representation evolves from the first time point to the second time points and to any additional time points to a final time point. This allows ruling out enriched gRNAs/targets due to cell growth advantages during the course of the screen by verifying gRNA abundance is unchanged between the first and second time points. As a specific example, the first time point can be after about 1 day, about 2 days, about 3 days, or about 4 days of culturing and expansion (e.g., at about 3 days of culture and expansion), and the second time point can be after about 5 days, about 6 days, about 7 days, about 8 days, about 9 days, about 10 days, or about 11 days of culturing and expansion. For example, the first time point can be after about 3 days of culturing and expansion, and the second time point can be after about 7 days or about 10 days of culturing and expansion.

In some methods, a gene can then be considered a genetic modifier of tau aggregation, wherein disruption (CRISPRn) or transcriptional activation (CRISPRa) of the gene promotes or enhances tau aggregation (or is expected to promote or enhance tau aggregation), if the abundance of a guide RNA targeting the gene relative to the total population of the plurality of unique guide RNAs is at least 1.5-fold higher in the aggregation-positive population of cells relative to the aggregation-negative population of cells, the cultured population of cells at the first time point, and the seeded population of cells at the second time point. Alternatively or additionally, a gene can then be considered a genetic modifier of tau aggregation, wherein disruption (CRISPRn) or transcriptional activation (CRISPRa) of the gene promotes or enhances tau aggregation (or is expected to promote or enhance tau aggregation), if the abundance of a guide RNA targeting the gene relative to the total population of the plurality of unique guide RNAs is at least 1.5-fold lower in the aggregation-negative population of cells relative to the aggregation-positive population of cells, the cultured population of cells at the first time point, and the seeded population of cells at the second time point. Alternatively or additionally, a gene can then be considered a genetic modifier of tau aggregation, wherein disruption (CRISPRn) or transcriptional activation (CRISPRa) of the gene promotes or enhances tau aggregation (or is expected to promote or enhance tau aggregation), if the abundance of a guide RNA targeting the gene relative to the total population of the plurality of unique guide RNAs is at least 1.5-fold lower in the aggregation-negative population of cells relative to the aggregation-positive population of cells and the seeded population of cells at the second time point.

In some CRISPRn methods, the following steps are taken to identify a gene as a genetic modifier of tau aggregation, wherein disruption of the gene prevents (or is expected to prevent) tau aggregation. Likewise, in some CRISPRa methods, the following steps are taken to identify a gene as a genetic modifier of tau aggregation, wherein transcriptional activation of the gene prevents (or is expected to prevent) tau aggregation. The first step comprises identifying which of the plurality of unique guide RNAs are present in the aggregation-negative population of cells. The second step comprises calculating the random chance of the guide RNAs identified being present using the formula $nC_{n'}*(x-n')C(m-n)/xCm$, where x is the variety of unique guide RNAs introduced into the population of cells, m is the variety of unique guide RNAs identified in step (1), n is the variety of unique guide RNAs introduced into the population of cells that target the gene, and n' is the variety of unique guide RNAs identified in step (1) that target the gene. The third step comprises calculating average enrichment scores for the guide RNAs identified in step (1). The enrichment score for a guide RNA is the relative abundance of the guide RNA in the aggregation-negative population of cells divided by the relative abundance of the guide RNA in the aggregation-positive cells or the population of cells cultured after introduction of the guide RNA library or the seeded population of cells. The relative abundance is the read count of the guide RNA divided by the read count of the total population of the plurality of unique guide RNAs. The fourth step comprises selecting the gene if a guide RNA targeting the gene is significantly below the random chance of being present and above a threshold enrichment score. Possible threshold enrichment scores are discussed above. As a specific example, the threshold enrichment score can be set at about 1.5-fold.

Alternatively, in some CRISPRn methods, the following steps are taken to identify a gene as a genetic modifier of tau aggregation, wherein disruption of the gene promotes or enhances (or is expected to promote or enhance) tau aggregation. Likewise, in some CRISPRa methods, the following steps are taken to identify a gene as a genetic modifier of tau aggregation, wherein transcriptional activation of the gene promotes or enhances (or is expected to promote or enhance) tau aggregation. The first step comprises identifying which of the plurality of unique guide RNAs are present in the aggregation-positive population of cells. The second step comprises calculating the random chance of the guide RNAs identified being present using the formula $nC_{n'}*(x-n')C(m-n)/xCm$, where x is the variety of unique guide RNAs introduced into the population of cells, m is the variety of unique guide RNAs identified in step (1), n is the variety of unique guide RNAs introduced into the population of cells that target the gene, and n' is the variety of unique guide RNAs identified in step (1) that target the gene. The third step comprises calculating average enrichment scores for the guide RNAs identified in step (1). The enrichment score for a guide RNA is the relative abundance of the guide RNA in the aggregation-positive population of cells divided by the relative abundance of the guide RNA in the aggregation-negative cells or the population of cells cultured after introduction of the guide RNA library or the seeded population of cells. The relative abundance is the read count of the guide RNA divided by the read count of the total population of the plurality of unique guide RNAs. The fourth step comprises selecting the gene if a guide RNA targeting the gene is significantly below the random chance of being present and above a threshold enrichment score. Possible threshold enrichment scores are discussed above. As a specific example, the threshold enrichment score can be set at about 1.5-fold.

Variety when used in the phrase variety of unique guide RNAs means the number of unique guide RNA sequences. It is not the abundance, but rather the qualitative "present" or "not present." Variety of unique guide RNAs means the number of unique guide RNA sequence. The variety of unique guide RNA is determined by next generation sequencing (NGS) to identify all the unique guide RNAs present in a cell population. It is done by using two primers that recognize the constant regions of the viral vector to amplify the gRNA that is between the constant regions and a primer that recognizes one constant region for sequencing. Each unique guide RNA present in the sample will generate read counts using the sequencing primer. The NGS results will include the sequence and also the number of reads corresponding to the sequence. The number of reads will be used for the enrichment score calculation for each guide RNA, and the presence of each unique sequence will tell us which guide RNAs are present. For instance, if there are three unique guide RNAs for a gene before selection, and all three are retained post-selection, then both n and n' are 3. These numbers are used for calculating the statistics but not the actual read counts. However, the read counts for each guide RNA (in one example, 100, 200, 50, which correspond to each of the 3 unique guide RNAs) will be used for the calculation of enrichment score.

VI. Methods of Screening for Genetic Modifiers of Tau Disaggregation

The Cas/tau biosensor cell lines disclosed herein can be used in methods of screening for genetic modifiers of tau disaggregation (e.g., that promote tau disaggregation). Such methods can comprise providing a population of tau-aggregation-positive Cas/tau biosensor cells as disclosed elsewhere herein, introducing a library comprising a plurality of unique guide RNAs, and assessing tau disaggregation in the targeted cells.

As one example, a method can comprise providing a population of Cas/tau biosensor cells (e.g., a population of cells comprising a Cas protein, a first tau repeat domain linked to a first reporter, and a second tau repeat domain linked to a second reporter), wherein the cells are tau-aggregation-positive cells in which a tau repeat domain stably presents in an aggregated state, introducing into the population of cells a library comprising a plurality of unique guide RNAs that target a plurality of genes, and culturing the population of cells to allow genome editing and expansion. The plurality of unique guide RNAs form complexes with the Cas protein, and the Cas protein cleaves the plurality of genes resulting in knockout of gene function to produce a genetically modified population of cells. The culturing results in an aggregation-positive population of cells and an aggregation-negative population of cells, which can then be identified. Finally, abundance of each of the plurality of unique guide RNAs can be determined in the aggregation-positive population of cells relative to the aggregation-negative population of cells and/or relative to the population of cells being cultured after introduction of the guide RNA library at one or more time points. Enrichment of a guide RNA in the aggregation-negative population of cells relative to the aggregation-positive population of cells and/or relative to the population of cells being cultured after introduction of the guide RNA library at one or more time points indicates that the gene targeted by the guide RNA is a genetic modifier of tau disaggregation, wherein disruption of the gene targeted by the guide RNA promotes tau disaggregation, or is a candidate genetic modifier of tau disaggregation (e.g., for further testing via secondary screens), wherein disruption of the gene targeted by the guide RNA is expected to promote tau disaggregation. Likewise, depletion of a guide RNA in the aggregation-positive population of cells relative to the aggregation-negative population of cells and/or relative to the population of cells being cultured after introduction of the guide RNA library at one or more time points indicates that the gene targeted by the guide RNA is a genetic modifier of tau disaggregation, wherein disruption of the gene targeted by the guide RNA promotes tau disaggregation, or is a candidate genetic modifier of tau disaggregation (e.g., for further testing via secondary screens), wherein disruption of the gene targeted by the guide RNA is expected to promote tau disaggregation. Enrichment of a guide RNA in the aggregation-positive population of cells relative to the aggregation-negative population of cells and/or relative to the population of cells being cultured after introduction of the guide RNA library at one or more time points indicates that the gene targeted by the guide RNA is a genetic modifier of tau aggregation, wherein disruption of the gene targeted by the guide RNA promotes or enhances tau aggregation, or is a candidate genetic modifier of tau aggregation (e.g., for further testing via secondary screens), wherein disruption of the gene targeted by the guide RNA is expected to promote or enhance tau aggregation. Likewise, depletion of a guide RNA in the aggregation-negative population of cells relative to the aggregation-positive population of cells and/or relative to the population of cells being cultured after introduction of the guide RNA library at one or more time points indicates that the gene targeted by the guide RNA is a genetic modifier of tau aggregation, wherein disruption of the gene targeted by the guide RNA promotes or enhances tau aggregation, or is a candidate genetic modifier of tau aggregation (e.g., for further testing via secondary screens), wherein disruption of the gene targeted by the guide RNA is expected to promote or enhance tau aggregation.

Similarly, the SAM/tau biosensor cell lines disclosed herein can be used in methods of screening for genetic modifiers of tau disaggregation (e.g., that promote tau disaggregation). Such methods can comprise providing a population of tau-aggregation-positive SAM/tau biosensor cells as disclosed elsewhere herein, introducing a library comprising a plurality of unique guide RNAs, and assessing tau disaggregation in the targeted cells.

As one example, a method can comprise providing a population of SAM/tau biosensor cells (e.g., a population of cells comprising a chimeric Cas protein comprising a nuclease-inactive Cas protein fused to one or more transcriptional activation domains, a chimeric adaptor protein comprising an adaptor protein fused to one or more transcriptional activation domains, a first tau repeat domain linked to a first reporter, and a second tau repeat domain linked to a second reporter), wherein the cells are tau-aggregation-positive cells in which a tau repeat domain stably presents in an aggregated state, introducing into the population of cells a library comprising a plurality of unique guide RNAs that target a plurality of genes, and culturing the population of cells to allow transcriptional activation and expansion. The plurality of unique guide RNAs form complexes with the chimeric Cas protein and the chimeric adaptor protein, and the complexes activate transcription of the plurality of genes resulting in increased gene expression and a modified population of cells. The culturing results in an aggregation-positive population of cells and an aggregation-negative population of cells, which can then be identified. Finally, abundance of each of the plurality of unique guide RNAs can be determined in the aggregation-positive population of cells relative to the aggregation-negative population of cells and/or relative to the population of cells being cultured after introduction of the guide RNA library at one or more time points. Enrichment of a guide RNA in the aggregation-negative population of cells relative to the aggregation-positive population of cells and/or relative to the population of cells being cultured after introduction of the guide RNA library at one or more time points indicates that the gene targeted by the guide RNA is a genetic modifier of tau disaggregation, wherein transcriptional activation of the gene targeted by the guide RNA promotes tau disaggregation, or is a candidate genetic modifier of tau disaggregation (e.g., for further testing via secondary screens), wherein transcriptional activation of the gene targeted by the guide RNA is expected to promote tau disaggregation. Likewise, depletion of a guide RNA in the aggregation-positive population of cells relative to the aggregation-negative population of cells and/or relative to the population of cells being cultured after introduction of the guide RNA library at one or more time points indicates that the gene targeted by the guide RNA is a genetic modifier of tau disaggregation, wherein transcriptional activation of the gene targeted by the guide RNA promotes tau disaggregation, or is a candidate genetic modifier of tau disaggregation (e.g., for further testing via secondary screens), wherein transcriptional activation of the gene targeted by the guide RNA is expected to promote tau disaggregation. Enrichment of a guide RNA in the aggregation-positive population of cells relative to the aggregation-negative population of cells and/or relative to the population of cells being cultured after introduction of the guide RNA library at one or more time points indicates that the gene targeted by the guide RNA is a genetic modifier of tau aggregation, wherein transcriptional activation of the gene targeted by the guide RNA promotes or enhances tau aggregation, or is a candidate genetic modifier of tau aggregation (e.g., for further testing via secondary screens), wherein transcriptional activation of the gene targeted by the guide RNA is expected to promote or enhance tau aggregation. Likewise, depletion of a guide RNA in the aggregation-negative population of cells relative to the aggregation-positive population of cells and/or relative to the population of cells being cultured after introduction of the guide RNA library at one or more time points indicates that the gene targeted by the guide RNA is a genetic modifier of tau aggregation, wherein transcriptional activation of the gene targeted by the guide RNA promotes or enhances tau aggregation, or is a candidate genetic modifier of tau aggregation (e.g., for further testing via secondary screens), wherein transcriptional activation of the gene targeted by the guide RNA is expected to promote or enhance tau aggregation.

The Cas/tau biosensor cells used in the method can be any of the Cas/tau biosensor cells disclosed elsewhere herein. Likewise, the SAM/tau biosensor cells used in the method can be any of the SAM/tau biosensor cells disclosed elsewhere herein. The first tau repeat domain and the second tau repeat domain can be different or can be similar or the same. The tau repeat domain can be any of the tau repeat domains disclosed elsewhere herein. For example, the first tau repeat domain and/or the second tau repeat domain can be a wild type tau repeat domain or can comprise a pro-aggregation mutation (e.g., a pathogenic, pro-aggregation mutation), such as a tau P301S mutation. The first tau repeat domain and/or the second tau repeat domain can comprise a tau four-repeat domain. As one specific example, the first tau repeat domain and/or the second tau repeat domain can comprise, consist essentially of, or consist of SEQ ID NO: 11 or a sequence at least about 90%, 91%, 92%, 93%, 94%, 95%, 96%, 97%, 98%, or 99% identical to SEQ ID NO: 11. In one specific example, the nucleic acid encoding the tau repeat domain can comprise, consist essentially of, or consist of SEQ ID NO: 12 or a sequence at least about 90%, 91%, 92%, 93%, 94%, 95%, 96%, 97%, 98%, or 99% identical to SEQ ID NO: 12, optionally wherein the nucleic acid encodes a protein comprising, consisting essentially of, or consisting of SEQ ID NO: 11.

The first tau repeat domain can be linked to the first reporter and the second tau repeat domain can be linked to the second reporter by any means. For example, the reporter can be fused to the tau repeat domain (e.g., as part of a fusion protein). The reporter proteins can be any pair of reporter proteins that produce a detectable signal when the first tau repeat domain linked to the first reporter is aggregated with the second tau repeat domain linked to the second reporter. As one example, the first and second reporters can be a split luciferase protein. As another example, the first and second reporter proteins can be a fluorescence resonance energy transfer (FRET) pair. FRET is a physical phenomenon in which a donor fluorophore in its excited state non-radiatively transfers its excitation energy to a neighboring acceptor fluorophore, thereby causing the acceptor to emit its characteristic fluorescence. Examples of FRET pairs (donor and acceptor fluorophores) are well known. See, e.g., Bajar et al. (2016) *Sensors (Basel)* 16(9):1488, herein incorporated by reference in its entirety for all purposes. As one specific example of a FRET pair, the first reporter can be cyan fluorescent protein (CFP) and the second reporter can be yellow fluorescent protein (YFP). As a specific example, the CFP can comprise, consist essentially of, or consist of SEQ ID NO: 13 or a sequence at least about 90%, 91%, 92%, 93%, 94%, 95%, 96%, 97%, 98%, or 99% identical to SEQ ID NO: 13. As another specific example, the YFP can comprise, consist essentially of, or consist of SEQ ID NO: 15 or a sequence at least about 90%, 91%, 92%, 93%, 94%, 95%, 96%, 97%, 98%, or 99% identical to SEQ ID NO: 15.

For the Cas/tau biosensor cells, the Cas protein can be any Cas protein disclosed elsewhere herein. As one example, the Cas protein can be a Cas9 protein. For example, the Cas9 protein can be a *Streptococcus pyogenes* Cas9 protein. As one specific example, the Cas protein can comprise, consist essentially of, or consist of SEQ ID NO: 21 or a sequence at least about 90%, 91%, 92%, 93%, 94%, 95%, 96%, 97%, 98%, or 99% identical to SEQ ID NO: 21.

One or more or all of the Cas protein, the first tau repeat domain linked to the first reporter, and the second tau repeat domain linked to the second reporter can be stably expressed in the population of cells. For example, nucleic acids encoding one or more or all of the Cas protein, the first tau repeat domain linked to the first reporter, and the second tau repeat domain linked to the second reporter can be genomically integrated in the population of cells. In one specific example, the nucleic acid encoding the Cas protein can comprise, consist essentially of, or consist of SEQ ID NO: 22 or a sequence at least about 90%, 91%, 92%, 93%, 94%, 95%, 96%, 97%, 98%, or 99% identical to SEQ ID NO: 22, optionally wherein the nucleic acid encodes a protein comprising, consisting essentially of, or consisting of SEQ ID NO: 21.

For the SAM/tau biosensor cells, the Cas protein can be any Cas protein disclosed elsewhere herein. As one example, the Cas protein can be a Cas9 protein. For example, the Cas9 protein can be a *Streptococcus pyogenes* Cas9 protein. As one specific example, the chimeric Cas protein can comprise the nuclease-inactive Cas protein fused to a VP64 transcriptional activation domain. For example, the chimeric Cas protein can comprise from N-terminus to C-terminus: the nuclease-inactive Cas protein; a nuclear localization signal; and the VP64 transcriptional activator domain. As one specific example, the adaptor protein can be an MS2 coat protein, and the one or more transcriptional activation domains in the chimeric adaptor protein can comprise a p65 transcriptional activation domain and an HSF1 transcriptional activation domain. For example, the chimeric adaptor protein can comprise from N-terminus to C-terminus: the MS2 coat protein; a nuclear localization signal; the p65 transcriptional activation domain; and the HSF1 transcriptional activation domain. In one specific example, the nucleic acid encoding the chimeric Cas protein can comprise, consist essentially of, or consist of SEQ ID NO: 38 or a sequence at least about 90%, 91%, 92%, 93%, 94%, 95%, 96%, 97%, 98%, or 99% identical to SEQ ID NO: 38, optionally wherein the nucleic acid encodes a protein comprising, consisting essentially of, or consisting of SEQ ID NO: 36. In one specific example, the nucleic acid encoding the chimeric adaptor protein can comprise, consist essentially of, or consist of SEQ ID NO: 39 or a sequence at least about 90%, 91%, 92%, 93%, 94%, 95%, 96%, 97%, 98%, or 99% identical to SEQ ID NO: 39, optionally wherein the nucleic acid encodes a protein comprising, consisting essentially of, or consisting of SEQ ID NO: 37.

One or more or all of the chimeric Cas protein, the chimeric adaptor protein, the first tau repeat domain linked to the first reporter, and the second tau repeat domain linked to the second reporter can be stably expressed in the population of cells. For example, nucleic acids encoding one or more or all of the chimeric Cas protein, the chimeric adaptor protein, the first tau repeat domain linked to the first reporter, and the second tau repeat domain linked to the second reporter can be genomically integrated in the population of cells.

As disclosed elsewhere herein, the cells can be any type of cells. For example, the cells can be eukaryotic cells, mammalian cells, or human cells (e.g., HEK293T cells or neuronal cells).

The plurality of unique guide RNAs can be introduced into the population of cells by any known means. In some methods, the guide RNAs are introduced into the population of cells by viral transduction, such as retroviral, adenoviral, or lentiviral transduction. In a specific example, the guide RNAs can be introduced by lentiviral transduction. Each of the plurality of unique guide RNAs can be in a separate viral vector. The population of cells can be infected at any multiplicity of infection. For example, the multiplicity of infection can be between about 0.1 and about 1.0, between about 0.1 and about 0.9, between about 0.1 and about 0.8, between about 0.1 and about 0.7, between about 0.1 and about 0.6, between about 0.1 and about 0.5, between about 0.1 and about 0.4, or between about 0.1 and about 0.3. Alternatively, the multiplicity of infection can be less than about 1.0, less than about 0.9, less than about 0.8, less than about 0.7, less than about 0.6, less than about 0.5, less than about 0.4, less than about 0.3, or less than about 0.2. In a specific example, the multiplicity of infection can be less than about 0.3.

The guide RNAs can be introduced into the population of cells together with a selection marker or reporter gene to select for cells that have the guide RNAs, and the method can further comprise selecting cells that comprise the selection marker or reporter gene. Examples of selection markers and reporter genes are provided elsewhere herein. As one example, the selection marker can be one that imparts resistance to a drug, such as neomycin phosphotransferase, hygromycin B phosphotransferase, puromycin-N-acetyltransferase, and blasticidin S deaminase. Another exemplary selection marker is bleomycin resistance protein, encoded by the Sh ble gene (*Streptoalloteichus hindustanus* bleomycin gene), which confers zeocin (phleomycin D1) resistance. For example, cells can be selected with a drug (e.g., puromycin) so that only cells transduced with a guide RNA construct are preserved for being used to carry out screening. For example, the drug can be puromycin or zeocin (phleomycin D1).

In some methods, the plurality of unique guide RNAs are introduced at a concentration selected such that a majority of the cells receive only one of the unique guide RNAs. For example, if the guide RNAs are being introduced by viral transduction, the cells can be infected at a low multiplicity of infection to ensure that most cells receive only one viral construct with high probability. As one specific example, the multiplicity of infection can be less than about 0.3.

The population of cells into which the plurality of unique guide RNAs is introduced can be any suitable number of cells. For example, the population of cells can comprise greater than about 50, greater than about 100, greater than about 200, greater than about 300, greater than about 400, greater than about 500, greater than about 600, greater than about 700, greater than about 800, greater than about 900, or greater than about 1000 cells per unique guide RNA. In a specific example, the population of cells comprises greater than about 300 cells or greater than about 500 cells per unique guide RNA.

The plurality of unique guide RNAs can target any number of genes. For example, the plurality of unique guide RNAs can target about 50 or more genes, about 100 or more genes, about 200 or more genes, about 300 or more genes, about 400 or more genes, about 500 or more genes, about 1000 or more genes, about 2000 or more genes, about 3000 or more genes, about 4000 or more genes, about 5000 or more genes, about 10000 or more genes, or about 20000 or more genes. In some methods, the guide RNAs can be selected to target genes in a particular signaling pathway. In some methods, the library of unique guide RNAs is a genome-wide library.

The plurality of unique guide RNAs can target any number of sequences within each individual targeted gene. In some methods, a plurality of target sequences are targeted on average in each of the targeted plurality of genes. For example, about 2 to about 10, about 2 to about 9, about 2 to about 8, about 2 to about 7, about 2 to about 6, about 2 to about 5, about 2 to about 4, or about 2 to about 3 unique target sequences can be targeted on average in each of the targeted plurality of genes. For example, at least about 2, at least about 3, at least about 4, at least about 5, or at least about 6 unique target sequences can be targeted on average in each of the targeted plurality of genes. As a specific example, about 6 target sequences can be targeted on average in each of the targeted plurality of genes. As another specific example, about 3 to about 6 or about 4 to about 6 target sequences are targeted on average in each of the targeted plurality of genes.

The guide RNAs can target any desired location in the target genes. In some CRISPRn methods using the Cas/tau biosensor cells, each guide RNA targets a constitutive exon if possible. In some methods, each guide RNA targets a 5' constitutive exon if possible. In some methods, each guide RNA targets a first exon, a second exon, or a third exon (from the 5' end of the gene) if possible. In some CRISPRa methods using the SAM/tau biosensor cells, each guide RNA can target a guide RNA target sequence within 200 bp upstream of a transcription start site, if possible. In some CRISPRa methods using the SAM/tau biosensor cells, wherein each guide RNA can comprise one or more adaptor-binding elements to which the chimeric adaptor protein can specifically bind. In one example, each guide RNA comprises two adaptor-binding elements to which the chimeric adaptor protein can specifically bind, optionally wherein a first adaptor-binding element is within a first loop of each of the one or more guide RNAs, and a second adaptor-binding element is within a second loop of each of the one or more guide RNAs. For example, the adaptor-binding element can comprise the sequence set forth in SEQ ID NO: 33. In a specific example, each of one or more guide RNAs is a single guide RNA comprising a CRISPR RNA (crRNA) portion fused to a transactivating CRISPR RNA (tracrRNA) portion, and the first loop is the tetraloop corresponding to residues 13-16 of SEQ ID NO: 17, 19, 30, or 31, and the second loop is the stem loop 2 corresponding to residues 53-56 of SEQ ID NO: 17, 19, 30, or 31.

The step of culturing the population of cells to allow genome editing and expansion can be any suitable period of time. For example, the culturing can be for between about 2 days and about 15 days, between about 3 days and about 14 days, between about 5 days and about 14 days, between about 7 days and about 14 days, between about 9 days and about 14 days, between about 10 days and about 14 days, between about 11 days and about 14 days, or between about 12 days and about 14 days. Likewise, the step of culturing the population of cells to allow transcriptional activation and expansion can be any suitable period of time. For example, the culturing can be for between about 2 days and about 15 days, between about 3 days and about 14 days, between about 5 days and about 14 days, between about 7 days and about 14 days, between about 9 days and about 14 days, between about 10 days and about 14 days, between about 11 days and about 14 days, or between about 12 days and about 14 days.

The step of identifying the aggregation-positive cell population and the aggregation-negative cell population can comprise synchronizing cell cycle progression. For example, this can be used to obtain a cell population predominantly enriched in the S phase or predominantly enriched in the G2 phase. As a specific example, the synchronization can be achieved by double thymidine block.

Aggregation can be determined by any suitable means, depending on the reporters used. For example, in methods in which the first reporter and the second reporter are a fluorescence resonance energy transfer (FRET) pair, the aggregation-positive population of cells can be identified by flow cytometry.

Abundance of guide RNAs can be determined by any suitable means. In a specific example, abundance is determined by next-generation sequencing. Next-generation sequencing refers to non-Sanger-based high-throughput DNA sequencing technologies. For example, determining abundance of a guide RNA can comprise measuring read counts of the guide RNA.

In some methods, a guide RNA is considered enriched in aggregation-negative cells if the abundance of the guide RNA relative to the total population of the plurality of unique guide RNAs is at least 1.5-fold higher in the aggregation-negative population of cells relative to the aggregation-positive population of cells and/or the cultured population of cells at one or more time points. In some methods, a guide RNA is considered depleted in aggregation-positive cells if the abundance of the guide RNA relative to the total population of the plurality of unique guide RNAs is at least 1.5-fold lower in the aggregation-positive population of cells relative to the aggregation-negative population of cells and/or the cultured population of cells at one or more time points. Different enrichment/depletion thresholds can also be used. For example, an enrichment/depletion threshold can be set higher to be more stringent (e.g., at least about 1.6-fold, at least about 1.7-fold, at least about 1.8-fold, at least about 1.9-fold, at least about 2-fold, at least about 2.5-fold, or at least about 2.5-fold). Alternatively, an enrichment/depletion threshold can be set lower to be less stringent (e.g., at least about 1.4-fold, at least about 1.3-fold, or at least about 1.2-fold).

In some methods, a guide RNA is considered enriched in aggregation-positive cells if the abundance of the guide RNA relative to the total population of the plurality of unique guide RNAs is at least 1.5-fold higher in the aggregation-positive population of cells relative to the aggregation-negative population of cells and/or the cultured population of cells at one or more time points. In some methods, a guide RNA is considered depleted in aggregation-negative cells if the abundance of the guide RNA relative to the total population of the plurality of unique guide RNAs is at least 1.5-fold lower in the aggregation-negative population of cells relative to the aggregation-positive population of cells and/or the cultured population of cells at one or more time points. Different enrichment/depletion thresholds can also be used. For example, an enrichment/depletion threshold can be set higher to be more stringent (e.g., at least about 1.6-fold, at least about 1.7-fold, at least about 1.8-fold, at least about 1.9-fold, at least about 2-fold, at least about 2.5-fold, or at least about 2.5-fold). Alternatively, an enrichment/depletion threshold can be set lower to be less stringent (e.g., at least about 1.4-fold, at least about 1.3-fold, or at least about 1.2-fold).

In one example, the step of determining abundance can comprise determining abundance of the plurality of unique guide RNAs in the aggregation-positive population relative to the aggregation-negative population and/or relative to the population of cells cultured after introduction of the guide RNA library at a first time point and/or relative to the population of cells cultured after introduction of the guide RNA library at a second time point. Likewise, the step of determining abundance can comprise determining abundance of the plurality of unique guide RNAs in the aggregation-negative population relative to the aggregation-positive population and/or relative to the population of cells cultured after introduction of the guide RNA library at a first time point and/or relative to the population of cells cultured after introduction of the guide RNA library at a second time point. For example, the first time point can be at a first passage of culturing the population of cells or in the middle of culturing the population of cells to allow genome editing and expansion, and the second time point can be in the middle of culturing the population of cells to allow genome editing and expansion. For example, the first time point can be after a sufficient amount of time for the guide RNAs to form complexes with the Cas protein, and for the Cas protein to cleave the plurality of genes resulting in knockout of gene function (CRISPRn) or to transcriptionally activate the plurality of genes (CRISPRa). However, in some cases, the first time point should ideally be at the first cell passage to determine the gRNA library representation soon after infection (i.e., before further expansion and genome editing) and to determine if each gRNA representation evolves from the first time point to the second time points and to any additional time points to a final time point. This allows ruling out enriched gRNAs/targets due to cell growth advantages during the course of the screen by verifying gRNA abundance is unchanged between the first and second time points. As a specific example, the first time point can be after about 1 day, about 2 days, about 3 days, about 4 days, about 5 days, about 6 days, about 7 days, or about 8 days of culturing and expansion (e.g., at about 7 days of culture and expansion), and the second time point can be after about 5 days, about 6 days, about 7 days, about 8 days, about 9 days, about 10 days, about 11 days, or about 12 days (e.g., about 10 days) of culturing and expansion. For example, the first time point can be after about 7 days of culturing and expansion, and the second time point can be after about 10 days of culturing and expansion.

In some methods, a gene can then be considered a genetic modifier of tau disaggregation, wherein disruption (CRISPRn) or transcriptional activation (CRISPRa) of the gene promotes (or is expected to promote) tau disaggregation, if the abundance of a guide RNA targeting the gene relative to the total population of the plurality of unique guide RNAs is at least 1.5-fold higher in the aggregation-negative population of cells relative to the aggregation-positive population of cells, the cultured population of cells at the first time point, and the cultured population of cells at the second time point. Alternatively or additionally, a gene can then be considered a genetic modifier of tau disaggregation, wherein disruption (CRISPRn) or transcriptional activation (CRISPRa) of the gene promotes (or is expected to promote) tau disaggregation, if the abundance of a guide RNA targeting the gene relative to the total population of the plurality of unique guide RNAs is at least 1.5-fold higher in the aggregation-negative population of cells relative to the aggregation-positive population of cells and the cultured population of cells at the second time point. Alternatively or additionally, a gene can then be considered a genetic modifier of tau disaggregation, wherein disruption (CRISPRn) or transcriptional activation (CRISPRa) of the gene promotes (or is expected to promote) tau disaggregation, if the abundance of a guide RNA targeting the gene relative to the total population of the plurality of unique guide RNAs is at least 1.5-fold lower in the aggregation-positive population of cells relative to the aggregation-negative population of cells, the cultured population of cells at the first time point, and the cultured population of cells at the second time point. Alternatively or additionally, a gene can then be considered a genetic modifier of tau disaggregation, wherein disruption (CRISPRn) or transcriptional activation (CRISPRa) of the gene promotes (or is expected to promote) tau disaggregation, if the abundance of a guide RNA targeting the gene relative to the total population of the plurality of unique guide RNAs is at least 1.5-fold lower in the aggregation-positive population of cells relative to the aggregation-negative population of cells and the cultured population of cells at the second time point.

In some methods, a gene can then be considered a genetic modifier of tau aggregation, wherein disruption (CRISPRn) or transcriptional activation (CRISPRa) of the gene promotes or enhances (or is expected to promote or enhance) tau aggregation, if the abundance of a guide RNA targeting the gene relative to the total population of the plurality of unique guide RNAs is at least 1.5-fold higher in the aggregation-positive population of cells relative to the aggregation-negative population of cells, the cultured population of cells at the first time point, and the cultured population of cells at the second time point. Alternatively or additionally, a gene can then be considered a genetic modifier of tau aggregation, wherein disruption (CRISPRn) or transcriptional activation (CRISPRa) of the gene promotes or enhances (or is expected to promote or enhance) tau aggregation, if the abundance of a guide RNA targeting the gene relative to the total population of the plurality of unique guide RNAs is at least 1.5-fold higher in the aggregation-positive population of cells relative to the aggregation-negative population of cells and the cultured population of cells at the second time point. Alternatively or additionally, a gene can then be considered a genetic modifier of tau aggregation, wherein disruption (CRISPRn) or transcriptional activation (CRISPRa) of the gene promotes or enhances (or is expected to promote or enhance) tau aggregation, if the abundance of a guide RNA targeting the gene relative to the total population of the plurality of unique guide RNAs is at least 1.5-fold lower in the aggregation-negative population of cells relative to the aggregation-positive population of cells, the cultured population of cells at the first time point, and the cultured population of cells at the second time point. Alternatively or additionally, a gene can then be considered a genetic modifier of tau aggregation, wherein disruption (CRISPRn) or transcriptional activation (CRISPRa) of the gene promotes or enhances (or is expected to promote or enhance) tau aggregation, if the abundance of a guide RNA targeting the gene relative to the total population of the plurality of unique guide RNAs is at least 1.5-fold lower in the aggregation-negative population of cells relative to the aggregation-positive population of cells and the cultured population of cells at the second time point.

In some CRISPRn methods, the following steps are taken to identify a gene as a genetic modifier of tau disaggregation, wherein disruption of the gene promotes (or is expected to promote) tau disaggregation. Likewise, in some CRISPRa methods, the following steps are taken to identify a gene as a genetic modifier of tau disaggregation, wherein transcriptional activation of the gene promotes (or is expected to promote) tau disaggregation. The first step comprises identifying which of the plurality of unique guide RNAs are present in the aggregation-negative population of cells. The second step comprises calculating the random chance of the guide RNAs identified being present using the formula $nC_{n'} * (x-n')C(m-n)/xCm$, where x is the variety of unique guide RNAs introduced into the population of cells, m is the variety of unique guide RNAs identified in step (1), n is the variety of unique guide RNAs introduced into the population of cells that target the gene, and n' is the variety of unique guide RNAs identified in step (1) that target the gene. The third step comprises calculating average enrichment scores for the guide RNAs identified in step (1). The enrichment score for a guide RNA is the relative abundance of the guide RNA in the aggregation-negative population of cells divided by the relative abundance of the guide RNA in the aggregation-positive cells or the population of cells cultured after introduction of the guide RNA library at the first or second time point. The relative abundance is the read count of the guide RNA divided by the read count of the total population of the plurality of unique guide RNAs. The fourth step comprises selecting the gene if a guide RNA targeting the gene is significantly below the random chance of being present and above a threshold enrichment score. Possible threshold enrichment scores are discussed above. As a specific example, the threshold enrichment score can be set at about 1.5-fold.

In some CRISPRn methods, the following steps are taken to identify a gene as a genetic modifier of tau aggregation, wherein disruption of the gene promotes or enhances (or is expected to promote or enhance) tau aggregation. Likewise, in some CRISPRa methods, the following steps are taken to identify a gene as a genetic modifier of tau aggregation, wherein transcriptional activation of the gene promotes or enhances (or is expected to promote or enhance) tau aggregation. The first step comprises identifying which of the plurality of unique guide RNAs are present in the aggregation-positive population of cells. The second step comprises calculating the random chance of the guide RNAs identified being present using the formula $nCn'*(x-n')C(m-n)/xCm$, where x is the variety of unique guide RNAs introduced into the population of cells, m is the variety of unique guide RNAs identified in step (1), n is the variety of unique guide RNAs introduced into the population of cells that target the gene, and n' is the variety of unique guide RNAs identified in step (1) that target the gene. The third step comprises calculating average enrichment scores for the guide RNAs identified in step (1). The enrichment score for a guide RNA is the relative abundance of the guide RNA in the aggregation-positive population of cells divided by the relative abundance of the guide RNA in the aggregation-negative cells or the population of cells cultured after introduction of the guide RNA library at the first or second time point. The relative abundance is the read count of the guide RNA divided by the read count of the total population of the plurality of unique guide RNAs. The fourth step comprises selecting the gene if a guide RNA targeting the gene is significantly below the random chance of being present and above a threshold enrichment score. Possible threshold enrichment scores are discussed above. As a specific example, the threshold enrichment score can be set at about 1.5-fold.

Variety when used in the phrase variety of unique guide RNAs means the number of unique guide RNA sequences. It is not the abundance, but rather the qualitative "present" or "not present." Variety of unique guide RNAs means the number of unique guide RNA sequence. The variety of unique guide RNA is determined by next generation sequencing (NGS) to identify all the unique guide RNAs present in a cell population. It is done by using two primers that recognize the constant regions of the viral vector to amplify the gRNA that is between the constant regions and a primer that recognizes one constant region for sequencing. Each unique guide RNA present in the sample will generate read counts using the sequencing primer. The NGS results will include the sequence and also the number of reads corresponding to the sequence. The number of reads will be used for the enrichment score calculation for each guide RNA, and the presence of each unique sequence will tell us which guide RNAs are present. For instance, if there are three unique guide RNAs for a gene before selection, and all three are retained post-selection, then both n and n' are 3. These numbers are used for calculating the statistics but not the actual read counts. However, the read counts for each guide RNA (in one example, 100, 200, 50, which correspond to each of the 3 unique guide RNAs) will be used for the calculation of enrichment score.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 2

Description of Sequences.

| SEQ ID NO | Type | Description |
|---|---|---|
| 1 | Protein | Tau R1 Repeat Domain |
| 2 | Protein | Tau R2 Repeat Domain |
| 3 | Protein | Tau R3 Repeat Domain |
| 4 | Protein | Tau R4 Repeat Domain |
| 5 | DNA | Tau R1 Repeat Domain Coding Sequence |
| 6 | DNA | Tau R2 Repeat Domain Coding Sequence |
| 7 | DNA | Tau R3 Repeat Domain Coding Sequence |
| 8 | DNA | Tau R4 Repeat Domain Coding Sequence |
| 9 | Protein | Tau Four-Repeat Domain (R1-R4; amino acids 243-375 of full-length (P10636-8) Tau) |
| 10 | DNA | Coding Sequence for Tau Four-Repeat Domain (R1-R4; coding sequence for amino acids 243-375 of full-length (P10636-8) Tau) |
| 11 | Protein | Tau Four-Repeat Domain (R1-R4) with P301S Mutation |
| 12 | DNA | Coding Sequence for Tau Four-Repeat Domain (R1-R4) with P301S Mutation |
| 13 | Protein | eCFP |
| 14 | DNA | eCFP Coding Sequence |

TABLE 2-continued

Description of Sequences.

| SEQ ID NO | Type | Description |
|---|---|---|
| 15 | Protein | eYFP |
| 16 | DNA | eYFP Coding Sequence |
| 17 | RNA | Guide RNA Scaffold V1 |
| 18 | RNA | Guide RNA Scaffold V2 |
| 19 | RNA | Guide RNA Scaffold V3 |
| 20 | RNA | Guide RNA Scaffold V4 |
| 21 | Protein | Cas9-FLAG |
| 22 | DNA | Cas9-FLAG Coding Sequence |
| 23 | RNA | crRNA Tail |
| 24 | RNA | TracrRNA |
| 25 | DNA | Guide RNA Target Sequence Plus PAM V1 |
| 26 | DNA | Guide RNA Target Sequence Plus PAM V2 |
| 27 | DNA | Guide RNA Target Sequence Plus PAM V3 |
| 28 | RNA | TracrRNA v2 |
| 29 | RNA | TracrRNA v3 |
| 30 | RNA | Guide RNA Scaffold V5 |
| 31 | RNA | Guide RNA Scaffold V6 |
| 32 | RNA | Guide RNA Scaffold V7 |
| 33 | RNA | MS2-binding loop |
| 34 | RNA | Guide RNA Scaffold with MS2-Binding Loops |
| 35 | RNA | Generic sgRNA with MS2-Binding Loops |
| 36 | Protein | dCas9-VP64 chimeric Cas protein |
| 37 | Protein | MCP-p65-HSF1 chimeric adaptor protein |
| 38 | DNA | DNA Encoding dCas9-VP64 chimeric Cas protein |
| 39 | DNA | DNA Encoding MCP-p65-HSF1 chimeric adaptor protein |
| 40 | Protein | MCP |
| 41 | DNA | DNA Encoding MCP |
| 42 | DNA | Lenti dCas9-VP64 |
| 43 | DNA | Lenti MCP-p65-HSF1 Hygro |

EXAMPLES

Example 1. Development of Genome-Wide CRISPR/Cas9 Screening Platform to Identify Genetic Modifiers of Tau Aggregation Abnormal aggregation or fibrillization of proteins is a defining feature of many diseases, notably including a number of neurodegenerative diseases such as Alzheimer's disease (AD), Parkinson's disease (PD), frontotemporal dementia (FTD), amyotrophic lateral sclerosis (ALS), chronic traumatic encephalopathy (CTE), Creutzfeldt-Jakob disease (CJD), and others. In many of these diseases, the fibrillization of certain proteins into insoluble aggregates is not only a hallmark of disease, but has also been implicated as a causative factor of neurotoxicity. Furthermore, these diseases are characterized by propagation of aggregate pathology through the central nervous system following stereotypical patterns, a process which correlates with disease progression. The identification of genes and genetic pathways that modify the processes of abnormal protein aggregation, or cell-to-cell propagation of aggregates, are therefore of great value in better understanding neurodegenerative disease etiology as well as in devising strategies for therapeutic intervention.

To identify genes and pathways that modify the processes of abnormal tau protein aggregation, a platform was developed for performing genome-wide screens with CRISPR nuclease (CRISPRn) sgRNA libraries to identify genes that regulate the potential of cells to be "seeded" by tau disease-associated protein aggregates (i.e. genes which, when disrupted, cause cells to be more susceptible to tau aggregate formation when exposed to a source of tau fibrillized protein). The identification of such genes may elucidate the mechanisms of tau cell-to-cell aggregate propagation and genetic pathways that govern the susceptibility of neurons to form tau aggregates in the context of neurodegenerative diseases.

Figure 1:
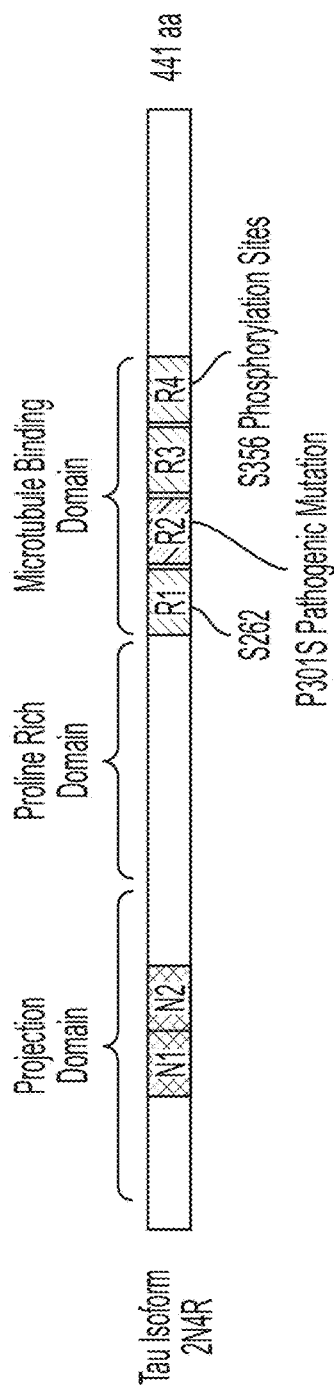
FIG. 1 (not to scale) shows a schematic of tau isoform 2N4R. The tau biosensor lines include only tau4RD-YFP and tau4RD-CFP as transgenes, not the full 2N4R.
Figure 2:
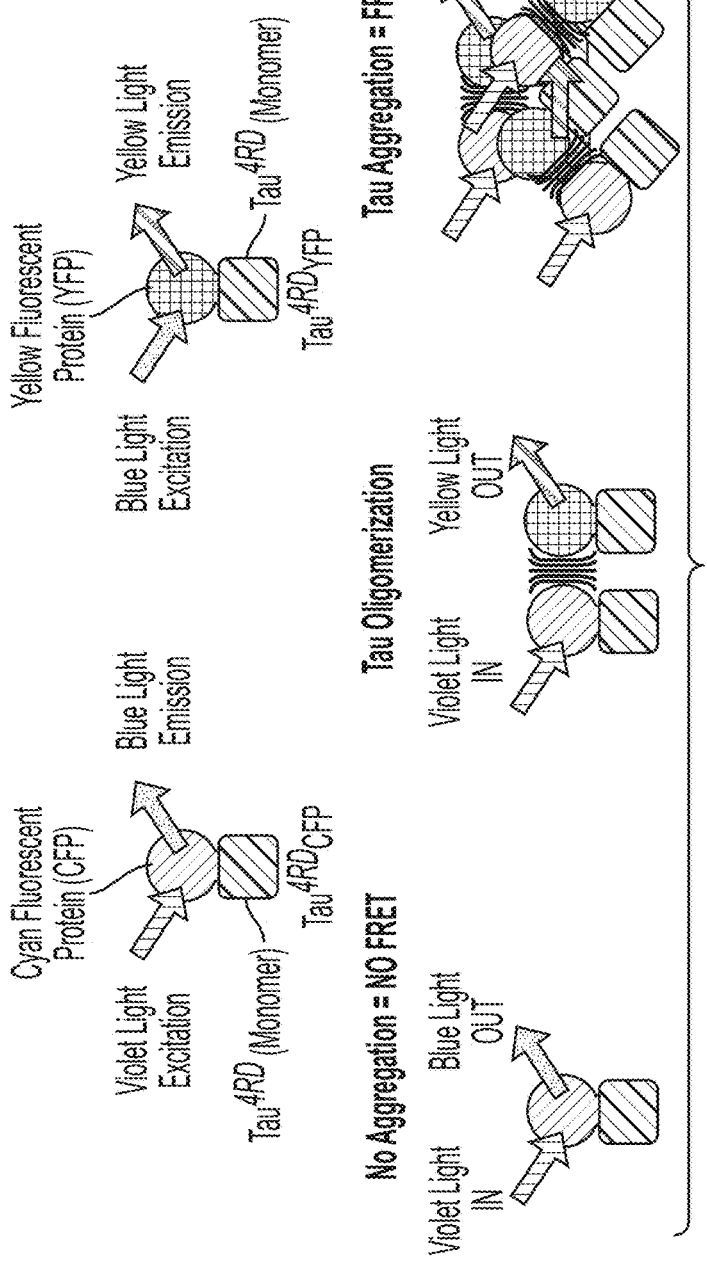
FIG. 2 shows a schematic of how aggregate formation is monitored by fluorescence resonance energy transfer (FRET) in tau biosensor cell lines. The tau$^{4RD}$-CFP protein is excited by violet light and emits blue light. The tau$^{4RD}$-YFP fusion protein is excited by blue light and emits yellow light. If there is no aggregation, excitation by violet light will not lead to FRET. If there is tau aggregation, excitation by violet light will lead to FRET and yellow light emission.

The screen employed a tau biosensor human cell line consisting of HEK293T cells stably expressing tau four-repeat domain, tau_4RD, comprising the tau microtubule binding domain (MBD) with the P301S pathogenic mutation, fused to either CFP or YFP. That is, the HEK293T cell lines contain two transgenes stably expressing disease-associated protein variants fused to the fluorescent protein CFP or the fluorescent protein YFP: tau$^{4RD}$-CFP/tau$^{4RD}$-YFP (TCY), wherein the tau repeat domain (4RD) comprises the P301S pathogenic mutation. See FIG. 1. In these biosensor lines, tau-CFP/tau-YFP protein aggregation produces a FRET signal, the result of a transfer of fluorescent energy from donor CFP to acceptor YFP. See FIG. 2. FRET-positive cells, which contain tau aggregates, can be sorted and isolated by flow cytometry. At baseline, unstimulated cells express the reporters in a stable, soluble state with minimal FRET signal. Upon stimulation (e.g., liposome transfection of seed particles), the reporter proteins form aggregates, producing a FRET signal. Aggregate-containing cells can be isolated by FACS. Stably propagating aggregate-containing cell lines, Agg[+], can be isolated by clonal serial dilution of Agg[−] cell lines.

Figure 3A:
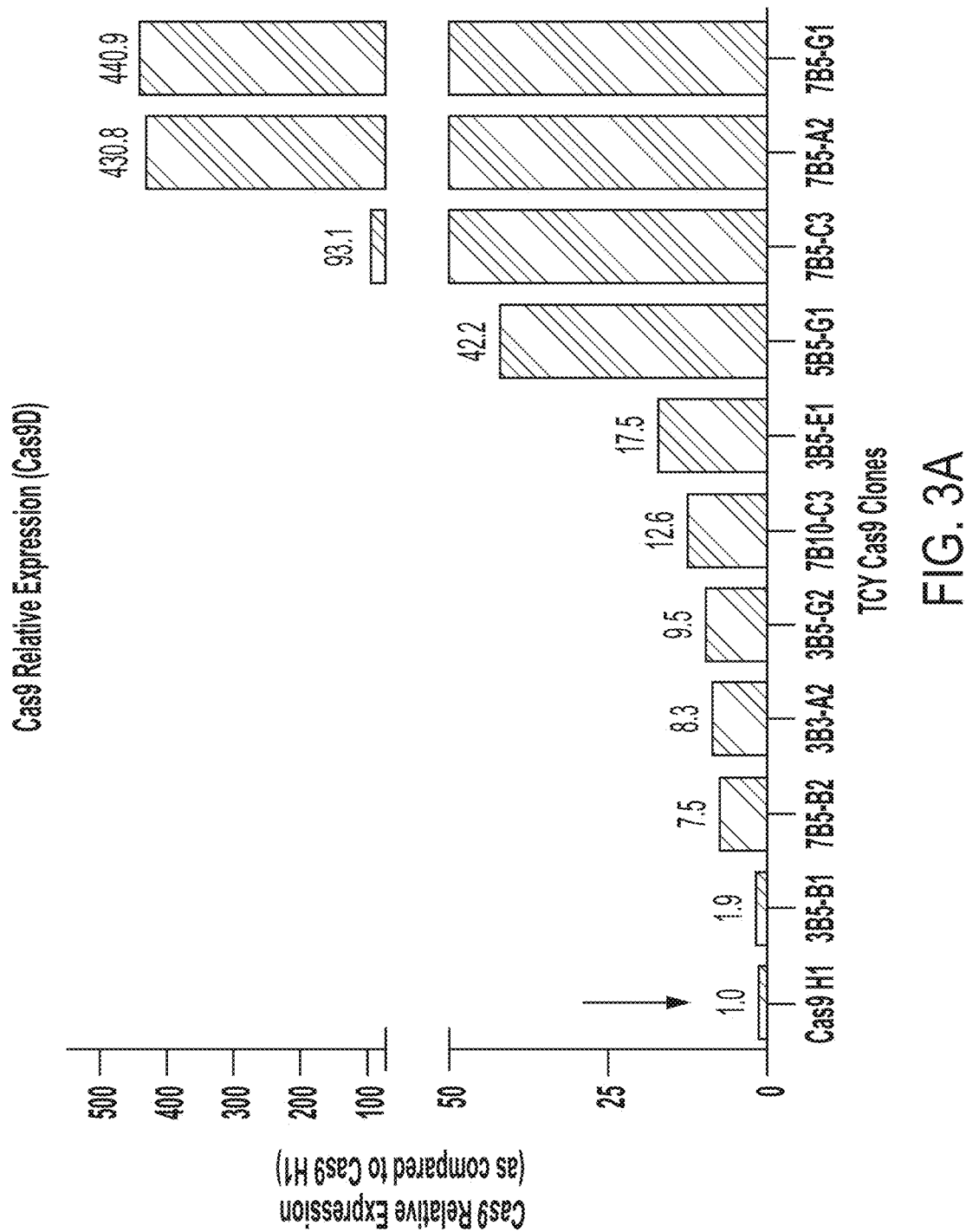
FIG. 3A shows relative Cas9 mRNA expression in tau$^{4RD}$-CFP/tau$^{4RD}$-YFP (TCY) biosensor cell clones transduced with lentiviral Cas9 expression constructs relative to clone Cas9H1, which is a control underperforming Cas9-expression TCY clone that was previously isolated.
Figure 3B:
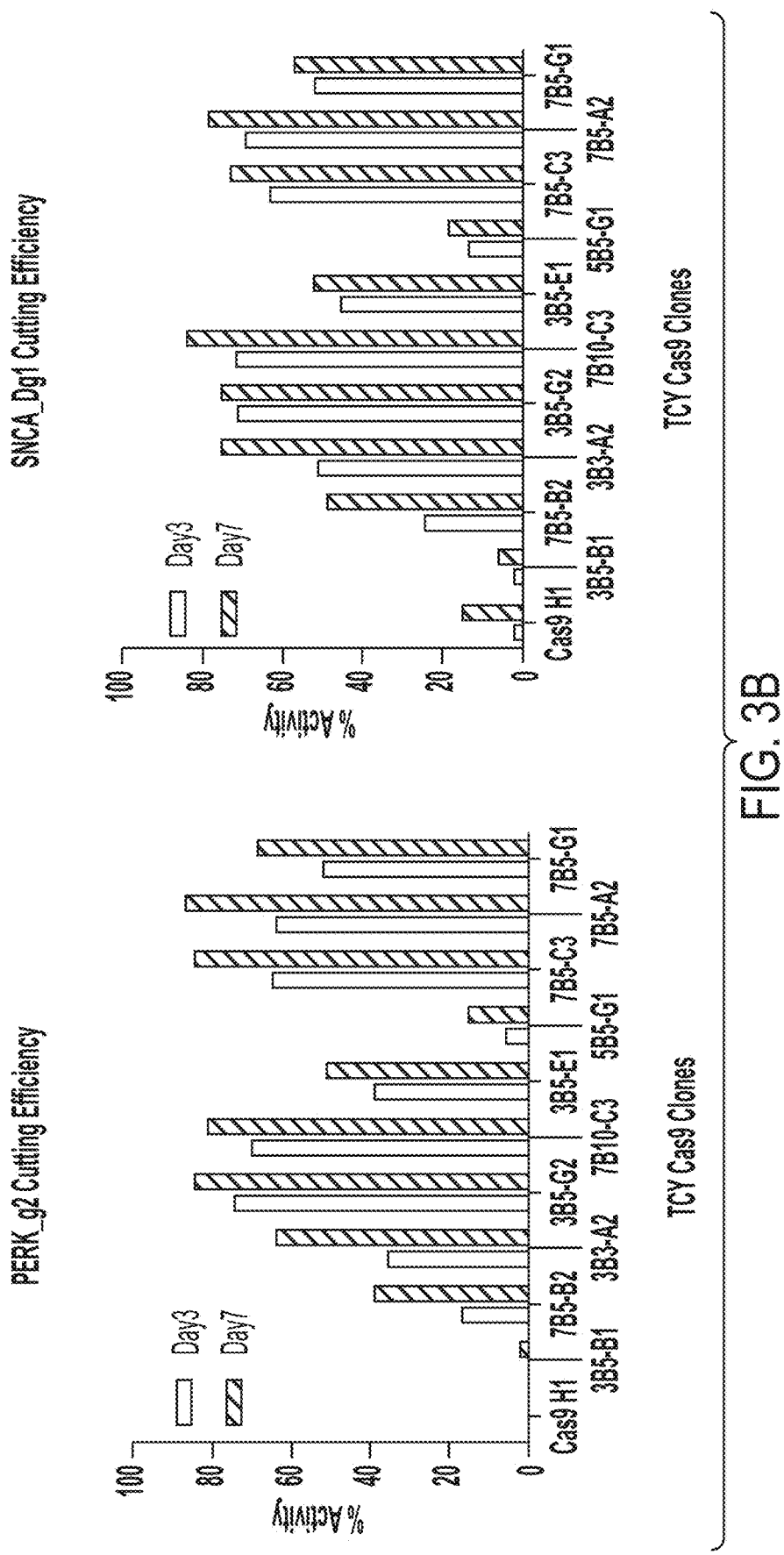
FIG. 3B shows cutting efficiency at the PERK locus and the SNCA locus in the Cas9 TCY clones three and seven days after transduction with sgRNAs targeting PERK and SNCA respectively.

Several modifications were made to this tau biosensor cell line to make it useful for genetic screening. First, these tau biosensor cells were modified by introducing a Cas9-expressing transgene (SpCas9) via a lentiviral vector. Clonal transgenic cell lines expressing Cas9 were selected with blasticidin and isolated by clonal serial dilution to obtain single-cell-derived clones. Clones were evaluated for level of Cas9 expression by qRT-PCR (FIG. 3A) and for DNA cleavage activity by digital PCR (FIG. 3B). Relative Cas9 expression levels are also shown in Table 3.

TABLE 3

Relative Cas9 Expression Levels.

| Clone Name | Cas9D Ct | | | | Cas9D AVG Ct | B2m AVG Ct | Cas9D-B2m delta Ct |
|---|---|---|---|---|---|---|---|
| | rep1 | rep2 | rep3 | rep4 | | | |
| 3B5-B1 | 26.22 | 26.31 | 26.36 | 26.45 | 26.33 | 22.01 | 4.33 |
| 3B5-G2 | 23.68 | 23.85 | 24.39 | 23.61 | 23.88 | 21.51 | 2.38 |
| 7B5-B2 | 23.63 | 23.60 | 24.12 | 23.50 | 23.71 | 21.38 | 2.34 |
| 3B3-A2 | 24.05 | 23.95 | 24.02 | 24.47 | 24.12 | 21.94 | 2.19 |
| 7B10-C3 | 22.58 | 22.71 | 22.67 | 23.20 | 22.79 | 21.19 | 1.59 |
| 3B5-E1 | 24.12 | 24.32 | 24.75 | 24.05 | 24.31 | 22.81 | 1.50 |
| 3B5-G1 | 21.16 | 21.14 | 21.09 | 21.43 | 21.20 | 21.35 | −0.15 |
| 7B5-C3 | 19.98 | 19.99 | 19.86 | 19.97 | 19.95 | 21.24 | −1.29 |
| 7B5-A2 | 18.84 | 18.74 | 19.33 | 18.99 | 18.97 | 22.10 | −3.12 |
| 7B5-G1 | 19.01 | 18.88 | 19.61 | 19.18 | 19.17 | 22.33 | −3.16 |

Specifically, Cas9 mutation efficiency was assessed by digital PCR 3 and 7 days after transduction of lentiviruses encoding gRNAs against two selected target genes. Cutting efficiency was limited by Cas9 levels in lower-expressing clones. A clone with an adequate level of Cas9 expression was needed to achieve maximum activity. Several derived clones with lower Cas9 expression were not able to cut target sequences efficiently, whereas clones with higher expression (including those used for screening) were able to generate mutations at target sequences in the genes PERK and SNCA with approximately 80% efficiency after three days in culture. Efficient cutting was observed already at 3 days after gRNA transduction with only marginal improvement after 7 days. Clone 7B10-C3 was selected as a high-performing clone to use for subsequent library screens.

Figure 5:
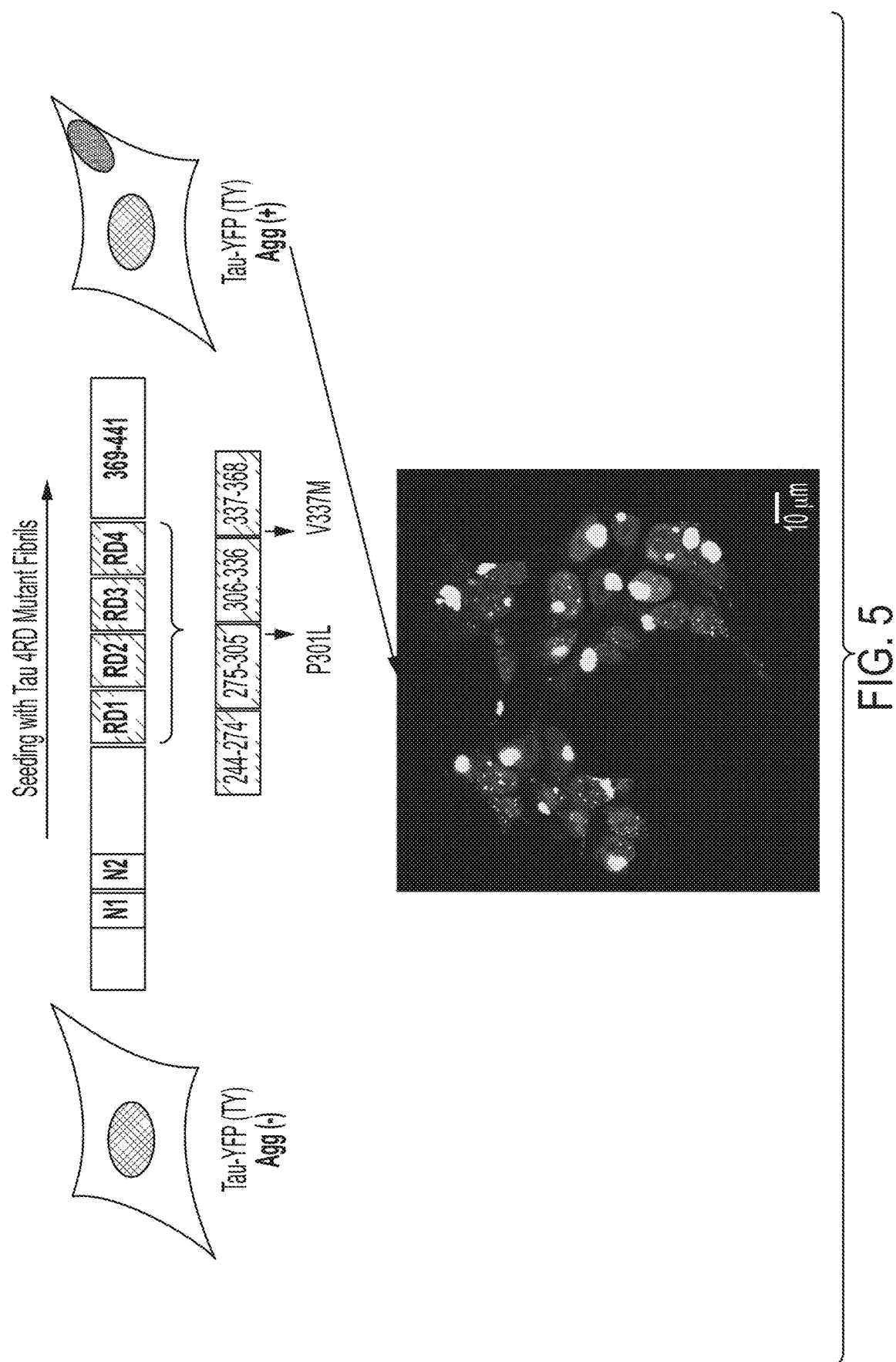
FIG. 5 is a schematic showing derivation of tau$^{4RD}$-YFP Agg[+] subclones containing stably propagating tau aggregates when tau$^{4RD}$-YFP cells are seeded with tau$^{41}$ fibrils. A fluorescence microscopy image showing the subclone with tau aggregates is also shown.
Figure 6:
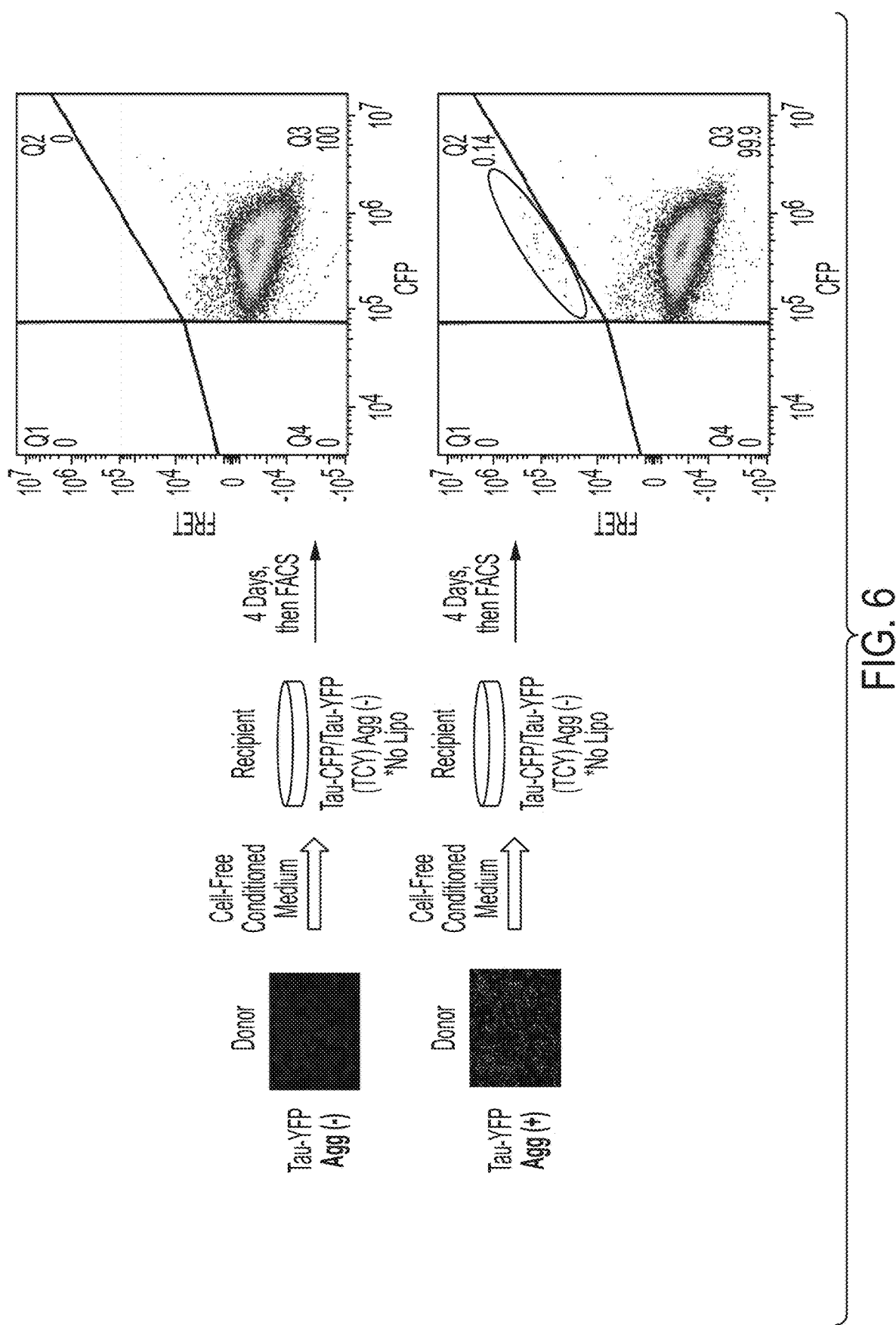
FIG. 6 is a schematic showing that conditioned medium from tau$^{4RD}$-YFP Agg[+] subclones collected after three days on confluent cells can provide a source of tau aggregation activity whereas medium from tau$^{4RD}$-YFP Agg[−] subclones does not. Conditioned medium was applied to recipient cells as 75% conditioned medium and 25% fresh medium. Fluorescence-activated cell sorting (FACS) analysis images are shown for each. The x-axis shows CFP (405 nm laser excitation), and the y-axis shows FRET (excitation from CFP emission). The upper right quadrant is FRET[+], the lower right quadrant is CFP[+], and the lower left quadrant is double-negative.

Second, reagents and a method were developed for sensitizing cells to tau seeding activity. Tau cell-to-cell propagation may result from tau aggregation activity secreted by aggregate-containing cells. To study cell propagation of tau aggregation, sub-clones were obtained of a tau-YFP cell line consisting of HEK293T cells stably expressing tau repeat domain, tau_4RD, comprising the tau microtubule binding domain (MBD) with the P301S pathogenic mutation, fused to YFP. See FIG. 5. Cells in which tau-YFP protein stably presents in an aggregated state (Agg[+]) were obtained by treating these tau-YFP cells with recombinant fibrillized tau mixed with lipofectamine reagent in order to seed the aggregation of the tau-YFP protein stably expressed by these cells. The "seeded" cells were then serially diluted to obtain single-cell-derived clones. These clones were then expanded to identify clonal cell lines in which tau-YFP aggregates stably persist in all cells with growth and multiple passages over time. One of these tau-YFP_Agg[+] clones, Clone_18, was used to produce conditioned medium by collecting medium that has been on confluent tau-YFP_Agg[+] cells for four days. Conditioned medium (CM) was then applied onto naïve biosensor tau-CFP/Tau-YFP cells at a ratio of 3:1 CM:fresh medium so that tau aggregation could be induced in a small percentage of these recipient cells. No lipofectamine was used. Lipofectamine was not used in order to have an assay that is as physiologic as possible, without tricking the recipient cells to force/increase tau aggregation using lipofectamine. As measured by using flow cytometry to assess the percentage of cells producing a FRET signal as a measure of aggregation, conditioned medium consistently induced FRET in approximately 0.1% of cells. See FIG. 6. In conclusion, tau-YFP_Agg[+] cells cannot produce a FRET signal, but they can provide a source of tau seeds.

Figure 4:
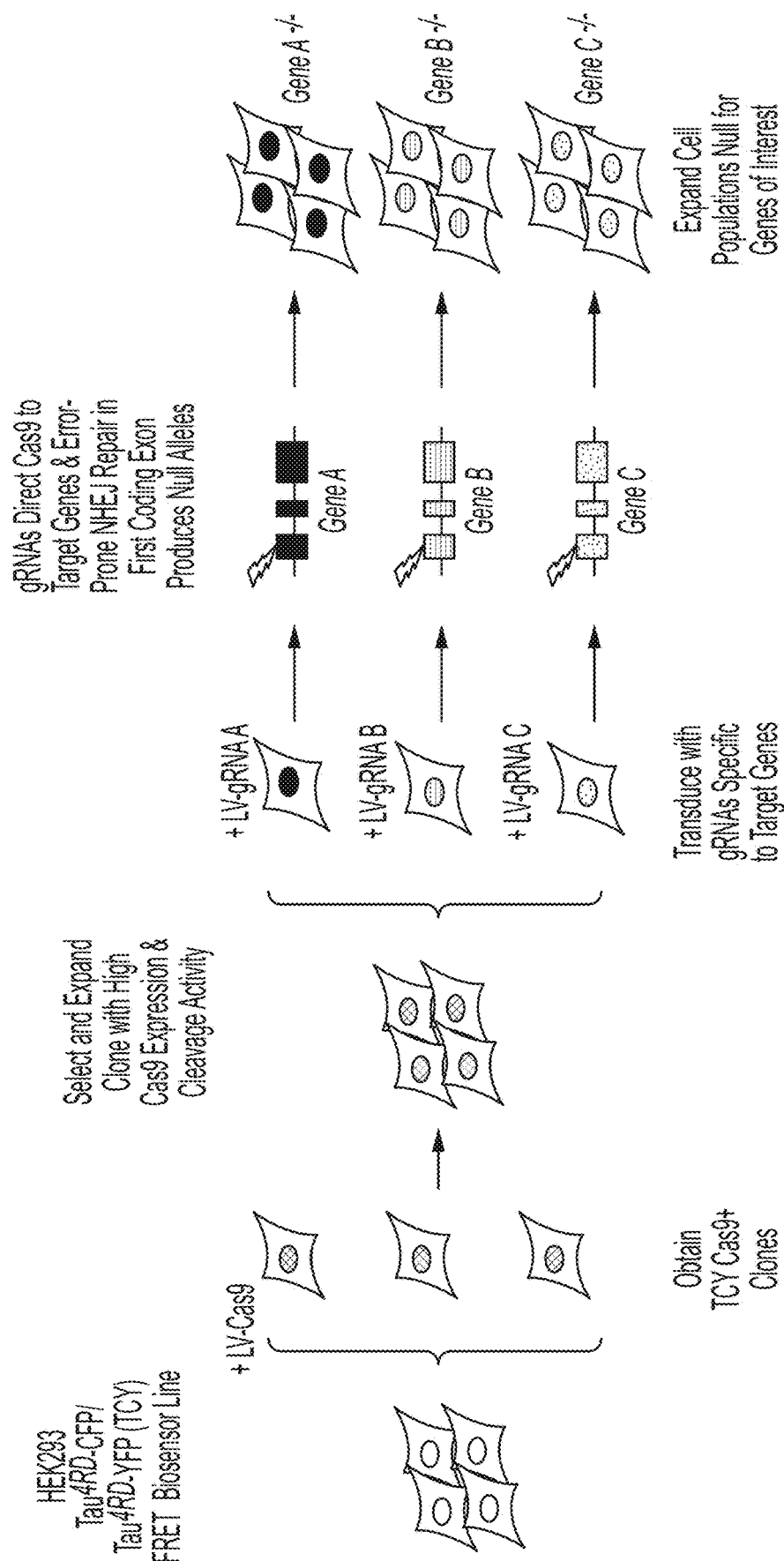
FIG. 4 shows a schematic of the strategy for disruption of target genes in Cas9 TCY biosensor cell using a genome-wide CRISPR/Cas9 sgRNA library.

Example 2. Genome-Wide CRISPR/Cas9 Screening to Identify Genetic Modifiers of Tau Aggregation To reveal modifier genes of tau aggregation as enriched sgRNAs in FRET[+] cells, the Cas9-expressing tau-CFP/tau-YFP biosensor cells without aggregates (Agg[−]) were transduced with two human genome-wide CRISPR sgRNA libraries using a lentiviral delivery approach to introduce knock-out mutations at each target gene. See FIG. 4. Each CRISPR sgRNA library targets 5' constitutive exons for functional knock-out with an average coverage of ~3 sgRNAs per gene (total of 6 gRNAs per gene in the two libraries combined). Read count distribution (i.e., the representation of each gRNA in the library) was normal and similar for each library. The sgRNAs were designed to avoid off-target effects by avoiding sgRNAs with two or fewer mismatches to off-target genomic sequences. The libraries cover 19,050 human genes and 1864 miRNA with 1000 non-targeting control sgRNAs. The libraries were transduced at a multiplicity of infection (MOI)<0.3 at a coverage of >300 cells per sgRNA. Tau biosensor cells were grown under puromycin selection to select cells with integration and expression of a unique sgRNA per cell. Puromycin selection began 24 h after transduction at 1 µg/mL. Five independent screening replicates were used in the primary screen.

Figure 7:
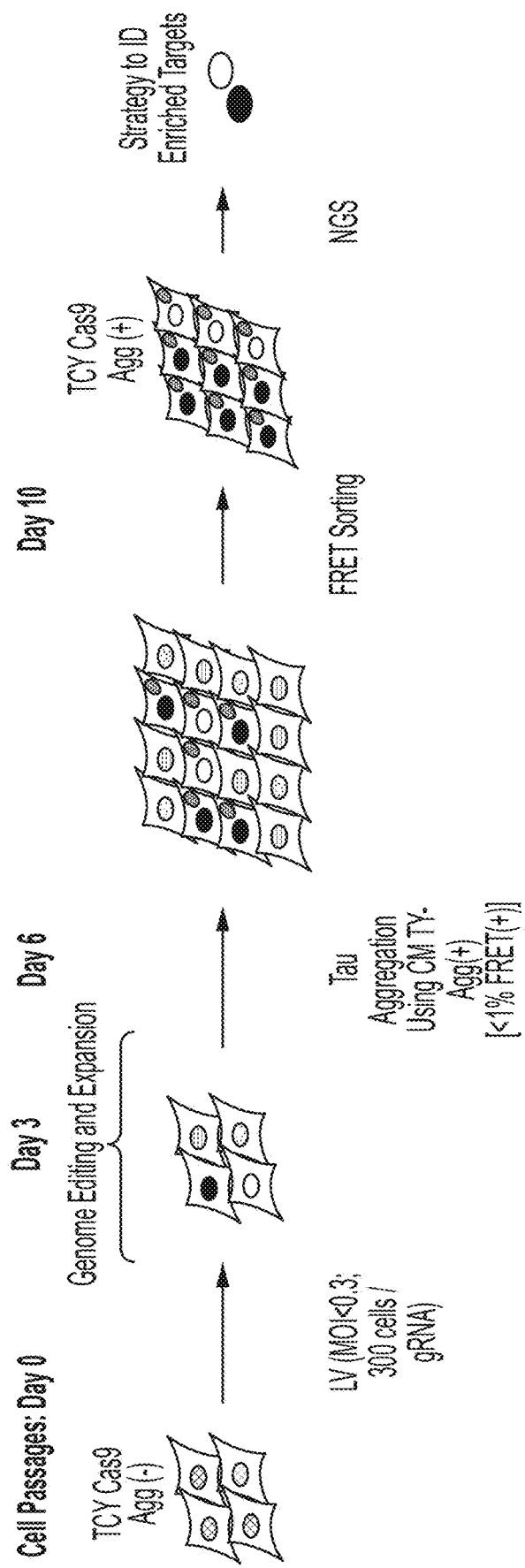
FIG. 7 is a schematic showing the strategy for a genome-wide CRISPR nuclease (CRISPRn) screen to identify modifier genes that promote tau aggregation.

Samples of the full, transduced cell population were collected upon cell passaging at Day 3 and Day 6 post-transduction. After the Day 6 passage, cells were grown in conditioned medium to sensitize them to the seeding activity. At Day 10, fluorescence-assisted cell sorting (FACS) was used to isolate specifically the sub-population of FRET [+] cells. See FIG. 7. The screening consisted of five replicated experiments. DNA isolation and PCR amplification of the integrated sgRNA constructs allowed a characterization by next generation sequencing (NGS) of the sgRNA repertoire at each time point.

Figure 8:
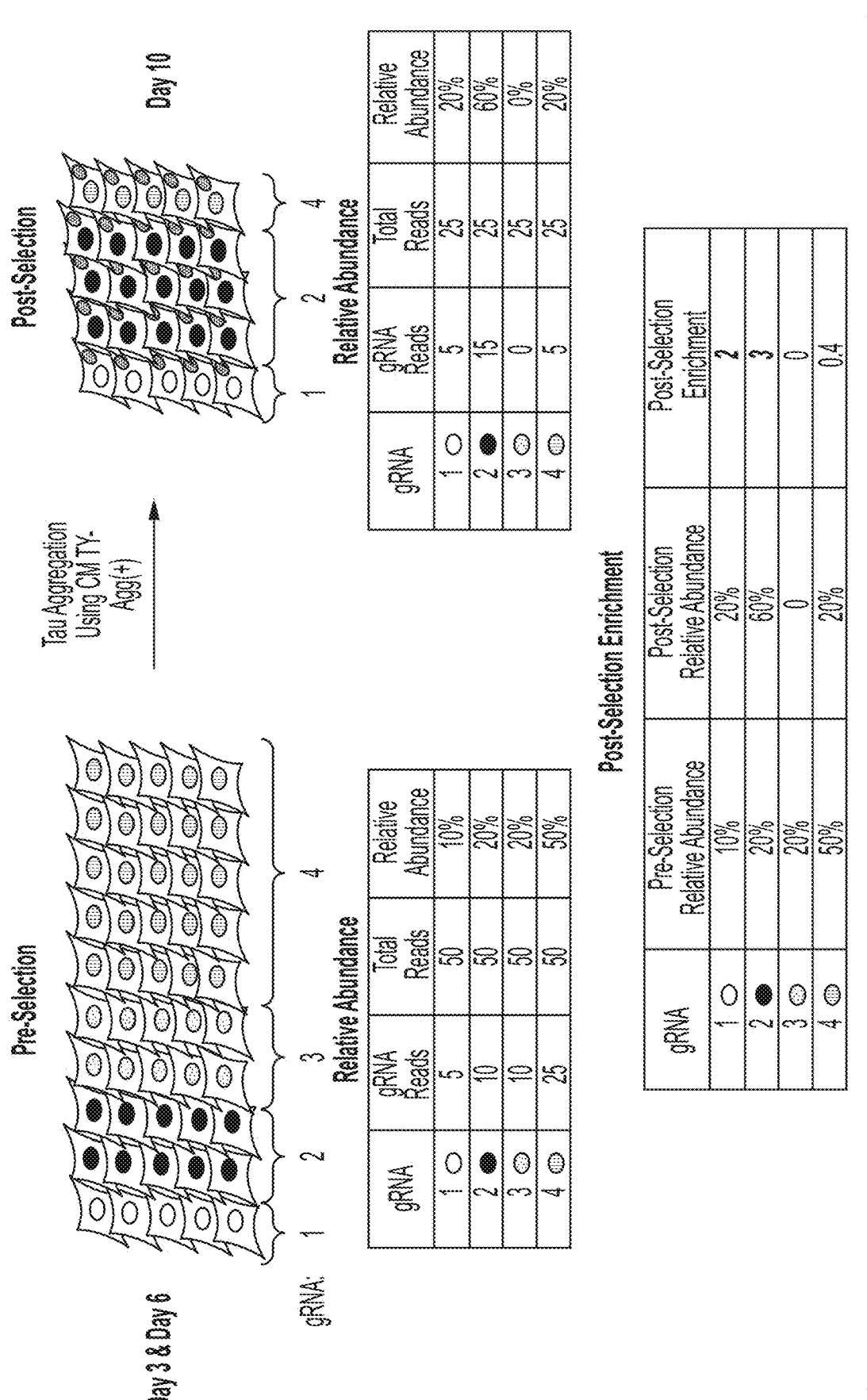
FIG. 8 is a schematic showing the concepts of abundance and enrichment for next-generation sequencing (NGS) analysis using the gnome-wide CRISPRn screen.

Statistical analysis of the NGS data enabled identification of sgRNAs enriched in the Day 10 FRET[+] sub-population of the five experiments as compared to the sgRNAs repertoire at earlier time points Day 3 and Day 6. The concepts of relative abundance and enrichment for NGS analysis are exemplified in FIG. 8. The first strategy to identify potential tau modifiers was to use DNA sequencing to produce sgRNA read counts in each sample using the DESeq algorithm to find the sgRNAs that are more abundant in Day 10 vs. Day 3 or Day 10 vs. Day 6 but not in Day 6 vs. Day 3 (fold change (fc) ≥1.5 and negative binomial test p<0.01). Fc≥1.5 means the ratio of (average of day 10 counts)/(average of day 3 or day 6 counts)≥1.5. P<0.01 means the chance that there is no statistical difference between Day 10 and Day 3 or Day 6 counts<0.01. The DESeq algorithm is a widely used algorithm for "differential expression analysis for sequence count data." See, e.g., Anders et al. (2010) *Genome Biology* 11: R106, herein incorporated by reference in its entirety for all purposes.

Specifically, two comparisons were used in each library to identify the significant sgRNAs: Day 10 vs. Day 3, and Day 10 vs. Day 6. For each of these four comparisons, the DESeq algorithm was used, and the cutoff threshold to be considered as significant was fold change≥1.5 as well as negative binomial test p<0.01. Once the significant guides were identified in each of these comparisons for each library, a gene was considered to be significant if it meets one of the two following criteria: (1) at least two sgRNAs corresponding to the that gene were considered to be significant in one comparison (either Day 10 vs. Day 3 or Day 10 vs. Day 6); and (2) at least one sgRNA was significant in both comparisons (Day 10 vs. Day 3 and Day 10 vs. Day 6). Using this algorithm, we identified five genes to be significant from the first library and four genes from the second library. See Table 4.

TABLE 4

| Genes Identified Using Strategy #1. | | | | | |
| --- | --- | --- | --- | --- | --- |
| Day 10 vs Day 3 | | Day 10 vs Day 6 | | Day 6 vs Day 3 | |
| Gene | Significant gRNAs | Gene | Significant gRNAs | Gene | Significant gRNAs |
| Library #1 | | | | | |
| Target Gene 1 | 1 | Target Gene 1 | 1 | Target Gene 1 | 0 |
| Target Gene 2 | 3 | Target Gene 2 | 1 | Target Gene 2 | 0 |
| Target Gene 15 | 1 | Target Gene 15 | 1 | Target Gene 15 | 0 |

TABLE 4-continued

Genes Identified Using Strategy #1.

| Day 10 vs Day 3 | | Day 10 vs Day 6 | | Day 6 vs Day 3 | |
|---|---|---|---|---|---|
| Gene | Significant gRNAs | Gene | Significant gRNAs | Gene | Significant gRNAs |
| Target Gene 16 | 1 | Target Gene 16 | 1 | Target Gene 16 | 0 |
| Target Gene 17 | 2 | Target Gene 17 | 0 | Target Gene 17 | 0 |
| | | Library #2 | | | |
| Target Gene 2 | 1 | Target Gene 2 | 1 | Target Gene 2 | 0 |
| Target Gene 18 | 1 | Target Gene 18 | 1 | Target Gene 18 | 0 |
| Target Gene 19 | 1 | Target Gene 19 | 1 | Target Gene 19 | 0 |
| Target Gene 20 | 1 | Target Gene 20 | 1 | Target Gene 20 | 0 |

However, the first strategy requires certain levels of read count homogeneity within each experiment group might be too stringent. For the same sgRNA, many factors could produce read count variability among the samples within each experiment group (Day 3, Day 6 or Day 10 samples), such as initial viral counts in the screening library, infection or gene editing efficiency, and relative growth rate post-gene editing. Thus, a second strategy was also used based on the positive occurrence (read count>30) of guides per gene in each sample at Day 10 (post-selection) instead of exact read count. Formal statistical p-value was calculated for positively observing a number of guides in the post-selection sample (n') given the library size (x), number of guides per gene (n), and the total number of positive guides in the post-selection sample (m) (the "number" refers to sgRNA type (i.e., unique guide RNA sequences), not read count) ($p_n'$=nCn'*(x−n')C(m−n)/xCm). The probability of n' guides being present by chance is: $p_n'$=nCn'*(x−n')C(m−n)/xCm. The probability of n' guides or more for gene g to be present by chance was calculated as:

$$p_g = \Sigma_{i=n'}^{n} p_i$$

The overall enrichment of read counts of a gene post-selection compared to pre-selection was used as additional parameter to identify positive genes: (Relative abundance=[read count of a gene]/[read count of all genes] and post-selection enrichment=[relative abundance post-selection]/[relative abundance pre-selection]).

More specifically, the second strategy is a new and more sensitive analysis method for CRISPR positive selection. The goal of CRISPR positive selection is to use DNA sequencing to identify genes for which perturbation by sgRNAs is correlated to the phenotype. To reduce the noise background, multiple sgRNAs for the same gene together with experiment replicates are usually used in these experiments. However, currently the commonly used statistical analysis methods, which require a certain degree of homogeneity/agreement among the sgRNAs for the same gene as well as among technical repeats, do not work well. This is because these methods cannot handle huge variation among sgRNAs and repeats for the same gene, due to many possible reasons (e.g., different infection or gene editing efficiency, initial viral counts in the screening library, and the presence of other sgRNAs with the same phenotype). In contrast, we developed a method that is robust to large variations. It is based on the positive occurrences of guides per gene in an individual experiment instead of the exact read count of each sgRNA. Formal statistical p-values are calculated for positively observing a number of sgRNAs over experiment repeats given the library size, number of sgRNAs per gene, and the totally number of positive sgRNAs in each experiment. Relative sgRNA sequence read enrichment before and after phenotype selection is also used as a parameter. Our method performs better than widely used methods up-to-date, including DESeq, MAGECK, and others. Specifically, this method includes the following steps:

(1) For each experiment, identifying any present guides in cells with positive phenotype.
(2) At the gene level, calculating the random chance of guides being present in each experiment: nCn'*(x−n')C(m−n)/xCm, where x is the variety of guides before phenotype selection, m is the variety of guides after phenotype selection, n is the variety of guides for a gene before phenotype selection, and n' is the variety of guides for the gene after phenotype selection. The overall chance of being present across multiple experiments (generating a single p value over p values generated from several experiments) is calculated by the Fisher's combined probability test (reference: Fisher, R. A.; Fisher, R. A (1948) "Questions and answers #14" The American Statistician). That is, a test statistic 0 is first computed using the p-values from the multiple experiments: $\phi = -2\Sigma_{k=1}^{K} p_k$, where $p_k$ is the p-value calculated for the kth experiment, and K is the total number of the experiments. Then, the combined p-value over the K experiments is equal to the probability of observing the value of φ under the chi-square distribution with the degree of freedom of 2*K. Alternatively, the overall chance of being present across multiple experiments is calculated by multiplying the above calculated possibility obtained from each experiment.
(3) Calculating the average enrichment of guides at gene level: Enrichment score=relative abundance post-selection/relative abundance pre-selection. Relative abundance=read count of guides for a gene/read count of all guides.
(4) Selecting genes significantly below the random chance of being present as well as above certain enrichment score.

Figure 9:
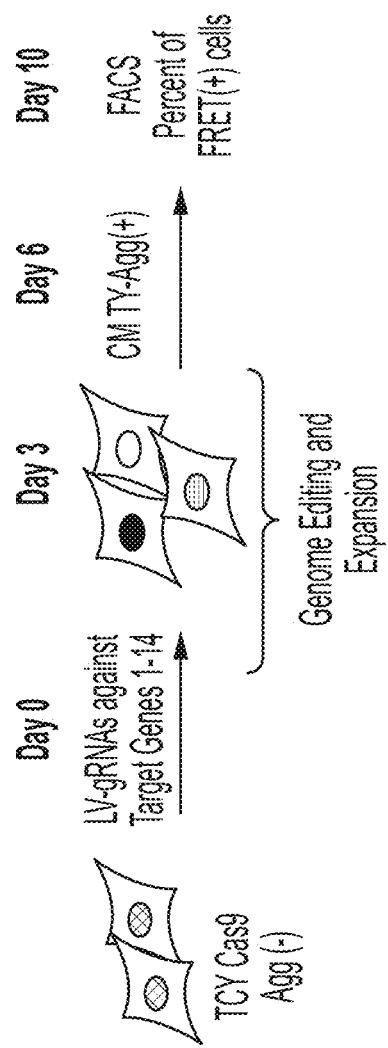
FIG. 9 shows a schematic for secondary screening for Target Genes 1-14 identified in the genome-wide screen for modifier genes that promote tau aggregation.
Figure 10:
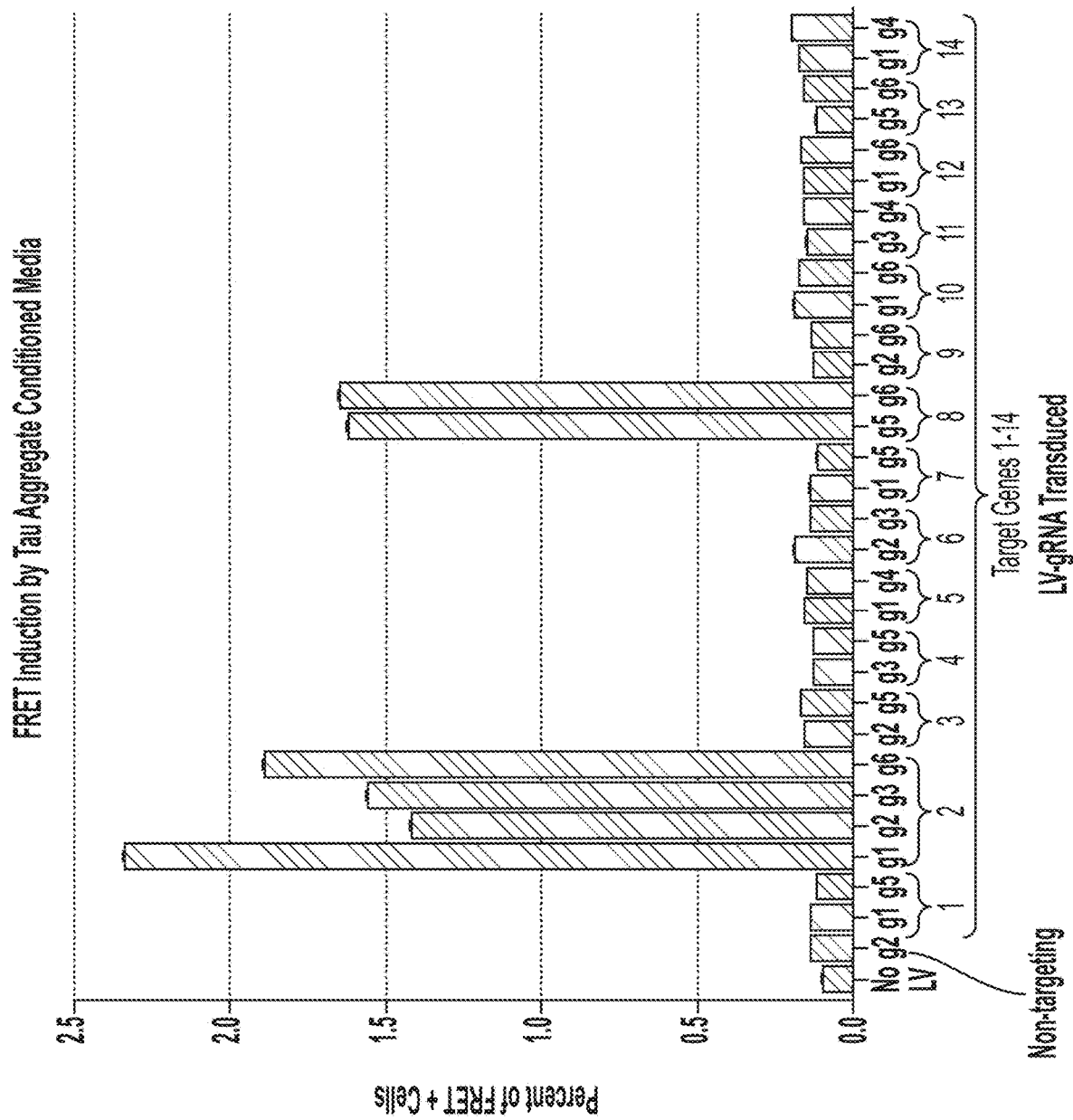
FIG. 10 is a graph showing FRET induction by tau aggregate conditioned medium in Cas9 TCY biosensor cells transduced with lentiviral expression constructs for sgRNAs targeting Target Genes 1-14. The secondary screen confirmed that Target Genes 2 and 8 modulate cell susceptibility to tau seeding/aggregation.
Figure 11:
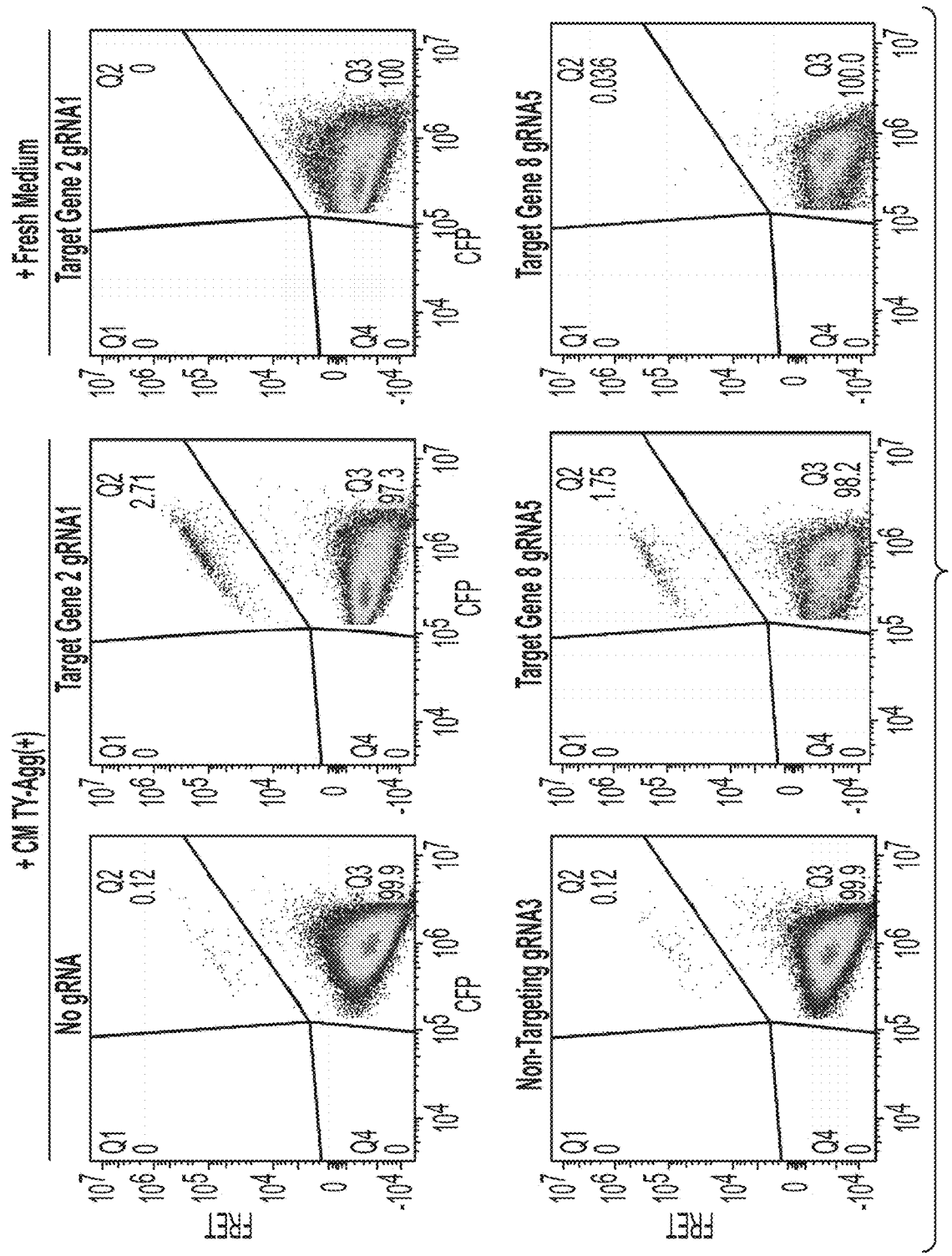
FIG. 11 shows FACS analysis images for Cas9 TCY biosensor cells transduced with lentiviral expression constructs for Target Gene 2 gRNA1, Target Gene 8 gRNA5, a non-targeting gRNA, and no gRNA. The cells were cultured in conditioned medium or fresh medium. The x-axis shows CFP (405 nm laser excitation), and the y-axis shows FRET (excitation from CFP emission). The upper right quadrant is FRET[+], the lower right quadrant is CFP[+], and the lower left quadrant is double-negative. Disruption of Target Gene 2 or 8 increases the formation of tau aggregates in response to tau aggregate conditioned medium but not fresh medium.

Fourteen of the target genes identified by the two different approaches (either approach or both) as being enriched in the FRET[+] cells were selected as top candidates for further validation after visual inspection based on read counts data. See Table 5. Thirty individual sgRNAs were tested in secondary screens for validation. A schematic of the secondary screens is shown in FIG. 9, and the results are shown in FIG. 10. Disruption of either Target Gene 2 or Target Gene 8, by multiple tested sgRNAs, increased the susceptibility of a cell to form tau aggregates in response to a source of tau seeding activity (conditioned medium). The induction of FRET signal increased by 15-20-fold in cells with disruption of either of these two targets. The disruption of these two target genes increased the formation of tau aggregates in response to conditioned medium but not fresh medium. See FIG. 11.

TABLE 5

Targets Identified.

| Target Gene | sgRNA |
|---|---|
| Target Gene 1 | g1 - Lib-A |
| Target Gene 1 | g5 - Lib-B |
| Target Gene 2 | g1 - Lib-A |
| Target Gene 2 | g2 - Lib-A |
| Target Gene 2 | g3 - Lib-A |
| Target Gene 2 | g6 - Lib-B |
| Target Gene 3 | g2 - Lib-A |
| Target Gene 3 | g5 - Lib-B |
| Target Gene 4 | g3 - Lib-A |
| Target Gene 4 | g5 - Lib-B |
| Target Gene 5 | g1 - Lib-A |
| Target Gene 5 | g4 - Lib-B |
| Target Gene 6 | g2 - Lib-A |
| Target Gene 6 | g5 - Lib-B |
| Target Gene 7 | g1 - Lib-A |
| Target Gene 7 | g5 - Lib-B |
| Target Gene 8 | g5 - Lib-B |
| Target Gene 8 | g6 - Lib-B |
| Target Gene 9 | g2 - Lib-A |
| Target Gene 9 | g6 - Lib-B |
| Target Gene 10 | g1 - Lib-A |
| Target Gene 10 | g6 - Lib-B |
| Target Gene 11 | g3 - Lib-A |
| Target Gene 11 | g4 - Lib-B |
| Target Gene 12 | g1 - Lib-A |
| Target Gene 12 | g6 - Lib-B |
| Target Gene 13 | g5 - Lib-B |
| Target Gene 13 | g6 - Lib-B |
| Target Gene 14 | g1 - Lib-A |
| Target Gene 14 | g4 - Lib-B |

Figure 12:
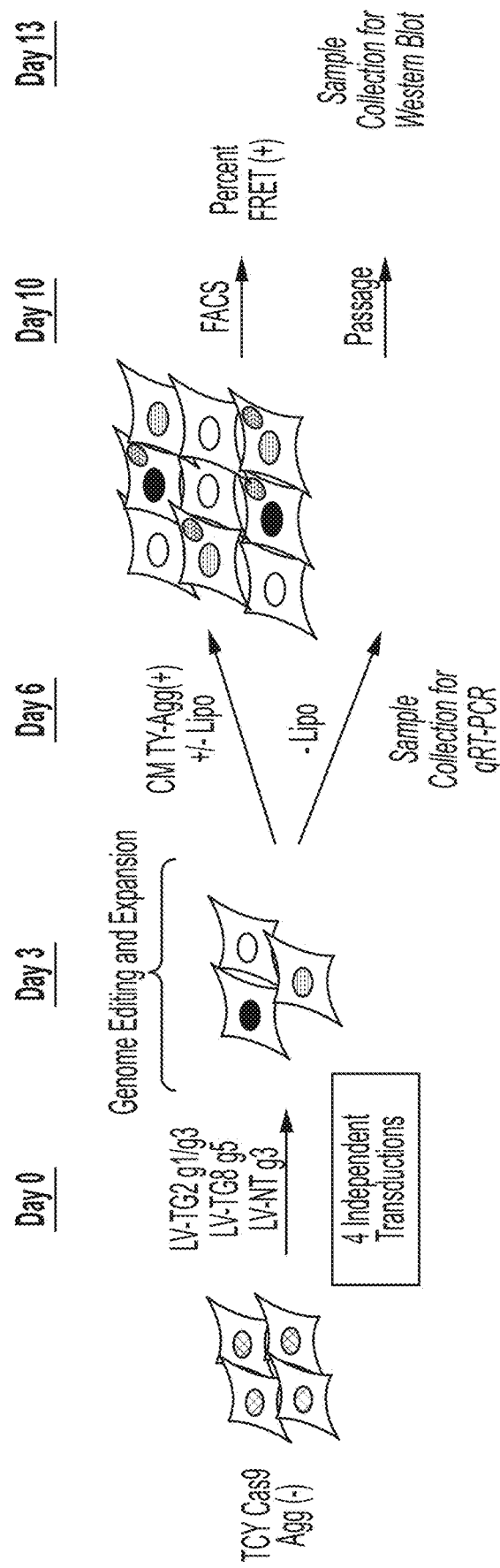
FIG. 12 shows a schematic for secondary screening in Cas9 TCY biosensor cells transduced with lentiviral expression constructs for sgRNAs targeting Target Genes 2 and 8, including mRNA expression analysis, protein expression analysis, and FRET analysis. Two sgRNAs were used against Target Gene 2 (g1 and g3), one sgRNA was used against Target Gene 8 (g5), and a non-targeting sgRNA (g3) was used as a non-targeting control.
Figure 13:
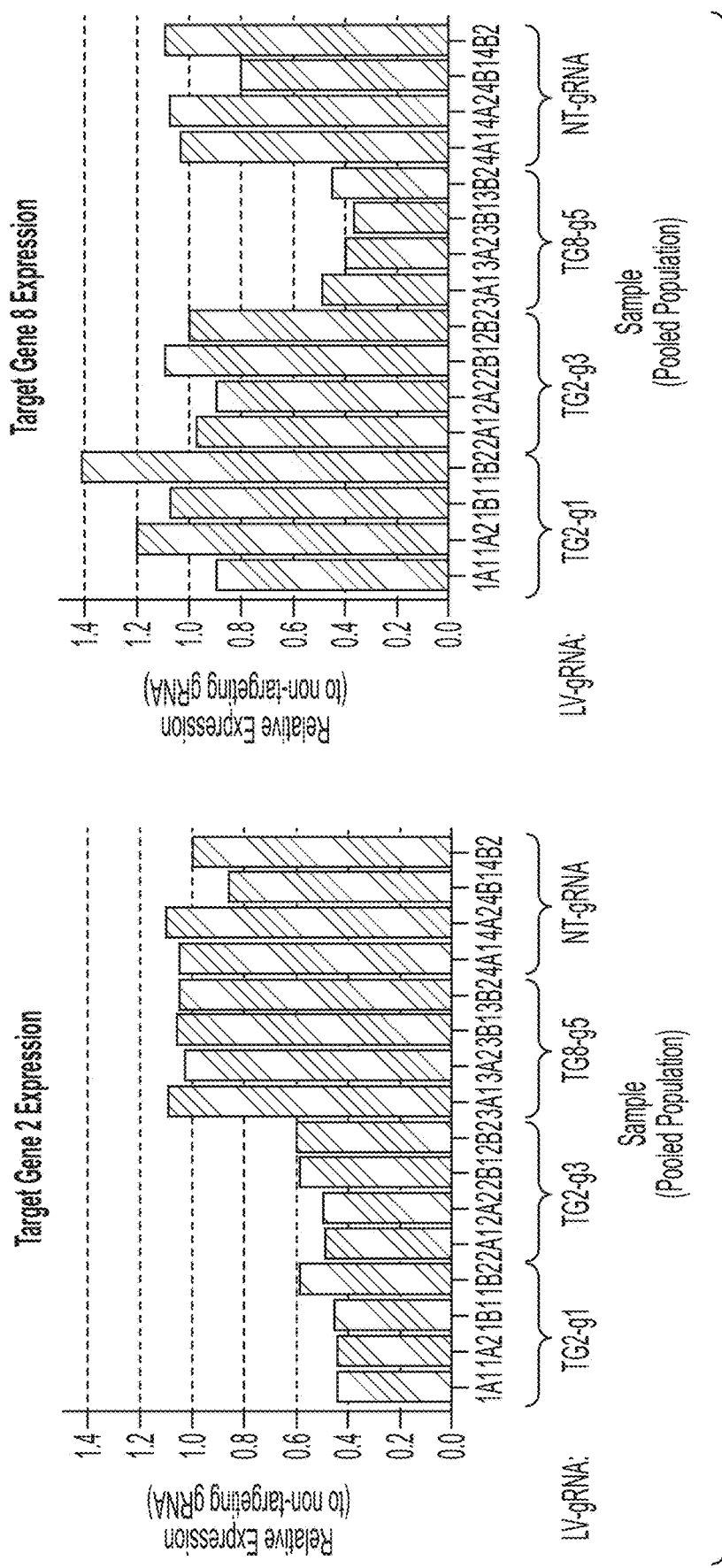
FIG. 13 shows relative expression of Target Gene 2 and Target Gene 8 in Cas9 TCY biosensor cells as assessed by qRT-PCR at Day 6 following transduction with the lentiviral sgRNA expression constructs.
Figure 14:
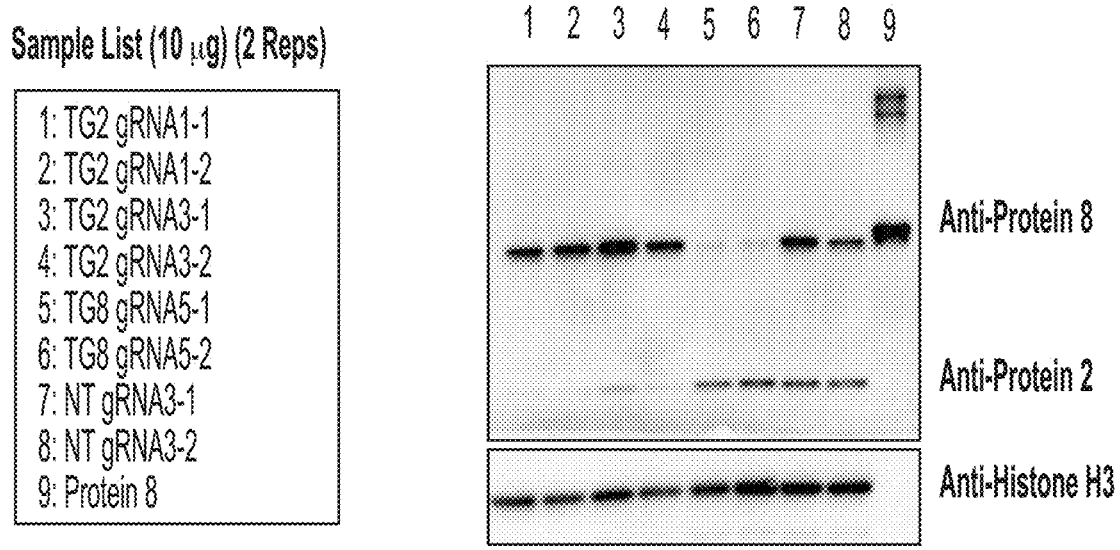
FIG. 14 shows expression of Protein 2 (encoded by Target Gene 2) and Protein 8 (encoded by Target Gene 8) in Cas9

Further experiments with Target Genes 2 and 8 were then performed to further validate that targeting of each gene promotes tau aggregation. See FIG. 12. Two different sgRNAs against Target Gene 2 were tested and one sgRNA against Target Gene 8 were used. A non-targeting sgRNA was used as a negative control. Four independent lentiviral transductions were done for each guide RNA on Day 0. On Day 6, tau seeding with conditioned medium was performed with or without lipofectamine and samples were collected for qRT-PCR. The qRT-PCR data are shown in FIG. 13. Each of the two sgRNAs targeting Target Gene 2 reduced Target Gene 2 mRNA expression, and the gRNA targeting Target Gene 8 reduced Target Gene 8 expression. On Day 10, FACS analysis was done to assess induction of FRET signal. Tau aggregation was increased by each of the two sgRNAs targeting Target Gene 2 and the gRNA targeting Target Gene 8. See FIG. 15. On Day 13, samples were collected for western blot analysis. The western blot results are shown in FIG. 14. Similar to the qRT-PCR experiments assessing mRNA expression, expression of Protein 2 was reduced by the two sgRNAs targeting Target Gene 2, and expression of Protein 8 was reduced by the sgRNA targeting Target Gene 8.

Further validation of Target Genes 2 and 8 as modifiers of tau aggregation was done by isolating individual Target Gene 2 knockdown clones and individual Target Gene 8 knockdown clones for validation. Cas9-expressing tau-CFP/tau-YFP biosensor cells without aggregates (Agg[−]) were transduced with lentivirus expressing Target Gene 2 sgRNA 1, Target Gene 8 sgRNA 5, or a non-targeting sgRNA. Serial clonal dilution was then undertaken to select individual clones. Levels of Target Gene 2 mRNA and Target Gene 8 mRNA were assessed by qRT-PCR, and levels of Protein 2 and Protein 8 were assessed by western blot. Each Target Gene 2 sgRNA clone had reduced Target Gene 2 mRNA expression (data not shown) and Protein 2 expression (FIG. 16), and each target Gene 8 sgRNA clone had reduced Target Gene 8 mRNA expression (data not shown) and Protein 8 expression (FIG. 16).

Next, each clone was seeded with conditioned medium for 4 days and FRET analysis was done to assess tau aggregation. The knockdown clones validate Target Genes 2 and 8 as modifiers of tau aggregation. See FIG. 17.

The individual clones were then further characterized by next-generation sequencing to determine what modifications were made that the Target Gene 2 and Target Gene 8 loci. The modifications are summarized in Table 6 below. Almost all of the mutant clones contain some percentage of wild type alleles. The percentage of FRET[+] cells (tau aggregation activity) correlated with the percentage of insertions/deletions caused by non-homologous end joining at the cleavage sites (i.e., tau aggregation was inversely correlated with the percentage of wild type alleles—the lower the percentage of wild type alleles, the higher the percentage of Fret[+] cells). See FIG. 16 and Table 6.

TABLE 6

Characterization of Target Gene 2 and Target Gene 8 Clones.

| Gene (Target) | Clone | Amplicon Sequenced | Allele Frequency (Reads ≥ 5%) | | |
|---|---|---|---|---|---|
| | | | WT | INDEL 1 | INDEL 2 |
| Target Gene 2 | MP1-3 | TG8_g5 | 98.80% | | |
| | | TG2_g1 | 11.30% | 49.9% (+1 bp) | 33.9% (Δ16 bp) |
| | MP1-10 | TG8_g5 | 98.60% | | |
| | | TG2_g1 | 16.50% | 79.1% (+1 bp) | |
| | MP1-13 | TG8_g5 | 98.80% | | |
| | | TG2_g1 | 14.90% | 35.9% (Δ6 bp) | 44.3% (+1 bp) |
| | MP1-23 | TG8_g5 | 98.70% | | |
| | | TG2_g1 | 20.20% | 71.4% (+1 bp) | |
| Target Gene 8 | MP5-7 | TG8_g5 | 0.00% | 54.8% (Δ3 bp + 6 bp) | 29.7% (C→T) |
| | | TG2_g1 | 99.5%% | | |
| | MP5-9 | TG8_g5 | 34.80% | 55.0% (Δ20 bp) | 6.8% (+1 bp) |
| | | TG2_g1 | 99.30% | | |

Tau phosphorylation was also assessed in each clone by western blot. Tau was found to be hyper-phosphorylated at S262 and S356 in Target Gene 8 sgRNA clone 5.7. See FIG.

18. Although clones in which tau was not hyperphosphorylated still appeared to enhance FRET induction in this experiment, clone 5.7 was quite unstable, and Target Gene 8 is involved in many biological processes, so no general conclusions could be drawn. Further experiments in mouse primary cortical neurons showed that phosho-tau (S356) staining is increased in the somatodendritic compartment in mouse primary cortical neurons treated with Cas9 and Target Gene2 sgRNA via lentiviral delivery and maintained for 14 days in culture (data not shown).

This validation confirmed the value of the primary screening approach in the identification of genes that can regulate the susceptibility of cells to tau seeding when exposed to an external source of tau seeding activity. Targets identified through the screening could be therefore relevant targets in the cell-to-cell propagation of tau pathology in the context of neurodegenerative disease and will be further explored.

Example 3. Development of Genome-Wide CRISPR/Cas9 Screening Platform to Identify Genetic Modifiers of Tau Aggregation Using a Transcriptional Activation CRISPR/Cas9 Library To further identify genes and pathways that modify the processes of abnormal tau protein aggregation, a platform was developed for performing genome-wide screens with transcriptional activation (hSAM) CRISPRa sgRNA libraries to identify genes that regulate the potential of cells to be "seeded" by tau disease-associated protein aggregates (i.e. genes which, when transcriptionally activated, cause cells to be more susceptible to tau aggregate formation when exposed to a source of tau fibrillized protein). The identification of such genes may elucidate the mechanisms of tau cell-to-cell aggregate propagation and genetic pathways that govern the susceptibility of neurons to form tau aggregates in the context of neurodegenerative diseases.

The screen employed a tau biosensor human cell line consisting of HEK293T cells stably expressing tau four-repeat domain, tau_4RD, comprising the tau microtubule binding domain (MBD) with the P301S pathogenic mutation, fused to either CFP or YFP. That is, the HEK293T cell lines contain two transgenes stably expressing disease-associated protein variants fused to the fluorescent protein CFP or the fluorescent protein YFP: tau$^{4RD}$-CFP/tau$^{4RD}$-YFP (TCY), wherein the tau repeat domain (4RD) comprises the P301S pathogenic mutation. See FIG. 1. In these biosensor lines, tau-CFP/tau-YFP protein aggregation produces a FRET signal, the result of a transfer of fluorescent energy from donor CFP to acceptor YFP. See FIG. 2. FRET-positive cells, which contain tau aggregates, can be sorted and isolated by flow cytometry. At baseline, unstimulated cells express the reporters in a stable, soluble state with minimal FRET signal. Upon stimulation (e.g., liposome transfection of seed particles), the reporter proteins form aggregates, producing a FRET signal. Aggregate-containing cells can be isolated by FACS. Stably propagating aggregate-containing cell lines, Agg[+], can be isolated by clonal serial dilution of Agg[−] cell lines.

Several modifications were made to this tau biosensor cell line to make it useful for genetic screening. First, this biosensor cell line was further transgenically modified to express the components of the CRISPR/Cas SAM transcriptional activation system: dCas9-VP64 and MS2-P65-HSF1. Lentiviral dCas9-VP64 and MS2-P65-HSF1 constructs are provided in SEQ ID NOS: 42 and 43, respectively. A clone was selected as a high-performing clone to use for subsequent library screens. This clone was validated for its efficacy in activating selected target genes.

Second, reagents and a method were developed for sensitizing cells to tau seeding activity as in Example 1. Alternatively, if more aggregation is needed, use of cell lysate from an Agg[+] clone can be used as in Example 5.

Example 4. Genome-Wide CRISPR/Cas9 Screening to Identify Genetic Modifiers of Tau Aggregation Using a Transcriptional Activation CRISPR/Cas9 Library To reveal further modifier genes of tau aggregation as enriched sgRNAs in FRET[+] cells, the SAM-expressing tau-CFP/tau-YFP biosensor cells without aggregates (Agg[−]) were transduced with a human genome-wide CRISPR hSAM sgRNA library using a lentiviral delivery approach to transcriptionally activate each target gene. The sgRNAs in the library target sites within 200 bp upstream of the transcription start site with an average coverage of ~3 sgRNAs per gene. The sgRNAs were designed to avoid off-target effects by avoiding sgRNAs with two or fewer mismatches to off-target genomic sequences. The library covers 18,946 human genes. The library was transduced at a multiplicity of infection (MOI)<0.3 at a coverage of >300 cells per sgRNA. Tau biosensor cells were grown under zeocin selection to select cells with integration and expression of a unique sgRNA per cell. Five independent screening replicates were used in the primary screen.

Samples of the full, transduced cell population were collected upon cell passaging at Day 3 and Day 6 post-transduction. After the Day 6 passage, cells were grown in conditioned medium to sensitize them to the seeding activity. At Day 10, fluorescence-assisted cell sorting (FACS) was used to isolate specifically the sub-population of FRET[+] cells. DNA isolation and PCR amplification of the integrated sgRNA constructs allowed a characterization by next generation sequencing (NGS) of the sgRNA repertoire at each time point.

Because data analysis and statistical analysis mirrored the approach used in Example 2, not all the details from Example 2 are repeated here. Statistical analysis of the NGS data enabled identification of sgRNAs enriched in the Day 10 FRET[+] sub-population of the multiple experiments as compared to the sgRNAs repertoire at earlier time points Day 3 and Day 6. The first strategy to identify potential tau modifiers was to use DNA sequencing to produce sgRNA read counts in each sample using the DESeq algorithm to find the sgRNAs that are more abundant in Day 10 vs. Day 3 or Day 10 vs. Day 6 but not in Day 6 vs. Day 3 (fold change (fc) ≥1.5 and negative binomial test p<0.01). Fc≥1.5 means the ratio of (average of day 10 counts)/(average of day 3 or day 6 counts)≥1.5. P<0.01 means the chance that there is no statistical difference between Day 10 and Day 3 or Day 6 counts<0.01. The DESeq algorithm is a widely used algorithm for "differential expression analysis for sequence count data." See, e.g., Anders et al. (2010) *Genome Biology* 11: R106, herein incorporated by reference in its entirety for all purposes.

Specifically, two comparisons were used in each library to identify the significant sgRNAs: Day 10 vs. Day 3, and Day 10 vs. Day 6. For each of these four comparisons, the DESeq algorithm was used, and the cutoff threshold to be considered as significant was fold change≥1.5 as well as negative binomial test p<0.01. Once the significant guides were identified in each of these comparisons for each library, a gene was considered to be significant if it meets one of the two following criteria: (1) at least two sgRNAs corresponding to the that gene were considered to be significant in one comparison (either Day 10 vs. Day 3 or Day 10 vs. Day 6); and (2) at least one sgRNA was significant in both comparisons (Day 10 vs. Day 3 and Day 10 vs. Day 6).

However, the first strategy requires certain levels of read count homogeneity within each experiment group might be too stringent. For the same sgRNA, many factors could produce read count variability among the samples within each experiment group (Day 3, Day 6 or Day 10 samples), such as initial viral counts in the screening library, infection or gene editing efficiency, and relative growth rate post-gene editing. Thus, a second strategy was also used based on the positive occurrence (read count>30) of guides per gene in each sample at Day 10 (post-selection) instead of exact read count. Formal statistical p-value was calculated for positively observing a number of guides in the post-selection sample (n') given the library size (x), number of guides per gene (n), and the total number of positive guides in the post-selection sample (m) (the "number" refers to sgRNA type (i.e., unique guide RNA sequences), not read count) $(p_n'=nCn'*(x-n')C(m-n)/xCm)$. The probability of n' guides being present by chance is: $p_n'=nCn'*(x-n')C(m-n)/xCm$. The probability of n' guides or more for gene g to be present by chance was calculated as:

$$p_g = \Sigma_{i=n}^{n} p_i$$

The overall enrichment of read counts of a gene post-selection compared to pre-selection was used as additional parameter to identify positive genes: (Relative abundance= [read count of a gene]/[read count of all genes] and post-selection enrichment=[relative abundance post-selection]/ [relative abundance pre-selection]).

More specifically, the second strategy is a new and more sensitive analysis method for CRISPR positive selection. The goal of CRISPR positive selection is to use DNA sequencing to identify genes for which transcriptional activation by sgRNAs is correlated to the phenotype. To reduce the noise background, multiple sgRNAs for the same gene together with experiment replicates are usually used in these experiments. However, currently the commonly used statistical analysis methods, which require a certain degree of homogeneity/agreement among the sgRNAs for the same gene as well as among technical repeats, do not work well. This is because these methods cannot handle huge variation among sgRNAs and repeats for the same gene, due to many possible reasons (e.g., different infection or gene editing efficiency, initial viral counts in the screening library, and the presence of other sgRNAs with the same phenotype). In contrast, we developed a method that is robust to large variations. It is based on the positive occurrences of guides per gene in an individual experiment instead of the exact read count of each sgRNA. Formal statistical p-values are calculated for positively observing a number of sgRNAs over experiment repeats given the library size, number of sgRNAs per gene, and the totally number of positive sgRNAs in each experiment. Relative sgRNA sequence read enrichment before and after phenotype selection is also used as a parameter. Our method performs better than widely used methods up-to-date, including DESeq, MAGECK, and others. Specifically, this method includes the following steps:
 (1) For each experiment, identifying any present guides in cells with positive phenotype.
 (2) At the gene level, calculating the random chance of guides being present in each experiment: $nCn'*(x-n')C(m-n)/xCm$, where x is the variety of guides before phenotype selection, m is the variety of guides after phenotype selection, n is the variety of guides for a gene before phenotype selection, and n' is the variety of guides for the gene after phenotype selection. The overall chance of being present across multiple experiments (generating a single p value over p values generated from several experiments) is calculated by the Fisher's combined probability test (reference: Fisher, R. A.; Fisher, R. A (1948) "Questions and answers #14" The American Statistician). That is, a test statistic $\phi$ is first computed using the p-values from the multiple experiments: $\phi = -2\Sigma_{k=1}^{K} p_k$, where $p_k$ is the p-value calculated for the kth experiment, and K is the total number of the experiments. Then, the combined p-value over the K experiments is equal to the probability of observing the value of $\phi$ under the chi-square distribution with the degree of freedom of 2*K. Alternatively, the overall chance of being present across multiple experiments is calculated by multiplying the above calculated possibility obtained from each experiment.
 (3) Calculating the average enrichment of guides at gene level: Enrichment score=relative abundance post-selection/relative abundance pre-selection. Relative abundance=read count of guides for a gene/read count of all guides.
 (4) Selecting genes significantly below the random chance of being present as well as above certain enrichment score.

A total of 34 target genes (targeted by 42 different sgRNAs) were identified by the two different approaches (either approach or both) as being enriched in the FRET[+] cells.

Example 5. Preparation and Validation of Tau-YFP Clone18 Agg[+] Cell Lysates for Tau Seeding We next wanted to identify target genes that, when disrupted, reduce tau aggregation (whether by blocking uptake of seeds, inhibiting the formation of oligomers or fibrils, promoting their disassembly, or by some other mechanism). To develop such a screen for sgRNAs that prevent tau aggregation, we needed a source of seeding activity that is potent and that we can easily generate in large quantities. As described in this example, we discovered that whole cell lysate from tau-YFP Agg[+] clone18 can induce tau aggregation and FRET signal, while lysate from tau-YFP Agg[−] does not. Whole cell lysate is much more potent at seeding tau activity (with no lipofectamine) than conditioned media or recombinant tau fibrils. To induce aggregation (FRET) in larger percentage of cells (e.g., >50%), we tried using whole cell lysate in combination with lipofectamine. We also needed to develop a method of collecting cell lysate in buffer that is not itself toxic to cells. In the experiments described herein, we used phosphate-buffered saline (PBS)+ protease inhibitors to collect cells and sonication to lyse cells. Cell lysate sonicated for 3 minutes worked best.

Cells were prepared for sonication as follows: (1) take 6× T175 plates of tau-YFP Agg[−] cells and 6×T175 plates of tau-YFP Clone18 Agg[+] cells (~50 million cells/T175); (2) rinse flask with 10 mL PBS, then scrape cells into 5 mL of PBS; (3) collect 2×T175 into a 15 mL tube, then rinse these 2×T175 with a total of 5 mL PBS and add it to the 15 mL tube for a final volume of 15 mL (should have 3 tubes of tau-YFP Agg[−] cells and 3 tubes of tau-YFP Clone18 Agg[+] cells); (4) spin the tubes @ 1000 rpm for 5 minutes, aspirate, add 4 mL PBS/tube+40 µL HALT™ (six broadspectrum protease inhibitors AEBSF, aprotinin, bestatin, E-64, leupeptin and pepstatin A stabilized in high-quality dimethylsulfoxide (DMSO))+40 µL ethylenediaminetetracetic acid (EDTA)/tube (protease inhibitors); and (5) transfer cell suspensions to 50 mL tubes (sonication tube holder can only hold 50 mL tube) and freeze at −80° C. until sonication.

Sonication to create cell lysates was performed as follows: (1) thaw cell suspensions in warm water bath; (2) sonicate for 1 minute, 3 minutes, or 6 minutes; (3) spin down sonicated samples @ 1000 rpm for 5 minutes, make 300 µL aliquots, and freeze at −80° C.

Tau biosensor cells tau-CFP/tau-YFP/Cas9 Clone 7B10C3 Agg[−] (C3) and FRET/FACS control cells tau-CFP, tau-YFP, HEK-HZ, tau-CFP/tau-YFP/Cas9 Clone 7B10C3-B2 Agg[+] (B2) were thawed and were plated in 12-well plates and were treated with 10 µg, 30 µg, or 100 µg of the cell lysate produced above. The results are shown in FIG. 19. A dose-dependent response was observed, and 3 minutes sonication worked best.

In a subsequent experiment, 150,000 of 7B10C3 Agg[−] cells were plated per well in 24-well plates in duplicate. We used 1 mL of fresh medium per well. We added 0 (control), 10, 25, or 50 µg of 3-min tau-YFP Agg[+] Clone18 cell lysate+/− lipofectamine (10 µL per 1 mL of medium). With the lipofectamine, all cells were Agg[+], but all cells were dead after 24 hours in the 25 and 50 µg lysate samples and after 48 hours in the 10 µg lysate samples.

We next tried decreasing the amount of lysate used. 150,000 of 7BOC3 Agg[−] cells were plated per well in 24-well plates in duplicate. We used 1 mL of fresh medium per well. We added 0 (control), 1, 5, or 10 µg of 3-min tau-YFP Agg[+] Clone18 cell lysate+/− lipofectamine (10 µL per 1 mL of medium). With the lipofectamine, all cells were Agg[+], but the cells looked unhealthy after 24 hours and were dead after 48 hours in the 5 and 10 µg lysate samples. In the 1 µg lysate samples, the cells were all Agg[+], but looked somewhat unhealthy at 24 hours. After 3 days, the cells were still alive and Agg[+].

We next tried decreasing the amount of lysate used and testing different lipofectamine concentrations. 150,000 of 7B10C3 Agg[−] cells were plated per well in 24-well plates in duplicate. We used 1 mL of fresh medium per well. We added 0 (control), 0.1, 0.5, or 1 ag of 3-min tau-YFP Agg[+] Clone18 cell lysate+/− lipofectamine (1, 5, or 10 µL per 1 mL of medium). With 10 µL lipofectamine, all cells were dead after 24 hours in all samples. With 5 µL lipofectamine and 0.5 µg lysate, the cells looked ok after 48 hours and most were Agg[+]. Similarly, with 5 µL lipofectamine and 1 µg lysate, the cells looked ok after 48 hours and all were Agg[+]. However, the 5 µL lipofectamine was toxic in the 0 ug and 0.1 µg samples, as the cells looked unhealthy after 48 hours. With 1 µL lipofectamine, the cells looked ok after 48 hours and were ~30% Agg[+] in the 0.1 µg lysate samples, were ~40% Agg[+] in the 0.5 µg lysate samples, and were ~50% Agg[+] in the 1 µg lysate samples. See FIG. 20. A similar experiment was done testing 3 µg, 5 µg, or 10 µg of cell lysate and 1 µL, 2 µL, or 3 µL of lipofectamine. The results are shown in FIG. 21. Yet another experiment was done testing 0.5 g, 0.7 µg, or 1 µg of cell lysate and 3.5 µL or 4 µL of lipofectamine. The percentage of aggregation-positive cells for each condition was as follows: 0.5 µg lysate/3.5 µL lipofectamine: 73.5%; 0.7 µg lysate/3.5 µL lipofectamine: 71.7%; 1 µg lysate/3.5 µL lipofectamine: 75.7%; 0.5 µg lysate/4 µL lipofectamine: 76.4%; 0.7 µg lysate/4 µL lipofectamine: 76.7%; and 1 µg lysate/4 L lipofectamine: 78.0%. In further experiments, 2 µL and 2.5 µL lipofectamine were not toxic to the cells, but 3 µL, 3.5 µL, 4 µL, 4.5 µL, and 5 µL were toxic to cells.

Next, we scaled up to T25 flasks, plating 2.8 million 7B10C3 cells+lysate+lipofectamine. FACS/FRET sorting was done after 2 days in culture. Two conditions were tested: (1) 1.5 µg lysate+2 µL lipofectamine per mL of fresh medium; and (2) 2 µg lysate+2 L lipofectamine per mL of fresh medium. In the first experiment, 965,880 cells were FRET[−](i.e., Agg[−]) and 984,760 cells were FRET[+] (i.e., Agg[+]). In the second experiment, 547,960 cells were FRET[−] (i.e., Agg[−]) and 855,900 cells were FRET[+] (i.e., Agg[+]). We concluded that for genome-wide screens we would use 2.5 µL lipofectamine per mL of fresh medium and compare two different doses of tau-YFP Agg[+] clone18 cell lysates (1.5 µg and 2 µg), which could potentially increase the percent of Agg[+] cells while keeping them healthy.

Example 6. Genome-Wide CRISPR/Cas9 Screening to Identify Genetic Modifiers that Prevent Tau Aggregation The goal of the screen in Example 2 was to identify modifier genes which, when disrupted, promote the formation of tau aggregates when stimulated with a weak tau seeding material. In contrast, in the screen described in this example, we treated our biosensor cells with a potent tau seeding material that normally causes tau aggregation and FRET induction in a majority of cells. This "maximal seeding" material consists of sonicated whole cell lysate from tau-YFP Agg[+] Clone18 cells, applied with lipofectamine transfection reagent. We took this approach to identify target genes that, when disrupted, reduce tau aggregation (whether by blocking uptake of seeds, inhibiting the formation of oligomers or fibrils, promoting their disassembly, or by some other mechanism). See FIG. 22.

The Cas9-expressing tau-CFP/tau-YFP biosensor cells without aggregates (Agg[−]) were transduced with two human genome-wide CRISPR sgRNA libraries using a lentiviral delivery approach to introduce knock-out mutations at each target gene. Each CRISPR sgRNA library targets 5' constitutive exons for functional knock-out with an average coverage of ~3 sgRNAs per gene (total of 6 gRNAs per gene in the two libraries combined). Read count distribution (i.e., the representation of each gRNA in the library) was normal and similar for each library. The sgRNAs were designed to avoid off-target effects by avoiding sgRNAs with two or fewer mismatches to off-target genomic sequences. The libraries cover 19,050 human genes and 1864 miRNA with 1000 non-targeting control sgRNAs. The libraries were transduced at a multiplicity of infection (MOI) <0.3 at a coverage of >300 cells per sgRNA. Tau biosensor cells were grown under puromycin selection to select cells with integration and expression of a unique sgRNA per cell. Puromycin selection began 24 h after transduction at 1 µg/mL. Five independent screening replicates were used in the primary screen.

In each replicate, samples of 7B10C3 biosensor cells were collected at Day 3 and Day 7 post-transduction of the lentivirally-packaged CRISPR libraries. At the Day 7 passage, the "maximal seeding" material was added to the cells, and after 48 hours (at Day 9), FACS was performed to separate and collect FRET[−] and FRET[+] populations. The screening consisted of five replicated experiments. DNA isolation and PCR amplification of the integrated sgRNA constructs allowed a characterization by next generation sequencing (NGS) of the sgRNA repertoire at each time point. There were 40 samples in total: 5 replicate screens*2 libraries*4 samples for each (Day 3, Day 7, Day 9 FRET[−], and Day 9 FRET[+]). For the "maximal seeding," 2.5 μL of lipofectamine was used per mL of fresh medium, and different amounts of cell lysate were tested per mL of fresh medium (2 μg, 4 μg, and 5 μg).

Data analysis and statistical analysis mirrored the approach used in Example 2, so the details from Example 2 are not repeated here. We compared (paired analysis) FRET (−) vs FRET(+) vs Day 7. We also performed a paired analysis by comparison to Day 3 (more stringent). Day 9 FRET[−] and FRET[+] samples were analyzed for sgRNAs whose enrichment or depletion may indicate an effect on the tau aggregation phenotype. sgRNAs that are enriched in Day 9 FRET[−] cells relative to Day 9 FRET[+], Day 3, and Day 7, and/or are depleted in Day 9 FRET[+] cells relative to Day 9 FRET[−], Day 3, and Day 7, indicate target genes that, when disrupted, may reduce or protect against tau aggregation. These sgRNA hits are of special interest as potential targets for therapeutic intervention. sgRNAs that are enriched in Day 9 FRET[+] cells relative to Day 9 FRET[−], Day 3, and Day 7, and/or are depleted in Day 9 FRET[−] cells relative to Day 9 FRET[+], Day 3, and Day 7, indicate target genes that, when disrupted, may promote or enhance tau aggregation. sgRNAs that are depleted in both Day 9 FRET[+] and FRET[−] relative to earlier timepoints are likely to represent essential genes that reduce cell viability over time when they are disrupted.

We identified 142 significant gRNAs that were enriched or depleted in FRET[−] cells (as compared to FRET[+] cells and Day 7 cells). Of these, 46 gRNAs were depleted in FRET[−] cells, 77 gRNAs were enriched in FRET[−] cells, and 20 gRNAs were enriched in FRET[−] cells compared to Day 7 (not significant as compared to Day 3). See FIGS. 23 and 24.

Next, 405 individual sgRNAs were tested in secondary screens for validation. A schematic of the secondary screens is shown in FIG. 25. Four experiments were done. The amount of cell lysate used in each was 5 μg/mL of fresh medium. Four different amounts of lipofectamine (per mL fresh medium) were tested: 1.5 μL, 2 μL, 2.5 μL, and 3.5 μL. This validation confirms the value of the primary screening approach in the identification of genes that can act as positive and negative modifiers of tau aggregation.

Example 7. Genome-Wide CRISPR/Cas9 Screening to Identify Genetic Modifiers that Prevent Tau Aggregation Using a Transcriptional Activation CRISPR/Cas9 Library Similar to Example 6, in the screen described in this example, we treated our biosensor cells with a potent tau seeding material that normally causes tau aggregation and FRET induction in a majority of cells. This "maximal seeding" material consists of sonicated whole cell lysate from tau-YFP Agg[+] Clone18 cells, applied with lipofectamine transfection reagent. We took this approach to identify target genes that, when transcriptionally activated, reduce tau aggregation (whether by blocking uptake of seeds, inhibiting the formation of oligomers or fibrils, promoting their disassembly, or by some other mechanism). See FIG. 26.

The SAM-expressing tau-CFP/tau-YFP biosensor cells without aggregates (Agg[−]) were transduced with a human genome-wide CRISPR hSAM sgRNA library using a lentiviral delivery approach to transcriptionally activate each target gene. The sgRNAs in the library target sites within 200 bp upstream of the transcription start site with an average coverage of ~3 sgRNAs per gene. The sgRNAs were designed to avoid off-target effects by avoiding sgRNAs with two or fewer mismatches to off-target genomic sequences. The library covers 18,946 human genes. The library was transduced at a multiplicity of infection (MOI) <0.3 at a coverage of >300 cells per sgRNA. Tau biosensor cells were grown under zeocin selection to select cells with integration and expression of a unique sgRNA per cell. Five independent screening replicates were used in the primary screen.

At Day 10 (PM) post-transduction of the lentivirally-packaged CRISPR libraries, the "maximal seeding" material was added to the cells, and at Day 13 (AM) FACS was performed to separate and collect FRET[−] and FRET[+] populations. See FIG. 26. The screening consisted of five replicated experiments. DNA isolation and PCR amplification of the integrated sgRNA constructs allowed a characterization by next generation sequencing (NGS) of the sgRNA repertoire at each time point. For the "maximal seeding," three amounts of lipofectamine were used per mL of fresh medium (2.5 μL, 3.5 μL, and 4 μL), and different amounts of cell lysate were tested per mL of fresh medium (3 μg, 4 μg, and 5 μg).

Day 13 FRET[−] and FRET[+] samples were analyzed for sgRNAs whose enrichment or depletion may indicate an effect on the tau aggregation phenotype. sgRNAs that are enriched in Day 13 FRET[−] cells relative to Day 13 FRET[+] and Day 10, and/or are depleted in Day 13 FRET[+] cells relative to Day 13 FRET[−] and Day 10 indicate target genes that, when transcriptionally activated, may reduce or protect against tau aggregation. These sgRNA hits are of special interest as potential targets for therapeutic intervention. sgRNAs that are enriched in Day 13 FRET[+] cells relative to Day 13 FRET[−] and Day 10, and/or are depleted in Day 13 FRET[−] cells relative to Day 13 FRET[+] and Day 10, indicate target genes that, when transcriptionally activated, may promote or enhance tau aggregation. Data are analyzed and tested in secondary screens for validation as in Example 6. Statistical analysis mirrors the approach used in Example 2. We compare (paired analysis) FRET(−) vs FRET(+) vs Day 10.

Example 8. Genome-Wide CRISPR/Cas9 Screening to Identify Genetic Modifiers of Tau Disaggregation In the above examples, we conducted two series of genome wide screens aiming at the identification of positive and negative regulators of tau aggregation. In our first screen, we have identified modifier genes which, when disrupted, promote the formation of tau aggregates when stimulated with a weak tau seeding material. This "minimal-seeding" material consists of a conditioned medium collected from tau-YFP aggregate[+] cells, applied directly to 7B10C3 cells to trigger ~0.1% FRET[+] cells after 3 Days In Vitro (DIV). In contrast, in the second screen we have treated our biosensor cells with a potent or maximal tau seeding material, that normally causes tau aggregation and FRET induction in a majority of cells. This "maximal-seeding" material consists of sonicated whole cell lysate from tau-YFP aggregate[+] cells, applied with lipofectamine transfection reagent.

Here, we transduced aggregate[+] 7B10C3-B2 or DC11-B6 cells with lentivirally-packaged CRISPR libraries. 7B10C3-B2 and DC11-B6 are clones that contains stably propagating Tau aggregates. This screen was done in HEK293 tau biosensor cells expressing Cas9 (clone 7B10C3) or dCas9-SAM (clone DC11), in which tau aggregation produces a FRET signal that can be detected and used as a means of cell sorting by FACS. The 7B10C3 and DC11 clones were further treated with tau fibrils in order to derive sub-clones that contains stably propagating Tau aggregates. Two of these aggregate-positive aggregate[+] stable sub-clones, called 7B10C3-B2 and DC11-B6, were selected for expansion and used for screening.

After two weeks in culture, we isolated and sequenced by next generation sequencing (NGS) to reveal depleted/enriched single guide RNAs (sgRNAs) in FRET[−] cells on the hypothesis that sgRNAs that cause a loss of tau aggregation through disruption of their specific targets will be enriched in the FRET[−] population. The FRET[−] cell population was predominantly composed by cells with no aggregates. However, we observed some FRET[−] cells showing speckles, composed by tiny aggregates that were not sufficient to emit FRET and thus not recognized as FRET[+] by FACS.

In order to reduce false positives in the FRET[−] population and to minimize the number of speckles[+] cells observed predominately on G1 phase after mitosis (see FIG. 28), we synchronized the cell cycle progression by double thymidine block, a DNA synthesis inhibitor (see FIG. 29). This novel application of this synchronization method allowed us to obtain a cell population predominantly enriched in S phase and thus to synchronize aggregate accumulation after mitosis.

Five replicate screens are performed for each library (two CRISPRn libraries and one CRISPRa library). In each replicate, samples of 7B10C3-B2 and DC11-B6 biosensor cells are collected at Day 7 and Day 10 post-transduction of the lentivirally-packaged CRISPR libraries. At Day 12, cells are grown in the presence thymidine for 21 hours. After the first block thymidine is removed (Day 13), cells are washed and grown in fresh medium for 8 hours to release cells from the block and incubated with thymidine again for the second block. As a result of this synchronization, cells progress synchronously through G2 and mitotic phase and are arrested at the beginning of S phase. At Day 14, cells are released by the second thymidine block and grown in fresh medium for 3 hours to let them progress synchronously through G2 phase. FACS is performed to separate and collect FRET[−] and FRET[+] populations. See FIG. 27.

Genomic DNA is collected from each sample, and the sgRNA repertoire amplified from each by PCR. There are 60 samples in total: 5 replicate screens*3 libraries*4 samples for each (Day 7, Day 10, Day 14 FRET[−], and Day 14 FRET[+]).

Data analysis and statistical analysis mirror the approach used in Example 2, so the details from Example 2 are not repeated here. sgRNAs that are enriched in Day 14 FRET[−] cells relative to Day 14 FRET[+], Day 7, and Day 10, and/or are depleted in Day 14 FRET[+] cells relative to Day 14 FRET[−], Day 7, and Day 10, may indicate target genes that, when disrupted (or transcriptionally activated in the case of the CRISPRa screen), induce tau disaggregation. These sgRNA hits are of special interest as potential targets for therapeutic intervention. sgRNAs that are enriched in Day 14 FRET[+] cells relative to Day 14 FRET[−], Day 7, and Day 10, and/or are depleted in Day 14 FRET[−] cells relative to Day 14 FRET[+], Day 7, and Day 10, may indicate target genes that, when disrupted (or transcriptionally activated in the case of the CRISPRa screen), promote or enhance tau aggregation.

We claim:

1. A method of screening for genetic modifiers of tau aggregation, comprising:
   (a) providing a population of cells comprising a chimeric Cas protein comprising a nuclease-inactive Cas protein fused to one or more transcriptional activation domains, a chimeric adaptor protein comprising an adaptor protein fused to one or more transcriptional activation domains, a first tau repeat domain linked to a first reporter, and a second tau repeat domain linked to a second reporter,
   wherein the cells are mammalian cells,
   wherein the first reporter and the second reporter are fluorescent proteins, and wherein the first reporter and the second reporter are a fluorescence resonance energy transfer (FRET) pair;
   (b) introducing into the population of cells a library comprising a plurality of unique guide RNAs that target a plurality of genes;
   (c) culturing the population of cells to allow transcriptional activation and expansion, wherein the plurality of unique guide RNAs form complexes with the chimeric Cas protein and the chimeric adaptor protein, and the complexes activate transcription of the plurality of genes resulting in increased gene expression to produce a genetically modified population of cells;
   (d) contacting the genetically modified population of cells with a tau seeding agent to produce a seeded population of cells,
   wherein step (d) comprises culturing the genetically modified population of cells in the presence of conditioned medium harvested from cultured tau-aggregation-positive cells in which a tau repeat domain stably presents in an aggregated state, wherein the conditioned medium was harvested after being on confluent tau-aggregation-positive cells for 1 to 7 days;
   (e) culturing the seeded population of cells to allow tau aggregates to form, wherein aggregates of the first tau repeat domain and the second tau repeat domain form in a subset of the seeded population of cells to produce an aggregation-positive population of cells; and
   (f) determining abundance of each of the plurality of unique guide RNAs in the aggregation-positive population of cells identified in step (e) relative to the genetically modified population of cells in step (c),
   wherein enrichment of a guide RNA in the aggregation-positive population of cells identified in step (e) relative to the cultured population of cells in step (c) indicates that the gene targeted by the guide RNA is a genetic modifier of tau aggregation, wherein transcriptional activation of the gene targeted by the guide RNA enhances tau aggregation.

2. The method of claim 1, wherein the Cas protein is a Cas9 protein.

3. The method of claim 2, wherein the Cas protein is *Streptococcus pyogenes* Cas9.

4. The method of claim 1, wherein the chimeric Cas protein comprises the nuclease-inactive Cas protein fused to a VP64 transcriptional activation domain, wherein the chimeric Cas protein comprises from N-terminus to C-terminus: the nuclease-inactive Cas protein; a nuclear localization signal; and the VP64 transcriptional activation domain.

5. The method of claim 1, wherein the adaptor protein is an MS2 coat protein, and wherein the one or more transcriptional activation domains in the chimeric adaptor protein comprise a p65 transcriptional activation domain and an HSF1 transcriptional activation domain, wherein the chimeric adaptor protein comprises from N-terminus to C-terminus: the MS2 coat protein; a nuclear localization signal; the p65 transcriptional activation domain; and the HSF1 transcriptional activation domain.

6. The method of claim 1, wherein the chimeric Cas protein comprises SEQ ID NO: 36, or wherein the chimeric Cas protein is encoded by a coding sequence comprising the sequence set forth in SEQ ID NO: 38.

7. The method of claim 1, wherein the chimeric adaptor protein comprises SEQ ID NO: 37, or wherein the chimeric adaptor protein is encoded by a coding sequence comprising the sequence set forth in SEQ ID NO: 39.

8. The method of claim 1, wherein the chimeric Cas protein, the chimeric adaptor protein, the first tau repeat domain linked to the first reporter, and the second tau repeat domain linked to the second reporter are stably expressed in the population of cells, and wherein nucleic acids encoding the chimeric Cas protein, the chimeric adaptor protein, the first tau repeat domain linked to the first reporter, and the second tau repeat domain linked to the second reporter are genomically integrated in the population of cells.

9. The method of claim 1, wherein each guide RNA targets a guide RNA target sequence within 200 bp upstream of a transcription start site.

10. The method of claim 1, wherein each guide RNA comprises two adaptor-binding elements to which the chimeric adaptor protein can specifically bind, wherein a first adaptor-binding element is within a first loop of each of the guide RNAs, and a second adaptor-binding element is within a second loop of each of the guide RNAs, wherein the adaptor-binding element comprises the sequence set forth in SEQ ID NO: 33, and
  wherein each of guide RNAs is a single guide RNA comprising a CRISPR RNA (crRNA) portion fused to a transactivating CRISPR RNA (tracrRNA) portion, and the first loop is the tetraloop corresponding to residues 13-16 of SEQ ID NO: 17, and the second loop is the stem loop 2 corresponding to residues 53-56 of SEQ ID NO: 17.

11. The method of claim 1, wherein step (c) is about 3 days to about 9 days.

12. The method of claim 11, wherein step (c) is about 6 days.

13. The method of claim 1, wherein the conditioned medium was harvested after being on confluent tau-aggregation-positive cells for about 4 days.

14. The method of claim 1, wherein step (d) comprises culturing the genetically modified population of cells in about 75% conditioned medium and about 25% fresh medium.

15. The method of claim 1, wherein the genetically modified population of cells is not co-cultured with the tau-aggregation-positive cells in which a tau repeat domain stably presents in an aggregated state.

16. The method of claim 1, wherein step (e) is about 2 days to about 6 days.

17. The method of claim 16, wherein step (e) is about 4 days.

18. The method of claim 1, wherein the aggregation-positive population of cells in step (e) is identified by flow cytometry.

19. The method of claim 1, wherein abundance is determined by next-generation sequencing.

20. The method of claim 1, wherein a guide RNA is considered enriched if the abundance of the guide RNA relative to the total population of the plurality of unique guide RNAs is at least 1.5-fold higher in the aggregation-positive population of cells in step (e) relative to the cultured population of cells in step (c).

21. The method of claim 1, wherein step (f) comprises determining abundance of each of the plurality of unique guide RNAs in the aggregation-positive population of cells in step (e) relative to the cultured population of cells in step (c) at a first time point in step (c) and/or a second time point in step (c).

22. The method of claim 21, wherein the first time point in step (c) is at a first passage of culturing the population of cells, and the second time point is in the middle of culturing the population of cells to allow transcriptional activation and expansion.

23. The method of claim 22, wherein the first time point in step (c) is after about three days of culturing, and the second time point in step (c) is after about six days of culturing.

24. The method of claim 21, wherein a gene is considered a genetic modifier of tau aggregation, wherein transcriptional activation of the gene enhances tau aggregation, if:
  (1) the abundance of a guide RNA targeting the gene relative to the total population of the plurality of unique guide RNAs is at least 1.5-fold higher in the aggregation-positive population of cells in step (e) relative to the cultured population of cells in step (c) at both the first time point in step (c) and the second time point in step (c); and/or
  (2) the abundance of at least two unique guide RNAs targeting the gene relative to the total population of the plurality of unique guide RNAs is at least 1.5-fold higher in the aggregation-positive population of cells in step (e) relative to the cultured population of cells in step (c) at either the first time point in step (c) or the second time point in step (c).

25. The method of claim 1, wherein the following steps are taken in step (f) to identify a gene as a genetic modifier of tau aggregation, wherein transcriptional activation of the gene enhances tau aggregation:
  (1) identifying which of the plurality of unique guide RNAs are present in the aggregation-positive population of cells produced in step (e);
  (2) calculating the random chance of the guide RNAs identified in step (f)(1) being present using the formula $nC_{n'}*(x-n')C(m-n)/xC_m$,
    wherein x is the variety of unique guide RNAs introduced into the population of cells in step (b),
    wherein m is the variety of unique guide RNAs identified in step (f)(1),
    wherein n is the variety of unique guide RNAs introduced into the population of cells in step (b) that target the gene, and
    wherein n' is the variety of unique guide RNAs identified in step (f)(1) that target the gene;
  (3) calculating average enrichment scores for the guide RNAs identified in step (f)(1),
    wherein the enrichment score for a guide RNA is the relative abundance of the guide RNA in the aggregation-positive population of cells produced in step (e) divided by the relative abundance of the guide RNA in the cultured population of cells in step (c), and
    wherein relative abundance is the read count of the guide RNA divided by the read count of the total population of the plurality of unique guide RNAs; and
  (4) selecting the gene if a guide RNA targeting the gene is significantly below the random chance of being present and above a threshold enrichment score.

26. The method of claim 1, wherein the first tau repeat domain and/or the second tau repeat domain is a human tau repeat domain.

27. The method of claim 1, wherein the first tau repeat domain and/or the second tau repeat domain comprises a pro-aggregation mutation, wherein the pro-aggregation mutation is a tau P301S mutation, which corresponds to position 59 of SEQ ID NO: 11.

28. The method of claim 1, wherein the first tau repeat domain and/or the second tau repeat domain comprises a tau four-repeat domain.

29. The method of claim 1, wherein the first tau repeat domain and/or the second tau repeat domain comprises SEQ ID NO: 11.

30. The method of claim 1, wherein the first tau repeat domain and the second tau repeat domain are the same and each comprises a tau four-repeat domain comprising a tau P301S mutation, which corresponds to position 59 of SEQ ID NO: 11.

31. The method of claim 1, wherein the first reporter is cyan fluorescent protein (CFP) and the second reporter is yellow fluorescent protein (YFP).

32. The method of claim 1, wherein the cells are human cells.

33. The method of claim 32, wherein the cells are HEK293T cells.

34. The method of claim 1, wherein the plurality of unique guide RNAs are introduced at a concentration selected such that a majority of the cells receive only one of the unique guide RNAs.

35. The method of claim 1, wherein the plurality of unique guide RNAs target 100 or more genes, 1000 or more genes, or 10000 or more genes.

36. The method of claim 1, wherein the library is a genome-wide library.

37. The method of claim 1, wherein a plurality of target sequences are targeted on average in each of the targeted plurality of genes.

38. The method of claim 37, wherein at least three target sequences are targeted on average in each of the targeted plurality of genes or wherein about three to about six target sequences are targeted on average in each of the targeted plurality of genes.

39. The method of claim 1, wherein the plurality of unique guide RNAs are introduced into the population of cells by lentiviral transduction, wherein each of the plurality of unique guide RNAs is in a separate viral vector.

40. The method of claim 39, wherein the population of cells is infected at a multiplicity of infection of less than 0.3.

41. The method of claim 1, wherein the plurality of unique guide RNAs are introduced into the population of cells together with a selection marker that imparts resistance to a drug, and step (b) further comprises selecting cells that comprise the selection marker.

42. The method of claim 1, wherein the population of cells into which the plurality of unique guide RNAs are introduced in step (b) comprises greater than 300 cells per unique guide RNA.

* * * * *

SEQUENCE LISTING

```
Sequence total quantity: 43
SEQ ID NO: 1            moltype = AA  length = 31
FEATURE                 Location/Qualifiers
REGION                  1..31
                        note = Synthetic
source                  1..31
                        mol_type = protein
                        organism = synthetic construct
SEQUENCE: 1
QTAPVPMPDL KNVKSKIGST ENLKHQPGGG K                                 31

SEQ ID NO: 2            moltype = AA  length = 31
FEATURE                 Location/Qualifiers
REGION                  1..31
                        note = Synthetic
source                  1..31
                        mol_type = protein
                        organism = synthetic construct
SEQUENCE: 2
VQIINKKLDL SNVQSKCGSK DNIKHVPGGG S                                 31

SEQ ID NO: 3            moltype = AA  length = 31
FEATURE                 Location/Qualifiers
REGION                  1..31
                        note = Synthetic
source                  1..31
                        mol_type = protein
                        organism = synthetic construct
SEQUENCE: 3
VQIVYKPVDL SKVTSKCGSL GNIHHKPGGG Q                                 31

SEQ ID NO: 4            moltype = AA  length = 32
FEATURE                 Location/Qualifiers
REGION                  1..32
                        note = Synthetic
source                  1..32
```

```
                        mol_type = protein
                        organism = synthetic construct
SEQUENCE: 4
VEVKSEKLDF KDRVQSKIGS LDNITHVPGG GN                                    32

SEQ ID NO: 5            moltype = DNA   length = 93
FEATURE                 Location/Qualifiers
misc_feature            1..93
                        note = Synthetic
source                  1..93
                        mol_type = other DNA
                        organism = synthetic construct
SEQUENCE: 5
cagacagccc ccgtgccat gccagacctg aagaatgtca agtccaagat cggctccact        60
gagaacctga agcaccagcc gggaggcggg aag                                   93

SEQ ID NO: 6            moltype = DNA   length = 93
FEATURE                 Location/Qualifiers
misc_feature            1..93
                        note = Synthetic
source                  1..93
                        mol_type = other DNA
                        organism = synthetic construct
SEQUENCE: 6
gtgcagataa ttaataagaa gctggatctt agcaacgtcc agtccaagtg tggctcaaag       60
gataatatca aacacgtccc gggaggcggc agt                                   93

SEQ ID NO: 7            moltype = DNA   length = 93
FEATURE                 Location/Qualifiers
misc_feature            1..93
                        note = Synthetic
source                  1..93
                        mol_type = other DNA
                        organism = synthetic construct
SEQUENCE: 7
gtgcaaatag tctacaaacc agttgacctg agcaaggtga cctccaagtg tggctcatta      60
ggcaacatcc atcataaacc aggaggtggc cag                                   93

SEQ ID NO: 8            moltype = DNA   length = 96
FEATURE                 Location/Qualifiers
misc_feature            1..96
                        note = Synthetic
source                  1..96
                        mol_type = other DNA
                        organism = synthetic construct
SEQUENCE: 8
gtggaagtaa aatctgagaa gcttgacttc aaggacagag tccagtcgaa gattgggtcc      60
ctggacaata tcacccacgt ccctggcgga ggaaat                                96

SEQ ID NO: 9            moltype = AA    length = 133
FEATURE                 Location/Qualifiers
REGION                  1..133
                        note = Synthetic
source                  1..133
                        mol_type = protein
                        organism = synthetic construct
SEQUENCE: 9
LQTAPVPMPD LKNVKSKIGS TENLKHQPGG GKVQIINKKL DLSNVQSKCG SKDNIKHVPG      60
GGSVQIVYKP VDLSKVTSKC GSLGNIHHKP GGGQVEVKSE KLDFKDRVQS KIGSLDNITH     120
VPGGGNKKIE THK                                                        133

SEQ ID NO: 10           moltype = DNA   length = 399
FEATURE                 Location/Qualifiers
misc_feature            1..399
                        note = Synthetic
source                  1..399
                        mol_type = other DNA
                        organism = synthetic construct
SEQUENCE: 10
ctgcagacag ccccgtgcc atgccagac ctgaagaatg tcaagtccaa gatcggctcc        60
actgagaacc tgaagcacca gccgggaggc gggaaggtgc agataattaa taagaagctg    120
gatcttagca acgtccagtc caagtgtggc tcaaaggata tatcaaaaca cgtcccggga    180
ggcggcagtg tgcaaatagt ctacaaacca gttgacctga gcaaggtgac ctccaagtgt    240
ggctcattag gcaacatcca tcataaacca ggaggtggcc aggtggaagt aaaatctgag    300
aagcttgact tcaaggacag agtccagtcg aagattgggt ccctggacaa tatcacccac    360
gtccctggcg gaggaaataa aaagattgaa acccacaag                            399

SEQ ID NO: 11           moltype = AA    length = 133
FEATURE                 Location/Qualifiers
```

```
REGION                       1..133
                             note = Synthetic
source                       1..133
                             mol_type = protein
                             organism = synthetic construct
SEQUENCE: 11
LQTAPVPMPD LKNVKSKIGS TENLKHQPGG GKVQIINKKL DLSNVQSKCG SKDNIKHVSG    60
GGSVQIVYKP VDLSKVTSKC GSLGNIHHKP GGGQVEVKSE KLDFKDRVQS KIGSLDNITH   120
VPGGGNKKIE THK                                                      133

SEQ ID NO: 12                moltype = DNA    length = 399
FEATURE                      Location/Qualifiers
misc_feature                 1..399
                             note = Synthetic
source                       1..399
                             mol_type = other DNA
                             organism = synthetic construct
SEQUENCE: 12
ctgcagacag cccccgtgcc catgccagac ctgaagaatg tcaagtccaa gatcggctcc    60
actgagaacc tgaagcacca gccgggaggc gggaaggtgc agataattaa taagaagctg   120
gatcttagca acgtccagtc caagtgtggc tcaaaggata tatcaaaca cgtctcggga   180
ggcggcagtg tgcaaatagt ctacaaacca gttgacctga gcaaggtgac ctccaagtgt   240
ggctcattag gcaacatcca tcataaacca ggaggtggcc aggtggaagt aaaatctgag   300
aagcttgact tcaaggacag agtccagtcg aagattgggt ccctggacaa tatcacccac   360
gtccctggcg gaggaaataa aaagattgaa acccacaag                          399

SEQ ID NO: 13                moltype = AA    length = 238
FEATURE                      Location/Qualifiers
REGION                       1..238
                             note = Synthetic
source                       1..238
                             mol_type = protein
                             organism = synthetic construct
SEQUENCE: 13
VSKGEELFTG VVPILVELDG DVNGHKFSVS GEGEGDATYG KLTLKFICTT GKLPVPWPTL    60
VTTLTWGVQC FSRYPDHMKQ HDFFKSAMPE GYVQERTIFF KDDGNYKTRA EVKFEGDTLV   120
NRIELKGIDF KEDGNILGHK LEYNYISHNV YITADKQKNG IKANFKIRHN IEDGSVQLAD   180
HYQQNTPIGD GPVLLPDNHY LSTQSALSKD PNEKRDHMVL LEFVTAAGIT LGMDELYK     238

SEQ ID NO: 14                moltype = DNA    length = 714
FEATURE                      Location/Qualifiers
misc_feature                 1..714
                             note = Synthetic
source                       1..714
                             mol_type = other DNA
                             organism = synthetic construct
SEQUENCE: 14
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg gcccaccctc   180
gtgaccaccc tgacctgggg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacatcag ccacaacgtc tatatcaccg ccgacaagca gaagaacggc   480
atcaaggcca acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccgccct gagcaaagac cccaacgaga gcgcgatca catggtcctg   660
ctggagttcg tgaccgccgc cgggatcact ctcggcatga cgagctgta caag          714

SEQ ID NO: 15                moltype = AA    length = 236
FEATURE                      Location/Qualifiers
REGION                       1..236
                             note = Synthetic
source                       1..236
                             mol_type = protein
                             organism = synthetic construct
SEQUENCE: 15
VSKGEELFTG VVPILVELDG DVNGHKFSVS GEGEGDATYG KLTLKFICTT GKLPVPWPTL    60
VTTFGYGLQC FARYPDHMKQ HDFFKSAMPE GYVQERTIFF KDDGNYKTRA EVKFEGDTLV   120
NRIELKGIDF KEDGNILGHK LEYNYNSHNV YIMADKQKNG IKVNFKIRHN IEDGSVQLAD   180
HYQQNTPIGD GPVLLPDNHY LSYQSALSKD PNEKRDHMVL LEFVTAAGIT LGMDEL       236

SEQ ID NO: 16                moltype = DNA    length = 708
FEATURE                      Location/Qualifiers
misc_feature                 1..708
                             note = Synthetic
source                       1..708
                             mol_type = other DNA
```

```
                            -continued
                        organism = synthetic construct
SEQUENCE: 16
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg gcccaccctc   180
gtgaccacct tcggctacgg cctgcagtgc ttcgcccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacaacag ccacaacgtc tatatcatgg ccgacaagca gaagaacggc   480
atcaaggtga acttcaagat ccgccacaac atcgaggacg gcagcgtgca gctcgccgac   540
cactaccagc agaacacccc catcggcgac ggccccgtgc tgctgcccga caaccactac   600
ctgagctacc agtccgccct gagcaaagac cccaacgaga gcgcgatca catggtcctg   660
ctggagttcg tgaccgccgc cgggatcact ctcggcatga cgagctg                 708

SEQ ID NO: 17          moltype = RNA length = 77
FEATURE                Location/Qualifiers
misc_feature           1..77
                       note = Synthetic
source                 1..77
                       mol_type = other RNA
                       organism = synthetic construct
SEQUENCE: 17
gttttagagc tagaaatagc aagttaaaat aaggctagtc cgttatcaac ttgaaaaagt    60
ggcaccgagt cggtgct                                                   77

SEQ ID NO: 18          moltype = RNA length = 82
FEATURE                Location/Qualifiers
misc_feature           1..82
                       note = Synthetic
source                 1..82
                       mol_type = other RNA
                       organism = synthetic construct
SEQUENCE: 18
gttggaacca ttcaaaacag catagcaagt taaaataagg ctagtccgtt atcaacttga    60
aaaagtggca ccgagtcggt gc                                             82

SEQ ID NO: 19          moltype = RNA length = 76
FEATURE                Location/Qualifiers
misc_feature           1..76
                       note = Synthetic
source                 1..76
                       mol_type = other RNA
                       organism = synthetic construct
SEQUENCE: 19
gttttagagc tagaaatagc aagttaaaat aaggctagtc cgttatcaac ttgaaaaagt    60
ggcaccgagt cggtgc                                                    76

SEQ ID NO: 20          moltype = RNA length = 86
FEATURE                Location/Qualifiers
misc_feature           1..86
                       note = Synthetic
source                 1..86
                       mol_type = other RNA
                       organism = synthetic construct
SEQUENCE: 20
gtttaagagc tatgctggaa acagcatagc aagtttaaat aaggctagtc cgttatcaac    60
ttgaaaaagt ggcaccgagt cggtgc                                         86

SEQ ID NO: 21          moltype = AA length = 1392
FEATURE                Location/Qualifiers
REGION                 1..1392
                       note = Synthetic
REGION                 1..1384
                       note = MISC_FEATURE - Cas9
REGION                 1385..1392
                       note = MISC_FEATURE - FLAG
source                 1..1392
                       mol_type = protein
                       organism = synthetic construct
SEQUENCE: 21
MDKKYSIGLD IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
```

```
VVDKGASAQS FIERMTNFDK NLPNEKVLPK HSLLYEYFTV YNELTKVKYV TEGMRKPAFL    540
SGEQKKAIVD LLFKTNRKVT VKQLKEDYFK KIECFDSVEI SGVEDRFNAS LGTYHDLLKI    600
IKDKDFLDNE ENEDILEDIV LTLTLFEDRE MIEERLKTYA HLFDDKVMKQ LKRRRYTGWG    660
RLSRKLINGI RDKQSGKTIL DFLKSDGFAN RNFMQLIHDD SLTFKEDIQK AQVSGQGDSL    720
HEHIANLAGS PAIKKGILQT VKVVDELVKV MGRHKPENIV IEMARENQTT QKGQKNSRER    780
MKRIEEGIKE LGSQILKEHP VENTQLQNEK LYLYYLQNGR DMYVDQELDI NRLSDYDVDH    840
IVPQSFLKDD SIDNKVLTRS DKNRGKSDNV PSEEVVKKMK NYWRQLLNAK LITQRKFDNL    900
TKAERGGLSE LDKAGFIKRQ LVETRQITKH VAQILDSRMN TKYDENDKLI REVKVITLKS    960
KLVSDFRKDF QFYKVREINN YHHAHDAYLN AVVGTALIKK YPKLESEFVY GDYKVYDVRK   1020
MIAKSEQEIG KATAKYFFYS NIMNFFKTEI TLANGEIRKR PLIETNGETG EIVWDKGRDF   1080
ATVRKVLSMP QVNIVKKTEV QTGGFSKESI LPKRNSDKLI ARKKDWDPKK YGGFDSPTVA   1140
YSVLVVAKVE KGKSKKLKSV KELLGITIME RSSFEKNPID FLEAKGYKEV KKDLIIKLPK   1200
YSLFELENGR KRMLASAGEL QKGNELALPS KYVNFLYLAS HYEKLKGSPE DNEQKQLFVE   1260
QHKHYLDEII EQISEFSKRV ILADANLDKV LSAYNKHRDK PIREQAENII HLFTLTNLGA   1320
PAAFKYFDTT IDRKRYTSTK EVLDATLIHQ SITGLYETRI DLSQLGGDKR PAATKKAGQA   1380
KKKKDYKDDD DK                                                       1392

SEQ ID NO: 22           moltype = DNA   length = 4176
FEATURE                 Location/Qualifiers
misc_feature            1..4176
                        note = Synthetic
misc_feature            1..4152
                        note = Cas9
misc_feature            4153..4176
                        note = FLAG
source                  1..4176
                        mol_type = other DNA
                        organism = synthetic construct
SEQUENCE: 22
atggacaaga agtacagcat cggcctggac atcggcacca actctgtggg ctgggccgtg    60
atcaccgacg agtacaaggt gcccagcaag aaattcaagg tgctgggcaa caccgaccgg   120
cacagcatca agaagaacct gatcggagcc ctgctgttcg acagcggcga aacagccgag   180
gccacccggc tgaagagaac cgccagaaga agatacacca cacggaagaa ccggatctgc   240
tatctgcaag agatcttcag caacgagatg gccaaggtgg acgacagctt cttccacaga   300
ctggaagagt ccttcctggt ggaagaggat aagaagcacg agcggcaccc catcttcggc   360
aacatcgtgg acgaggtggc ctaccacgag aagtacccca ccatcctacc cctgagaaag   420
aaactggtgg acagcaccga caaggccgac tgcggctga tctatctggc cctgcccac    480
atgatcaagt tccggggcca cttcctgatc gagggcgacc tgaaccccga caacagcgac   540
gtggacaagc tgttcatcca gctggtgcag acctacaacc agctgttcga ggaaaaccct   600
atcaacgcca gcggcgtgga cgccaaggcc atcctgtctg ccagactgag caagagcaga   660
cggctgaaaa tcctgatcgc ccagctgccc ggcgagaaga gaatggcct gttcggaaac   720
ctgattgccc tgagcctggg cctgaccccc aacttcaaga gcaacttcga cctggccgag   780
gatgccaaac tgcagctgag caaggacacc tacgacgacg acctgctgac                840
cagatcggcg accagtacgc cgacctgttt ctggccgcca gaacctgtc cgacgccatc   900
ctgctgagcg acatcctgag agtgaacacc gagatcacca aggcccccct gagcgcctct   960
atgatcaaga gatacgacga gcaccaccag gacctgaccc tgctgaaagc tctcgtgcgc  1020
cagcagctgc ctgagaagta caaagagatt tcttcgaca agcaggaa cggctacgcc    1080
ggctacattg acggcggagc cagccaggaa gagttctaca gttcatcaa gcccatcctg  1140
gaaaagatgg acggcaccga ggaactgctc gtgaagctga acagagagga cctgctgcgg  1200
aagcagcgga ccttcgacaa cggcagcatc cccaccagat ccacctgggc agagctgcac  1260
gccattctgc ggcggcagga agattttac ccattcctga aggacaaccg ggaaaagatc  1320
gagaagatcc tgaccttccg catccctac tacgtgggcc ctctggcag gggaaacagc  1380
agattcgcct ggatgaccag aaagagcgag gaaaccatca ccccctgaa cttcgaggaa  1440
gtggtggaca agggcgcttc cgcccagagc ttcatcgagc ggatgaccaa cttcgataag  1500
aacctgccca acgagaaggt gctgcccaag cacagcctgc tgtacgagta cttcaccgtg  1560
tataacgagc tgaccaaagt gaaatacgtg accgagggaa tgagaaagcc cgccttcctg  1620
agcggcgagc agaaaaaggc catcgtggac ctgctgttca gaccaaccg aaagtgacc  1680
gtgaagcagc tgaaagagga ctacttcaag aaaatcgagt gcttcgactc cgtggaaatc  1740
tccggcgtgg aagatcggtt caacgcctcc ctgggcacat accacgatct gctgaaaatt  1800
atcaaggaca aggacttcct ggacaatgag gaaaacgagg acattctgga agatatcgtg  1860
ctgaccctga cactgtttga ggacagagag atgatcgagg aacggctgaa aacctatgcc  1920
cacctgttcg acgacaaagt gatgaagcag ctgaagcggc ggagatacac cggctggggc  1980
aggctgagcc ggaagctgat caacggcatc cgggacaagc agtccggcaa gacaatcctg  2040
gatttcctga gtccgacgg cttcgccaac agaaacttca tgcagctgat ccacgacgac  2100
agcctgacct ttaaagagga catccagaaa gccaaggtgt ccggccaggg cgatagcctg  2160
cacgagcaca ttgccaatct ggccggcagc cccgccatta gaagggcat cctgcagaca  2220
gtgaaggtgt tggacgagct cgtgaaagtg atgggccggc acaagcccga gaacatcgtg  2280
atcgaaatgg ccagagagaa ccagaccacc cagaagggac agaaacag ccgcgagaga  2340
atgaagcgga tcgaagagg catcaaagag ctgggcagcc agatcctgaa agaacacccc  2400
gtggaaaaca cccagctgca gaacgagaag ctgtacctgt actacctgca gaatgggcgg  2460
gatatgtacg tggaccagga actggacatc aaccggctgt ccgactacga tgtggaccat  2520
atcgtgcctc agagctttct gaaggacgac tccatcgaca caaggtgct gaccagaagc  2580
gacaagaacc ggggcaagag cgacaacgtg ccctccgaag aggtcgtgaa aagatgaag  2640
aactactggc ggcagctgct gaacgccaag ctgattacac agagaaagtt cgacaatctg  2700
accaaggccg agaggcgg cctgagcgaa ctgataagg ccggcttcat caagagacag  2760
ctggtggaaa cccggcagat cacaaagcac gtggcacaga tcctggactc ccggatgaac  2820
actaagtacg acgagaatga caagctgatc cgggaagtga aagtgatcac cctgaagtcc  2880
aagctggtgt ccgatttccg gaaggatttc cagttttaca agtgcgcga gatcaacaac  2940
taccaccacg cccacgacgc ctacctgaac gccgtcgtgg gaaccgccct gatcaaaaag  3000
```

```
tacccctaagc tggaaagcga gttcgtgtac ggcgactaca aggtgtacga cgtgcggaag  3060
atgatcgcca agagcgagca ggaaatcggc aaggctaccg ccaagtactt cttctacagc  3120
aacatcatga acttttttcaa gaccgagatt accctggcca acggcgagat ccggaagcgg  3180
cctctgatcg agacaaacgg cgaaaccggg gagatcgtgt gggataaggg ccgggatttt  3240
gccaccgtgc ggaaagtgct gagcatgccc caagtgaata tcgtgaaaaa gaccgaggtg  3300
cagacaggcg gcttcagcaa agagtctatc ctgcccaaga ggaacagcga taagctgatc  3360
gccagaaaga aggactggga ccctaagaag tacggcggct tcgacagccc caccgtggcc  3420
tattctgtgc tggtggtggc caaagtggaa aagggcaagt ccaagaaact gaagagtgtg  3480
aaagagctac tgggatcac catcatgaga agaagcagct tcgagaagaa tcccatcgaa  3540
tttctggaag ccaagggcta caagaagtg aaaaaggacc tgatcatcaa gctgcctaag  3600
tactccctgt tcgagctgga aaacggccgg aagagaatgc tggcctctgc cggcgaactg  3660
cagaagggaa acgaactggc cctgcctcc aaatatgtga acttcctgta cctgccagc  3720
cactatgaga agctgaaggg ctcccccgag gataatgagc agaaacagct gtttgtggaa  3780
cagcacaagc actacctgga cgagatcatc gagcagatca gcgagttctc caagagagtg  3840
atcctggccg acgctaatct ggacaaagtg ctgtccgcct acaacaagca ccgggataag  3900
cccatcagag agcaggccga gaatatcatc cacctgttta ccctgaccaa tctgggagcc  3960
cctgccgcct tcaagtactt tgacaccacc atcgaccgga gaggtacac cagcaccaaa  4020
gaggtgctgg acgccaccct gatccaccag agcatcaccg gcctgtacga gacaggatc  4080
gacctgtctc agctgggagg cgacaagcga cctgccgcca caagaaggc tggacaggct  4140
aagaagaaga aagattacaa agacgatgac gataag                            4176

SEQ ID NO: 23           moltype = RNA   length = 16
FEATURE                 Location/Qualifiers
misc_feature            1..16
                        note = Synthetic
source                  1..16
                        mol_type = other RNA
                        organism = synthetic construct
SEQUENCE: 23
gttttagagc tatgct                                                   16

SEQ ID NO: 24           moltype = RNA   length = 67
FEATURE                 Location/Qualifiers
misc_feature            1..67
                        note = Synthetic
source                  1..67
                        mol_type = other RNA
                        organism = synthetic construct
SEQUENCE: 24
agcatagcaa gttaaaataa ggctagtccg ttatcaactt gaaaaagtgg caccgagtcg   60
gtgcttt                                                             67

SEQ ID NO: 25           moltype =    length =
SEQUENCE: 25
000

SEQ ID NO: 26           moltype =    length =
SEQUENCE: 26
000

SEQ ID NO: 27           moltype =    length =
SEQUENCE: 27
000

SEQ ID NO: 28           moltype = RNA   length = 72
FEATURE                 Location/Qualifiers
misc_feature            1..72
                        note = Synthetic
source                  1..72
                        mol_type = other RNA
                        organism = synthetic construct
SEQUENCE: 28
aaacagcata gcaagttaaa ataaggctag tccgttatca acttgaaaaa gtggcaccga   60
gtcggtgctt tt                                                       72

SEQ ID NO: 29           moltype = RNA   length = 82
FEATURE                 Location/Qualifiers
misc_feature            1..82
                        note = Synthetic
source                  1..82
                        mol_type = other RNA
                        organism = synthetic construct
SEQUENCE: 29
gttggaacca ttcaaaaacag catgcaagt taaataagg ctagtccgtt atcaacttga    60
aaaagtggca ccgagtcggt gc                                            82

SEQ ID NO: 30           moltype = RNA   length = 83
FEATURE                 Location/Qualifiers
misc_feature            1..83
```

```
                        note = Synthetic
source                  1..83
                        mol_type = other RNA
                        organism = synthetic construct
SEQUENCE: 30
gttttagagc tagaaatagc aagttaaaat aaggctagtc cgttatcaac ttgaaaaagt    60
ggcaccgagt cggtgctttt ttt                                            83

SEQ ID NO: 31           moltype = RNA   length = 80
FEATURE                 Location/Qualifiers
misc_feature            1..80
                        note = Synthetic
source                  1..80
                        mol_type = other RNA
                        organism = synthetic construct
SEQUENCE: 31
gttttagagc tagaaatagc aagttaaaat aaggctagtc cgttatcaac ttgaaaaagt    60
ggcaccgagt cggtgctttt                                                80

SEQ ID NO: 32           moltype = RNA   length = 92
FEATURE                 Location/Qualifiers
misc_feature            1..92
                        note = Synthetic
source                  1..92
                        mol_type = other RNA
                        organism = synthetic construct
SEQUENCE: 32
gtttaagagc tatgctggaa acagcatagc aagtttaaat aaggctagtc cgttatcaac    60
ttgaaaaagt ggcaccgagt cggtgctttt tt                                  92

SEQ ID NO: 33           moltype = RNA   length = 34
FEATURE                 Location/Qualifiers
misc_feature            1..34
                        note = Synthetic
source                  1..34
                        mol_type = other RNA
                        organism = synthetic construct
SEQUENCE: 33
ggccaacatg aggatcaccc atgtctgcag ggcc                                34

SEQ ID NO: 34           moltype = RNA   length = 137
FEATURE                 Location/Qualifiers
misc_feature            1..137
                        note = Synthetic
source                  1..137
                        mol_type = other RNA
                        organism = synthetic construct
SEQUENCE: 34
gttttagagc taggccaaca tgaggatcac ccatgtctgc agggcctagc aagttaaaat    60
aaggctagtc cgttatcaac ttggccaaca tgaggatcac ccatgtctgc agggccaagt   120
ggcaccgagt cggtgct                                                  137

SEQ ID NO: 35           moltype = RNA   length = 157
FEATURE                 Location/Qualifiers
misc_feature            1..157
                        note = Synthetic
misc_difference         1..20
                        note = n is a, c, g, or u
source                  1..157
                        mol_type = other RNA
                        organism = synthetic construct
SEQUENCE: 35
nnnnnnnnnn nnnnnnnnnn gttttagagc taggccaaca tgaggatcac ccatgtctgc    60
agggcctagc aagttaaaat aaggctagtc cgttatcaac ttggccaaca tgaggatcac   120
ccatgtctgc agggccaagt ggcaccgagt cggtgct                            157

SEQ ID NO: 36           moltype = AA    length = 1471
FEATURE                 Location/Qualifiers
REGION                  1..1471
                        note = Synthetic
REGION                  1..1384
                        note = MISC_FEATURE - dCas9
REGION                  1405..1409
                        note = MISC_FEATURE - NLS
REGION                  1410..1471
                        note = MISC_FEATURE - VP64
source                  1..1471
                        mol_type = protein
                        organism = synthetic construct
```

```
SEQUENCE: 36
MKRPAATKKA GQAKKKKDKK YSIGLAIGTN SVGWAVITDE YKVPSKKFKV LGNTDRHSIK      60
KNLIGALLFD SGETAEATRL KRTARRRYTR RKNRICYLQE IFSNEMAKVD DSFFHRLEES     120
FLVEEDKKHE RHPIFGNIVD EVAYHEKYPT IYHLRKKLVD STDKADLRLI YLALAHMIKF     180
RGHFLIEGDL NPDNSDVDKL FIQLVQTYNQ LFEENPINAS GVDAKAILSA RLSKSRRLEN     240
LIAQLPGEKK NGLFGNLIAL SLGLTPNFKS NFDLAEDAKL QLSKDTYDDD LDNLLAQIGD     300
QYADLFLAAK NLSDAILLSD ILRVNTEITK APLSASMIKR YDEHHQDLTL LKALVRQQLP     360
EKYKEIFFDQ SKNGYAGYID GGASQEEFYK FIKPILEKMD GTEELVKLN REDLLRKQRT      420
FDNGSIPHQI HLGELHAILR RQEDFYPFLK DNREKIEKIL TFRIPYYVGP LARGNSRFAW     480
MTRKSEETIT PWNFEEVVDK GASAQSFIER MTNFDKNLPN EKVLPKHSLL YEYFTVYNEL     540
TKVKYVTEGM RKPAFLSGEQ KKAIVDLLFK TNRKVTVKQL KEDYFKKIEC FDSVEISGVE     600
DRFNASLGTY HDLLKIIKDK DFLDNEENED ILEDIVLTLT LFEDREMIEE RLKTYAHLFD     660
DKVMKQLKRR RYTGWGRLSR KLINGIRDKQ SGKTILDFLK SDGFANRNFM QLIHDDSLTF    720
KEDIQKAQVS GQGDSLHEHI ANLAGSPAIK KGILQTVKVV DELVKVMGRH KPENIVIEMA     780
RENQTTQKGQ KNSRERMKRI EEGIKELGSQ ILKEHPVENT QLQNEKLYLY YLQNGRDMYV     840
DQELDINRLS DYDVDHIVPQ SFLKDDSIDN KVLTRSDKAR GKSDNVPSEE VVKKMKNYWR     900
QLLNAKLITQ RKFDNLTKAE RGGLSELDKA GFIKRQLVET RQITKHVAQI LDSRMNTKYD     960
ENDKLIREVK VITLKSKLVS DFRKDFQFYK VREINNYHHA HDAYLNAVVG TALIKKYPKL    1020
ESEFVYGDYK VYDVRKMIAK SEQEIGKATA KYFFYSNIMN FFKTEITLAN GEIRKRPLIE    1080
TNGETGEIVW DKGRDFATVR KVLSMPQVNI VKKTEVQTGG FSKESILPKR NSDKLIARKK    1140
DWDPKKYGGF DSPTVAYSVL VVAKVEKGKS KKLKSVKELL GITIMERSSF EKNPIDFLEA    1200
KGYKEVKKDL IIKLPKYSLF ELENGRKRML ASAGELQKGN ELALPSKYVN FLYLASHYEK    1260
LKGSPEDNEQ KQLFVEQHKH YLDEIIEQIS EFSKRVILAD ANLDKVLSAY NKHRDKPIRE    1320
QAENIIHLFT LTNLGAPAAF KYFDTTIDRK RYTSTKEVLD ATLIHQSITG LYETRIDLSQ    1380
LGGDSAGGGG SGGGGSGGGG SGPKKKRKVA AAGSGRADAL DDFDLDMLGS DALDDFDLDM    1440
LGSDALDDFD LDMLGSDALD DFDLDMLINC T                                  1471

SEQ ID NO: 37           moltype = AA   length = 473
FEATURE                 Location/Qualifiers
REGION                  1..473
                        note = Synthetic
REGION                  1..130
                        note = MISC_FEATURE - MCP
REGION                  151..155
                        note = MISC_FEATURE - NLS
REGION                  161..341
                        note = MISC_FEATURE - P65
REGION                  350..473
                        note = MISC_FEATURE - HSF1
source                  1..473
                        mol_type = protein
                        organism = synthetic construct
SEQUENCE: 37
MASNFTQFVL VDNGGTGDVT VAPSNFANGV AEWISSNSRS QAYKVTCSVR QSSAQKRKYT      60
IKVEVPKVAT QTVGGVELPV AAWRSYLNME LTIPIFATNS DCELIVKAMQ GLLKDGNPIP     120
SAIAANSGIY SAGGGGSGGG GSGGGGSGPK KKRKVAAAGS PSGQISNQAL ALAPSSAPVL     180
AQTMVPSSAM VPLAQPPAPA PVLTGPPPQS LSAPVPKSTQ AGEGTLSEAL LHLQFDADED    240
LGALLGNSTD PGVFTDLASV DNSEFQQLLN QGVSMSHSTA EPMLMEYPEA ITRLVTGSQR    300
PPDPAPTPLG TSGLPNGLSG DEDFSSIADM DFSALLSQIS SSGQGGGGSG FSVDTSALLD    360
LFSPSVTVPD MSLPDLDSSL ASIQELLSPQ EPPRPPEAEN SSPDSGKQLV HYTAQPLFLL    420
DPGSVDTGSN DLPVLFELGE GSYFSEGDGF AEDPTISLLT GSEPPKAKDP TVS           473

SEQ ID NO: 38           moltype = DNA   length = 4413
FEATURE                 Location/Qualifiers
misc_feature            1..4413
                        note = Synthetic
misc_feature            1..4152
                        note = dCas9
misc_feature            4213..4227
                        note = NLS
misc_feature            4228..4413
                        note = VP64
source                  1..4413
                        mol_type = other DNA
                        organism = synthetic construct
SEQUENCE: 38
atgaaaaggc cggcgccac gaaaaaggcc ggcaggcaa aaagaaaaa ggacaagaag         60
tacagcatcg gcctggccat cggcaccaac tctgtgggct gggccgtgat caccgacgag    120
tacaaggtgc ccagcaagaa attcaaggtg ctgggcaaca ccgaccggca cagcatcaag    180
aagaacctga tcggagccct gctgttcgac agcggcgaaa cagccgaggc cacccggctg    240
aagagaaccg ccagaagaag atacaccaga cggaagaacc ggatctgcta tctgcaagag    300
atcttcagca acgagatggc caaggtggac gacagcttct tccacagact ggaagagtcc    360
ttcctggtgg aagaggataa gaagcacgag cggcacccca tcttcggcaa catcgtggac    420
gaggtggcct accacgagaa gtaccccacc atctaccatc tgagaaagaa actggtggac    480
agcaccgaca aggccgacct gcggctgatc tatctggccc tggcccacat gatcaagttc    540
cggggccact cctgatcga gggcgacctg aaccccgaca acagcgacgt ggacaagctg    600
ttcatccagc tggtgcagac ctacaaccag ctgttcgagg aaaacccat caacgccagc    660
ggcgtggacg ccaaggccat cctgtctgcc agactgagca gagcagacg gctgaaaat    720
ctgatcgccc agctgcccgg cgagaagaag aatggcctgt tcggcaacct gattgccctg    780
```

```
agcctgggcc tgaccccaa cttcaagagc aacttcgacc tggccgagga tgccaaactg    840
cagctgagca aggacaccta cgacgacgac ctggacaacc tgctggccca gatcggcgac    900
cagtacgccg acctgtttct ggccgccaag aacctgtccg acgccatcct gctgagcgac    960
atcctgagag tgaacaccga gatcaccaag gcccccctga cgcctctat gatcaagaga   1020
tacgacgagc accaccagga cctgaccctg ctgaaagctc tcgtgcggca gcagctgcct   1080
gagaagtaca agagatttt cttcgaccag agcaagaacg gctacgccgg ctacattgac   1140
ggcggagcca gccaggaaga gttctacaag ttcatcaagc ccatcctgga aaagatggac   1200
ggcaccgagg aactgctcgt gaagctgaac agagaggacc tgctgcgaa gcagcggacc   1260
ttcgacaacg gcagcatccc ccaccagatc cacctgggag agctgcacgc cattctgcgg   1320
cggcaggaag atttttaccc attcctgaag gacaaccgga aaaagatcga gaagatcctg   1380
accttccgca tcccctacta cgtgggccct ctggccaggg aaacagcag attcgcctgg   1440
atgaccagaa agagcgagga aaccatcacc ccctggaact tcgaggaagt ggtggacaag   1500
ggcgcttccg cccagagctt catcgagcgg atgaccaact tcgataagaa cctgcccaac   1560
gagaaggtgc tgcccaagca cagcctgctg tacgagtact tcaccgtgta taacgagctg   1620
accaaagtga atacgtgac cgagggaatg agaaagcccg ccttcctgag cggcgagcag   1680
aaaaaggcca tcgtggacct gctgttcaag accaaccgga agtgaccgt gaagcagctg   1740
aaagaggact acttcaagaa aatcgagtgc ttcgactccg tggaaatctc cggcgtggaa   1800
gatcggttca acgcctccct gggcacatac cacgatctgc tgaaaattat caaggacaag   1860
gacttcctgg acaatggagga aaacgaggac attctggaag atatcgtgct gaccctgaca   1920
ctgtttgagg acagagagat gatcgaggaa cggctgaaaa cctatgccca cctgttcgac   1980
gacaaagtga tgaagcagct gaagcggcgg agatacaccg ctggggcag ctgagccgag   2040
aagctgatca acggcatccg ggacaagcag tccggcaaga caatcctgga tttcctgaag   2100
tccgacggct tcgccaacag aaacttcatg cagctgatcc acgacgacag cctgaccttt   2160
aaagaggaca tccagaaagc ccaggtgtcc ggccagggcg atagcctgca cgagcacatt   2220
gccaatctgg ccgcagccc cgccattaag aaggggcatc tgcagacagt gaaggtggtg   2280
gacgagctcg tgaaagtgat gggccggcac aagcccgaca acatcgtgat cgaaatggcc   2340
agagagaacc agaccaccca aagggacaa aagaacagcc gcgagagaat gaagcggatc   2400
gaagagggca tcaaagagct gggcagccag atcctgaaag aacaccccgt ggaaaacacc   2460
cagctgcaga acgagaagct gtacctgtac tacctgcaga atgggcggga tatgtacgtg   2520
gaccaggaac tggacatcaa ccggctgtcc gactacgatg tggaccacat cgtgcctcag   2580
agctttctga aggacgactc catcgacaac aaggtgctga ccagaagcga caaggcccgg   2640
ggcaagagcg acaacgtgcc ctccgaagag gtcgtgaaga agatgaagaa ctactggcgg   2700
cagctgctga acgccaagct gattacccag agaaagttcg acaatctgac caaggccgag   2760
agaggcggcc tgagcgaact ggataaggcc ggcttcatca agagacagct ggtggaaacc   2820
cggcagatca caaagcacgt ggcacagatc ctggactccc ggatgaacac taagtacgac   2880
gagaatgaca agctgatccg ggaagtgaaa gtgatcaccc tgaagtccaa gctggtgtcc   2940
gatttccgga aggatttcca gttttacaaa gtgcgcgaga tcaacaacta ccaccacgcc   3000
cacgacgcct acctgaacgc cgtcgtggga accgcctga tcaaaaagta ccctaagctg   3060
gaaagcgagt tcgtgtacgg cgactacaag gtgtacgacg tgcggaagt gatcgccaag   3120
agcgagcagg aaatcggcaa ggctaccgcc aagtactct tctacagcaa catcatgaac   3180
ttttcaaga ccgagattac cctgccaac ggcgagatcc ggaagcggcc tctgatcgag   3240
acaaacggcg aaaccgggga gatcgtgtgg gataagggcc gggattttgc caccgtgcgg   3300
aaagtgctga gcatgcccca agtgaatatc gtgaaaaaga ccgaggtgca gacaggcggc   3360
ttcagcaaag agtctatcct gcccaagagg aacagcgata gctgatcgc agaaagaag   3420
gactgggacc ctaagaagta cggcggcttc gacagcccca ccgtgccta ttctgtgctg   3480
gtggtggcca agtggaaaa gggcaagtcc aagaactga agagtgtgaa agagctgctg   3540
gggatcacca tcatggaag aagcagcttc gagaagaatc ccatcgactt tctggaagcc   3600
aagggctaca agaagtgaa aaaggacctg atcatcaagc tgcctaagta ctccctgttc   3660
gagctggaaa acgccggaa gagaatgctg gcctctgccg gcgaactgca aagggaaac   3720
gaactggccc tgccctccaa atatgtgaac ttcctgtacc tggccagcca ctatgagaag   3780
ctgaagggct ccccccagga taatgagcag aaacagctga ttgtggaaca gcacaagcac   3840
tacctggacg agatcatcga gcagatcagc gagttctcca agagagtgat cctggccgac   3900
gctaatctgg acaaagtgct gtccgcctac aacaagcacc gggataagcc catcagagag   3960
caggccgaga atatcatcca cctgtttacc ctgaccaatc tgggagcccc tgccgccttc   4020
aagtactttg acaccaccat cgaccggaag aggtacacca gcaccaaaga ggtgctggac   4080
gccaccctga tccaccagag catcaccggc ctgtacgaa cacgatcga cctgtctcag   4140
ctgggaggcg acagcgctgg aggaggtgga gcggaggag gagaagcgg aggaggagt   4200
agcggaccta agaaaagag gaaggtgcg gccgctggat ccggacgggc tgacgcattg   4260
gacgattttg atctggatat gctgggaagt gacgccctcg atgatttga ccttgacatg   4320
cttggttcgg atgcccttga tgactttgac ctcgacatgc tcggcagtga cgcccttgat   4380
gatttcgacc tggacatgct gattaactgt aca                              4413
```

SEQ ID NO: 39    moltype = DNA   length = 1419
FEATURE          Location/Qualifiers
misc_feature     1..1419
                 note = Synthetic
misc_feature     1..390
                 note = MCP
misc_feature     451..465
                 note = NLS
misc_feature     481..1023
                 note = P65
misc_feature     1048..1419
                 note = HSF1
source           1..1419
                 mol_type = other DNA
                 organism = synthetic construct
SEQUENCE: 39
atggcttcaa actttactca gttcgtgctc gtggacaatg gtgggacagg ggatgtgaca    60

```
gtggctcctt ctaatttcgc taatggggtg gcagagtgga tcagctccaa ctcacggagc   120
caggcctaca aggtgacatg cagcgtcagg cagtctagtg cccagaagag aaagtatacc   180
atcaaggtgg aggtccccaa agtggctacc cagacagtgg gcggagtcga actgcctgtc   240
gccgcttgga ggtcctacct gaacatggag ctcactatcc aattttcgc taccaattct    300
gactgtgaac tcatcgtgaa ggcaatgcag gggctcctca aagacggtaa tcctatccct   360
tccgccatcg ccgctaactc aggtatctac agcgctggag gaggtggaag cggaggagga   420
ggaagcggag gaggagtag cggacctaag aaaaagagga aggtggcggc cgctggatcc    480
ccttcagggc agatcagcaa ccaggccctg gctctggccc ctagctccgc tccagtgctg   540
gcccagacta tggtgccctc tagtgctatg ggcctctgg cccagccacc tgctccagcc    600
cctgtgctga ccccaggacc accccagtca ctgagcgctc cagtgcccaa gtctacacag   660
gccggcgagg ggactctgag tgaagctctg ctgcacctgc agttcgacgc tgatgaggac   720
ctgggagctc tgctgggaa cagcaccgat cccggagtgt tcacagatct ggcctccgtg    780
gacaactctg agtttcagca gctgctgaat cagggcgtgt ccatgtctca tagtacagcc   840
gaaccaatgc tgatggagta cccgaagcc attacccggc tggtgaccgg cagccagcgg   900
ccccccgacc ccgctccaac tccctggga accagcggcc tgcctaatgg gctgtccgga   960
gatgaagact tctcaagcat cgctgatatg gactttagtg ccctgctgtc acagatttcc  1020
tctagtgggc agggaggagg tggaagcgga ttcagcgtgg acaccagtgc cctgctggac  1080
ctgttcagcc cctcggtgac cgtgcccgac atgagcctgc ctgaccttga cagcagcctg  1140
gccagtatcc aagagctcct gtctccccag gagcccccca ggcctcccga ggcagagaac  1200
agcagcccgg attcagggaa gcagctggtg cactacacag cgcagccgct gttcctgctg  1260
gaccccggct ccgtggacac cgggagcaac gacctgccgg tgctgtttga gctgggagag  1320
ggctcctact ctccgaagg gacggcttc gccgaggacc ccaccatctc cctgctgaca   1380
ggctcggagc tcccaaagc caaggacccc actgtctcc                          1419

SEQ ID NO: 40            moltype = AA   length = 130
FEATURE                  Location/Qualifiers
REGION                   1..130
                         note = Synthetic
source                   1..130
                         mol_type = protein
                         organism = synthetic construct
SEQUENCE: 40
MASNFTQFVL VDNGGTGDVT VAPSNFANGV AEWISSNSRS QAYKVTCSVR QSSAQKRKYT    60
IKVEVPKVAT QTVGGVELPV AAWRSYLNME LTIPIFATNS DCELIVKAMQ GLLKDGNPIP   120
SAIAANSGIY                                                          130

SEQ ID NO: 41            moltype = DNA   length = 390
FEATURE                  Location/Qualifiers
misc_feature             1..390
                         note = Synthetic
source                   1..390
                         mol_type = other DNA
                         organism = synthetic construct
SEQUENCE: 41
atggcttcaa actttactca gttcgtgctc gtggacaatg gtgggacagg ggatgtgaca    60
gtggctcctt ctaatttcgc taatggggtg gcagagtgga tcagctccaa ctcacggagc   120
caggcctaca aggtgacatg cagcgtcagg cagtctagtg cccagaagag aaagtatacc   180
atcaaggtgg aggtccccaa agtggctacc cagacagtgg gcggagtcga actgcctgtc   240
gccgcttgga ggtcctacct gaacatggag ctcactatcc aattttcgc taccaattct    300
gactgtgaac tcatcgtgaa ggcaatgcag gggctcctca aagacggtaa tcctatccct   360
tccgccatcg ccgctaactc aggtatctac                                    390

SEQ ID NO: 42            moltype = DNA   length = 6673
FEATURE                  Location/Qualifiers
misc_feature             1..6673
                         note = Synthetic
source                   1..6673
                         mol_type = other DNA
                         organism = synthetic construct
SEQUENCE: 42
gtgcccgtca gtgggcagag cgcacatcgc ccacagtccc cgagaagttg ggggagggg    60
tcggcaattg aaccggtgcc tagagaaggt ggcgcgggt aaactgggaa agtgatgtcg    120
tgtactggct ccgccttttt cccgagggtg ggggagaacc gtatataagt gcagtagtcg   180
ccgtgaacgt tcttttttcg aacgggtttg ccgcagaac acaggtaagt gccgtgtgtg   240
gttcccgcgg gcctggcctc tttacgggtt atgccccttg cgtgccttga attacttcca   300
cctggctgca gtacgtgatt cttgatcccg agcttcgggt tggaagtggg tgggagagtt   360
cgaggccttg cgcttaagga gcccttcgc ctcgtgcttg agttgaggcc tggcctgggc   420
gctggggccg ccgcgtgcga atctggtggc accttcgcgc ctgtctcgct gctttcgata  480
agtctctagc catttaaaat ttttgatgac ctgctgcgac gctttttttc tggcaagata   540
gtcttgtaaa tgcgggccaa gatctgcaca ctggtatttc ggttttttggg gccgcgggcg   600
gcgacgggc ccgtgcgtcc cagcgcacat gttcggcgag gcggggcctg cgagcgcggc    660
caccgagaat cggacggggg tagtctcaag ctggccggcc tgctctggtg cctggcctcg   720
cgccgccgtg tatcgccccg ccctgggcgg caaggctggc ccgtcggca ccagttgcgt    780
gagcggaaga atgccgcctt cccggccgcg ctgcagggag ctcaaaatgg aggacgcggt   840
gctcgggaga gcggcggggt gagtcaccca cacaaaggaa aagggccttt ccgtcctcag   900
ccgtcgcttc atgtgactcc acggagtacc gggcgccgtc caggcacctc gattagttct   960
cgagcttttg gagtacgtcg tctttaggtt ggggggaggg gttttatgcg atggagtttc  1020
cccacactga gtgggtggag actgaagtta ggccagcttg gcacttgatg taattctcct  1080
tggaatttgc ccttttttgag tttggatctt ggttcattct caagcctcag acagtggttc  1140
```

```
aaagttttttt tcttccattt caggtgtcgt gacgtacggc caccatgaaa aggccggcgg  1200
ccacgaaaaa ggccggccag gcaaaaaaga aaaaggacaa gaagtacagc atcggcctgg  1260
ccatcggcac caactctgtg ggctgggccg tgatcaccga cgagtacaag gtgcccagca  1320
agaaattcaa ggtgctgggc aacaccgacc ggcacagcat caagaagaac ctgatcggag  1380
ccctgctgtt cgacagcggc gaaacagccg aggccacccg gctgaagaga accgccagaa  1440
gaagatacac cagacggaag aaccggatct gctatctgca agagatcttc agcaacgaga  1500
tggccaaggt ggacgacagc ttcttccaca gactggaaga gtccttcctg gtggaagagg  1560
ataagaagca cgagcggcac cccatcttcg gcaacatcgt ggacgaggtg gcctaccacg  1620
agaagtaccc caccatctac cacctgagaa agaaactggt ggacagcacc gacaaggccg  1680
acctgcggct gatctatctg gccctggccc acatgatcaa gttccggggc cacttcctga  1740
tcgagggcga cctgaacccc gacaacagcg acgtggacaa gctgttcatc cagctggtgc  1800
agacctacaa ccagctgttc gaggaaaacc ccatcaacgc cagcggcgtg gacgccaagg  1860
ccatcctgtc tgccagactg agcaagagca cgacggctgga aaatctgatc gcccagctgc  1920
ccggcgagaa gaagaatggc ctgttcggca acctgattgc cctgagcctg ggcctgaccc  1980
ccaacttcaa gagcaacttc gacctggccg aggatgccaa actgcagctg agcaaggaca  2040
cctacgacga cgacctggac aacctgctgg cccagatcgg cgaccagtac gccgacctgt  2100
ttctggccgc caagaacctg tccgacgcca tcctgctgag cgacatcctg agagtgaaca  2160
ccgagatcac caaggccccc ctgagcgcct ctatgatcaa agatacgac gagcaccacc  2220
aggacctgac cctgctgaaa gctctcgtgc ggcagcagct gcctgagaag tacaaagaga  2280
ttttcttcga ccagagcaag aacggctacg ccggctacat tgacggcgga gccagccagg  2340
aagagttcta caagttcatc aagcccatcc tggaaaagat ggacggcacc gaggaactgc  2400
tcgtgaagct gaacagagag gacctgctgc ggaagcagcg gaccttcgac aacggcagca  2460
tccccccacca gatccacctg ggagagctgc acgccattct gcggcggcag gaagattttt  2520
acccattcct gaaggacaac cgggaaaaga tcgagaagat cctgaccttc cgcatcccct  2580
actacgtggg ccctctggcc aggggaaaca gcagattcgc ctggatgacc agaaagagcg  2640
aggaaaccat cacccctgg aacttcgagg aagtggtgga caaggcgct tccgcccaga  2700
gcttcatcga gcggatgacc aacttcgata agaacctgcc caacgagaag gtgctgccca  2760
agcacagcct gctgtacgag tacttcaccg tgtataacga gctgaccaaa gtgaaatacg  2820
tgaccgaggg aatgagaaag cccgccttcc tgagcggcga gcagaaaaag gccatcgtgg  2880
acctgctgtt caagaccaac cggaaagtga ccgtgaagca gctgaaagag gactacttca  2940
agaaaatcga gtgcttcgac tccgtgaaa tctccggcgt ggaagatcgg ttcaacgcct  3000
ccctgggcac ataccacgat ctgctgaaaa ttatcaagga caaggacttc ctggacaatg  3060
aggaaaacga ggacattctg gaagatatcg tgctgaccct gacactgttt gaggacagag  3120
agatgatcga ggaacggctg aaaacctatg cccacctgtt cgacgacaaa gtgatgaagc  3180
agctgaagcg gcggagatac accggctggg gcaggctgag ccggaagctg atcaacgcga  3240
tccgggacaa gcagtccggc aagacaatcc tggatttcct gaagtccgac ggcttcgcca  3300
acagaaactt catgcagctg atccacgacg acagcctgac cttttaagag gacatccaga  3360
aagcccaggt gtccggccag ggcgtagcc tgcacgagca cattgccaat ctggccggca  3420
gccccgccat taagaagggc atcctgcaga cagtgaaagt ggtggacgag ctcgtgaaag  3480
tgatgggccg gcacaagccc gagaacatcg tgatcgaaat ggccagagag aaccagacca  3540
cccagaaggg acagaagaac agccgcgaga gaatgaagcg gatcgaagag ggcatcaaag  3600
agctgggcag ccagatcctg aaagaacacc ccgtggaaaa cacccagctg cagaacgaga  3660
agctgtacct gtactacctg cagaatgggc gggatatgta cgtggaccag gaactggaca  3720
tcaaccggct gtccgactac gatgtggacc acatcgtgcc tcagagcttt ctgaaggacg  3780
actccatcga caacaaggtg ctgaccagaa gcgacaaggc ccggggcaag agcgacaacg  3840
tgccctccga gaggtcgtg aagaagatga aaactactg gcggcagctg ctgaacgcca  3900
agctgattac ccagagaaag ttcgacaatc tgaccaaggc cgagagggc ggcctgagcg  3960
aactggataa ggccggcttc atcaagagac agctggtgga aacccggcag atcacaaagc  4020
acgtggcaca gatcctggac tccggatga acactaagta cgacgagaat gacaagctga  4080
tccgggaagt gaaagtgatc accctgaagt ccaagctggt gtccgatttc cggaaggatt  4140
tccagttta caaagtgcgc gagatcaaca actaccacca cgcccacgac gcctacctga  4200
acgccgtcgt gggaaccgcc ctgatcaaaa agtaccctaa gctggaaagc gagttcgtgt  4260
acggcgacta caaggtgtac gacgtgcgga agatgatcgc caagagcgag caggaaatcg  4320
gcaaggctac cgccaagtac ttcttctaca gcaacatcat gaacttttc aagaccgaga  4380
ttacctggc caacggcgag atccggaagc ggcctctgat cgagacaaac ggcgaaaccg  4440
gggagatcgt gtgggataag gccgggatt ttgccaccgt gcggaaagtg ctgagcatgc  4500
cccaagtgaa tatcgtgaaa aagaccgagg tgcagacagg cggcttcagc aaagagtcta  4560
tcctgcccaa gaggaacagc gataagctga tcgccagaaa aaaggactgg gaccctaaga  4620
agtacggcgg cttcgacagc cccaccgtgg cctattctgt gctggtggtg gccaaagtgg  4680
aaaagggcaa gtccaagaaa ctgaagagtg tgaaagagct gctggggatc accatcatgg  4740
aaagaagcag cttcgagaag aatcccatcg acttttctgga agcaaggc tacaaagaag  4800
tgaaaaagga cctgatcatc aagctgccta gtactccct gttcgagctg gaaacggcc  4860
ggaagagaat gctggcctct gccggcgaac tgcagaaggg aaacgaactg gccctgccct  4920
ccaaatatgt gaacttcctg tacctggcca gccactatga gaagctgaag ggctccccag  4980
aggataatga gcagaaacag ctgtttgtgg aacagcacaa gcactacctg gacgagatca  5040
tcgagcagat cagcgagttc tccaagagag tgatcctggc cgacgctaat ctggacaaag  5100
tgctgtccgc ctacaacaag caccgggata agccatcag agagcaggcc gagaatatca  5160
tccacctgtt taccctgacc aatctgggag ccctgcgcgc cttcaagtac tttgacacca  5220
ccatcgaccg gaagaggtac accagcacca aagaggtgct ggacgccacc ctgatccacc  5280
agagcatcac cggcctgtac gagacacgga tcgacctgtc tcagctggga ggcgacagcg  5340
ctggaggagg tggaagcgga ggaggaggaa gcggaggagg aggtagcgga cctaagaaaa  5400
agaggaaggt ggcggccgct ggatccgac gggctgacgc attggacgat tttgatctgg  5460
atatgctggg aagtgacgcc ctcgatgatt ttgaccttga catgcttggt tcggatgccc  5520
ttgatgactt tgacctcgac atgctgggca gtgacgccct tgatgatttc gacctgacca  5580
tgctgattaa ctgtacaggc agtgagaggc gcagaggaag tctgctaaca tgcggtgacg  5640
tcgaggagaa tcctgcccca atggccaagc ttttgtctca agaagaatcc accctcattg  5700
aaagagcaac ggctacaatc aacagcatcc ccatctctga agactacagc gtcgccagcg  5760
cagctctctc tagcgacggc cgcatcttca ctggtgtcaa tgtatatcat tttactgggg  5820
gaccttgtgc agaactcgtg gtgctgggca ctgctgctgc tgcggcagct ggcaacctga  5880
```

```
cttgtatcgt cgcgatcgga aatgagaaca ggggcatctt gagcccctgc ggacggtgcc   5940
gacaggtgct tctcgatctg catcctggga tcaaagccat agtgaaggac agtgatggac   6000
agccgacggc agttgggatt cgtgaattgc tgccctctgg ttatgtgtgg gagggctaag   6060
aattcgatat caagcttatc ggtaatcaac ctctggatta caaatttgt gaaagattga    6120
ctggtattct taactatgtt gctccttta cgctatgtgg atacgctgct ttaatgcctt    6180
tgtatcatgc tattgcttcc cgtatggctt tcatttctc ctccttgtat aaatcctggt    6240
tgctgtctct ttatgaggag ttgtggcccg ttgtcaggca acgtggcgtg gtgtgcactg    6300
tgtttgctga cgcaaccccc actggttggg gcattgccac cacctgtcag ctcctttccg    6360
ggactttcgc tttccccctc cctattgcca cggcggaact catcgccgcc tgccttgccc    6420
gctgctggac aggggctcgg ctgttgggca ctgacaattc cgtggtgttg tcggggaaat    6480
catcgtcctt tccttggctg ctcgcctgtg ttgccacctg gattctgcgc gggacgtcct    6540
tctgctacgt cccttcggcc ctcaatccag cggaccttcc ttcccgcggc ctgctgccgg    6600
ctctgcggcc tcttccgcgt cttcgccttc gccctcagac gagtcggatc tccctttggg    6660
ccgcctcccc gca                                                      6673

SEQ ID NO: 43          moltype = DNA   length = 4324
FEATURE                Location/Qualifiers
misc_feature           1..4324
                       note = Synthetic
source                 1..4324
                       mol_type = other DNA
                       organism = synthetic construct
SEQUENCE: 43
gtgcccgtca gtgggcagag cgcacatcgc ccacagtccc cgagaagttg gggggagggg     60
tcggcaattg aaccggtgcc tagagaaggt ggcgcggggt aaactgggaa agtgatgtcg    120
tgtactggct ccgccttttt cccgagggtg gggagaaacc gtatataagt gcagtagtcg    180
ccgtgaacgt tctttttcgc aacgggtttt ccgccagaac acaggtaagt gccgtgtgtg    240
gttcccgcgg gcctggcctc tttacgggtt atgcccttg cgtgccttga attacttcca     300
cctggctgca gtacgtgatt cttgatcccg agcttcgggt tggaagtggg tgggagagtt    360
cgaggccttg cgcttaagga gccccttcgc ctcgtgcttg agttgaggcc tggcctgggc    420
gctggggccg ccgcgtgcga atcggtggc accttcgcgc ctgtctcgct gcttcgata     480
agtctctagc cattaaaaat ttttgatgac ctgctgcgac gcttttttc tggcaagata    540
gtcttgtaaa tgcgggccaa gatctgcaca ctggtatttc ggttttggg gccgcgggcg    600
gcgacggggc ccgtgcgtcc cagcgcacat gttcggcgag gcggggcctg cgagcgcggc    660
caccgagaat cggacggggg tagtctcaag ctggccgagc tgtctggtg cctggcctcg    720
cgccgccgtg tatcgccccg ccctgggcgg caaggctggc ccgtcggca ccagttgcgt    780
gagcggaaaa atgccgcgct tccggccctg ctgcaggga ctcaaaatgg aggacgcggc    840
gctcgggaga gcgggcgggt gagtcaccca cacaaaggaa aagggccttt ccgtcctcag    900
ccgtcgcttc atgtgactcc acggagtacc gggcgccgtc caggcacctc gattagttct    960
cgagcttttg gagtacgtcg tctttaggtt gggggagg gttttatgcg atggagtttc    1020
cccacactga gtgggtggag actgaagtta ggccagcttg gcacttgatg taattctcct   1080
tggaatttgc ccttttgag tttggatctt ggttcattct caagcctcag acagtggttc    1140
aaagtttttt tcttccattt caggtgtcgt gacgtacggc caccatgcct tcaaacttta   1200
ctcagttcgt gctcgtggac aatggtggga caggggatgt gacagtggct ccttctaatt   1260
tcgctaatgg ggtggcagag tggatcagct ccaactcacg gagccaggcc tacaaggtga   1320
catgcagcgt caggcagtct agtgcccaga agagaaagta taccatcaag gtggaggtcc   1380
ccaaagtggc tacccagaca gtgggcggga tcgaactgcc tgtcgccgct tggaggtcct   1440
acctgaacat ggagctcact atcccaattt tcgctaccaa ttctgactgt gaactcatcg   1500
tgaaggcaat gcagggggctc ctcaaagacg gtaatcctat cccttccgcc atcgccgcta   1560
actcaggtat ctacagcgct ggaggaggtg aagcggagg aggaggaagc ggaggaggag   1620
gtagcggacc taagaaaaag aggaaggtgg cggccgctgg atcccctttca gggcagatca   1680
gcaaccaggc cctggctctg gcccctagct ccgctccagt gctggcccag actatggtgc   1740
cctctagtgc tatggtgcct ctgcccagc cacctgctcc agcccctgtg ctgacccag    1800
gaccacccca gtcactgagc gctccagtgc ccaagtctac acaggccggc gaggggactc    1860
tgagtgaagc tctgctgcac ctgcagttcg acgctgatga ggacctggga gctctgctgg    1920
ggaacagcac cgatcccgga gtgttcacga atctggcctc cgtggacaac tctgagtttc    1980
agcagctgct gaatcagggc gtgtccatgt ctcatagtac agccgaacca atgctgatgg    2040
agtacccga agccattacc cggctggtga ccggcagcca gcggcccccc gaccccgctc     2100
caactcccct gggaaccagc ggcctgccta atgggctgtc cggagatgaa gacttctcaa    2160
gcatcgctga tatggacttt agtgccctgc tgtcacagat ttcctctagt gggcagggaa    2220
gaggtggaag cggcttcagc gtggacacca gtgccctgct ggacctgttc agcccctcgg    2280
tgaccgtgcc cgacatgagc ctgcctgacc ttgacagcag cctggccagt atccaagagc    2340
tcctgtctcc caggagcccc ccaggcctcc cgaggcaga aacagcagc ccggattcag     2400
ggaagcagct ggtgcactac acagcggcagc cgctgttcct ggtggaccc gctccggtgg    2460
acaccgggag caacgacctg ccggtgctgt ttgagctggg agagggctcc tacttctccg    2520
aagggacgg cttcgccgag gaccccacca tctccctgct gacaggctcg gagcctccca    2580
aagccaagga cccactgtc tcctgtacag gcagtggaga gggcagagga agtctgctaa    2640
catgcggtga cgtcgaggag aatcctggcc caaccatgaa aaagcctgaa ctcaccgcta    2700
cctctgtcga gaagtttctg atcgaaaagt tcgacagcgt ctccgacctg atgcagctct    2760
ccgagggcga agaatctcgg gcttcagct tcgatgtggg agggcgtgga tatgtcctgc    2820
gggtgaatag ctgcgccgat ggttctaca aagatcgcta tgttatcgg cacttttgcat    2880
ccgccgctct cccctattccc gaagtgcttg acattgggga gttcagcgag agcctgacct    2940
attgcatctc ccgccgtgca cagggtgtca ccttgcaaga cctgcctgaa accgaactgc    3000
ccgctgttct ccagccgctc gccgaggcca tggatgccgt gccgcc gatcttagcc        3060
agaccagcgc gttcggccca ttcggacctc aaggaatcgg tcaatacact acatggcgcg    3120
atttcatctg cgctattgct gatcccatg tgtatcactg gcaaactgtg atggacacaa    3180
ccgtcagtgc ctccgtcgcc caggctccg atgagctgat gctttgggcc gaggactgcc    3240
ccgaagtccg gcacctcgtg cacgccgatt tcggctccaa caatgtcctg accgacaatg    3300
gccgcataac agccgtcatt gactgagcg aggccatgtt cggggattcc caatacgagg    3360
```

-continued

```
tcgccaacat cttcttctgg aggccctggt tggcttgtat ggagcagcag acccgctact    3420
tcgagcggag gcatcccgag cttgcaggat ctcctcggct ccgggcttat atgctccgca    3480
ttggtcttga ccaactctat cagagcttgg ttgacggcaa tttcgatgat gcagcttggg    3540
ctcagggtcg ctgcgacgca atcgtccggt ccggagccgg gactgtcggg cgtacacaaa    3600
tcgcccgcag aagcgctgcc gtctggaccg atggctgtgt ggaagtgctc gccgatagtg    3660
gaaacagacg ccccagcact cgtcctaggg caaaggatct gcagtaatga gaattcgata    3720
tcaagcttat cggtaatcaa cctctggatt acaaaatttg tgaaagattg actggtattc    3780
ttaactatgt tgctcctttt acgctatgtg gatacgctgc tttaatgcct ttgtatcatg    3840
ctattgcttc ccgtatggct ttcattttct cctccttgta taaatcctgg ttgctgtctc    3900
tttatgagga gttgtggccc gttgtcaggc aacgtgcgt ggtgtgcact gtgtttgctg     3960
acgcaacccc cactggttgg ggcattgcca ccacctgtca gctcctttcc gggactttcg    4020
ctttccccct ccctattgcc acggcggaac tcatcgccgc ctgccttgcc cgctgctgga    4080
caggggctcg gctgttgggc actgacaatt ccgtggtgtt gtcggggaaa tcatcgtcct    4140
ttccttggct gctcgcctgt gttgccacct ggattctgcg cgggacgtcc ttctgctacg    4200
tcccttcggc cctcaatcca gcggaccttc cttcccgcgg cctgctgccg gctctgcggc    4260
ctcttccgcg tcttcgcctt cgccctcaga cgagtcggat ctccctttgg gccgcctccc    4320
cgca                                                                 4324
```